United States Patent
Kühn et al.

(10) Patent No.: US 11,891,635 B2
(45) Date of Patent: Feb. 6, 2024

(54) NUCLEIC ACID SEQUENCE REPLACEMENT BY NHEJ

(71) Applicant: Max-Delbrück-Centrum für Molekulare Medizin in der Helmholtz-Gemeinschaft, Berlin (DE)

(72) Inventors: Ralf Kühn, Berlin (DE); Eric Danner, Berlin (DE)

(73) Assignee: Max-Delbrück-Centrum für Molekulare Medizin in der Helmholtz-Gemeinschaft, Berlin (DE)

( * ) Notice: Subject to any disclaimer, the term of this patent is extended or adjusted under 35 U.S.C. 154(b) by 340 days.

(21) Appl. No.: 16/956,365

(22) PCT Filed: Dec. 21, 2018

(86) PCT No.: PCT/EP2018/086508
§ 371 (c)(1),
(2) Date: Jun. 19, 2020

(87) PCT Pub. No.: WO2019/122302
PCT Pub. Date: Jun. 27, 2019

(65) Prior Publication Data
US 2022/0090035 A1 Mar. 24, 2022

(30) Foreign Application Priority Data
Dec. 21, 2017 (EP) ..................... 17209549

(51) Int. Cl.
| | | |
|---|---|---|
| C12N 9/22 | (2006.01) | |
| A61K 31/7088 | (2006.01) | |
| A61K 38/46 | (2006.01) | |
| C12N 15/01 | (2006.01) | |
| C12N 15/90 | (2006.01) | |
| C12N 15/11 | (2006.01) | |

(52) U.S. Cl.
CPC ............ *C12N 9/22* (2013.01); *A61K 31/7088* (2013.01); *A61K 38/465* (2013.01); *C12N 15/11* (2013.01); *C12N 15/907* (2013.01); *C12N 2310/20* (2017.05); *C12N 2800/80* (2013.01)

(58) Field of Classification Search
CPC .......................... C12N 15/102; C12N 15/907; C12N 2310/20; C12N 15/63; C12N 15/11; C12N 9/22; C12N 2800/80; A61K 38/465; A61K 31/7088
See application file for complete search history.

(56) References Cited

U.S. PATENT DOCUMENTS 9,005,973 B2    4/2015   Cost et al.
2016/0058889 A1*  3/2016   Olson .................. A61P 21/00
                                                             424/94.6

FOREIGN PATENT DOCUMENTS

| CA | 3 021 647 A1 | 10/2017 |
| WO | WO 2017/095967 A2 | 6/2017 |
| WO | WO 2017/185054 A1 | 10/2017 |
| WO | WO 2017/193029 A2 | 11/2017 |

OTHER PUBLICATIONS

Chen et al., CRISPR-Cas 12a target binding unleashes single-stranded DNase activity. bioRxiv, Nov. 29, 2017, pp. 1-29. (Year: 2017).*
Gao et al., Genome Editing in Cotton with the CRISPR/Cas9 System. Frontiers in Plant Science, 2017, vol. 8, Article 1364, pp. 1-12. (Year: 2017).*
He et al., Knock-in of large reporter genes in human cells via CRISPR/Cas9-induced homology-dependent and independent DNA repair. Nuc. Acids Res., 2016, vol. 44(9), e85, pp. 1-14. (Year: 2016).*
Horii et al., Efcient generation of conditional knockout mice via sequential introduction of lox sites. Nature, Scientific reports, 2017, vol. 7: 7891, pp. 1-8. (Year: 2017).*
Liu et al., Delivery methods for site-specific nucleases: Achieving the full potential of therapeutic gene editing. J. Controlled Release., 2016, vol. 244: 83-97. (Year: 2016).*
Ran et al., Double nicking by RNA-guided CRISPR Cas9 enhanced genome editing specificity. Cell, 2013, vol. 154: 1380-1389. ( Year: 2013).*
Stella et al., Conformational activation promotes CRISPR Cas12a catalysis and resetting of the endonuclease activity. Cell, 2018, vol. 175: 1856-1871. (Year: 2018).*
Swarts et al., Structural basis for guide RNA processing and seed-dependent DNA targeting by CRISPR-Cas12a. Mol. Cell, 2017, vol. 66: 221-233. (Year: 2017).*
Geisinger et al., In vivo blunt-end cloning through CRISPR/Cas9-facilitated non-homologous end-joining. Nuc. Acids Res., 2016, vol. 44(8): e76, pp. 1-15. (Year: 2016).*
Suzuki et al., In vivo genome editing via CRISPR/Cas9 mediated homology-independent targeted integration. Nature, 2016, vol. 540: 144-149. (Year: 2016).*
Geisinger, Jonathan M., et al. "In vivo blunt-end cloning through CRISPR/Cas9-facilitated non-homologous end-joining, " Nucleic Acids Research Nucleic Acids Res May 5, 2016;44(8):e76.
Jinek, Martin, et al., "RNA-programmed genome editing in human cells," eLife 2013;2:e00471.
Mali, Prashant, et al., "RNA-Guided Human Genome Engineering via Cas9," Science, Feb. 15, 2013; 339(6121): 823-826.
Orlando, Salvatore J., et al., "Zinc-finger nuclease-driving targeted integration into mammalian genomes using donors with limited chromosomal homology," Nucleic Acids Research, 2010, vol. 38, No. 15 e152.

(Continued)

*Primary Examiner* — Ganapathirama Raghu
(74) *Attorney, Agent, or Firm* — Knobbe Martens Olson & Bear LLP

(57) ABSTRACT

A method for modifying double stranded DNA (dsDNA) employing an RNA guided DNA endonuclease to generate two double strand breaks in the dsDNA molecule to be modified, and replacement of the sequence positioned between the double strand breaks with a substitute DNA sequence using the non-homologous end joining (NHEJ) pathway, and corresponding kits and compositions for modifying double stranded DNA molecules.

14 Claims, 15 Drawing Sheets

Specification includes a Sequence Listing.

(56) References Cited

OTHER PUBLICATIONS

Suzuki, Keiichiro, et al., "In vivo genome editing via CRISPR/Cas9 mediated homology-independent targeted integration," Nature, Dec. 1, 2016, 540(7631): 144-149.

International Search Report and Written Opinion, PCT/EP2018/086508, dated Feb. 12, 2019.

Li, J. et al., 2016 "Gene replacements and insertions in rice by intron targeting using CRISPR-Cas9", *Nature Plants*, vol. 2, No. 10: 16139 (in 6 pages).

Weinthal, D.M et al., 2013 "Nonhomologous End Joining-Mediated Gene Replacement in Plant Cells", *Plant Physiology*, vol. 162, No. 1: 390-400.

Auer, T. O. et al., 2013 "Highly efficient CRISPR/Cas9-mediated knock-in in zebrafish by homology-independent DNA repair", *Genome Research*, vol. 24: 142-153.

He, X. et al., 2016 "Knock-in of large reporter genes in human cells via CRISPR/Cas9-induced homology-dependent and independent DNA repair", *Nucleic Acids Research*, vol. 44, No. 9: e85 (in 14 pages).

Danner, E. et al., 2017 "Control of gene editing by manipulation of DNA repair mechanisms" Mamm Genome vol. 28, No. 7. p. 262-274.

Komor, A.C. et al., 2017 "CRISPR-Based Technologies for the Manipulation of Eukaryotic Genomes", *Cell, Cell Press*, Amsterdam, NL, vol. 168, No. 1: p. 20-36.

\* cited by examiner

A)

B)

A)

X-CGD and α-Sarcoglycan Treatment

Fig. 15 (cont.)

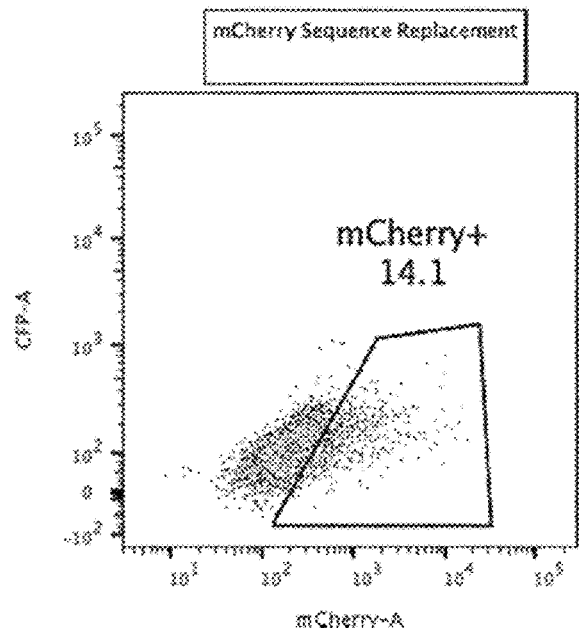

Fig. 16

Replacement of Exon in Polb

WT-Allele:

```
        Protospacer    Upstream                    Protospacer    Downstream
                       PAM                                        PAM
        TTGTGTGGGTCA CCCAGGCAAATG — 400bp of Exon 5 — CCAGTTTGGTTA CCCAGGCAGAAA
                (SEQ ID NO: 77)                             (SEQ ID NO: 78)
Correctly                        Sequence Replaced
Targeted:
        TTGTGTGGGTCA TGACCCACACAA — SA-2A-mCherry-pA — AGAAGTCCTGGG CCCAGGCAGAAA
                (SEQ ID NO: 79)                             (SEQ ID NO: 80)
```

| | | | | (Respective SEQ ID NOs) |
|---|---|---|---|---|
| Theory: | TTGTGTGGGTCA TGACCCACACAA | -- SA 2A-mCherry-pA -- | AGAAGTCCTGGG- CCCAGGCAGAAA | 79, 80 |
| Cl1. | TTGTGTGGGTCA TGACCCACACAA | ----------126----- | --- CAGGCAGAAA | 79, 81 |
| Cl2. | TTGTGTGGGTCA CTGACCCACACAA | | AGAAGTCCTGGG- CCCAGGCAGAAA | 82, 80 |
| Cl3. | TTGTGTGGGT -- TGACCCACACAA | | -----------16 -16---------- | 83 |
| Cl4. | TTGTGTGGGTCA TGACCCACACAA | | AGAAGTCCTGGG- CCCAGGCAGAAA | 79, 80 |
| Cl5. | TTGTGTGGGTCA TGACCCACACAA | | AGAAGTCCTGGG TCCCAGGCAGAAA | 84, 80 |
| Cl6. | TTGTGTGGGTCA TGACCCACACAA | | AGAAGTCCTGGG- CCCAGGCAGAAA | 79, 80 |
| Cl7. | TTGTGTGGGTCA TGACCCACACAA | | AGAAGTCCTGGG- CCCAGGCAGAAA | 79, 80 |
| Cl8. | TTGTGTGGGTCA TGACCCACACAA | | AGAAGTCCTGGG ACCCAGGCAGAAA | 79, 85 |
| Cl9. | TTGTGTGGGTCA TGACCCACACAA | | AGAAGTCCTGGG- CCCAGGCAGAAA | 79, 80 |
| Cl10. | TTGTGTGGGTCA TGACCCACACAA | | AGAAGTCCTGGG- CCCAGGCAGAAA | 79, 80 |

SEQUENCE LISTING

<160> NUMBER OF SEQ ID NOS: 86

<210> SEQ ID NO 1
<211> LENGTH: 9178
<212> TYPE: DNA
<213> ORGANISM: Artificial Sequence
<220> FEATURE:
<223> OTHER INFORMATION: Plasmid Target Site A-sgRNA CAG-Cas9-2A-Puro
      for targeting Reporter 1 (#481)

<400> SEQUENCE: 1

| | | | | | |
|---|---|---|---|---|---|
| actgcggcca | acttacttct | gacaacgatc | ggaggaccga | aggagctaac | cgcttttttg | 60 |
| cacaacatgg | gggatcatgt | aactcgcctt | gatcgttggg | aaccggagct | gaatgaagcc | 120 |
| ataccaaacg | acgagcgtga | caccacgatg | cctgtagcaa | tggcaacaac | gttgcgcaaa | 180 |
| ctattaactg | gcgaactact | tactctagct | tcccggcaac | aattaataga | ctggatggag | 240 |
| gcggataaag | ttgcaggacc | acttctgcgc | tcggcccttc | cggctggctg | gtttattgct | 300 |
| gataaatctg | gagccggtga | gcgtggaagc | cgcggtatca | ttgcagcact | ggggccagat | 360 |
| ggtaagccct | cccgtatcgt | agttatctac | acgacgggga | gtcaggcaac | tatggatgaa | 420 |
| cgaaatagac | agatcgctga | gataggtgcc | tcactgatta | agcattggta | actgtcagac | 480 |
| caagtttact | catatatact | ttagattgat | ttaaaacttc | attttaatt | taaaaggatc | 540 |
| taggtgaaga | tcctttttga | taatctcatg | accaaaatcc | cttaacgtga | gttttcgttc | 600 |
| cactgagcgt | cagaccccgt | agaaaagatc | aaaggatctt | cttgagatcc | ttttttctg | 660 |
| cgcgtaatct | gctgcttgca | aacaaaaaaa | ccaccgctac | cagcggtggt | ttgtttgccg | 720 |
| gatcaagagc | taccaactct | tttccgaag | gtaactggct | tcagcagagc | gcagatacca | 780 |
| aatactgtcc | ttctagtgta | gccgtagtta | ggccaccact | tcaagaactc | tgtagcaccg | 840 |
| cctacatacc | tcgctctgct | aatcctgtta | ccagtggctg | ctgccagtgg | cgataagtcg | 900 |
| tgtcttaccg | ggttggactc | aagacgatag | ttaccggata | aggcgcagcg | gtcgggctga | 960 |
| acggggggtt | cgtgcacaca | gcccagcttg | gagcgaacga | cctacaccga | actgagatac | 1020 |
| ctacagcgtg | agctatgaga | aagcgccacg | cttcccgaag | ggagaaaggc | ggacaggtat | 1080 |
| ccggtaagcg | gcagggtcgg | aacaggagag | cgcacgaggg | agcttccagg | gggaaacgcc | 1140 |
| tggtatcttt | atagtcctgt | cgggtttcgc | cacctctgac | ttgagcgtcg | attttttgtga | 1200 |
| tgctcgtcag | gggggcggag | cctatggaaa | aacgccagca | acgcggcctt | tttacggttc | 1260 |
| ctggcctttt | gctggccttt | tgctcacatg | tgagggccta | tttcccatga | ttccttcata | 1320 |
| tttgcatata | cgatacaagg | ctgttagaga | gataattgga | attaatttga | ctgtaaacac | 1380 |
| aaagatatta | gtacaaaata | cgtgacgtag | aaagtaataa | ttcttgggt | agtttgcagt | 1440 |
| tttaaaatta | tgttttaaaa | tggactatca | tatgcttacc | gtaacttgaa | agtatttcga | 1500 |
| tttcttggct | ttatatatct | tgtggaaagg | acgaaacacc | gactccagtc | tttctagaag | 1560 |
| agttttagag | ctagaaatag | caagttaaaa | taaggctagt | ccgttatcaa | cttgaaaaag | 1620 |
| tggcaccgag | tcggtgcttt | tttgttttag | agctagaaat | agcaagttaa | aataaggcta | 1680 |
| gtccgttttt | agcgcgtgcg | ccaattctgc | agacaaatgg | ctctagaggt | acccgttaca | 1740 |
| taacttacgg | taaatggccc | gcctggctga | ccgcccaacg | acccccgccc | attgacgtca | 1800 |
| atagtaacgc | caatagggac | tttccattga | cgtcaatggg | tggagtattt | acggtaaact | 1860 |
| gcccacttgg | cagtacatca | agtgtatcat | atgccaagta | cgccccctat | tgacgtcaat | 1920 |
| gacggtaaat | ggcccgcctg | gcattgtgcc | cagtacatga | ccttatggga | ctttcctact | 1980 |

```
tggcagtaca tctacgtatt agtcatcgct attaccatgg tcgaggtgag ccccacgttc    2040
tgcttcactc tccccatctc ccccccctcc ccaccccaa ttttgtattt atttattttt     2100
taattatttt gtgcagcgat ggggggcggg gggggggggg ggcgcgcgcc aggcggggcg    2160
gggcggggcg aggggcgggg cggggcgagg cggagaggtg cggcggcagc caatcagagc    2220
ggcgcgctcc gaaagtttcc ttttatggcg aggcggcggc ggcggcggcc ctataaaaag    2280
cgaagcgcgc ggcgggcggg agtcgctgcg acgctgcctt cgccccgtgc cccgctccgc    2340
cgccgcctcg cgccgcccgc cccggctctg actgaccgcg ttactcccac aggtgagcgg    2400
gcgggacggc ccttctcctc cgggctgtaa ttagctgagc aagaggtaag ggtttaaggg    2460
atggttggtt ggtggggtat taatgtttaa ttacctggag cacctgcctg aaatcacttt    2520
ttttcaggtt ggaccggtgc caccatggac tataaggacc acgacggaga ctacaaggat    2580
catgatattg attacaaaga cgatgacgat aagatggccc caaagaagaa gcggaaggtc    2640
ggtatccacg gagtcccagc agccgacaag aagtacagca tcggcctgga catcggcacc    2700
aactctgtgg gctgggccgt gatcaccgac gagtacaagg tgcccagcaa gaaattcaag    2760
gtgctgggca acaccgaccg gcacagcatc aagaagaacc tgatcggagc cctgctgttc    2820
gacagcggcg aaacagccga ggccacccgg ctgaagagaa ccgccagaag aagatacacc    2880
agacggaaga accggatctg ctatctgcaa gagatcttca gcaacgagat ggccaaggtg    2940
gacgacagct tcttccacag actggaagag tccttcctgg tggaagagga taagaagcac    3000
gagcggcacc ccatcttcgg caacatcgtg gacgaggtgg cctaccacga gaagtacccc    3060
accatctacc acctgagaaa gaaactggtg gacagcaccg acaaggccga cctgcggctg    3120
atctatctgg ccctggccca catgatcaag ttccggggcc acttcctgat cgagggcgac    3180
ctgaaccccg acaacagcga cgtggacaag ctgttcatcc agctggtgca gacctacaac    3240
cagctgttcg aggaaaaccc catcaacgcc agcggcgtgg acgccaaggc catcctgtct    3300
gccagactga gcaagagcag acggctggaa aatctgatcg cccagctgcc cggcgagaag    3360
aagaatggcc tgttcggaaa cctgattgcc ctgagcctgg gcctgacccc caacttcaag    3420
agcaacttcg acctggccga ggatgccaaa ctgcagctga gcaaggacac ctacgacgac    3480
gacctggaca acctgctggc ccagatcggc gaccagtacg ccgacctgtt tctggccgcc    3540
aagaacctgt ccgacgccat cctgctgagc gacatcctga gagtgaacac cgagatcacc    3600
aaggcccccc tgagcgcctc tatgatcaag agatacgacg agcaccacca ggacctgacc    3660
ctgctgaaag ctctcgtgcg gcagcagctg cctgagaagt acaaagagat tttcttcgac    3720
cagagcaaga acggctacgc cggctacatt gacggcggag ccagccagga agagttctac    3780
aagttcatca agcccatcct ggaaaagatg gacggcaccg aggaactgct cgtgaagctg    3840
aacagagagg acctgctgcg gaagcagcgg accttcgaca acggcagcat cccccaccag    3900
atccacctgg gagagctgca cgccattctg cggcggcagg aagattttta cccattcctg    3960
aaggacaacc gggaaaagat cgagaagatc ctgaccttcc gcatccccta ctacgtgggc    4020
cctctggcca ggggaaacag cagattcgcc tggatgacca aaagagcga ggaaaccatc    4080 accccctgga acttcgagga agtggtggac aagggcgctt ccgcccagag cttcatcgag    4140
cggatgacca acttcgataa gaacctgccc aacgagaagg tgctgcccaa gcacagcctg    4200
ctgtacgagt acttcaccgt gtataacgag ctgaccaaag tgaaatacgt gaccgaggga    4260
atgagaaagc ccgccttcct gagcggcgag cagaaaaagg ccatcgtgga cctgctgttc    4320
aagaccaacc ggaaagtgac cgtgaagcag ctgaaagagg actacttcaa gaaaatcgag    4380
```

```
tgcttcgact ccgtggaaat ctccggcgtg gaagatcggt tcaacgcctc cctgggcaca      4440
taccacgatc tgctgaaaat tatcaaggac aaggacttcc tggacaatga ggaaaacgag      4500
gacattctgg aagatatcgt gctgaccctg acactgtttg aggacagaga gatgatcgag      4560
gaacggctga aaacctatgc ccacctgttc gacgacaaag tgatgaagca gctgaagcgg      4620
cggagataca ccggctgggg caggctgagc cggaagctga tcaacggcat ccgggacaag      4680
cagtccggca gacaatcct ggatttcctg aagtccgacg gcttcgccaa cagaaacttc       4740
atgcagctga tccacgacga cagcctgacc tttaaagagg acatccagaa agcccaggtg      4800
tccggccagg gcgatagcct gcacgagcac attgccaatc tggccggcag ccccgccatt      4860
aagaagggca tcctgcagac agtgaaggtg gtggacgagc tcgtgaaagt gatgggccgg      4920
cacaagcccg agaacatcgt gatcgaaatg gccagagaga accagaccac ccagaaggga      4980
cagaagaaca gccgcgagag aatgaagcgg atcgaagagg gcatcaaaga gctgggcagc      5040
cagatcctga agaacacccc cgtggaaaac acccagctgc agaacgagaa gctgtacctg      5100
tactacctgc agaatgggcg ggatatgtac gtggaccagg aactggacat caaccggctg      5160
tccgactacg atgtggacca tatcgtgcct cagagctttc tgaaggacga ctccatcgac      5220
aacaaggtgc tgaccagaag cgacaagaac cggggcaaga gcgacaacgt gccctccgaa      5280
gaggtcgtga agaagataaa gaactactgg cggcagctgc tgaacgccaa gctgattacc      5340
cagagaaagt tcgacaatct gaccaaggcc gagagaggcg gcctgagcga actggataag      5400
gccggcttca tcaagagaca gctggtggaa acccggcaga tcacaaagca cgtggcacag      5460
atcctggact cccggatgaa cactaagtac gacgagaatg acaagctgat ccgggaagtg      5520
aaagtgatca ccctgaagtc caagctggtg tccgatttcc ggaaggattt ccagttttac      5580
aaagtgcgcg agatcaacaa ctaccaccac gcccacgacg cctacctgaa cgccgtcgtg      5640
ggaaccgccc tgatcaaaaa gtaccctaag ctggaaagcg agttcgtgta cggcgactac      5700
aaggtgtacg acgtgcggaa gatgatcgcc aagagcgagc aggaaatcgg caaggctacc      5760
gccaagtact tcttctacag caacatcatg aactttttca agaccgagat taccctggcc      5820
aacgcgaga tccggaagcg gcctctgatc gagacaaacg gcgaaaccgg ggagatcgtg      5880
tgggataagg ccgggatttt tgccaccgtg cggaaagtgc tgagcatgcc ccaagtgaat      5940
atcgtgaaaa agaccgaggt gcagacaggc ggcttcagca agagtctat cctgcccaag      6000
aggaacagcg ataagctgat cgccagaaag aaggactggg accctaagaa gtacggcggc      6060
ttcgacagcc ccaccgtggc ctattctgtg ctggtggtgg ccaaagtgga aaagggcaag      6120
tccaagaaac tgaagagtgt gaaagagctg ctggggatca ccatcatgga aagaagcagc      6180
ttcgagaaga tcccatcga ctttctggaa gccaagggct acaaagaagt gaaaaaggac      6240
ctgatcatca gctgcctaa gtactccctg ttcgagctgg aaaacggccg gaagagaatg      6300
ctggcctctg ccggcgaact gcagaaggga aacgaactgg ccctgccctc caaatatgtg      6360
aacttcctgt acctggccag ccactatgag aagctgaagg gctcccccga ggataatgag      6420
cagaaacagc tgtttgtgga acagcacaag cactacctgg acgagatcat cgagcagatc      6480
agcgagttct ccaagagagt gatcctggcc gacgctaatc tggacaaagt gctgtccgcc      6540
tacaacaagc accgggataa gcccatcaga gagcaggccg agaatatcat ccacctgttt      6600
accctgacca atctgggagc ccctgccgcc ttcaagtact tgacaccac catcgaccgg      6660
aagaggtaca ccagcaccaa agaggtgctg gacgccaccc tgatccacca gagcatcacc      6720
```

```
ggcctgtacg agacacggat cgacctgtct cagctgggag gcgacaaaag gccggcggcc    6780
acgaaaaagg ccggccaggc aaaaagaaa aaggaattcg gcagtggaga gggcagagga     6840
agtctgctaa catgcggtga cgtcgaggag aatcctggcc caatgaccga gtacaagccc    6900
acggtgcgcc tcgccacccg cgacgacgtc cccaggcccg tacgcaccct cgccgccgcg    6960
ttcgccgact accccgccac gcgccacacc gtcgatccgg accgccacat cgagcgggtc    7020
accgagctgc aagaactctt cctcacgcgc gtcgggctcg acatcggcaa ggtgtgggtc    7080
gcggacgacg gcgccgcggt ggcggtctgg accacgccgg agagcgtcga agcgggggcg    7140
gtgttcgccg agatcggccc cgcatggcc gagttgagcg gttcccggct ggccgcgcag     7200
caacagatgg aaggcctcct ggcgccgcac cggcccaagg agcccgcgtg gttcctggcc    7260
accgtcggag tctcgcccga ccaccagggc aagggtctgg gcagcgccgt cgtgctcccc    7320
ggagtggagg cggccgagcg cgccggggtg cccgccttcc tggagacctc cgcgccccgc    7380
aacctcccct tctacgagcg gctcggcttc accgtcaccg ccgacgtcga ggtgcccgaa    7440
ggaccgcgca cctggtgcat gacccgcaag cccggtgcct gagaattcta actagagctc    7500
gctgatcagc ctcgactgtg ccttctagtt gccagccatc tgttgtttgc ccctcccccg    7560
tgccttcctt gaccctggaa ggtgccactc ccactgtcct ttcctaataa aatgaggaaa    7620
ttgcatcgca ttgtctgagt aggtgtcatt ctattctggg gggtggggtg gggcaggaca    7680
gcaaggggga ggattgggaa gagaatagca ggcatgctgg ggagcggccg caggaacccc    7740
tagtgatgga gttggccact ccctctctgc gcgctcgctc gctcactgag gccgggcgac    7800
caaaggtcgc ccgacgcccg ggcttttgccc gggcggcctc agtgagcgag cgagcgcgca    7860
gctgcctgca ggggcgcctg atgcggtatt ttctccttac gcatctgtgc ggtatttcac    7920
accgcatacg tcaaagcaac catagtacgc gccctgtagc ggcgcattaa gcgcggcggg    7980
tgtggtggtt acgcgcagcg tgaccgctac acttgccagc gccctagcgc ccgctccttt    8040
cgctttcttc ccttcctttc tcgccacgtt cgccggcttt ccccgtcaag ctctaaatcg    8100
ggggctccct ttagggttcc gatttagtgc tttacggcac ctcgacccca aaaaacttga    8160
tttgggtgat ggttcacgta gtgggccatc gccctgatag acggttttc gccctttgac     8220
gttggagtcc acgttcttta atagtggact cttgttccaa actggaacaa cactcaaccc    8280
tatctcgggc tattcttttg atttataagg gattttgccg atttcggcct attggttaaa    8340
aaatgagctg atttaacaaa aatttaacgc gaatttaac aaaatattaa cgtttacaat     8400
tttatggtgc actctcagta caatctgctc tgatgccgca tagttaagcc agccccgaca    8460
cccgccaaca cccgctgacg cgccctgacg gcttgtctg ctcccggcat ccgcttacag     8520
acaagctgtg accgtctccg ggagctgcat gtgtcagagg ttttcaccgt catcaccgaa    8580
acgcgcgaga cgaaagggcc tcgtgatacg cctatttta taggttaatg tcatgataat     8640
aatggtttct tagacgtcag gtggcacttt tcggggaaat gtgcgcggaa cccctatttg    8700
tttatttttc taaatacatt caaatatgta tccgctcatg agacaataac cctgataaat    8760
gcttcaataa tattgaaaaa ggaagagtat gagtattcaa catttccgtg tcgcccttat    8820
tccctttttt gcggcatttt gccttcctgt ttttgctcac ccagaaacgc tggtgaaagt    8880
aaaagatgct gaagatcagt tgggtgcacg agtgggttac atcgaactgg atctcaacag    8940
cggtaagatc cttgagagtt ttcgccccga agaacgtttt ccaatgatga gcacttttaa    9000
agttctgcta tgtggcgcgg tattatcccg tattgacgcc gggcaagagc aactcggtcg    9060
ccgcatacac tattctcaga atgacttggt tgagtactca ccagtcacag aaaagcatct    9120
```

```
tacggatggc atgacagtaa gagaattatg cagtgctgcc ataaccatga gtgataac      9178
```

<210> SEQ ID NO 2
<211> LENGTH: 23
<212> TYPE: DNA
<213> ORGANISM: Artificial Sequence
<220> FEATURE:
<223> OTHER INFORMATION: PAM+Protospacer for Target Site A Sequence used
      for Cas9 cleavage in Reporter 1

<400> SEQUENCE: 2

```
actccagtct ttctagaaga tgg                                            23
```

<210> SEQ ID NO 3
<211> LENGTH: 4004
<212> TYPE: DNA
<213> ORGANISM: Artificial Sequence
<220> FEATURE:
<223> OTHER INFORMATION: Reporter 1 sequence (Figure 2) integrated into
      the AAVS1 loci

<400> SEQUENCE: 3

```
ctagttatta atagtaatca attacggggt cattagttca tagcccatat atggagttcc      60
gcgttacata acttacggta atggcccgc ctggctgacc gcccaacgac ccccgcccat     120
tgacgtcaat aatgacgtat gttcccatag taacgccaat agggactttc cattgacgtc    180
aatgggtgga gtatttacgg taaactgccc acttggcagt acatcaagtg tatcatatgc    240
caagtacgcc ccctattgac gtcaatgacg gtaaatggcc cgcctggcat tatgcccagt    300
acatgacctt atgggacttt cctacttggc agtacatcta cgtattagtc atcgctatta    360
ccatggtcga ggtgagcccc acgttctgct tcactctccc catctccccc ccctccccac    420
ccccaatttt gtatttattt attttttaat tattttgtgc agcgatgggg gcggggggg    480 gggggggcg cgcgccaggc ggggcgggc ggggcgaggg gcgggcggg gcgaggcgga    540 gaggtgcggc ggcagccaat cagagcggcg cgctccgaaa gtttccttt atggcgaggc    600 ggcggcggcg gcggccccat aaaaagcgaa gcgcgcggcg ggcggggagt cgctgcgacg    660
ctgccttcgc cccgtgcccc gctccgccgc cgcctcgcgc cgcccgcccc ggctctgact    720
gaccgcgtta ctcccacagg tgagcgggcg ggacggccct tctcctccgg gctgtaatta    780
gcgcttggtt taatgacggc ttgtttcttt tctgtggctg cgtgaaagcc ttgaggggct    840 ccggagggc cctttgtgcg gggggagcgg ctcggggggt gcgtgcgtgt gtgtgtgcgt    900
ggggagcgcc gcgtgcggct ccgcgctgcc cggcggctgt gagcgctgcg ggcgcggcgc    960
ggggctttgt gcgctccgca gtgtgcgcga ggggagcgcg gccggggcg gtgccccgcg   1020 gtgcggggg gctgcgagg ggaacaaagg ctgcgtgcgg ggtgtgtgcg tggggggtg    1080 agcaggggt gtgggcgcgt cggtcgggct gcaaccccc ctgcacccc ctccccgagt    1140 tgctgagcac ggcccggctt cgggtgcggg gctccgtacg ggcgtggcg cggggctcgc    1200 cgtgccgggc gggggtggc ggcaggtggg ggtgccgggc ggggcgggc cgcctcgggc    1260 cggggagggc tcgggggagg ggcgcggcgg cccccggagc gccggcggct gtcgaggcgc    1320
ggcgagccgc agccattgcc ttttatggta atcgtgcgag agggcgcagg gacttccttt    1380
gtcccaaatc tgtgcggagc cgaaatctgg gaggcgccgc cgcacccct ctagcgggcg    1440 cggggcgaag cggtgcggcg ccggcaggaa ggaaatgggc ggggagggcc ttcgtgcgtc    1500
gccgcgccgc cgtccccttc tccctctcca gcctcggggc tgtccgcggg gggacggctg    1560
```

-continued

```
ccttcggggg ggacggggca gggcggggtt cggcttctgg cgtgtgaccg gcggctctag    1620
agcctctgct aaccatgttc atgccttctt cttttttccta cagctcctgg caacgtgct    1680
ggttattgtg ctgtctcatc attttggcaa agaattccgc tccatcttct agaaagactg    1740
gagtgcgatc gcgccaccat ggtgagcaag ggcgaggagc tgttcaccgg ggtggtgccc    1800
atcctggtcg agctggacgg cgacgtaaac ggccacaagt tcagcgtgag ggcgagggc     1860
gagggcgatc ccaccaacgg caagctgacc ctgaagttca tctgcaccac cggcaagctg    1920
cccgtgccct ggcccaccct cgtgaccacc ctgagccacg gcgtgcagtg cttcgcccgc    1980
taccccgacc acatgaagca gcacgacttc ttcaagtccg ccatgcccga aggctacgtc    2040
caggagcgca ccatcttctt caaggacgac ggcacctaca agacccgcgc cgaggtgaag    2100
ttcgagggcg acaccctggt gaaccgcatc gagctgaagg gcgtcgactt caaggaggac    2160
ggcaacatcc tggggcacaa gctggagtac aacttcaaca gccacaacat ctatatcatg    2220
gccgtcaagc agaagaacgg catcaaggtg aacttcaaga tccgccacaa cgtggaggac    2280
ggcagcgtgc agctcgccga ccactaccag cagaacaccc ccatcggcga cggccccgtg    2340
ctgctgcccg acagccacta cctgagcacc cagtccgtgc tgagcaaaga ccccaacgag    2400
aagcgcgatc acatggtcct gctggagttc gtcaccgccg ccgggatcac tctcggcatg    2460
gacgagctgt acaagtgaga attcctagag ctcgctgatc agcctcgact gtgccttcta    2520
gttgccagcc atctgttgtt tgcccctccc ccgtgccttc cttgaccctg gaaggtgcca    2580
ctcccactgt cctttcctaa taaaatgagg aaattgcatc gcattgtctg agtaggtgtc    2640
attctattct gggggggtggg gtggggcagg acagcaaggg ggaggattgg gaagagaata    2700
gcaggcatgc ctccatcttc tagaaagact ggagtttaat taagccacca tggtgagcaa    2760
gggcgaggag ctgttcaccg gggtggtgcc catcctggtc gagctggacg gcgacgtaaa    2820
cggccacaag ttcagcgtgt ccggcgaggg cgagggcgat gccacctacg gcaagctgac    2880
cctgaagctg atctgcacca ccggcaagct gcccgtgccc tggcccaccc tcgtgaccac    2940
cctgggctac ggcctgcagt gcttcgcccg ctaccccgac cacatgaagc agcacgactt    3000
cttcaagtcc gccatgcccg aaggctacgt ccaggagcgc accatcttct tcaaggacga    3060
cggcaactac aagacccgcg ccgaggtgaa gttcgagggc gacaccctgg tgaaccgcat    3120
cgagctgaag ggcatcgact tcaaggagga cggcaacatc ctggggcaca gctggagta    3180
caactacaac agccacaacg tctatatcac cgccgacaag cagaagaacg gcatcaaggc    3240
caacttcaag atccgccaca catcgagga cggcggcgtg cagctcgccg accactacca    3300
gcagaacacc cccatcggcg acggccccgt gctgctgccc gacaaccact acctgagcta    3360
ccagtccgcc ctgagcaaag accccaacga gaagcgcgat cacatggtcc tgctggagtt    3420
cgtgaccgcc gccgggatca ctctcggcat ggacgagctg tacaagtaac gcgtgaattc    3480
actcctcagg tgcaggctgc ctatcagaag gtggtggctg gtgtggccaa tgccctggct    3540
cacaaatacc actgagatct ttttccctct gccaaaaatt atgggacat catgaagccc    3600
cttgagcatc tgacttctgg ctaataaagg aaatttattt tcattgcaat agtgtgttgg    3660
aattttttgt gtctctcact cggaaggaca tatgggaggg caaatcattt aaaacatcag    3720
aatgagtatt tggtttagag tttggcaaca tatgcccata tgctggctgc catgaacaaa    3780
ggttggctat aaagaggtca tcagtatatg aaacagcccc tgctgtcca ttccttattc     3840
catagaaaag ccttgacttg aggttagatt ttttttatat tttgttttgt gttattttt     3900
tcttaacat ccctaaaatt tccttacat gttttactag ccagatttt cctcctctcc       3960
```

```
tgactactcc cagtcatagc tgtccctctt ctcttatgga gatc            4004
```

<210> SEQ ID NO 4
<211> LENGTH: 3799
<212> TYPE: DNA
<213> ORGANISM: Artificial Sequence
<220> FEATURE:
<223> OTHER INFORMATION: Reporter 1 with mCherry Replacing BFP in the
      AAVSI loci

<400> SEQUENCE: 4

```
ctagttatta atagtaatca attacggggt cattagttca tagcccatat atggagttcc    60
gcgttacata acttacggta aatggcccgc ctggctgacc gcccaacgac ccccgcccat   120
tgacgtcaat aatgacgtat gttcccatag taacgccaat agggactttc cattgacgtc   180
aatgggtgga gtatttacgg taaactgccc acttggcagt acatcaagtg tatcatatgc   240
caagtacgcc ccctattgac gtcaatgacg gtaaatggcc cgcctggcat tatgcccagt   300
acatgacctt atgggacttt cctacttggc agtacatcta cgtattagtc atcgctatta   360
ccatggtcga ggtgagcccc acgttctgct tcactctccc catctccccc ccctccccac   420
ccccaatttt gtatttattt attttttaat tattttgtgc agcgatgggg gcggggggg    480
gggggggcg cgcgccaggc ggggcgggc ggggcgaggg gcgggcggg gcgaggcgga    540
gaggtgcggc ggcagccaat cagagcggcg cgctccgaaa gtttcctttt atggcgaggc   600
ggcggcggcg gcggccctat aaaaagcgaa gcgcgcggcg ggcggggagt cgctgcgacg   660
ctgccttcgc cccgtgcccc gctccgccgc cgcctcgcgc cgcccgcccc ggctctgact   720
gaccgcgtta ctcccacagg tgagcgggcg ggacggccct tctcctccgg gctgtaatta   780
gcgcttggtt taatgacggc ttgtttcttt tctgtggctg cgtgaaagcc ttgagggct    840
ccgggagggc cctttgtgcg ggggagcgg ctcggggggt gcgtgcgtgt gtgtgtgcgt   900
ggggagcgcc gcgtgcggct ccgcgctgcc cggcggctgt gagcgctgcg ggcgcggcgc   960
ggggctttgt gcgctccgca gtgtgcgcga ggggagcgcg gccggggggcg gtgccccgcg  1020
gtgcggggg ggctgcgagg ggaacaaagg ctgcgtgcgg ggtgtgtgcg tggggggtg    1080
agcaggggt gtgggcgcgt cggtcgggct gcaaccccc ctgcacccc ctccccgagt    1140
tgctgagcac ggcccggctt cgggtgcggg gctccgtacg gggcgtggcg cgggctcgc   1200
cgtgccgggc gggggtggc ggcaggtggg ggtgccgggc ggggcgggc cgcctcgggc   1260
cggggagggc tcgggggagg ggcgcggcgg ccccccgagc gccggcggct gtcgaggcgc   1320
ggcgagccgc agccattgcc ttttatggta atcgtgcgag agggcgcagg gacttccttt   1380
gtcccaaatc tgtgcggagc cgaaatctgg gaggcgccgc cgcacccct ctagcgggcg   1440
cggggcgaag cggtgcggcg ccggcaggaa ggaaatgggc ggggagggcc ttcgtgcgtc   1500
gccgcgccgc cgtccccttc tccctctcca gcctcgggc tgtccgcggg ggacggctg    1560
ccttcggggg gacggggca gggcggggtt cggcttctgg cgtgtgaccg gcggctctag   1620
agcctctgct aaccatgttc atgccttctt cttttttccta cagctcctgg caacgtgct   1680
ggttattgtg ctgtctcatc attttggcaa agaattccgc tccatctaga tggggggacg   1740
tggttttcct ttgaaaaaca cgatgataat atggccacaa ccatggtgag caagggcgag   1800
gaggataaca tggccatcat caaggagttc atgcgcttca aggtgcacat ggagggctcc   1860
gtgaacggcc acgagttcga gatcgagggc gagggcgagg gccgccccta cgagggcacc   1920
cagaccgcca agctgaaggt gaccaagggt ggccccctgc ccttcgcctg ggacatcctg  1980
```

```
tcccctcagt tcatgtacgg ctccaaggcc tacgtgaagc accccgccga catccccgac    2040
tacttgaagc tgtccttccc cgagggcttc aagtgggagc gcgtgatgaa cttcgaggac    2100
ggcggcgtgg tgaccgtgac ccaggactcc tccctgcagg acggcgagtt catctacaag    2160
gtgaagctgc gcggcaccaa cttccctcc gacggcccg taatgcagaa gaagaccatg     2220
ggctgggagg cctcctccga gcggatgtac cccgaggacg gcgccctgaa gggcgagatc    2280
aagcagaggc tgaagctgaa ggacggcggc cactacgacg ctgaggtcaa gaccacctac    2340
aaggccaaga gcccgtgca gctgcccggc gcctacaacg tcaacatcaa gttggacatc    2400
acctcccaca cgaggacta caccatcgtg aacagtacg aacgcgccga gggccgccac     2460
tccaccggcg gcatggacga gctgtacaag taatgaactc cagtctttct agatctagaa    2520
agactggagt ttaattaagc caccatggtg agcaagggcg aggagctgtt caccggggtg    2580
gtgcccatcc tggtcgagct ggacggcgac gtaaacggcc acaagttcag cgtgtccggc    2640
gagggcgagg gcgatgccac ctacggcaag ctgaccctga agctgatctg caccaccggc    2700
aagctgcccg tgccctggcc caccctcgtg accaccctgg gctacggcct gcagtgcttc    2760
gcccgctacc ccgaccacat gaagcagcac gacttcttca gtccgccat gcccgaaggc     2820 tacgtccagg agcgcaccat cttcttcaag gacgacggca actacaagac ccgcgccgag    2880
gtgaagttcg agggcgacac cctggtgaac cgcatcgagc tgaagggcat cgacttcaag    2940
gaggacggca acatcctggg gcacaagctg gagtacaact acaacagcca caacgtctat    3000
atcaccgccg acaagcagaa gaacggcatc aaggccaact tcaagatccg ccacaacatc    3060
gaggacggcg gcgtgcagct cgccgaccac taccagcaga cacccccat cggcgacggc     3120 cccgtgctgc tgcccgacaa ccactacctg agctaccagt ccgccctgag caaagacccc    3180
aacgagaagc gcgatcacat ggtcctgctg gagttcgtga ccgccgccgg gatcactctc    3240
ggcatggacg agctgtacaa gtaacgcgtg aattcactcc tcaggtgcag gctgcctatc    3300
agaaggtggt ggctggtgtg gccaatgccc tggctcacaa ataccactga gatctttttc    3360
cctctgccaa aaattatggg gacatcatga agccccttga gcatctgact tctggctaat    3420
aaaggaaatt tattttcatt gcaatagtgt gttggaattt tttgtgtctc tcactcggaa    3480
ggacatatgg gagggcaaat catttaaaac atcagaatga gtatttggtt tagagtttgg    3540
caacatatgc ccatatgctg gctgccatga acaaaggttg gctataaaga ggtcatcagt    3600
atatgaaaca gccccctgct gtccattcct tattccatag aaaagccttg acttgaggtt    3660 agatttttt tatattttgt tttgtgttat ttttttcttt aacatcccta aaattttcct    3720
tacatgtttt actagccaga ttttcctcc tctcctgact actcccagtc atagctgtcc    3780
ctcttctctt atggagatc                                                 3799
```

<210> SEQ ID NO 5
<211> LENGTH: 1425
<212> TYPE: PRT
<213> ORGANISM: Artificial Sequence
<220> FEATURE:
<223> OTHER INFORMATION: Cas9 protein (Amino acid sequence)

<400> SEQUENCE: 5

```
Met Asp Tyr Lys Asp His Asp Gly Asp Tyr Lys Asp His Asp Ile Asp
1               5                   10                  15

Tyr Lys Asp Asp Asp Asp Lys Met Ala Pro Lys Lys Arg Lys Val
            20                  25                  30
```

```
Gly Ile His Gly Val Pro Ala Ala Asp Lys Lys Tyr Ser Ile Gly Leu
            35                  40                  45

Asp Ile Gly Thr Asn Ser Val Gly Trp Ala Val Ile Thr Asp Glu Tyr
50                  55                  60

Lys Val Pro Ser Lys Lys Phe Lys Val Leu Gly Asn Thr Asp Arg His
65                  70                  75                  80

Ser Ile Lys Lys Asn Leu Ile Gly Ala Leu Leu Phe Asp Ser Gly Glu
                85                  90                  95

Thr Ala Glu Ala Thr Arg Leu Lys Arg Thr Ala Arg Arg Arg Tyr Thr
            100                 105                 110

Arg Arg Lys Asn Arg Ile Cys Tyr Leu Gln Glu Ile Phe Ser Asn Glu
            115                 120                 125

Met Ala Lys Val Asp Asp Ser Phe Phe His Arg Leu Glu Glu Ser Phe
130                 135                 140

Leu Val Glu Glu Asp Lys Lys His Glu Arg His Pro Ile Phe Gly Asn
145                 150                 155                 160

Ile Val Asp Glu Val Ala Tyr His Glu Lys Tyr Pro Thr Ile Tyr His
                165                 170                 175

Leu Arg Lys Lys Leu Val Asp Ser Thr Asp Lys Ala Asp Leu Arg Leu
            180                 185                 190

Ile Tyr Leu Ala Leu Ala His Met Ile Lys Phe Arg Gly His Phe Leu
            195                 200                 205

Ile Glu Gly Asp Leu Asn Pro Asp Asn Ser Asp Val Asp Lys Leu Phe
            210                 215                 220

Ile Gln Leu Val Gln Thr Tyr Asn Gln Leu Phe Glu Glu Asn Pro Ile
225                 230                 235                 240

Asn Ala Ser Gly Val Asp Ala Lys Ala Ile Leu Ser Ala Arg Leu Ser
                245                 250                 255

Lys Ser Arg Arg Leu Glu Asn Leu Ile Ala Gln Leu Pro Gly Glu Lys
            260                 265                 270

Lys Asn Gly Leu Phe Gly Asn Leu Ile Ala Leu Ser Leu Gly Leu Thr
            275                 280                 285

Pro Asn Phe Lys Ser Asn Phe Asp Leu Ala Glu Asp Ala Lys Leu Gln
290                 295                 300

Leu Ser Lys Asp Thr Tyr Asp Asp Asp Leu Asp Asn Leu Leu Ala Gln
305                 310                 315                 320

Ile Gly Asp Gln Tyr Ala Asp Leu Phe Leu Ala Ala Lys Asn Leu Ser
                325                 330                 335

Asp Ala Ile Leu Leu Ser Asp Ile Leu Arg Val Asn Thr Glu Ile Thr
            340                 345                 350

Lys Ala Pro Leu Ser Ala Ser Met Ile Lys Arg Tyr Asp Glu His His
            355                 360                 365

Gln Asp Leu Thr Leu Leu Lys Ala Leu Val Arg Gln Gln Leu Pro Glu
370                 375                 380

Lys Tyr Lys Glu Ile Phe Phe Asp Gln Ser Lys Asn Gly Tyr Ala Gly
385                 390                 395                 400

Tyr Ile Asp Gly Gly Ala Ser Gln Glu Glu Phe Tyr Lys Phe Ile Lys
                405                 410                 415

Pro Ile Leu Glu Lys Met Asp Gly Thr Glu Glu Leu Leu Val Lys Leu
            420                 425                 430

Asn Arg Glu Asp Leu Leu Arg Lys Gln Arg Thr Phe Asp Asn Gly Ser
            435                 440                 445

Ile Pro His Gln Ile His Leu Gly Glu Leu His Ala Ile Leu Arg Arg
```

```
            450             455             460
Gln Glu Asp Phe Tyr Pro Phe Leu Lys Asp Asn Arg Glu Lys Ile Glu
465                 470                 475                 480

Lys Ile Leu Thr Phe Arg Ile Pro Tyr Tyr Val Gly Pro Leu Ala Arg
                485                 490                 495

Gly Asn Ser Arg Phe Ala Trp Met Thr Arg Lys Ser Glu Glu Thr Ile
            500                 505                 510

Thr Pro Trp Asn Phe Glu Glu Val Val Asp Lys Gly Ala Ser Ala Gln
                515                 520                 525

Ser Phe Ile Glu Arg Met Thr Asn Phe Asp Lys Asn Leu Pro Asn Glu
            530                 535                 540

Lys Val Leu Pro Lys His Ser Leu Leu Tyr Glu Tyr Phe Thr Val Tyr
545                 550                 555                 560

Asn Glu Leu Thr Lys Val Lys Tyr Val Thr Glu Gly Met Arg Lys Pro
                565                 570                 575

Ala Phe Leu Ser Gly Glu Gln Lys Lys Ala Ile Val Asp Leu Leu Phe
            580                 585                 590

Lys Thr Asn Arg Lys Val Thr Val Lys Gln Leu Lys Glu Asp Tyr Phe
                595                 600                 605

Lys Lys Ile Glu Cys Phe Asp Ser Val Glu Ile Ser Gly Val Glu Asp
            610                 615                 620

Arg Phe Asn Ala Ser Leu Gly Thr Tyr His Asp Leu Leu Lys Ile Ile
625                 630                 635                 640

Lys Asp Lys Asp Phe Leu Asp Asn Glu Glu Asn Glu Asp Ile Leu Glu
                645                 650                 655

Asp Ile Val Leu Thr Leu Thr Leu Phe Glu Asp Arg Glu Met Ile Glu
            660                 665                 670

Glu Arg Leu Lys Thr Tyr Ala His Leu Phe Asp Asp Lys Val Met Lys
                675                 680                 685

Gln Leu Lys Arg Arg Arg Tyr Thr Gly Trp Gly Arg Leu Ser Arg Lys
            690                 695                 700

Leu Ile Asn Gly Ile Arg Asp Lys Gln Ser Gly Lys Thr Ile Leu Asp
705                 710                 715                 720

Phe Leu Lys Ser Asp Gly Phe Ala Asn Arg Asn Phe Met Gln Leu Ile
                725                 730                 735

His Asp Asp Ser Leu Thr Phe Lys Glu Asp Ile Gln Lys Ala Gln Val
            740                 745                 750

Ser Gly Gln Gly Asp Ser Leu His Glu His Ile Ala Asn Leu Ala Gly
            755                 760                 765

Ser Pro Ala Ile Lys Lys Gly Ile Leu Gln Thr Val Lys Val Val Asp
770                 775                 780

Glu Leu Val Lys Val Met Gly Arg His Lys Pro Glu Asn Ile Val Ile
785                 790                 795                 800

Glu Met Ala Arg Glu Asn Gln Thr Thr Gln Lys Gly Gln Lys Asn Ser
                805                 810                 815

Arg Glu Arg Met Lys Arg Ile Glu Glu Gly Ile Lys Glu Leu Gly Ser
            820                 825                 830

Gln Ile Leu Lys Glu His Pro Val Glu Asn Thr Gln Leu Gln Asn Glu
            835                 840                 845

Lys Leu Tyr Leu Tyr Tyr Leu Gln Asn Gly Arg Asp Met Tyr Val Asp
            850                 855                 860

Gln Glu Leu Asp Ile Asn Arg Leu Ser Asp Tyr Asp Val Asp His Ile
865                 870                 875                 880
```

```
-continued

Val Pro Gln Ser Phe Leu Lys Asp Asp Ser Ile Asp Asn Lys Val Leu
            885                 890                 895

Thr Arg Ser Asp Lys Asn Arg Gly Lys Ser Asp Asn Val Pro Ser Glu
            900                 905                 910

Glu Val Val Lys Lys Met Lys Asn Tyr Trp Arg Gln Leu Leu Asn Ala
            915                 920                 925

Lys Leu Ile Thr Gln Arg Lys Phe Asp Asn Leu Thr Lys Ala Glu Arg
    930                 935                 940

Gly Gly Leu Ser Glu Leu Asp Lys Ala Gly Phe Ile Lys Arg Gln Leu
945                 950                 955                 960

Val Glu Thr Arg Gln Ile Thr Lys His Val Ala Gln Ile Leu Asp Ser
            965                 970                 975

Arg Met Asn Thr Lys Tyr Asp Glu Asn Asp Lys Leu Ile Arg Glu Val
            980                 985                 990

Lys Val Ile Thr Leu Lys Ser Lys Leu Val Ser Asp Phe Arg Lys Asp
            995                 1000                1005

Phe Gln Phe Tyr Lys Val Arg Glu Ile Asn Asn Tyr His His Ala His
            1010                1015                1020

Asp Ala Tyr Leu Asn Ala Val Val Gly Thr Ala Leu Ile Lys Lys Tyr
1025                1030                1035                1040

Pro Lys Leu Glu Ser Glu Phe Val Tyr Gly Asp Tyr Lys Val Tyr Asp
            1045                1050                1055

Val Arg Lys Met Ile Ala Lys Ser Glu Gln Glu Ile Gly Lys Ala Thr
            1060                1065                1070

Ala Lys Tyr Phe Phe Tyr Ser Asn Ile Met Asn Phe Phe Lys Thr Glu
            1075                1080                1085

Ile Thr Leu Ala Asn Gly Glu Ile Arg Lys Arg Pro Leu Ile Glu Thr
            1090                1095                1100

Asn Gly Glu Thr Gly Glu Ile Val Trp Asp Lys Gly Arg Asp Phe Ala
1105                1110                1115                1120

Thr Val Arg Lys Val Leu Ser Met Pro Gln Val Asn Ile Val Lys Lys
            1125                1130                1135

Thr Glu Val Gln Thr Gly Gly Phe Ser Lys Glu Ser Ile Leu Pro Lys
            1140                1145                1150

Arg Asn Ser Asp Lys Leu Ile Ala Arg Lys Lys Asp Trp Asp Pro Lys
            1155                1160                1165

Lys Tyr Gly Gly Phe Asp Ser Pro Thr Val Ala Tyr Ser Val Leu Val
            1170                1175                1180

Val Ala Lys Val Glu Lys Gly Lys Ser Lys Lys Leu Lys Ser Val Lys
1185                1190                1195                1200

Glu Leu Leu Gly Ile Thr Ile Met Glu Arg Ser Ser Phe Glu Lys Asn
            1205                1210                1215

Pro Ile Asp Phe Leu Glu Ala Lys Gly Tyr Lys Glu Val Lys Lys Asp
            1220                1225                1230

Leu Ile Ile Lys Leu Pro Lys Tyr Ser Leu Phe Glu Leu Glu Asn Gly
            1235                1240                1245

Arg Lys Arg Met Leu Ala Ser Ala Gly Glu Leu Gln Lys Gly Asn Glu
            1250                1255                1260

Leu Ala Leu Pro Ser Lys Tyr Val Asn Phe Leu Tyr Leu Ala Ser His
1265                1270                1275                1280

Tyr Glu Lys Leu Lys Gly Ser Pro Glu Asp Asn Glu Gln Lys Gln Leu
            1285                1290                1295
```

```
Phe Val Glu Gln His Lys His Tyr Leu Asp Glu Ile Ile Glu Gln Ile
            1300                1305                1310

Ser Glu Phe Ser Lys Arg Val Ile Leu Ala Asp Ala Asn Leu Asp Lys
        1315                1320                1325

Val Leu Ser Ala Tyr Asn Lys His Arg Asp Lys Pro Ile Arg Glu Gln
        1330                1335                1340

Ala Glu Asn Ile Ile His Leu Phe Thr Leu Thr Asn Leu Gly Ala Pro
1345                1350                1355                1360

Ala Ala Phe Lys Tyr Phe Asp Thr Thr Ile Asp Arg Lys Arg Tyr Thr
                1365                1370                1375

Ser Thr Lys Glu Val Leu Asp Ala Thr Leu Ile His Gln Ser Ile Thr
            1380                1385                1390

Gly Leu Tyr Glu Thr Arg Ile Asp Leu Ser Gln Leu Gly Gly Asp Lys
        1395                1400                1405

Arg Pro Ala Ala Thr Lys Lys Ala Gly Gln Ala Lys Lys Lys Lys Glu
    1410                1415                1420

Phe
1425

<210> SEQ ID NO 6
<211> LENGTH: 3106
<212> TYPE: DNA
<213> ORGANISM: Artificial Sequence
<220> FEATURE:
<223> OTHER INFORMATION: Plasmid containing mCherry flanked by two cut
      sites for Integration in Reporter 1

<400> SEQUENCE: 6
ctaaattgta agcgttaata ttttgttaaa attcgcgtta aattttgtt aaatcagctc      60 attttttaac caataggccg aaatcggcaa atcccttat aaatcaaaag aatagaccga    120
gatagggttg agtggccgct acagggcgct cccattcgcc attcaggctg cgcaactgtt   180
gggaagggcg tttcggtgcg ggcctcttcg ctattacgcc agctggcgaa agggggatgt   240
gctgcaaggc gattaagttg ggtaacgcca gggttttccc agtcacgacg ttgtaaaacg   300
acggccagtg agcgcgacgt aatacgactc actatagggc gaattgaagg aaggccgtca   360
aggccgcatt taattaaact ccagtctttc tagaagatgg ggggacgtgg ttttcctttg   420
aaaaacacga tgataatatg gccacaacca tggtgagcaa gggcgaggag ataacatgg    480 ccatcatcaa ggagttcatg cgcttcaagg tgcacatgga gggctccgtg aacggccacg   540
agttcgagat cgagggcgag ggcgagggcc gcccctacga gggcacccag accgccaagc   600
tgaaggtgac caagggtggc cccctgccct tcgcctggga catcctgtcc cctcagttca   660
tgtacggctc caaggcctac gtgaagcacc ccgccgacat ccccgactac ttgaagctgt   720
ccttccccga gggcttcaag tgggagcgcg tgatgaactt cgaggacggc ggcgtggtga   780
ccgtgaccca ggactcctcc ctgcaggacg gcgagttcat ctacaaggtg aagctgcgcg   840
gcaccaactt cccctccgac ggccccgtaa tgcagaagaa gaccatgggc tgggaggcct   900
cctccgagcg gatgtacccc gaggacggcg ccctgaaggg cgagatcaag cagaggctga   960
agctgaagga cggcggccac tacgacgctg aggtcaagac cacctacaag gccaagaagc  1020
ccgtgcagct gcccggcgcc tacaacgtca acatcaagtt ggacatcacc tcccacaacg  1080
aggactacac catcgtggaa cagtacgaac gcgccgaggg ccgccactcc accggcggca  1140
tggacgagct gtacaagtaa tgaactccag tctttctaga agatggcgat cgatcatctg  1200
ggcctcatgg gccttccttt cactgcccgc tttccagtcg ggaaacctgt cgtgccagct  1260
```

-continued

```
gcattaacat ggtcatagct gtttccttgc gtattgggcg ctctccgctt cctcgctcac    1320
tgactcgctg cgctcggtcg ttcgggtaaa gcctggggtg cctaatgagc aaaaggccag    1380
caaaaggcca ggaaccgtaa aaaggccgcg ttgctggcgt ttttccatag gctccgcccc    1440
cctgacgagc atcacaaaaa tcgacgctca agtcagaggt ggcgaaaccc gacaggacta    1500
taaagatacc aggcgtttcc ccctggaagc tccctcgtgc gctctcctgt tccgaccctg    1560
ccgcttaccg gatacctgtc cgcctttctc ccttcgggaa gcgtggcgct ttctcatagc    1620
tcacgctgta ggtatctcag ttcggtgtag tcgttcgct  ccaagctggg ctgtgtgcac    1680
gaaccccccg ttcagcccga ccgctgcgcc ttatccggta actatcgtct tgagtccaac    1740
ccggtaagac acgacttatc gccactggca gcagccactg gtaacaggat tagcagagcg    1800
aggtatgtag gcggtgctac agagttcttg aagtggtggc ctaactacgg ctacactaga    1860
agaacagtat ttggtatctg cgctctgctg aagccagtta ccttcggaaa aagagttggt    1920
agctcttgat ccggcaaaca aaccaccgct ggtagcggtg gtttttttgt ttgcaagcag    1980
cagattacgc gcagaaaaaa aggatctcaa gaagatcctt tgatcttttc tacggggtct    2040
gacgctcagt ggaacgaaaa ctcacgttaa gggattttgg tcatgagatt atcaaaaagg    2100
atcttcacct agatcctttt aaattaaaaa tgaagtttta aatcaatcta agtatatat     2160 gagtaaactt ggtctgacag ttattagaaa aattcatcca gcagacgata aaacgcaata    2220
cgctggctat ccggtgccgc aatgccatac agcaccagaa acgatccgc  ccattcgccg    2280 cccagttctt ccgcaatatc acgggtggcc agcgcaatat cctgataacg atccgccacg    2340
cccagacggc cgcaatcaat aaagccgcta aacggccat  tttccaccat aatgttcggc    2400
aggcacgcat caccatgggt caccaccaga tcttcgccat ccggcatgct cgctttcaga    2460
cgcgcaaaca gctctgccgg tgccaggccc tgatgttctt catccagatc atcctgatcc    2520
accaggcccg cttccatacg ggtacgcgca cgttcaatac gatgtttcgc ctgatgatca    2580
aacggacagg tcgccgggtc cagggtatgc agacgacgca tggcatccgc cataatgctc    2640 acttttctg  ccggcgccag atggctagac agcagatcct gacccggcac ttcgcccagc    2700
agcagccaat cacggcccgc ttcggtcacc acatccagcc ccgccgcaca cggaacaccg    2760
gtggtggcca gccagctcag acgcgccgct tcatcctgca gctcgttcag cgcaccgctc    2820
agatcggttt tcacaaacag caccggacga ccctgcgcgc tcagacgaaa caccgccgca    2880
tcagagcagc caatggtctg ctgcgcccaa tcatagccaa acagacgttc cacccacgct    2940
gccgggctac ccgcatgcag gccatcctgt tcaatcatac tcttccttt  tcaatattat    3000 tgaagcattt atcagggtta ttgtctcatg agcggataca tatttgaatg tatttagaaa    3060
aataaacaaa tagggggttcc gcgcacattt ccccgaaaag tgccac                  3106
```

<210> SEQ ID NO 7
<211> LENGTH: 842
<212> TYPE: DNA
<213> ORGANISM: Artificial Sequence
<220> FEATURE:
<223> OTHER INFORMATION: MC plasmid mCherry Insert for Integrating in Reporter 1

<400> SEQUENCE: 7

```
ttgggctccc cgggcgcgac tagtgaattc agatctgata tctctagagt cgagctagca     60
ctccagtctt tctagaagaa gggccacaac catggtgagc aagggcgagg aggataacat    120
ggccatcatc aaggagttca tgcgcttcaa ggtgcacatg gagggctccg tgaacggcca    180
```

```
cgagttcgag atcgagggcg agggcgaggg ccgcccctac gagggcaccc agaccgccaa    240
gctgaaggtg accaagggtg gcccctgcc cttcgcctgg acatcctgt cccctcagtt     300 catgtacggc tccaaggcct acgtgaagca ccccgccgac atccccgact acttgaagct    360
gtccttcccc gagggcttca agtgggagcg cgtgatgaac ttcgaggacg gcggcgtggt    420
gaccgtgacc caggactcct ccctgcagga cggcgagttc atctacaagg tgaagctgcg    480
cggcaccaac ttcccctccg acggccccgt aatgcagaag aagaccatgg gctgggaggc    540
ctcctccgag cggatgtacc ccgaggacgg cgccctgaag ggcgagatca agcagaggct    600
gaagctgaag gacggcggcc actacgacgc tgaggtcaag accacctaca aggccaagaa    660
gcccgtgcag ctgcccggcg cctacaacgt caacatcaag ttggacatca cctcccacaa    720
cgaggactac accatcgtgg aacagtacga acgcgccgag ggccgccact ccaccggcgg    780
catggacgag ctgtacaagt aatgagtcga cccatggggg cccgccccaa ctggggtaac    840
ct                                                                   842

<210> SEQ ID NO 8
<211> LENGTH: 668
<212> TYPE: DNA
<213> ORGANISM: Artificial Sequence
<220> FEATURE:
<223> OTHER INFORMATION: Example full PCR product of 5 prime end
      sequencing in Reporter 1

<400> SEQUENCE: 8
ttgtcccaaa tctgtgcgga gccgaaatct gggaggcgcc gccgcacccc ctctagcggg     60
cgcggggcga agcggtgcgg cgccggcagg aaggaaatgg gcggggaggg ccttcgtgcg    120
tcgccgcgcc gccgtcccct tctccctctc cagcctcggg gctgtccgcg gggggacggc    180
tgccttcggg ggggacgggg cagggcgggg ttcggcttct ggcgtgtgac cggcggctct    240
agagcctctg ctaaccatgt tcatgccttc ttcttttttcc tacagctcct gggcaacgtg    300
ctggttattg tgctgtctca tcattttggc aaagaattcc gctccatcta gatgggggga    360
cgtggttttc ctttgaaaaa cacgatgata atatggccac aaccatggtg agcaagggcg    420
aggaggataa catggccatc atcaaggagt tcatgcgctt caaggtgcac atggagggct    480
ccgtgaacgg ccacgagttc gagatcgagg gcgagggcga gggccgcccc tacgagggca    540
cccagaccgc caagctgaag gtgaccaagg gtggcccccct gcccttcgcc tgggacatcc    600 tgtccccctca gttcatgtac ggctccaagg cctacgtgaa gcaccccgcc gacatccccg    660
actacttg                                                             668

<210> SEQ ID NO 9
<211> LENGTH: 1076
<212> TYPE: DNA
<213> ORGANISM: Artificial Sequence
<220> FEATURE:
<223> OTHER INFORMATION: Example full PCR product of 3 prime end
      sequencing in Reporter 1

<400> SEQUENCE: 9
gactacacca tcgtggaaca gtacgaacgc gccgagggcc gccactccac cggcggcatg     60
gacgagctgt acaagtaatg aactccagtc tttctagatc tagaaagact ggagtttaat    120
taagccacca tggtgagcaa gggcgaggag ctgttcaccg gggtggtgcc catcctggtc    180
gagctggacg gcgacgtaaa cggccacaag ttcagcgtgt ccggcgaggg cgagggcgat    240
```

```
gccacctacg gcaagctgac cctgaagctg atctgcacca ccggcaagct gcccgtgccc    300
tggcccaccc tcgtgaccac cctgggctac ggcctgcagt gcttcgcccg ctaccccgac    360
cacatgaagc agcacgactt cttcaagtcc gccatgcccg aaggctacgt ccaggagcgc    420
accatcttct tcaaggacga cggcaactac aagacccgcg ccgaggtgaa gttcgagggc    480
gacaccctgg tgaaccgcat cgagctgaag ggcatcgact tcaaggagga cggcaacatc    540
ctggggcaca gcctggagta caactacaac agccacaacg tctatatcac cgccgacaag    600
cagaagaacg gcatcaaggc caacttcaag atccgccaca acatcgagga cggcggcgtg    660
cagctcgccg accactacca gcagaacacc cccatcggcg acggccccgt gctgctgccc    720
gacaaccact acctgagcta ccagtccgcc ctgagcaaag accccaacga aagcgcgat    780 cacatggtcc tgctggagtt cgtgaccgcc gccgggatca ctctcggcat ggacgagctg    840
tacaagtaac gcgtgaattc actcctcagg tgcaggctgc ctatcagaag gtggtggctg    900
gtgtggccaa tgccctggct cacaaatacc actgagatct ttttcccctct gccaaaaatt    960 atggggacat catgaagccc cttgagcatc tgacttctgg ctaataaagg aaatttattt   1020
tcattgcaat agtgtgttgg aattttttgt gtctctcact cggaaggaca tatggg       1076
```

<210> SEQ ID NO 10
<211> LENGTH: 3501
<212> TYPE: DNA
<213> ORGANISM: Artificial Sequence
<220> FEATURE:
<223> OTHER INFORMATION: Reporter 2 sequence in the AAVSI loci in HEK293
       Cells

<400> SEQUENCE: 10

```
gacattgatt attgactagt tattaatagt aatcaattac ggggtcatta gttcatagcc     60
catatatgga gttccgcgtt acataactta cggtaaatgg cccgcctggc tgaccgccca    120
acgacccccg cccattgacg tcaataatga cgtatgttcc catagtaacg ccaatagggga   180 ctttccattg acgtcaatgg gtggactatt tacggtaaac tgcccacttg gcagtacatc    240
aagtgtatca tatgccaagt acgccccta ttgacgtcaa tgacggtaaa tggcccgcct    300
ggcattatgc ccagtacatg accttatggg actttcctac ttggcagtac atctacgtat    360
tagtcatcgc tattaccatg gtcgaggtg agccccacgt tctgcttcac tctccccatc    420 tccccccct cccaccccc aattttgtat ttatttattt tttaattatt ttgtgcagcg    480 atggggcgg ggggggggg ggcgcgcgcc aggcggggcg gggcggggcg aggggcgggg    540
cggggcgagg cggagaggtg cggcggcagc caatcagagc ggcgcgctcc gaaagtttcc    600
ttttatggcg aggcggcggc ggcggcggcc ctataaaaag cgaagcgcgc ggcgggcggg    660
agtcgctgcg ttgccttcgc cccgtgcccc gctccgcgcc gcctcgcgcc gcccgccccg    720
gctctgactg accgcgttac tcccacaggt gagcgggcgg gacggccctt ctcctccggg    780
ctgtaattag cgcttggttt aatgacggct cgtttctttt ctgtggctgc gtgaaagcct    840
taaagggctc cggagggccc tttgtgcgg ggggagcgc ctcgggggt gcgtgcgtgt    900 gtgtgtgcgt ggggagcgcc gcgtgcggcc cgcgctgccc ggcggctgtg agcgctgcgg    960
gcgcggcgcg gggctttgtg cgctccgcgt gtgcgcgagg ggagcgcggc cggggcggt   1020 gccccgcggt gcgggggggc tgcgagggga acaaaggctg cgtgcggggt gtgtgcgtgg   1080
gggggtgagc aggggggtgtg ggcgcggcgg tcggctgta accccccct gcacccccct   1140 ccccgagttg ctgagcacgg cccggcttcg ggtgcgggc tccgtgcggg gcgtggcgcg   1200
```

```
gggctcgccg tgccgggcgg ggggtggcgg caggtgggggg tgccgggcgg ggcggggccg    1260
cctcgggccg gggagggctc gggggagggg cgcggcggcc ccggagcgcc ggcggctgtc    1320
gaggcgcggc gagccgcagc cattgccttt tatggtaatc gtgcgagagg cgcagggac    1380
ttcctttgtc ccaaatctgg cggagccgaa atctgggagg cgccgccgca cccctctag    1440
cgggcgcggg cgaagcggtg cggcgccggc aggaaggaaa tgggcgggga gggccttcgt    1500
gcgtcgccgc gccgccgtcc ccttctccat ctccagcctc ggggctgccg caggggacg    1560
gctgccttcg gggggacgg ggcagggcgg ggttcggctt ctggcgtgtg accggcggct    1620
ctagagcctc tgctaaccat gttcatgcct tcttcttttt cctacagatc cttaattaag    1680
ccgccaccat ggtgagcaag ggcgaggagc tgttcaccgg ggtggtgccc atcctggtcg    1740
agctggacgg cgacgtaaac ggccacaagt tcagcgtgtc cggcgagggc gagggcgatg    1800
ccacctacgg caagctgacc ctgaagctga tctgcaccac cggcaagctg cccgtgccct    1860
ggcccaccct cgtgaccacc ctgggctacg gcctgcagtg cttcgcccgc tacccgacc    1920
acatgaagca gcacgacttc ttcaagtccg ccatgcccga aggctacgtc caggagcgca    1980
ccatcttctt caaggacgac ggcaactaca agacccgcgc cgaggtgaag ttcgagctgc    2040
aactccagtc tttctagaag atgggcggga gtcttctggg caggcttata tcaagcgcta    2100
tgtgcaccaa aacttctcct cgcactaccg ggccaccatt ggtgatcacc gccgacaagc    2160
agaagaacgc catcaaggcc aacttcaaga tccgccacaa catcgaggac ggcggcgtgc    2220
agctcgccga ccactaccag cagaacaccc ccatcggcga cggccccgtg ctgctgcccg    2280
acaaccacta cctgagctac cagtccgccc tgagcaaaga ccccaacgag aagcgcgatc    2340
acatggtcct gctggagttc gtgaccgccg ccgggatcac tctcggcatg gacgagctgt    2400
acaagtagac gcgttggcca cgaacttctc tctgttaaag caagcaggag atgttgaaga    2460
aaaccccggg cctatggtgt ctaagggcga agagctgatt aaggagaaca tgcacatgaa    2520
gctgtacatg gagggcaccg tgaacaacca ccacttcaag tgcacatccg agggcgaagg    2580
caagccctac gagggcaccc agaccatgag aatcaaggtg gtcgagggcg ccctctccc    2640
cttcgccttc gacatcctgg ctaccagctt catgtacggc agcagaacct tcatcaacca    2700
cacccagggc atccccgact tctttaagca gtccttccct gagggcttca catgggagag    2760
agtcaccaca tacgaagacg ggggcgtgct gaccgctacc caggacacca gcctccagga    2820
cggctgcctc atctacaacg tcaagatcag aggggtgaac ttcccatcca acggccctgt    2880
gatgcagaag aaaacactcg gctgggaggc aacaccgag atgctgtacc ccgctgacgg    2940
cggcctggaa ggcagaagcg acatggccct gaagctcgtg ggcgggggcc acctgatctg    3000
caacttcaag accacataca gatccaagaa acccgctaag aacctcaaga tgcccggcgt    3060
ctactatgtg gaccacagac tggaaagaat caaggaggcc gacaaagaga cctacgtcga    3120
gcagcacgag gtggctgtgg ccagatactg cgacctccct agcaaactgg ggcacaaact    3180
taattgagcg atcgcacgcg taaatgattg cagatccact agttctagag ctcgctgatc    3240
agcctcgact gtgccttcta gttgccagcc atctgttgtt tgcccctccc ccgtgccttc    3300
cttgaccctg gaaggtgcca ctcccactgt ccttttcctaa taaaatgagg aaattgcatc    3360
gcattgtctg agtaggtgtc attctattct gggggggtggg gtggggcagg acagcaaggg    3420
ggaggattgg gaagacaata gcaggcatgc tggggatgcg gtgggctcta tggcttctga    3480
ggcggaaaga accagctggg g                                              3501
```

<210> SEQ ID NO 11
<211> LENGTH: 6650
<212> TYPE: DNA
<213> ORGANISM: Artificial Sequence
<220> FEATURE:
<223> OTHER INFORMATION: Plasmid targeting replacement of sequence in
      Reporter 2: All-in-one plasmid containing sequence for replacement
      (turboGFP), Cas9, guide RNA

<400> SEQUENCE: 11

| | | | | | |
|---|---|---|---|---|---|
| cccggattcg | acattgatta | ttgactagtc | catggtggcg | gcttaattaa | ggatcgattt | 60 |
| agcagccacc | atggtgagca | agggcgagga | ggataacatg | gcctctctcc | cagcgacaca | 120 |
| tgagttacac | atctttggct | ccatcaacgg | tgtggacttt | gacatggtgg | gtcagggcac | 180 |
| cggcaatcca | aatgatggtt | atgaggagtt | aaacctgaag | tccaccaagg | gtgacctcca | 240 |
| gttctccccc | tggattctgg | tccctcatat | cgggtatggc | ttccatcagt | acctgcccta | 300 |
| ccctgacggg | atgtcgcctt | ccaggccgc | catggtagat | ggctccggat | accaagtcca | 360 |
| tcgcacaatg | cagtttgaag | atggtgcctc | ccttactgtt | aactaccgct | acacctacga | 420 |
| gggaagccac | atcaaaggag | aggcccaggt | gaaggggact | ggtttccctg | ctgacggtcc | 480 |
| tgtgatgacc | aactcgctga | ccgctgcgga | ctggtgcagg | tcgaagaaga | cttaccccaa | 540 |
| cgacaaaacc | atcatcagta | cctttaagtg | gagttacacc | actggaaatg | gcaagcgcta | 600 |
| ccggagcact | gcgcggacca | cctacacctt | tgccaagcca | atggcggcta | actatctgaa | 660 |
| gaaccagccg | atgtacgtgt | tccgtaagac | ggagctcaag | cactccaaga | ccgagctcaa | 720 |
| cttcaaggag | tggcaaaagg | cctttaccga | tgtgatgggc | atggacgagc | tgtacaagta | 780 |
| aatcgattgc | agatcccctg | ggtgtggttg | atgaaggtcg | attaataata | cgactcacta | 840 |
| taggggccgc | caccatggga | cctaagaaaa | agaggaaggt | ggcggccccg | gtgcctagag | 900 |
| aaggtggcgc | ggggtaaact | gggaaagtga | tgtcgtgtac | tggctccgcc | ttttcccga | 960 |
| gggtggggga | gaaccgtata | taagtgcagt | agtcgccgtg | aacgttcttt | ttcgcaacgg | 1020 |
| gtttgccgcc | agaacacagg | taagtgccgt | gtgtggttcc | cgcgggcctg | gcctctttac | 1080 |
| gggttatggc | ccttgcgtgc | cttgaattac | ttccacctgg | ctgcagtacg | tgattcttga | 1140 |
| tcccgagctt | cgggttggaa | gtgggtggga | gagttcgagg | ccttgcgctt | aaggagcccc | 1200 |
| ttcgcctcgt | gcttgagttg | aggcctggcc | tgggcgctgg | ggccgccgcg | tgcgaatctg | 1260 |
| gtggcacctt | cgcgcctgtc | tcgctgcttt | cgataagtct | ctagccattt | aaaatttttg | 1320 |
| atgacctgct | gcgacgcttt | ttttctggca | agatagtctt | gtaaatgcgg | gccaagatct | 1380 |
| gcacactggt | atttcggttt | ttggggccgc | gggcggcgac | ggggcccgtg | cgtcccagcg | 1440 |
| cacatgttcg | gcgaggcggg | gcctgcgagc | gcggccaccg | agaatcggac | ggggtagtc | 1500 |
| tcaagctggc | cggcctgctc | tggtgcctgg | cctcgcgccg | ccgtgtatcg | ccccgccctg | 1560 |
| ggcggcaagg | ctggcccggt | cggcaccagt | tgcgtgagcg | gaaagatggc | cgcttcccgg | 1620 |
| ccctgctgca | gggagctcaa | aatggaggac | gcggcgctcg | ggagagcggg | cgggtgagtc | 1680 |
| acccacacaa | aggaaaaggg | cctttccgtc | ctcagccgtc | gcttcatgtg | actccacgga | 1740 |
| gtaccgggcg | ccgtccaggc | acctcgatta | gttctcgagc | ttttggagta | cgtcgtcttt | 1800 |
| aggttggggg | gaggggtttt | atgcgatgga | gtttccccac | actgagtggg | tggagactga | 1860 |
| agttaggcca | gcttggcact | tgatgtaatt | ctccttggaa | tttgcccttt | ttgagtttgg | 1920 |
| atcttggttc | attctcaagc | ctcagacagt | ggttcaaagt | ttttttcttc | catttcaggt | 1980 |
| gtcgtgagcg | atcgcatcga | cagtgtttaa | acgccaccat | ggtgagcaag | ggcgaggagc | 2040 |

```
tgttcaccgg ggtggtgccc atcctggtcg agctggacgg cgacgtaaac ggccacaagt    2100
tcagcgtgag gggcgagggc gagggcgatg ccaccaacgg caagctgacc ctgaagttca    2160
tctgcaccac cggcaagctg cccgtgccct ggcccaccct cgtgaccacc ctgagccacg    2220
gcgtgcagtg cttcgcccgc tacccgacc acatgaagca gcacgacttc ttcaagtccg     2280
ccatgcccga aggctacgtc caggagcgca ccatcttctt caaggacgac ggcacctaca    2340
agacccgcgc cgaggtgaag ttcgagggcg acaccctggt gaaccgcatc gagctgaagg    2400
gcgtcgactt caaggaggac ggcaacatcc tggggcacaa gctggagtac aacttcaaca    2460
gccacaacat ctatatcatg gccgtcaagc agaagaacgg catcaaggtg aacttcaaga    2520
tccgccacaa cgtggaggac ggcagcgtgc agctcgccga ccactaccag cagaacaccc    2580
ccatcggcga cggccccgtg ctgctgcccg acaaccacta cctgagcacc cagtccgtgc    2640
tgagcaaaga ccccaacgag aagcgcgatc acatggtcct gctggagttc gcaccgccg     2700
ccgggatcac tctcggcatg gacgagctgt acaagtgaga attcctagag ctcgctgatc    2760
agcctcgact gtgccttcta gttgccagcc atctgttgtt tgcccctccc ccgtgccttc    2820
cttgaccctg gaaggtgcca ctcccactgt cctttcctaa taaaatgagg aaattgcatc    2880
gcattgtctg agtaggtgtc attctattct ggggggtggg gtggggcagg acagcaaggg    2940
ggaggattgg gaagagaata gcaggcatgc gtttaaacat tagtcgacag gccgccact    3000
ggccgtcgtt ttacaacgtc gtgactggga aaacccgggc gttacccaac ttaatcgcct    3060
tgcagcacat ccccctttcg ccagctggcg taatagcgaa gaggcccgca ccgatcgccc    3120
ttcccaacag ttgcgcagcc tgaatggcga atgggacgcg ccctgtagcg gcgcattaag    3180
cgcggcgggt gtggtggtta cgcgcagcgt gaccgctaca cttgccagcg ccctagcgcc    3240
cgctcctttc gctttcttcc cttcctttct cgccacgttc gccggctttc cccgtcaagc    3300
tctaaatcgg gggctccctt tagggttccg atttagtgct ttacggcacc tcgaccccaa    3360
aaaacttgat tagggtgatg gttcacgtag tgggccatcg ccctgataga cggtttttcg    3420
ccctttgacg ttggagtcca cgttctttaa tagtggactc ttgttccaaa ctggaacaac    3480
actcaaccct atctcggtct attcttttga tttataaggg attttgccga tttcggccta    3540
ttggttaaaa aatgagctga tttaacaaaa atttaacgcg aattttaaca aaatattaac    3600
gcttacaatt taggtggcac ttttcgggga aatgtgcgcg gaaccccctat tgtttatttt    3660
ttctaaatac attcaaatat gtatccgctc atgagacaat aaccctgata aatgcttcaa    3720
taatattgaa aaaggaagag tatgagtatt caacatttcc gtgtcgccct tattcccttt    3780
tttgcggcat tttgccttcc tgttttgct cacccagaaa cgctggtgaa agtaaaagat     3840
gctgaagatc agttgggtgc acgagtgggt tacatcgaac tggatctcaa cagcggtaag    3900
atccttgaga gttttcgccc cgaagaacgt tttccaatga tgagcacttt taaagttctg    3960
ctatgtggcg cggtattatc ccgtattgac gccgggcaag agcaactcgg tcgccgcata    4020
cactattctc agaatgactt ggttgagtac tcaccagtca cagaaaagca tcttacggat    4080
ggcatgacag taagagaatt atgcagtgct gccataacca tgagtgataa cactgcggcc    4140
aacttacttc tgacaacgat cggaggaccg aaggagctaa ccgcttttt gcacaacatg    4200
ggggatcatg taactcgcct tgatcgttgg gaaccggagc tgaatgaagc cataccaaac    4260
gacgagcgtg acaccacgat gcctgtagca atggcaacaa cgttgcgcaa actattaact    4320
ggcgaactac ttactctagc ttcccggcaa caattaatag actggatgga gcggataaa    4380
gttgcaggac cacttctgcg ctcggccctt ccggctggct ggtttattgc tgataaatct    4440
```

```
ggagccggtg agcgtgggtc tcgcggtatc attgcagcac tggggccaga tggtaagccc    4500
tcccgtatcg tagttatcta cacgacgggg agtcaggcaa ctatggatga acgaaataga    4560
cagatcgctg ataggtgc ctcactgatt aagcattggt aactgtcaga ccaagtttac      4620
tcatatatac tttagattga tttaaaactt cattttaat ttaaaggat ctaggtgaag      4680 atccttttg ataatctcat gaccaaaatc ccttaacgtg agttttcgtt ccactgagcg     4740
tcagaccccg tagaaaagat caaggatct tcttgagatc ctttttttct gcgcgtaatc    4800
tgctgcttgc aaacaaaaaa accaccgcta ccagcggtgg tttgtttgcc ggatcaagag    4860
ctaccaactc ttttccgaa ggtaactggc ttcagcagag cgcagatacc aaatactgtc     4920
cttctagtgt agccgtagtt aggccaccac ttcaagaact ctgtagcacc gcctacatac    4980
ctcgctctgc taatcctgtt accagtggct gctgccagtg gcgataagtc gtgtcttacc    5040
gggttggact caagacgata gttaccggat aaggcgcagc ggtcgggctg aacggggggt    5100
tcgtgcacac agcccagctt ggagcgaacg acctacaccg aactgagata cctacagcgt    5160
gagctatgag aaagcgccac gcttcccgaa gggagaaagg cggacaggta tccggtaagc    5220
ggcagggtcg gaacaggaga gcgcacgagg gagcttccag ggggaaacgc ctggtatctt    5280
tatagtcctg tcgggtttcg ccacctctga cttgagcgtc gatttttgtg atgctcgtca    5340 gggggggcgga gcctatggaa aaacgccagc aacgcggcct ttttacggtt cctggccttt    5400
tgctggcctt ttgctcacat gttctttcct gcgttatccc ctgattctgt ggataaccgt    5460
attaccgcct ttgagtgagc tgataccgct cgccgcagcc gaacgaccga gcgcagcgag    5520
tcagtgagcg aggaagcgga agagcgccca atacgcaaac cgcctctccc cgcgcgttgg    5580
ccgattcatt aatgcagctg gcacgacagg tttcccgact ggaaagcggg cagtgagcgc    5640
aacgcaatta atgtgagtta gctcactcat taggcacccc aggctttaca ctttatgctt    5700
ccggctcgta tgttgtgtgg aattgtgagc ggataacaat ttcacacagg aaacagctat    5760
gaccatgagg ggccccttc accgagggcc tatttcccat gattccttca tatttgcata    5820
tacgatacaa ggctgttaga gagataattg gaattaattt gactgtaaac acaaagatat    5880
tagtacaaaa tacgtgacgt agaaagtaat aatttcttgg gtagtttgca gttttaaaat    5940
tatgttttaa aatggactat catatgctta ccgtaacttg aaagtatttc gatttcttgg    6000
ctttatatat cttgtggaaa ggacgaaaca ccgccttaat taagccgcca ccagttttag    6060
agctaggcca acatgaggat cacccatgtc tgcagggcct agcaagttaa aataaggcta    6120
gtccgttatc aacttggcca acatgaggat cacccatgtc tgcagggcca agtggcaccg    6180
agtcggtgct ttttttgatc acagcatcgg cctggccatc gggccccctt caccgagggc    6240
ctatttccca tgattccttc atatttgcat atacgataca aggctgttag agagataatt    6300
ggaattaatt tgactgtaaa cacaaagata ttagtacaaa atacgtgacg tagaaagtaa    6360
taatttcttg ggtagtttgc agttttaaaa ttatgtttta aatggactat catatgctt    6420 accgtaactt gaaagtattt cgatttcttg ctttatata tcttgtggaa aggacgaaac    6480
accgaccttc atcaaccaca cccagttta gagctaggcc aacatgagga tcacccatgt    6540
ctgcagggcc tagcaagtta aaataaggct agtccgttat caacttggcc aacatgagga    6600
tcacccatgt ctgcagggcc aagtggcacc gagtcggtgc ttttttgat                6650
```

<210> SEQ ID NO 12
<211> LENGTH: 23
<212> TYPE: DNA

```
<213> ORGANISM: Artificial Sequence
<220> FEATURE:
<223> OTHER INFORMATION: Target Site B PAM+Protospacer Sequence for
      targeting Reporter 2 in HEK293 Cells

<400> SEQUENCE: 12
ccatggtggc ggcttaatta agg                                             23

<210> SEQ ID NO 13
<211> LENGTH: 23
<212> TYPE: DNA
<213> ORGANISM: Artificial Sequence
<220> FEATURE:
<223> OTHER INFORMATION: Target Site C PAM+Protospacer Sequence for
      targeting Reporter 2 in HEK293 Cells

<400> SEQUENCE: 13
ccctgggtgt ggttgatgaa ggt                                             23

<210> SEQ ID NO 14
<211> LENGTH: 665
<212> TYPE: DNA
<213> ORGANISM: Homo sapiens
<220> FEATURE:
<223> OTHER INFORMATION: Human Lamin A Exon 2 Sequence

<400> SEQUENCE: 14
aggcaagcag atgcaaacca acctaatgca aggatgccct ctcctggtaa ttgcaggcat     60
agcagcgcca gcccccatgg ctgacctcct gggagcctgg cactgtctag gcacacagac    120
tccttctctt aaatctactc tcccctctct tctttagcaa taccaagaag gagggtgacc    180
tgatagctgc tcaggctcgg ctgaaggacc tggaggctct gctgaactcc aaggaggccg    240
cactgagcac tgctctcagt gagaagcgca cgctggaggg cgagctgcat gatctgcggg    300
gccaggtggc caaggtgagg ccaccctgca gggcccaccc atggcccac ctaacacatg     360 tacactcact cttctaccta ggccctcccc catgtggtgc ctggtctgac ctgtcacctg    420
atttcagagc cattcacctg tcctagagtc attttaccca ctgaggtcac atcttatcct    480
aatttggctg ccaatgggat ctaccacagt gaatttaaaa taatccagga ggccgggcat    540
ggtggttcac gcctgtaatc ccagcacttt aggaggccga ggtgggccga tcacgaggtc    600
aggagatcga gatcatcctg actaacatgg tgaaaccccg tctctactaa aaatacaaaa    660
aatta                                                                665

<210> SEQ ID NO 15
<211> LENGTH: 102
<212> TYPE: DNA
<213> ORGANISM: Artificial Sequence
<220> FEATURE:
<223> OTHER INFORMATION: hLMNA guide 1

<400> SEQUENCE: 15
gctcccagga ggtcagccat gttttagagc tagaaatagc aagttaaaat aaggctagtc     60
cgttatcaac ttgaaaaagt ggcaccgagt cggtgctttt tt                       102

<210> SEQ ID NO 16
<211> LENGTH: 102
<212> TYPE: DNA
<213> ORGANISM: Artificial Sequence
<220> FEATURE:
<223> OTHER INFORMATION: hLMNA guide 2

<400> SEQUENCE: 16
```

```
ttcactgtgg tagatcccat gttttagagc tagaaatagc aagttaaaat aaggctagtc    60
cgttatcaac ttgaaaaagt ggcaccgagt cggtgctttt tt                      102
```

<210> SEQ ID NO 17
<211> LENGTH: 102
<212> TYPE: DNA
<213> ORGANISM: Artificial Sequence
<220> FEATURE:
<223> OTHER INFORMATION: hLMNA Deleted Section guide 3

<400> SEQUENCE: 17

```
ttcactgtgg tagatcccat gttttagagc tagaaatagc aagttaaaat aaggctagtc    60
cgttatcaac ttgaaaaagt ggcaccgagt cggtgctttt tt                      102
```

<210> SEQ ID NO 18
<211> LENGTH: 3936
<212> TYPE: DNA
<213> ORGANISM: Artificial Sequence
<220> FEATURE:
<223> OTHER INFORMATION: hLMNA Replacement Sequence Plasmid

<400> SEQUENCE: 18

```
actcgacatt gattattgac tagtgctccc aggaggtcag ccatgggggg agcctggcac    60
tgtctaggca cacagactcc ttctcttaaa tctactctcc cctctcttct ttagcaatga   120
gggcagagga agtctgctaa catgcggtga cgtggaggag aatcccggcc ctgctagcat   180
ggtgagcaag ggcgaggagg ataacatggc catcatcaag gagttcatgc gcttcaaggt   240
gcacatggag ggctccgtga acggccacga gttcgagatc gagggcgagg gcgagggccg   300
cccctacgag ggcacccaga ccgccaagct gaaggtgacc aagggtggcc ccctgccctt   360
cgcctgggac atcctgtccc ctcagttcat gtacggctcc aaggcctacg tgaagcaccc   420
cgccgacatc cccgactact gaagctgtc cttccccgag ggcttcaagt gggagcgcgt   480
gatgaacttc gaggacggcg gcgtggtgac cgtgacccag gactcctccc tgcaggacgg   540
cgagttcatc tacaaggtga agctgcgcgc caccaacttc ccctcagacg gccccgtaat   600
gcagaagaaa accatgggct gggaggcctc ctccgagcgg atgtacccg aggacggcgc   660 cctgaagggc gagatcaagc agaggctgaa gctgaaggac ggcggccact acgacgctga   720
ggtcaagacc acctacaagg ccaagaagcc cgtgcagctg cccggcgcct acaacgtcaa   780
catcaagttg gacatcaccc cccacaacga ggactacacc atcgtggaac agtacgaacg   840
cgccgagggc cgccactcca ccggcggcat ggacgagctg tacaagtaag aattcctaga   900
gctcgctgat cagcctcgac tgtgccttct agttgccagc catctgttgt ttgcccctcc   960
cccgtgcctt ccttgaccct ggaaggtgcc actcccactg tcctttccta ataaaatgag  1020
gaaattgcat cgcattgtct gagtaggtgt cattctattc tggggggtgg ggtggggcag  1080
gacagcaagg gggaggattg ggaagagaat agcaggcatg ctgggggctc caggaggtc   1140 agccatgggt taattaataa tacgactcac tatagggcc gccccgccac tggccgtcgt  1200
tttacaacgt cgtgactggg aaaaccctgg cgttacccaa cttaatcgcc ttgcagcaca  1260
tccccctttc gccagctggc gtaatagcga agaggcccgc accgatcgcc cttcccaaca  1320
gttgcgcagc ctgaatggcg aatgggacgc gccctgtagc ggcgcattaa gcgcggcggg  1380
tgtggtggtt acgcgcagcg tgaccgctac acttgccagc gccctagcgc ccgctccttt  1440
cgctttcttc ccttcctttc tcgccacgtt cgccggcttt ccccgtcaag ctctaaatcg  1500
```

```
ggggctccct  ttagggttcc  gatttagtgc  tttacggcac  ctcgacccca  aaaaacttga    1560
ttagggtgat  ggttcacgta  gtgggccatc  gccctgatag  acggttttc   gcccttgac     1620 gttggagtcc  acgttcttta  atagtggact  cttgttccaa  actggaacaa  cactcaaccc    1680
tatctcggtc  tattcttttg  atttataagg  gattttgccg  atttcggcct  attggttaaa    1740
aaatgagctg  atttaacaaa  aatttaacgc  gaattttaac  aaaatattaa  cgcttacaat    1800
ttaggtggca  cttttcgggg  aaatgtgcgc  ggaaccccta  tttgtttatt  tttctaaata    1860
cattcaaata  tgtatccgct  catgagacaa  taaccctgat  aaatgcttca  ataatattga    1920
aaaaggaaga  gtatgagtat  tcaacatttc  cgtgtcgccc  ttattccctt  ttttgcggca    1980
ttttgccttc  ctgttttgc   tcacccagaa  acgctggtga  agtaaaaga   tgctgaagat    2040 cagttgggtg  cacgagtggg  ttacatcgaa  ctggatctca  acagcggtaa  gatccttgag    2100
agttttcgcc  ccgaagaacg  ttttccaatg  atgagcactt  ttaaagttct  gctatgtggc    2160
gcggtattat  cccgtattga  cgccgggcaa  gagcaactcg  gtcgccgcat  acactattct    2220
cagaatgact  tggttgagta  ctcaccagtc  acagaaaagc  atcttacgga  tggcatgaca    2280
gtaagagaat  tatgcagtgc  tgccataacc  atgagtgata  acactgcggc  caacttactt    2340
ctgacaacga  tcggaggacc  gaaggagcta  accgcttttt  tgcacaacat  ggggatcat     2400 gtaactcgcc  ttgatcgttg  ggaaccggag  ctgaatgaag  ccataccaaa  cgacgagcgt    2460
gacaccacga  tgcctgtagc  aatggcaaca  acgttgcgca  aactattaac  tggcgaacta    2520
cttactctag  cttcccggca  acaattaata  gactggatgg  aggcggataa  agttgcagga    2580
ccacttctgc  gctcggccct  tccggctggc  tggtttattg  ctgataaatc  tggagccggt    2640
gagcgtgggt  ctcgcggtat  cattgcagca  ctggggccag  atggtaagcc  ctcccgtatc    2700
gtagttatct  acacgacggg  gagtcaggca  actatggatg  aacgaaatag  acagatcgct    2760
gagataggtg  cctcactgat  taagcattgg  taactgtcag  accaagttta  ctcatatata    2820
ctttagattg  atttaaaact  tcattttaa   tttaaaagga  tctaggtgaa  gatccttttt    2880
gataatctca  tgaccaaaat  cccttaacgt  gagttttcgt  tccactgagc  gtcagacccc    2940
gtagaaaaga  tcaaaggatc  ttcttgagat  cctttttttc  tgcgcgtaat  ctgctgcttg    3000
caaacaaaaa  aaccaccgct  accagcggtg  gtttgtttgc  cggatcaaga  gctaccaact    3060 cttttccga   aggtaactgg  cttcagcaga  gcgcagatac  caaatactgt  ccttctagtg    3120
tagccgtagt  taggccacca  cttcaagaac  tctgtagcac  cgcctacata  cctcgctctg    3180
ctaatcctgt  taccagtggc  tgctgccagt  ggcgataagt  cgtgtcttac  cgggttggac    3240
tcaagacgat  agttaccgga  taaggcgcag  cggtcgggct  gaacggggg   ttcgtgcaca    3300 cagcccagct  tggagcgaac  gacctacacc  gaactgagat  acctacagcg  tgagctatga    3360
gaaagcgcca  cgcttcccga  agggagaaag  gcggacaggt  atccggtaag  cggcagggtc    3420
ggaacaggag  agcgcacgag  ggagcttcca  gggggaaacg  cctggtatct  ttatagtcct    3480
gtcgggtttc  gccacctctg  acttgagcgt  cgatttttgt  gatgctcgtc  aggggggcgg    3540
agcctatgga  aaaacgccag  caacgcggcc  tttttacggt  tcctggcctt  tgctggcct    3600 tttgctcaca  tgttctttcc  tgcgttatcc  cctgattctg  tggataaccg  tattaccgcc    3660
tttgagtgag  ctgataccgc  tcgccgcagc  cgaacgaccg  agcgcagcga  gtcagtgagc    3720
gaggaagcgg  aagagcgccc  aatacgcaaa  ccgcctctcc  ccgcgcgttg  gccgattcat    3780
taatgcagct  ggcacgacag  gtttcccgac  tggaaagcgg  gcagtgagcg  caacgcaatt    3840
aatgtgagtt  agctcactca  ttaggcaccc  caggctttac  actttatgct  tccggctcgt    3900
```

```
atgttgtgtg gaattgtgag cggataacaa tttcac                                3936

<210> SEQ ID NO 19
<211> LENGTH: 573
<212> TYPE: DNA
<213> ORGANISM: Homo sapiens
<220> FEATURE:
<223> OTHER INFORMATION: Human Sarcoglycan A (hSCGA) Exon 7 with
      mutation (premature stop codon)

<400> SEQUENCE: 19
cttgtctgag tctggattca aaccaggagg tcagacccta gagctgtgcg ctaaccagtg      60
cactgtcccg cctctgctgg actttgtgtc tcctgcctcc tagtcctggc ccctgccatg     120
ttcctgggga cctctgtgtc cagccagcca cttcctgcgt cagccctgag ctctctgtgc     180
aggtggataa gtaagtgccg gagcctgcag atgaggtgcc caccccaggt gatgggatcc     240
tggagcatga cccgttcttc tgcccaccca ctgaggcccc agaccgtgac ttcttggtgg     300
atgctctggt caccctcctg gtgccctgc tggtggccct gcttctcacc ttgctgctgg      360
cctatgtcat gtgctgccgg cgggagggaa ggtgaatgtg ggcatgaagg gcggggagc      420 acctgctgga gctcacaccc atgggactca gagtggcact tgtgctgtat gggacccaga     480
caccatggga atggggttct caggcacaaa aggagtgtgg ggccccttc taggcaactt      540 ggggcttgag acctgcctgg cctggcacca gga                                  573

<210> SEQ ID NO 20
<211> LENGTH: 4952
<212> TYPE: DNA
<213> ORGANISM: Artificial Sequence
<220> FEATURE:
<223> OTHER INFORMATION: hSCGA guide 1, 2, and 3 in AAV

<400> SEQUENCE: 20
ttaccggata aggcgcagcg gtcgggctga acggggggtt cgtgcacaca gcccagcttg      60
gagcgaacga cctacaccga actgagatac ctacagcgtg agctatgaga aagcgccacg     120
cttcccgaag ggagaaaggc ggacaggtat ccggtaagcg gcagggtcgg aacaggagag     180
cgcacgaggg agcttccagg gggaaacgcc tggtatcttt atagtcctgt cgggtttcgc     240
cacctctgac ttgagcgtcg attttttgtga tgctcgtcag gggggcgag cctatggaaa      300 aacgccagca acgcggcctt tttacggttc ctggccttt gctggccttt tgctcacatg       360
tcctgcaggc agctgcgcgc tcgctcgctc actgaggccg cccgggcgtc gggcgacctt     420
tggtcgcccg gcctcagtga gcgagcgagc gcgcagagag ggagtggcca actccatcac     480
taggggttcc tgcggccgca gaaatagcaa tttcccatga ttccttcata tttgcatata     540
cgatacaagg ctgttagaga gataattgga attaatttga ctgtaaacac aaagatatta     600
gtacaaaata cgtgacgtag aaagtaataa tttcttgggt agtttgcagt tttaaaatta     660
tgttttaaaa tggactatca tatgcttacc gtaacttgaa agtatttcga tttcttggct     720
ttatatatct tgtggaaagg acgaaacacc gagctctagg gtctgacctc cgttttagag     780
ctagaaatag caagttaaaa taaggctagt ccgttatcaa cttgaaaaag tggcaccgag     840
tcggtgcttt tttgcttgct agaaatagca atttcccatg attccttcat atttgcatat     900
acgatacaag ctgttagag agataattgg aattaatttg actgtaaaca caaagatatt     960
agtacaaaat acgtgacgta gaaagtaata atttcttggg tagtttgcag ttttaaaatt    1020
atgttttaaa atggactatc atatgcttac cgtaacttga agtatttcg atttcttggc     1080
```

-continued

```
tttatatatc ttgtggaaag gacgaaacac cgaagcccca agttgcctag aagttttaga    1140
gctagaaata gcaagttaaa ataaggctag tccgttatca acttgaaaaa gtggcaccga    1200
gtcggtgctt ttttgcttgg gctcgagttt cccatgattc cttcatattt gcatatacga    1260
tacaaggctg ttagagagat aattggaatt aatttgactg taaacacaaa gatattagta    1320
caaaatacgt gacgtagaaa gtaataattt cttgggtagt ttgcagtttt aaaattatgt    1380
tttaaaatgg actatcatat gcttaccgta acttgaaagt atttcgattt cttggcttta    1440
tatatcttgt ggaaaggacg aaacaccgaa gccccaagtt gcctatccgt tttagagcta    1500
gaaatagcaa gttaaaataa ggctagtccg ttatcaactt gaaaaagtgg caccgagtcg    1560
gtgcttttttt tgcttaagga tggtgagcaa gggcgaggag ctgttcaccg ggtggtgcc    1620
catcctggtc gagctggacg cgacgtaaa cggccacaag ttcagcgtga ggggcgaggg    1680
cgagggcgat gccaccaacg gcaagctgac cctgaagttc atctgcacca ccggcaagct    1740
gcccgtgccc tggcccaccc tcgtgaccac cctgagccac ggcgtgcagt gcttcgcccg    1800
ctaccccgac cacatgaagc agcacgactt cttcaagtcc gccatgcccg aaggctacgt    1860
ccaggagcgc accatcttct tcaaggacga cggcacctac aagacccgcg ccgaggtgaa    1920
gttcgagggc gacaccctgg tgaaccgcat cgagctgaag ggcgtcgact tcaaggagga    1980
cggcaacatc ctggggcaca agctggagta caacttcaac agccacaaca tctatatcat    2040
ggccgtcaag cagaagaacg gcatcaaggt gaacttcaag atccgccaca acgtggagga    2100
cggcagcgtg cagctcgccg accactacca gcagaacacc cccatcggcg acggccccgt    2160
gctgctgccc gacagccact acctgagcac ccagtccgtg ctgagcaaag accccaacga    2220
gaagcgcgat cacatggtcc tgctggagtt ccgcaccgcc gccgggatca ctctcggcat    2280
ggacgagctg tacaagtgag aattcctaga gctcgctgat cagcctcgac tgtgccttct    2340
agttgccagc catctgttgt ttgcccctcc cccgtgcctt ccttgaccct ggaaggtgcc    2400
actcccactg tccttttccta ataaaatgag gaaattgcat cgcattgtct gagtaggtgt    2460
cattctattc tggggggtgg ggtggggcag gacagcaagg gggaggattg ggaagagaat    2520
agcaggcatg cgcttaatta atatgctagc cagcacgtgc ggaccgagcg gccgcaggaa    2580
cccctagtga tggagttggc cactccctct ctgcgcgctc gctcgctcac tgaggccggg    2640
cgaccaaagg tcgcccgacg cccgggcttt gcccgggcgg cctcagtgag cgagcgagcg    2700
cgcagctgcc tgcaggggcg cctgatgcgg tattttctcc ttacgcatct gtgcggtatt    2760
tcacaccgca tacgtcaaag caaccatagt acgcgcctg tagcggcgca ttaagcgcgg    2820
cgggtgtggt ggttacgcgc agcgtgaccg ctacacttgc cagcgcccta gcgcccgctc    2880
ctttcgcttt cttcccttcc tttctcgcca cgttcgccgg cttccccgt caagctctaa    2940
atcggggggct cccctttaggg ttccgattta gtgctttacg gcacctcgac cccaaaaaac    3000
ttgatttggg tgatggttca cgtagtgggc catcgccctg atagacggtt tttcgccctt    3060
tgacgttgga gtccacgttc tttaatagtg gactcttgtt ccaaactgga acaacactca    3120
accctatctc gggctattct tttgatttat aagggatttt gccgatttcg gcctattggt    3180
taaaaaatga gctgatttaa caaaaattta acgcgaattt taacaaaata ttaacgttta    3240
caatttatg gtgcactctc agtacaatct gctctgatgc cgcatagtta agccagcccc    3300
gacacccgcc aacacccgct gacgcgccct gacgggcttg tctgctcccg gcatccgctt    3360
acagacaagc tgtgaccgtc tccgggagct gcatgtgtca gaggttttca ccgtcatcac    3420
```

| | |
|---|---|
| cgaaacgcgc gagacgaaag ggcctcgtga tacgcctatt tttataggtt aatgtcatga | 3480 |
| taataatggt ttcttagacg tcaggtggca cttttcgggg aaatgtgcgc ggaacccta | 3540 |
| tttgtttatt tttctaaata cattcaaata tgtatccgct catgagacaa taaccctgat | 3600 |
| aaatgcttca ataatattga aaaggaaga gtatgagtat tcaacatttc cgtgtcgccc | 3660 |
| ttattccctt ttttgcggca ttttgccttc ctgttttgc tcacccagaa acgctggtga | 3720 |
| aagtaaaaga tgctgaagat cagttgggtg cacgagtggg ttacatcgaa ctggatctca | 3780 |
| acagcggtaa gatccttgag agttttcgcc ccgaagaacg ttttccaatg atgagcactt | 3840 |
| ttaaagttct gctatgtggc gcggtattat cccgtattga cgccgggcaa gagcaactcg | 3900 |
| gtcgccgcat acactattct cagaatgact tggttgagta ctcaccagtc acagaaaagc | 3960 |
| atcttacgga tggcatgaca gtaagagaat tatgcagtgc tgccataacc atgagtgata | 4020 |
| acactgcggc caacttactt ctgacaacga tcggaggacc gaaggagcta accgcttttt | 4080 |
| tgcacaacat gggggatcat gtaactcgcc ttgatcgttg ggaaccggag ctgaatgaag | 4140 |
| ccataccaaa cgacgagcgt gacaccacga tgcctgtagc aatggcaaca acgttgcgca | 4200 |
| aactattaac tggcgaacta cttactctag cttcccggca acaattaata gactggatgg | 4260 |
| aggcggataa agttgcagga ccacttctgc gctcggccct tccggctggc tggtttattg | 4320 |
| ctgataaatc tggagccggt gagcgtgggt ctcgcggtat cattgcagca ctggggccag | 4380 |
| atggtaagcc ctcccgtatc gtagttatct acacgacggg gagtcaggca actatggatg | 4440 |
| aacgaaatag acagatcgct gagataggtg cctcactgat taagcattgg taactgtcag | 4500 |
| accaagttta ctcatatata ctttagattg atttaaaact tcatttttaa tttaaaagga | 4560 |
| tctaggtgaa gatcctttt gataatctca tgaccaaaat cccttaacgt gagttttcgt | 4620 |
| tccactgagc gtcagacccc gtagaaaaga tcaaaggatc ttcttgagat cctttttttc | 4680 |
| tgcgcgtaat ctgctgcttg caaacaaaaa aaccaccgct accagcggtg tttgtttgc | 4740 |
| cggatcaaga gctaccaact ctttttccga aggtaactgg cttcagcaga gcgcagatac | 4800 |
| caaatactgt ccttctagtg tagccgtagt taggccacca cttcaagaac tctgtagcac | 4860 |
| cgcctacata cctcgctctg ctaatcctgt taccagtggc tgctgccagt ggcgataagt | 4920 |
| cgtgtcttac cgggttggac tcaagacgat ag | 4952 |

<210> SEQ ID NO 21
<211> LENGTH: 4416
<212> TYPE: DNA
<213> ORGANISM: Artificial Sequence
<220> FEATURE:
<223> OTHER INFORMATION: hSCGA replacement in AAV with no premature stop
    codon

<400> SEQUENCE: 21

| | |
|---|---|
| ttaccggata aggcgcagcg gtcgggctga acggggggtt cgtgcacaca gcccagcttg | 60 |
| gagcgaacga cctacaccga actgagatac ctacagcgtg agctatgaga aagcgccacg | 120 |
| cttcccgaag ggagaaaggc ggacaggtat ccggtaagcg gcagggtcgg aacaggagag | 180 |
| cgcacgaggg agcttccagg gggaaacgcc tggtatcttt atagtcctgt cgggtttcgc | 240 |
| cacctctgac ttgagcgtcg atttttgtga tgctcgtcag ggggcggag cctatggaaa | 300 |
| aacgccagca acgcggcctt tttacggttc ctggccttt gctggccttt tgctcacatg | 360 |
| tcctgcaggc agctgcgcgc tcgctcgctc actgaggccg cccgggcgtc gggcgacctt | 420 |
| tggtcgcccg gcctcagtga gcgagcgagc gcgcagagag ggagtggcca actccatcac | 480 |

```
tagggggttcc tgcggccgca gaaatagcaa agctctaggg tctgacctcc tgggtgcgct    540
aaccagtgca ctgtcccgcc tctgctggac tttgtgtctc ctgcctccta gtcctggccc    600
ctgccatgtt cctggggacc tctgtgtcca gccagccact tcctgcgtca gccctgagct    660
ctctgtgcag gtggataagt cagtgccgga gcctgcagat gaggtgccca ccccaggtga    720
tgggatcctg gagcatgacc cgttcttctg cccacccact gaggcccag accgtgactt     780 cttggtggat gctctggtca ccctcctggt gccctgctg gtggccctgc ttctcacctt     840
gctgctggcc tatgtcatgt gctgccggcg ggagggaagg tgaatgtggg catgaagggc    900
gggggagcac ctgctggagc tcacacccat gggactcaca gtggcacttg tgctgtatgg    960
gacccagaca ccatgggaat ggggttctca ggcacaaaag gagtgtgggg ccagctctag   1020
ggtctgacct cctgggctta aggatggtga gcaagggcga ggagctgttc accgggtgg    1080 tgcccatcct ggtcgagctg gacggcgacg taaacggcca caagttcagc gtgaggggcg   1140
agggcgaggg cgatgccacc aacggcaagc tgaccctgaa gttcatctgc accaccggca   1200
agctgcccgt gccctggccc accctcgtga ccaccctgag ccacggcgtg cagtgcttcg   1260
cccgctaccc cgaccacatg aagcagcacg acttcttcaa gtccgccatg cccgaaggct   1320
acgtccagga gcgcaccatc ttcttcaagg acgacggcac ctacaagacc cgcgccgagg   1380
tgaagttcga gggcgacacc ctggtgaacc gcatcgagct gaagggcgtc gacttcaagg   1440
aggacggcaa catcctgggg cacaagctgg agtacaactt caacagccac aacatctata   1500
tcatggccgt caagcagaag aacggcatca aggtgaactt caagatccgc cacaacgtgg   1560
aggacggcag cgtgcagctc gccgaccact accagcagaa caccccatc ggcgacggcc    1620 ccgtgctgct gcccgacagc cactacctga gcacccagtc cgtgctgagc aaagaccca    1680 acgagaagcg cgatcacatg gtcctgctgg agttccgcac cgccgccggg atcactctcg   1740
gcatggacga gctgtacaag tgagaattcc tagagctcgc tgatcagcct cgactgtgcc   1800
ttctagttgc cagccatctg ttgtttgccc ctcccccgtg ccttccttga ccctggaagg   1860
tgccactccc actgtccttt cctaataaaa tgaggaaatt gcatcgcatt gtctgagtag   1920
gtgtcattct attctggggg gtggggtggg caggacagc aaggggagg attgggaaga    1980 gaatagcagg catgcgctta attaatatgc tagccagcac gtgcggaccg agcggccgca   2040
ggaaccccta gtgatggagt tggccactcc ctctctgcgc gctcgctcgc tcactgaggc   2100
cgggcgacca aggtcgcccc gacgcccggg ctttgcccgg gcggcctcag tgagcgagcg   2160
agcgcgcagc tgcctgcagg ggcgcctgat gcggtatttt ctccttacgc atctgtgcgg   2220
tatttcacac cgcatacgtc aaagcaacca tagtacgcgc cctgtagcgg cgcattaagc   2280
gcggcgggtg tggtggttac gcgcagcgtg accgctacac ttgccagcgc cctagcgccc   2340
gctcctttcg ctttcttccc ttcctttctc gccacgttcg ccggctttcc ccgtcaagct   2400
ctaaatcggg ggctcccttt agggttccga tttagtgctt tacggcacct cgaccccaaa   2460
aaacttgatt tgggtgatgg ttcacgtagt gggccatcgc cctgatagac ggtttttcgc   2520
cctttgacgt tggagtccac gttctttaat agtggactct tgttccaaac tggaacaaca   2580
ctcaacccta tctcgggcta ttcttttgat ttataaggga ttttgccgat ttcggcctat   2640
tggttaaaaa atgagctgat ttaacaaaaa tttaacgcga attttaacaa atattaacg    2700 tttacaattt tatggtgcac tctcagtaca atctgctctg atgccgcata gttaagccag   2760
ccccgacacc cgccaacacc cgctgacgcg ccctgacggg cttgtctgct cccggcatcc   2820
gcttacagac aagctgtgac cgtctccggg agctgcatgt gtcagaggtt ttcaccgtca   2880
```

```
tcaccgaaac gcgcgagacg aaagggcctc gtgatacgcc tattttttata ggttaatgtc    2940
atgataataa tggtttctta gacgtcaggt ggcacttttc ggggaaatgt gcgcggaacc    3000
cctatttgtt tattttttcta aatacattca aatatgtatc cgctcatgag acaataaccc    3060
tgataaatgc ttcaataata ttgaaaaagg aagagtatga gtattcaaca tttccgtgtc    3120
gcccttattc cctttttgc ggcatttgc cttcctgttt ttgctcaccc agaaacgctg    3180
gtgaaagtaa aagatgctga agatcagttg ggtgcacgag tgggttacat cgaactggat    3240
ctcaacagcg gtaagatcct tgagagtttt cgccccgaag aacgttttcc aatgatgagc    3300
acttttaaag ttctgctatg tggcgcggta ttatcccgta ttgacgccgg gcaagagcaa    3360
ctcggtcgcc gcatacacta ttctcagaat gacttggttg agtactcacc agtcacagaa    3420
aagcatctta cggatggcat gacagtaaga gaattatgca gtgctgccat aaccatgagt    3480
gataacactg cggccaactt acttctgaca acgatcggag gaccgaagga gctaaccgct    3540
tttttgcaca acatggggga tcatgtaact cgccttgatc gttgggaacc ggagctgaat    3600
gaagccatac caaacgacga gcgtgacacc acgatgcctg tagcaatggc aacaacgttg    3660
cgcaaactat taactggcga actacttact ctagcttccc ggcaacaatt aatagactgg    3720
atggaggcgg ataaagttgc aggaccactt ctgcgctcgg cccttccggc tggctggttt    3780
attgctgata atctggagc cggtgagcgt gggtctcgcg gtatcattgc agcactgggg    3840
ccagatggta agccctcccg tatcgtagtt atctacacga cggggagtca ggcaactatg    3900
gatgaacgaa atagacagat cgctgagata ggtgcctcac tgattaagca ttggtaactg    3960
tcagaccaag tttactcata tatactttag attgatttaa aacttcattt ttaatttaaa    4020
aggatctagg tgaagatcct ttttgataat ctcatgacca aaatccctta acgtgagttt    4080
tcgttccact gagcgtcaga ccccgtagaa aagatcaaag gatcttcttg agatcctttt    4140
tttctgcgcg taatctgctg cttgcaaaca aaaaaaccac cgctaccagc ggtggtttgt    4200
ttgccggatc aagagctacc aactcttttt ccgaaggtaa ctggcttcag cagagcgcag    4260
ataccaaata ctgtccttct agtgtagccg tagttaggcc accacttcaa gaactctgta    4320
gcaccgccta catacctcgc tctgctaatc ctgttaccag tggctgctgc cagtggcgat    4380
aagtcgtgtc ttaccgggtt ggactcaaga cgatag                              4416
```

<210> SEQ ID NO 22
<211> LENGTH: 7389
<212> TYPE: DNA
<213> ORGANISM: Artificial Sequence
<220> FEATURE:
<223> OTHER INFORMATION: spCas9 in AAV

<400> SEQUENCE: 22

```
ggcgtcgggc gacctttggt cgcccggcct cagtgagcga gcgagcgcgc agagagggag      60
tggccaactc catcactagg ggttcctgcg gcctctagaa agcttagctg aatgggtcc     120
gcctcttttc cctgcctaaa cagacaggaa ctcctgccaa ttgagggcgt caccgctaag    180
gctccgcccc agcctgggct ccacaaccaa tgaagggtaa tctcgacaaa gagcaagggg    240
tggggcgcgg gcgcgcaggt gcagcagcac acaggctggt cggagggcg gggcgcgacg    300
tctgccgtgc ggggtccgg catcggttgc gcgcaccggt gccaccatgt acccatacga    360
tgttccagat tacgcttcgc cgaagaaaaa gcgcaaggtc gaagcgtccg acaagaagta    420
cagcatcggc ctggacatcg gcaccaactc tgtgggctgg gccgtgatca ccgacgagta    480
```

```
caaggtgccc agcaagaaat tcaaggtgct gggcaacacc gaccggcaca gcatcaagaa    540
gaacctgatc ggagccctgc tgttcgacag cggcgaaaca gccgaggcca cccggctgaa    600
gagaaccgcc agaagaagat acaccagacg gaagaaccgg atctgctatc tgcaagagat    660
cttcagcaac gagatggcca aggtggacga cagcttcttc cacagactgg aagagtcctt    720
cctggtggaa gaggataaga agcacgagcg gcaccccatc ttcggcaaca tcgtggacga    780
ggtggcctac cacgagaagt accccaccat ctaccacctg agaaagaaac tggtggacag    840
caccgacaag gccgacctgc ggctgatcta tctggccctg gcccacatga tcaagttccg    900
gggccacttc ctgatcgagg gcgacctgaa ccccgacaac agcgacgtgg acaagctgtt    960
catccagctg gtgcagacct acaaccagct gttcgaggaa aaccccatca acgccagcgg    1020
cgtggacgcc aaggccatcc tgtctgccag actgagcaag agcagacggc tggaaaatct    1080
gatcgcccag ctgcccggcg agaagaagaa tggcctgttc ggaaacctga ttgccctgag    1140
cctgggcctg accccaact tcaagagcaa cttcgacctg gccgaggatg ccaaactgca    1200
gctgagcaag gacacctacg acgacgacct ggacaacctg ctggcccaga tcggcgacca    1260
gtacgccgac ctgtttctgg ccgccaagaa cctgtccgac gccatcctgc tgagcgacat    1320
cctgagagtg aacaccgaga tcaccaaggc cccctgagc gcctctatga tcaagagata    1380
cgacgagcac caccaggacc tgaccctgct gaaagctctc gtgcggcagc agctgcctga    1440
gaagtacaaa gagattttct tcgaccagag caagaacggc tacgccggct acattgacgg    1500
cggagccagc caggaagagt tctacaagtt catcaagccc atcctggaaa agatggacgg    1560
caccgaggaa ctgctcgtga agctgaacag agaggacctg ctgcggaagc agcggaccttt  1620 cgacaacggc agcatccccc accagatcca cctgggagag ctgcacgcca ttctgcggcg    1680
gcaggaagat ttttacccat tcctgaagga caacagggaa agatcgaga gatcctgac     1740 cttccgcatc ccctactacg tgggccctct ggccagggga acagcagat tcgcctggat    1800 gaccagaaag agcgaggaaa ccatcacccc ctggaacttc gaggaagtgg tggacaaggg    1860
cgcttccgcc cagagcttca tcgagcggat gaccaacttc gataagaacc tgcccaacga    1920
gaaggtgctg cccaagcaca gcctgctgta cgagtacttc accgtgtata acagctgac    1980 caaagtgaaa tacgtgaccg agggaatgag aaagcccgcc ttcctgagcg gcgagcagaa    2040
aaaggccatc gtggacctgc tgttcaagac caaccgggaaa gtgaccgtga agcagctgaa    2100
agaggactac ttcaagaaaa tcgagtgctt cgactccgtg gaaatctccg gcgtggaaga    2160
tcggttcaac gcctccctgg gcacatacca cgatctgctg aaaattatca aggacaagga    2220
cttcctggac aatgaggaaa acgaggacat tctggaagat atcgtgctga ccctgacact    2280
gtttgaggac agagagatga tcgaggaacg gctgaaaacc tatgcccacc tgttcgacga    2340
caaagtgatg aagcagctga gcggcggag atacaccggc tggggcaggc tgagccggaa    2400
gctgatcaac ggcatccggg acaagcagtc cggcaagaca atcctggatt tcctgaagtc    2460
cgacggcttc gccaacagaa acttcatgca gctgatccac gacgacagcc tgaccttta   2520 agaggacatc cagaaagccc aggtgtccgg ccagggcgat agcctgcacg agcacattgc    2580
caatctggcc ggcagcccg ccattaagaa gggcatcctg cagacagtga aggtggtgga    2640
cgagctcgtg aaagtgatgg gccggcacaa gcccgagaac atcgtgatcg aaatggccag    2700
agagaaccag accacccaga agggacagaa gaacagccgc gagagaatga gcggatcga    2760 agaggcatc aaagagctgg gcagccagat cctgaaagaa caccccgtgg aaaacaccca    2820
gctgcagaac gagaagctgt acctgtacta cctgcagaat gggcgggata tgtacgtgga    2880
```

```
ccaggaactg gacatcaacc ggctgtccga ctacgatgtg gaccatatcg tgcctcagag    2940
ctttctgaag gacgactcca tcgacaacaa ggtgctgacc agaagcgaca agaaccgggg    3000
caagagcgac aacgtgccct ccgaagaggt cgtgaagaag atgaagaact actggcggca    3060
gctgctgaac gccaagctga ttacccagag aaagttcgac aatctgacca aggccgagag    3120
aggcggcctg agcgaactgg ataaggccgg cttcatcaag agacagctgg tggaaacccg    3180
gcagatcaca aagcacgtgg cacagatcct ggactcccgg atgaacacta agtacgacga    3240
gaatgacaag ctgatccggg aagtgaaagt gatcaccctg aagtccaagc tggtgtccga    3300
tttccggaag gatttccagt tttacaaagt gcgcgagatc aacaactacc accacgccca    3360
cgacgcctac ctgaacgccg tcgtgggaac cgccctgatc aaaaagtacc ctaagctgga    3420
aagcgagttc gtgtacggcg actacaaggt gtacgacgtg cggaagatga tcgccaagag    3480
cgagcaggaa atcggcaagg ctaccgccaa gtacttcttc tacagcaaca tcatgaactt    3540
tttcaagacc gagattaccc tggccaacgg cgagatccgg aagcggcctc tgatcgagac    3600
aaacggcgaa accggggaga tcgtgtggga taagggccgg attttgcca ccgtgcggaa    3660 agtgctgagc atgccccaag tgaatatcgt gaaaaagacc gaggtgcaga caggcggctt    3720
cagcaaagag tctatcctgc caagaggaa cagcgataag ctgatcgcca gaagaagga    3780 ctgggacact aagaagtacg gcggcttcga cagccccacc gtggcctatt ctgtgctggt    3840
ggtggccaaa gtggaaaagg gcaagtccaa gaaactgaag agtgtgaaag gctgctggg    3900 gatcaccatc atgaaagaa gcagcttcga gaagaatccc atcgactttc tggaagccaa    3960
gggctacaaa gaagtgaaaa aggacctgat catcaagctg cctaagtact ccctgttcga    4020 gctgaaaac ggccggaaga gaatgctggc ctctgccggc gaactgcaga gggaaacga    4080 actgccctg ccctccaaat atgtgaactt cctgtacctg gccagccact atgagaagct    4140
gaagggctcc cccgaggata tgagcagaa acagctgttt gtggaacagc acaagcacta    4200
cctggacgag atcatcgagc agatcagcga gttctccaag agagtgatcc tggccgacgc    4260
taatctggac aaagtgctgt ccgcctacaa caagcaccgg gataagccca tcagagagca    4320
ggccgagaat atcatccacc tgtttaccct gaccaatctg ggagcccctg ccgccttcaa    4380
gtactttgac accaccatcg accggaagag gtacaccagc accaaagagg tgctggacgc    4440
caccctgatc caccagagca tcaccggcct gtacgagaca cggatcgacc tgtctcagct    4500
gggaggcgac agccccaaga agagagaaa ggtggaggcc agctaagaat tcaataaaag    4560
atctttattt tcattagatc tgtgtgttgg ttttttgtgt gcggccgcag gaaccctag    4620 tgatggagtt ggccactccc tctctgcgcg ctcgctcgct cactgaggcc gggcgaccaa    4680
aggtcgcccg acgcccggc tttgcccggg cggcctcagt gagcgagcga gcgcgcagct    4740
gcctgcaggg gcgcctgatg cggtattttc tccttacgca tctgtgcggt atttcacacc    4800
gcatacgtca aagcaaccat agtacgcgcc ctgtagcggc gcattaagcg cggcgggtgt    4860
ggtggttacg cgcagcgtga ccgctacact tgccagcgcc ttagcgcccg ctcctttcgc    4920
tttcttccct tcctttctcg ccacgttcgc cggctttccc cgtcaagctc taaatcgggg    4980
gctcccttta gggttccgat ttagtgcttt acggcacctc gaccccaaaa aacttgattt    5040
gggtgatggt tcacgtagtg gccatcgcc ctgatagacg ttttttcgcc ctttgacgtt    5100
ggagtccacg ttctttaata gtggactctt gttccaaact ggaacaacac tcaactctat    5160
ctcgggctat tcttttgatt tataagggat tttgccgatt tcggtctatt ggttaaaaaa    5220
```

```
tgagctgatt taacaaaaat ttaacgcgaa ttttaacaaa atattaacgt ttacaatttt    5280
atggtgcact ctcagtacaa tctgctctga tgccgcatag ttaagccagc ccgacaccc     5340 gccaacaccc gctgacgcgc cctgacgggc ttgtctgctc ccggcatccg cttacagaca    5400
agctgtgacc gtctccggga gctgcatgtg tcagaggttt tcaccgtcat caccgaaacg    5460
cgcgagacga aagggcctcg tgatacgcct atttttatag gttaatgtca tgataataat    5520
ggtttcttag acgtcaggtg gcacttttcg gggaaatgtg cgcggaaccc ctatttgttt    5580 attttttctaa atacattcaa atatgtatcc gctcatgaga caataaccct gataaatgct    5640
tcaataatat tgaaaaagga gagtatgag tattcaacat ttccgtgtcg cccttattcc     5700
cttttttgcg gcattttgcc ttcctgtttt tgctcaccca gaaacgctgg tgaaagtaaa    5760
agatgctgaa gatcagttgg gtgcacgagt gggttacatc gaactggatc tcaacagcgg    5820
taagatcctt gagagttttc gccccgaaga acgttttcca atgatgagca cttttaaagt    5880
tctgctatgt ggcgcggtat tatcccgtat tgacgccggg caagagcaac tcggtcgccg    5940
catacactat tctcagaatg acttggttga gtactcacca gtcacagaaa agcatcttac    6000
ggatggcatg acagtaagag aattatgcag tgctgccata accatgagtg ataacactgc    6060
ggccaactta cttctgacaa cgatcggagg accgaaggag ctaaccgctt ttttgcacaa    6120
catgggggat catgtaactc gccttgatcg ttgggaaccg gagctgaatg aagccatacc    6180
aaacgacgag cgtgacacca cgatgcctgt agcaatggca acaacgttgc gcaaactatt    6240
aactggcgaa ctacttactc tagcttcccg gcaacaatta atagactgga tggaggcgga    6300
taaagttgca ggaccacttc tgcgctcggc ccttccggct ggctggttta ttgctgataa    6360
atctggagcc ggtgagcgtg gaagccgcgg tatcattgca gcactggggc cagatggtaa    6420
gccctcccgt atcgtagtta tctacacgac ggggagtcag gcaactatgg atgaacgaaa    6480
tagacagatc gctgagatag gtgcctcact gattaagcat tggtaactgt cagaccaagt    6540
ttactcatat atactttaga ttgatttaaa acttcatttt taatttaaaa ggatctaggt    6600
gaagatcctt tttgataatc tcatgaccaa aatcccttaa cgtgagtttt cgttccactg    6660
agcgtcagac cccgtagaaa agatcaaagg atcttcttga gatcctttt tttctgcgcgt    6720 aatctgctgc ttgcaaacaa aaaaaccacc gctaccagcg gtggtttgtt tgccggatca    6780
agagctacca actcttttc cgaaggtaac tggcttcagc agagcgcaga taccaaatac    6840
tgttcttcta gtgtagccgt agttaggcca ccacttcaag aactctgtag caccgcctac    6900
atacctcgct ctgctaatcc tgttaccagt ggctgctgcc agtggcgata agtcgtgtct    6960
taccgggttg gactcaagac gatagttacc ggataaggcg cagcggtcgg gctgaacggg    7020
gggttcgtgc acacagccca gcttggagcg aacgacctac accgaactga gatacctaca    7080
gcgtgagcta tgagaaagcg ccacgcttcc cgaagggaga aaggcggaca ggtatccggt    7140
aagcggcagg gtcggaacag gagagcgcac gagggagctt ccaggggaa acgcctggta     7200 tctttatagt cctgtcgggt ttcgccacct ctgacttgag cgtcgatttt tgtgatgctc    7260
gtcagggggg cggagcctat ggaaaaacgc cagcaacgcg gcctttttac ggttcctggc    7320
cttttgctgg ccttttgctc acatgtcctg caggcagctg cgcgctcgct cgctcactga    7380
ggccgcccg                                                             7389
```

<210> SEQ ID NO 23
<211> LENGTH: 28
<212> TYPE: DNA
<213> ORGANISM: Artificial Sequence

```
<220> FEATURE:
<223> OTHER INFORMATION: Figure 3, Genomic Site 3 prime end

<400> SEQUENCE: 23
ccgctccatc ttctagaaag actggagt                                            28

<210> SEQ ID NO 24
<211> LENGTH: 27
<212> TYPE: DNA
<213> ORGANISM: Artificial Sequence
<220> FEATURE:
<223> OTHER INFORMATION: Figure 3, mCherry insert 5 prime end

<400> SEQUENCE: 24
actccagtct ttctagaaga tgggggg                                             27

<210> SEQ ID NO 25
<211> LENGTH: 21
<212> TYPE: DNA
<213> ORGANISM: Artificial Sequence
<220> FEATURE:
<223> OTHER INFORMATION: Figure 3, Theory = Cl2 = Cl4 = Cl5 = Cl6 = Cl8
      = Cl9 = Cl10

<400> SEQUENCE: 25
ccgctccatc tagatggggg g                                                   21

<210> SEQ ID NO 26
<211> LENGTH: 22
<212> TYPE: DNA
<213> ORGANISM: Artificial Sequence
<220> FEATURE:
<223> OTHER INFORMATION: Figure 3, Cl1

<400> SEQUENCE: 26
ccgctccatc ttagatgggg gg                                                  22

<210> SEQ ID NO 27
<211> LENGTH: 22
<212> TYPE: DNA
<213> ORGANISM: Artificial Sequence
<220> FEATURE:
<223> OTHER INFORMATION: Figure 3, Cl3

<400> SEQUENCE: 27
ccgctccatc taagatgggg gg                                                  22

<210> SEQ ID NO 28
<211> LENGTH: 24
<212> TYPE: DNA
<213> ORGANISM: Artificial Sequence
<220> FEATURE:
<223> OTHER INFORMATION: Figure 3, Cl7

<400> SEQUENCE: 28
ccgctccatc tttgagatgg gggg                                                24

<210> SEQ ID NO 29
<211> LENGTH: 31
<212> TYPE: DNA
<213> ORGANISM: Artificial Sequence
<220> FEATURE:
<223> OTHER INFORMATION: Figure 4, mCherry insert 3 prime end

<400> SEQUENCE: 29
gtaatgaact ccagtctttc tagaagatgg g                                        31
```

<210> SEQ ID NO 30
<211> LENGTH: 31
<212> TYPE: DNA
<213> ORGANISM: Artificial Sequence
<220> FEATURE:
<223> OTHER INFORMATION: Figure 4, Insert Site 5 prime end

<400> SEQUENCE: 30
ctccatcttc tagaaagact ggagtttaat t                              31

<210> SEQ ID NO 31
<211> LENGTH: 20
<212> TYPE: DNA
<213> ORGANISM: Artificial Sequence
<220> FEATURE:
<223> OTHER INFORMATION: Figure 4, Theory = C11 = C12 = C13 = C14 = C16
      = C17 = C18 = C19

<400> SEQUENCE: 31
tctttctaga tctagaaaga                                           20

<210> SEQ ID NO 32
<211> LENGTH: 16
<212> TYPE: DNA
<213> ORGANISM: Artificial Sequence
<220> FEATURE:
<223> OTHER INFORMATION: Figure 4, C15

<400> SEQUENCE: 32
tctttctcta gaaaga                                               16

<210> SEQ ID NO 33
<211> LENGTH: 22
<212> TYPE: DNA
<213> ORGANISM: Artificial Sequence
<220> FEATURE:
<223> OTHER INFORMATION: PAM Protospacer
<220> FEATURE:
<221> NAME/KEY: misc_feature
<222> LOCATION: 3..3
<223> OTHER INFORMATION: n is a, c, g or t

<400> SEQUENCE: 33
ggnatgccta attgatcctg at                                        22

<210> SEQ ID NO 34
<211> LENGTH: 22
<212> TYPE: DNA
<213> ORGANISM: Artificial Sequence
<220> FEATURE:
<223> OTHER INFORMATION: Religation
<220> FEATURE:
<221> NAME/KEY: misc_feature
<222> LOCATION: 3..3
<223> OTHER INFORMATION: n is a, c, g or t

<400> SEQUENCE: 34
ccntacggat taactaggac ta                                        22

<210> SEQ ID NO 35
<211> LENGTH: 24
<212> TYPE: DNA
<213> ORGANISM: Artificial Sequence
<220> FEATURE:
<223> OTHER INFORMATION: Religation
<220> FEATURE:
<221> NAME/KEY: misc_feature -continued

```
<222> LOCATION: 3..3
<223> OTHER INFORMATION: n is a, c, g or t

<400> SEQUENCE: 35
ggnatgcccc taattgatcc tgat                                          24

<210> SEQ ID NO 36
<211> LENGTH: 24
<212> TYPE: DNA
<213> ORGANISM: Artificial Sequence
<220> FEATURE:
<223> OTHER INFORMATION: Religation
<220> FEATURE:
<221> NAME/KEY: misc_feature
<222> LOCATION: 3..3
<223> OTHER INFORMATION: n is a, c, g or t

<400> SEQUENCE: 36
ccntacgggg attaactagg acta                                          24

<210> SEQ ID NO 37
<211> LENGTH: 28
<212> TYPE: DNA
<213> ORGANISM: Artificial Sequence
<220> FEATURE:
<223> OTHER INFORMATION: Figure 9 b, Genomic Site 3 prime end

<400> SEQUENCE: 37
ccttaattaa gccgccacca tggtgagc                                      28

<210> SEQ ID NO 38
<211> LENGTH: 28
<212> TYPE: DNA
<213> ORGANISM: Artificial Sequence
<220> FEATURE:
<223> OTHER INFORMATION: Figure 9 b, turboGFP insert 5 prime end

<400> SEQUENCE: 38
ctagtccatg gtggcggctt aattaagg                                      28

<210> SEQ ID NO 39
<211> LENGTH: 34
<212> TYPE: DNA
<213> ORGANISM: Artificial Sequence
<220> FEATURE:
<223> OTHER INFORMATION: Figure 9 b, Theory

<400> SEQUENCE: 39
ccttaattaa gccgccatgg cggcttaatt aagg                               34

<210> SEQ ID NO 40
<211> LENGTH: 19
<212> TYPE: DNA
<213> ORGANISM: Artificial Sequence
<220> FEATURE:
<223> OTHER INFORMATION: Figure 9 b, Cl1 = Cl2 = Cl3

<400> SEQUENCE: 40
ccttaatcct taattaagg                                                19

<210> SEQ ID NO 41
<211> LENGTH: 33
<212> TYPE: DNA
<213> ORGANISM: Artificial Sequence
<220> FEATURE:
<223> OTHER INFORMATION: Figure 9 c, turboGFP insert 3 prime end
```

<400> SEQUENCE: 41
attgcagatc ccctgggtgt ggttgatgaa ggt                          33

<210> SEQ ID NO 42
<211> LENGTH: 33
<212> TYPE: DNA
<213> ORGANISM: Artificial Sequence
<220> FEATURE:
<223> OTHER INFORMATION: Figure 9 c, Genomic Site 5 prime end

<400> SEQUENCE: 42
accttcatca accacaccca gggcatcccc gac                          33

<210> SEQ ID NO 43
<211> LENGTH: 32
<212> TYPE: DNA
<213> ORGANISM: Artificial Sequence
<220> FEATURE:
<223> OTHER INFORMATION: Figure 9 c, Theory

<400> SEQUENCE: 43
attgcagatc ccctggccag ggcatccccg ac                           32

<210> SEQ ID NO 44
<211> LENGTH: 33
<212> TYPE: DNA
<213> ORGANISM: Artificial Sequence
<220> FEATURE:
<223> OTHER INFORMATION: Figure 9 c, Cl1 = Cl 4

<400> SEQUENCE: 44
attgcagatc ccctggccca gggcatcccc gac                          33

<210> SEQ ID NO 45
<211> LENGTH: 19
<212> TYPE: DNA
<213> ORGANISM: Artificial Sequence
<220> FEATURE:
<223> OTHER INFORMATION: Figure 9 c, Cl2

<400> SEQUENCE: 45
attgcagggc atccccgac                                          19

<210> SEQ ID NO 46
<211> LENGTH: 25
<212> TYPE: DNA
<213> ORGANISM: Artificial Sequence
<220> FEATURE:
<223> OTHER INFORMATION: Figure 9 c, Cl3

<400> SEQUENCE: 46
attgcagatc ccctggatcc ccgac                                   25

<210> SEQ ID NO 47
<211> LENGTH: 20
<212> TYPE: DNA
<213> ORGANISM: Artificial Sequence
<220> FEATURE:
<223> OTHER INFORMATION: 5 prime junction PCR primer 1 (PCR 1 on Figure
      2)

<400> SEQUENCE: 47
ttgtcccaaa tctgtgcgga                                         20

<210> SEQ ID NO 48

```
<211> LENGTH: 20
<212> TYPE: DNA
<213> ORGANISM: Artificial Sequence
<220> FEATURE:
<223> OTHER INFORMATION: 5 prime junction PCR primer 2 (PCR 1 on Figure
      2)

<400> SEQUENCE: 48
caagtagtcg gggatgtcgg                                                   20

<210> SEQ ID NO 49
<211> LENGTH: 22
<212> TYPE: DNA
<213> ORGANISM: Artificial Sequence
<220> FEATURE:
<223> OTHER INFORMATION: 3 prime junction PCR primer 1 (mCherry insert
      with the 5 prime region of genomic DNA, PCR 2 noted on Figure 2)

<400> SEQUENCE: 49
ccgactactt gaagctgtcc tt                                                22

<210> SEQ ID NO 50
<211> LENGTH: 22
<212> TYPE: DNA
<213> ORGANISM: Artificial Sequence
<220> FEATURE:
<223> OTHER INFORMATION: 3 prime junction PCR primer 2 (mCherry insert
      with the 5 prime region of genomic DNA, PCR 2 noted on Figure 2)

<400> SEQUENCE: 50
cccatatgtc cttccgagtg ag                                                22

<210> SEQ ID NO 51
<211> LENGTH: 22
<212> TYPE: DNA
<213> ORGANISM: Artificial Sequence
<220> FEATURE:
<223> OTHER INFORMATION: 5 prime end PCR primer 1 (HEK293 Cells with
      Reporter 2)

<400> SEQUENCE: 51
cgtaggtgta gcggtagtta ac                                                22

<210> SEQ ID NO 52
<211> LENGTH: 21
<212> TYPE: DNA
<213> ORGANISM: Artificial Sequence
<220> FEATURE:
<223> OTHER INFORMATION: 5 prime end PCR primer 2 (HEK293 Cells with
      Reporter 2)

<400> SEQUENCE: 52
ttcggcttct ggcgtgtgac c                                                 21

<210> SEQ ID NO 53
<211> LENGTH: 22
<212> TYPE: DNA
<213> ORGANISM: Artificial Sequence
<220> FEATURE:
<223> OTHER INFORMATION: 3 prime end PCR primer 1 (HEK293 Cells with
      Reporter 2)

<400> SEQUENCE: 53
gttaactacc gctacaccta cg                                                22

<210> SEQ ID NO 54
<211> LENGTH: 21
```

```
<212> TYPE: DNA
<213> ORGANISM: Artificial Sequence
<220> FEATURE:
<223> OTHER INFORMATION: 3 prime end PCR primer 2 (HEK293 Cells with
      Reporter 2)

<400> SEQUENCE: 54
ggtacagcat ctcggtgttg g                                        21

<210> SEQ ID NO 55
<211> LENGTH: 1230
<212> TYPE: DNA
<213> ORGANISM: Artificial Sequence
<220> FEATURE:
<223> OTHER INFORMATION: Example 5: Polb-Minicircle

<400> SEQUENCE: 55
tgacccacac aaaattagtc ttttagcaga ctggtatgtt tccaataaga tcatttaagt    60
cctcaaagca ttcctaaatc attgttagac tttttttttt cttaaagatt gagggcagag   120
gaagtctgct aacatgcggt gacgtggagg agaatcccgg ccctgctagc atggtgagca   180
agggcgagga ggataacatg gccatcatca aggagttcat gcgcttcaag gtgcacatgg   240
agggctccgt gaacggccac gagttcgaga tcgagggcga gggcgagggc cgcccctacg   300
agggcaccca gaccgccaag ctgaaggtga ccaagggtgg ccccctgccc ttcgcctggg   360
acatcctgtc ccctcagttc atgtacggct ccaaggccta cgtgaagcac cccgccgaca   420
tccccgacta cttgaagctg tccttccccg agggcttcaa gtgggagcgc gtgatgaact   480
tcgaggacgg cggcgtggtg accgtgaccc aggactcctc cctgcaggac ggcgagttca   540
tctacaaggt gaagctgcgc ggcaccaact cccctcaga cggccccgta atgcagaaga    600
aaaccatggg ctgggaggcc tcctccgagc ggatgtaccc cgaggacggc gccctgaagg   660
gcgagatcaa gcagaggctg aagctgaagg acggcggcca ctacgacgct gaggtcaaga   720
ccacctacaa ggccaagaag cccgtgcagc tgccccggcgc ctacaacgtc aacatcaagt   780
tggacatcac ctcccacaac gaggactaca ccatcgtgga acagtacgaa cgcgccgagg   840
gccgccactc caccggcggc atggacgagc tgtacaagta agaattccta gagctcgctg   900
atcagcctcg actgtgcctt ctagttgcca gccatctgtt gtttgcccct ccccgtgcc    960 ttccttgacc ctggaaggtg ccactcccac tgtccttcc taataaaatg aggaaattgc    1020
atcgcattgt ctgagtaggt gtcattctat tctggggggt ggggtggggc aggacagcaa   1080
gggggaggat tgggaagaga atagcaggca tgctggggg atccctgcag gagctcgtcg   1140
acccatgggg gcccgcccca actggggtaa cctttgggct ccccgggcgc gactagtgaa   1200
ttcagatctg atatctctag aagtcctggg                                   1230

<210> SEQ ID NO 56
<211> LENGTH: 17
<212> TYPE: DNA
<213> ORGANISM: Artificial Sequence
<220> FEATURE:
<223> OTHER INFORMATION: Example 5: Mini circle target 1

<400> SEQUENCE: 56
tgacccacac aaaatta                                             17

<210> SEQ ID NO 57
<211> LENGTH: 89
<212> TYPE: DNA
<213> ORGANISM: Artificial Sequence
```

<220> FEATURE:
<223> OTHER INFORMATION: Example 5: Native gene exon splice acceptor

<400> SEQUENCE: 57
gtcttttagc agactggtat gtttccaata agatcattta agtcctcaaa gcattcctaa    60
atcattgtta gactttttt tttcttaaa                                       89

<210> SEQ ID NO 58
<211> LENGTH: 54
<212> TYPE: DNA
<213> ORGANISM: Artificial Sequence
<220> FEATURE:
<223> OTHER INFORMATION: Example 5: 2A sequence

<400> SEQUENCE: 58
gagggcagag gaagtctgct aacatgcggt gacgtggagg agaatcccgg ccct          54

<210> SEQ ID NO 59
<211> LENGTH: 711
<212> TYPE: DNA
<213> ORGANISM: Artificial Sequence
<220> FEATURE:
<223> OTHER INFORMATION: Example 5: mCherry seq

<400> SEQUENCE: 59
atggtgagca agggcgagga ggataacatg gccatcatca aggagttcat gcgcttcaag    60
gtgcacatgg agggctccgt gaacggccac gagttcgaga tcgagggcga gggcgagggc   120
cgcccctacg agggcaccca gaccgccaag ctgaaggtga ccaagggtgg ccccctgccc   180
ttcgcctggg acatcctgtc ccctcagttc atgtacggct ccaaggccta cgtgaagcac   240
cccgccgaca tccccgacta cttgaagctg tccttcccccg agggcttcaa gtgggagcgc   300
gtgatgaact tcgaggacgg cggcgtggtg accgtgaccc aggactcctc cctgcaggac   360
ggcgagttca tctacaaggt gaagctgcgc ggcaccaact tcccctcaga cggccccgta   420
atgcagaaga aaaccatggg ctgggaggcc tcctccgagc ggatgtaccc cgaggacggc   480
gccctgaagg gcgagatcaa gcagaggctg aagctgaagg acggcggcca ctacgacgct   540
gaggtcaaga ccacctacaa ggccaagaag cccgtgcagc tgcccggcgc ctacaacgtc   600
aacatcaagt tggacatcac ctcccacaac gaggactaca ccatcgtgga acagtacgaa   660
cgcgccgagg gccgccactc caccggcggc atggacgagc tgtacaagta a            711

<210> SEQ ID NO 60
<211> LENGTH: 237
<212> TYPE: DNA
<213> ORGANISM: Artificial Sequence
<220> FEATURE:
<223> OTHER INFORMATION: Example 5: pA

<400> SEQUENCE: 60
gaattcctag agctcgctga tcagcctcga ctgtgccttc tagttgccag ccatctgttg    60
tttgcccctc ccccgtgcct tccttgaccc tggaaggtgc cactcccact gtcctttcct   120
aataaaatga ggaaattgca tcgcattgtc tgagtaggtg tcattctatt ctggggggtg   180 ggtggggca ggacagcaag ggggaggatt gggaagagaa tagcaggcat gctgggg       237

<210> SEQ ID NO 61
<211> LENGTH: 22
<212> TYPE: DNA
<213> ORGANISM: Artificial Sequence
<220> FEATURE:

<223> OTHER INFORMATION: Example 5: PolbP1 primer

<400> SEQUENCE: 61
ccatacccgg ccatctttta ga                                              22

<210> SEQ ID NO 62
<211> LENGTH: 22
<212> TYPE: DNA
<213> ORGANISM: Artificial Sequence
<220> FEATURE:
<223> OTHER INFORMATION: Example 5: PolbP2 primer

<400> SEQUENCE: 62
gcttgagggc ttgttccaaa tt                                              22

<210> SEQ ID NO 63
<211> LENGTH: 22
<212> TYPE: DNA
<213> ORGANISM: Artificial Sequence
<220> FEATURE:
<223> OTHER INFORMATION: Example 5: PolbP3 primer

<400> SEQUENCE: 63
ccatacccgg ccatctttta ga                                              22

<210> SEQ ID NO 64
<211> LENGTH: 22
<212> TYPE: DNA
<213> ORGANISM: Artificial Sequence
<220> FEATURE:
<223> OTHER INFORMATION: Example 5: PolbP4 primer

<400> SEQUENCE: 64
actccttgat gatggccatg tt                                              22

<210> SEQ ID NO 65
<211> LENGTH: 22
<212> TYPE: DNA
<213> ORGANISM: Artificial Sequence
<220> FEATURE:
<223> OTHER INFORMATION: Example 5: PolbP5 primer

<400> SEQUENCE: 65
atcaagttgg acatcacctc cc                                              22

<210> SEQ ID NO 66
<211> LENGTH: 22
<212> TYPE: DNA
<213> ORGANISM: Artificial Sequence
<220> FEATURE:
<223> OTHER INFORMATION: Example 5: PolbP6 primer

<400> SEQUENCE: 66
gcttgagggc ttgttccaaa tt                                              22

<210> SEQ ID NO 67
<211> LENGTH: 9346
<212> TYPE: DNA
<213> ORGANISM: Artificial Sequence
<220> FEATURE:
<223> OTHER INFORMATION: Example 5: Plasmid DNA (circular): Expression
      vector for Cas9

<400> SEQUENCE: 67
ccgttacata acttacggta aatggcccgc ctggctgacc gcccaacgac ccccgcccat     60

```
tgacgtcaat agtaacgcca atagggactt ccattgacg tcaatgggtg gagtatttac    120
ggtaaactgc ccacttggca gtacatcaag tgtatcatat gccaagtacg cccctattg    180
acgtcaatga cggtaaatgg cccgcctggc attgtgccca gtacatgacc ttatgggact    240
ttcctacttg gcagtacatc tacgtattag tcatcgctat taccatggtc gaggtgagcc    300
ccacgttctg cttcactctc cccatctccc cccctcccc accccaatt ttgtatttat    360
ttattttta attattttgt gcagcgatgg gggcggggg gggggggggg cgcgcgccag    420
gcggggcggg gcggggcgag gggcggggcg gggcgaggcg gagaggtgcg gcggcagcca    480
atcagagcgg cgcgctccga aagtttcctt ttatggcgag gcggcggcgg cggcggccct    540
ataaaagcg aagcgcgcgg cgggcgggag tcgctgcgac gctgccttcg ccccgtgccc    600
cgctccgccg ccgcctcgcg ccgcccgccc cggctctgac tgaccgcgtt actcccacag    660
gtgagcgggc gggacggccc ttctcctccg ggctgtaatt agctgagcaa gaggtaaggg    720
tttaagggat ggttggttgg tggggtatta atgtttaatt acctggagca cctgcctgaa    780
atcacttttt ttcaggttgg accggtgcca ccatggacta taaggaccac gacggagact    840
acaaggatca tgatattgat tacaaagacg atgacgataa gatggccca aagaagaagc    900
ggaaggtcgg tatccacgga gtcccagcag ccgacaagaa gtacagcatc ggcctggaca    960
tcggcaccaa ctctgtgggc tgggccgtga tcaccgacga gtacaaggtg cccagcaaga   1020
aattcaaggt gctgggcaac accgaccggc acagcatcaa gaagaacctg atcggagccc   1080
tgctgttcga cagcggcgaa acagccgagg ccacccggct gaagagaacc gccagaagaa   1140
gatacaccag acggaagaac cggatctgct atctgcaaga gatcttcagc aacgagatgg   1200
ccaaggtgga cgacagcttc ttccacagac tggaagagtc cttcctggtg gaagaggata   1260
agaagcacga gcggcacccc atcttcggca acatcgtgga cgaggtggcc taccacgaga   1320
agtaccccac catctaccac ctgagaaaga aactggtgga cagcaccgac aaggccgacc   1380
tgcggctgat ctatctggcc ctggcccaca tgatcaagtt ccggggccac ttcctgatcg   1440
agggcgacct gaaccccgac aacagcgacg tggacaagct gttcatccag ctggtgcaga   1500
cctacaacca gctgttcgag gaaaaccca tcaacgccag cggcgtggac gccaaggcca   1560
tcctgtctgc cagactgagc aagagcagac ggctggaaaa tctgatcgcc cagctgcccg   1620
gcgagaagaa gaatggcctg ttcggaaacc tgattgccct gagcctgggc ctgaccccca   1680
acttcaagag caacttcgac ctggccgagg atgccaaact gcagctgagc aaggacacct   1740
acgacgacga cctggacaac ctgctggccc agatcggcga ccagtacgcc gacctgtttc   1800
tggccgccaa gaacctgtcc gacgccatcc tgctgagcga catcctgaga gtgaacaccg   1860
agatcaccaa ggccccctg agcgcctcta tgatcaagag atacgacgag caccaccagg   1920
acctgaccct gctgaaagct ctcgtgcggc agcagctgcc tgagaagtac aaagagattt   1980
tcttcgacca gagcaagaac ggctacgccg gctacattga cggcggagcc agccaggaag   2040
agttctacaa gttcatcaag cccatcctgg aaaagatgga cggcaccgag gaactgctcg   2100
tgaagctgaa cagagaggac ctgctgcgga agcagcggac cttcgacaac ggcagcatcc   2160
cccaccagat ccacctggga gagctgcacg ccattctgcg gcggcaggaa gattttacc   2220
cattcctgaa ggacaaccgg gaaaagatcg agaagatcct gaccttccgc atcccctact   2280
acgtgggccc tctggccagg ggaaacagca gattcgcctg gatgaccaga aagagcgagg   2340
aaaccatcac cccctggaac ttcgaggaag tggtggacaa gggcgcttcc gcccagagct   2400
tcatcgagcg gatgaccaac ttcgataaga acctgcccaa cgagaaggtg ctgcccaagc   2460
```

```
acagcctgct gtacgagtac ttcaccgtgt ataacgagct gaccaaagtg aaatacgtga    2520
ccgagggaat gagaaagccc gccttcctga gcggcgagca gaaaaaggcc atcgtggacc    2580
tgctgttcaa gaccaaccgg aaagtgaccg tgaagcagct gaaagaggac tacttcaaga    2640
aaatcgagtg cttcgactcc gtggaaatct ccggcgtgga agatcggttc aacgcctccc    2700
tgggcacata ccacgatctg ctgaaaatta tcaaggacaa ggacttcctg gacaatgagg    2760
aaaacgagga cattctggaa gatatcgtgc tgaccctgac actgtttgag gacagagaga    2820
tgatcgagga acggctgaaa acctatgccc acctgttcga cgacaaagtg atgaagcagc    2880
tgaagcggcg gagatacacc ggctggggca ggctgagccg gaagctgatc aacggcatcc    2940
gggacaagca gtccggcaag acaatcctgg atttcctgaa gtccgacggc ttcgccaaca    3000
gaaacttcat gcagctgatc cacgacgaca gcctgacctt taaagaggac atccagaaag    3060
cccaggtgtc cggccagggc gatagcctgc acgagcacat tgccaatctg gccggcagcc    3120
ccgccattaa gaagggcatc ctgcagacag tgaaggtggt ggacgagctc gtgaaagtga    3180
tgggccggca aagcccgag aacatcgtga tcgaaatggc cagagagaac cagaccaccc    3240
agaagggaca aagaacagc cgcgagagaa tgaagcggat cgaagagggc atcaaagagc    3300
tgggcagcca gatcctgaaa gaacaccccg tggaaaacac ccagctgcag aacgagaagc    3360
tgtacctgta ctacctgcag aatgggcggg atatgtacgt ggaccaggaa ctggacatca    3420
accggctgtc cgactacgat gtggaccata tcgtgcctca gagctttctg aaggacgact    3480
ccatcgacaa caaggtgctg accagaagcg acaagaaccg gggcaagagc gacaacgtgc    3540
cctccgaaga ggtcgtgaag aagatgaaga actactggcg gcagctgctg aacgccaagc    3600
tgattaccca gagaaagttc gacaatctga ccaaggccga gagaggcggc ctgagcgaac    3660
tggataaggc cggcttcatc aagagacagc tggtggaaac ccggcagatc acaaagcacg    3720
tggcacagat cctggactcc cggatgaaca ctaagtacga cgagaatgac aagctgatcc    3780
gggaagtgaa agtgatcacc ctgaagtcca agctggtgtc cgatttccgg aaggatttcc    3840
agttttacaa agtgcgcgag atcaacaact accaccacgc ccacgacgcc tacctgaacg    3900
ccgtcgtggg aaccgccctg atcaaaaagt accctaagct ggaaagcgag ttcgtgtacg    3960
gcgactacaa ggtgtacgac gtgcggaaga tgatcgccaa gagcgagcag gaaatcggca    4020
aggctaccgc caagtacttc ttctacagca acatcatgaa cttttcaag accgagatta    4080 ccctggccaa cggcgagatc cggaagcggc ctctgatcga gacaaacggc gaaaccgggg    4140
agatcgtgtg ggataagggc cgggattttg ccaccgtgcg gaaagtgctg agcatgcccc    4200
aagtgaatat cgtgaaaaag accgaggtgc agacaggcgg cttcagcaaa gagtctatcc    4260
tgcccaagag gaacagcgat aagctgatcg ccagaaagaa ggactgggac cctaagaagt    4320
acggcggctt cgacagcccc accgtggcct attctgtgct ggtggtggcc aaagtggaaa    4380
agggcaagtc caagaaactg aagagtgtga agagctgct ggggatcacc atcatggaaa    4440
gaagcagctt cgagaagaat cccatcgact ttctggaagc caagggctac aaagaagtga    4500
aaaaggacct gatcatcaag ctgcctaagt actccctgtt cgagctggaa aacggccgga    4560
agagaatgct ggcctctgcc ggcgaactgc agaagggaaa cgaactggcc ctgccctcca    4620
aatatgtgaa cttcctgtac ctggccagcc actatgagaa gctgaagggc tcccccgagg    4680
ataatgagca gaaacagctg tttgtggaac agcacaagca ctacctggac gagatcatcg    4740
agcagatcag cgagttctcc aagagagtga tcctggccga cgctaatctg gacaaagtgc    4800
```

```
tgtccgccta caacaagcac cgggataagc ccatcagaga gcaggccgag aatatcatcc    4860
acctgtttac cctgaccaat ctgggagccc ctgccgcctt caagtacttt gacaccacca    4920
tcgaccggaa gaggtacacc agcaccaaag aggtgctgga cgccaccctg atccaccaga    4980
gcatcaccgg cctgtacgag acacggatcg acctgtctca gctggaggc gacaaaaggc     5040
cggcggccac gaaaaaggcc ggccaggcaa aaagaaaaa ggaattcggc agtggagagg     5100
gcagaggaag tctgctaaca tgcggtgacg tcgaggagaa tcctggccca atgaccgagt    5160
acaagcccac ggtgcgcctc gccacccgcg acgacgtccc cagggccgta cgcaccctcg    5220
ccgccgcgtt cgccgactac cccgccacgc gccacaccgt cgatccggac cgccacatcg    5280
agcgggtcac cgagctgcaa gaactcttcc tcacgcgcgt cgggctcgac atcggcaagg    5340
tgtgggtcgc ggacgacggc gccgcggtgg cggtctggac cacgccggag agcgtcgaag    5400
cgggggcggt gttcgccgag atcggcccgc gcatggccga gttgagcggt tcccggctgg    5460
ccgcgcagca acagatggaa ggcctcctgg cgccgcaccg gcccaaggag cccgcgtggt    5520
tcctggccac cgtcggagtc tcgcccgacc accaggcaa gggtctgggc agcgccgtcg     5580
tgctccccgg agtggaggcg gccgagcgcg ccggggtgcc cgccttcctg gagacctccg    5640
cgccccgcaa cctccccttc tacgagcggc tcggcttcac cgtcaccgcc gacgtcgagg    5700
tgcccgaagg accgcgcacc tggtgcatga cccgcaagcc cggtgcctga gaattctaac    5760
tagagctcgc tgatcagcct cgactgtgcc ttctagttgc cagccatctg ttgtttgccc    5820
ctcccccgtg ccttccttga ccctggaagg tgccactccc actgtccttt cctaataaaa    5880
tgaggaaatt gcatcgcatt gtctgagtag gtgtcattct attctggggg gtggggtggg    5940
gcaggacagc aaggggagg attgggaaga gaatagcagg catgctgggg agcggccgca     6000
ggaacccta gtgatggagt tggccactcc ctctctgcgc gctcgctcgc tcactgaggc     6060
cgggcgacca aggtcgccc gacgcccggg cttttgcccgg gcggcctcag tgagcgagcg    6120
agcgcgcagc tgcctgcaat cactacattc acatctgatt tcagtagttc cttacgagag    6180
ttcctccgcg cgggtttaaa gggcctcgtg atacgcctat ttttataggt taatgtcatg    6240
ataataatgg tttcttagac gtcaggtggc acttttcggg gaaatgtgcg cggaacccct    6300
atttgtttat ttttctaaat acattcaaat atgtatccgc tcatgagaca ataaccctga    6360
taaatgcttc aataatattg aaaaaggaag agtatgagta ttcaacattt ccgtgtcgcc    6420
cttattccct tttttgcggc attttgcctt cctgttttg ctcacccaga aacgctggtg     6480
aaagtaaaag atgctgaaga tcagttgggt gcacgagtgg gttacatcga actggatctc    6540
aacagcggta agatccttga gagttttcgc cccgaagaac gttttccaat gatgagcact    6600
tttaaagttc tgctatgtgg cgcggtatta tcccgtattg acgccgggca agagcaactc    6660
ggtcgccgca tacactattc tcagaatgac ttggttgagt actcaccagt cacagaaaag    6720
catcttacgg atggcatgac agtaagagaa ttatgcagtg ctgccataac catgagtgat    6780
aacactgcgg ccaacttact tctgacaacg atcggaggac cgaaggagct aaccgctttt    6840
ttgcacaaca tgggggatca tgtaactcgc cttgatcgtt gggaaccgga gctgaatgaa    6900
gccataccaa acgacgagcg tgacaccacg atgcctgtag caatggcaac aacgttgcgc    6960
aaactattaa ctggcgaact acttactcta gcttcccggc aacaattaat agactggatg    7020
gaggcggata aagttgcagg accacttctg cgctcggccc ttccggctgg ctggtttatt    7080
gctgataaat ctggagccgg tgagcgtgga agccgcggta tcattgcagc actggggcca    7140
gatggtaagc cctcccgtat cgtagttatc tacacgacgg ggagtcaggc aactatggat    7200
```

```
gaacgaaata gacagatcgc tgagataggt gcctcactga ttaagcattg gtaactgtca    7260
gaccaagttt actcatatat actttagatt gatttaaaac ttcattttta atttaaaagg    7320
atctaggtga agatccttt tgataatctc atgaccaaaa tcccttaacg tgagttttcg    7380
ttccactgag cgtcagaccc cgtagaaaag atcaaaggat cttcttgaga tccttttttt    7440
ctgcgcgtaa tctgctgctt gcaaacaaaa aaaccaccgc taccagcggt ggtttgtttg    7500
ccggatcaag agctaccaac tcttttccg aaggtaactg gcttcagcag agcgcagata    7560
ccaaatactg tccttctagt gtagccgtag ttaggccacc acttcaagaa ctctgtagca    7620
ccgcctacat acctcgctct gctaatcctg ttaccagtgg ctgctgccag tggcgataag    7680
tcgtgtctta ccgggttgga ctcaagacga tagttaccgg ataaggcgca gcggtcgggc    7740
tgaacggggg gttcgtgcac acagcccagc ttggagcgaa cgacctacac cgaactgaga    7800
tacctacagc gtgagctatg agaaagcgcc acgcttcccg aagggagaaa ggcggacagg    7860
tatccggtaa gcggcagggt cggaacagga gagcgcacga gggagcttcc agggggaaac    7920
gcctggtatc tttatagtcc tgtcgggttt cgccacctct gacttgagcg tcgatttttg    7980
tgatgctcgt caggggggcg gagcctatgg aaaaacgcca gcaacgcggc ctttttacgg    8040
ttcctggcct tttgctggcc ttttgctcac atgtgagggc ctatttccca tgattccttc    8100
atatttgcat atacgataca aggctgttag agagataatt ggaattaatt tgactgtaaa    8160
cacaaagata ttagtacaaa atacgtgacg tagaaagtaa taattcttg ggtagtttgc     8220 agttttaaaa ttatgtttta aaatggacta tcatatgctt accgtaactt gaaagtattt    8280
cgatttcttg gctttatata tcttgtggaa aggacgaaac accgggtctt cgagaagacc    8340
tgttttagag ctagaaatag caagttaaaa taaggctagt ccgttatcaa cttgaaaaag    8400
tggcaccgag tcggtgcttt tttgttttag agctagaaat agcaagttaa aataaggcta    8460
gtccgttttt agcgcgtgcg ccaattctgc agacaaatgg ctctagagcg agggcctatt    8520
tcccatgatt ccttcatatt tgcatatacg atacaaggct gttagagaga taattggaat    8580
taatttgact gtaaacacaa agatattagt acaaaatacg tgacgtagaa agtaataatt    8640
tcttgggtag tttgcagttt taaaattatg ttttaaaatg gactatcata tgcttaccgt    8700
aacttgaaag tatttcgatt tcttggcttt atatatcttg tggaaggac gaaacaccgt     8760 aattttgtgt gggtcacccg ttttagagct aggccaacat gaggatcacc catgtctgca    8820
gggcctagca agttaaaata aggctagtcc gttatcaact tggccaacat gaggatcacc    8880
catgtctgca gggccaagtg gcaccgagtc ggtgcttttt ttgagatatc cgagggccta    8940
tttcccatga ttccttcata tttgcatata cgatacaagg ctgttagaga gataattgga    9000
attaatttga ctgtaaacac aaagatatta gtacaaaata cgtgacgtag aaagtaataa    9060
tttcttgggt agtttgcagt tttaaaatta tgttttaaaa tggactatca tatgcttacc    9120
gtaacttgaa agtatttcga tttcttggct ttatatatct tgtggaaagg acgaaacacc    9180
gtgaaaccag tttggttacc cgttttagag ctaggccaac atgaggatca cccatgtctg    9240
cagggcctag caagttaaaa taaggctagt ccgttatcaa cttggccaac atgaggatca    9300
cccatgtctg cagggccaag tggcaccgag tcggtgcttt ttttga                  9346
```

<210> SEQ ID NO 68
<211> LENGTH: 5990
<212> TYPE: DNA
<213> ORGANISM: Artificial Sequence
<220> FEATURE:

<223> OTHER INFORMATION: Example 5: Cbh promoter

<400> SEQUENCE: 68

```
cgttacataa cttacggtaa atggcccgcc tggctgaccg cccaacgacc cccgcccatt        60
gacgtcaata gtaacgccaa tagggacttt ccattgacgt caatgggtgg agtatttacg       120
gtaaactgcc cacttggcag tacatcaagt gtatcatatg ccaagtacgc ccctattga       180
cgtcaatgac ggtaaatggc ccgcctggca ttgtgcccag tacatgacct tatgggactt       240
tcctacttgg cagtacatct acgtattagt catcgctatt accatggtcg aggtgagccc       300
cacgttctgc ttcactctcc ccatctcccc ccctcccca ccccaatttt gtatttatt        360
tattttttaa ttatttttgtg cagcgatggg ggcggggggg ggggggggc gcgcgccagg       420
cggggcgggg cggggcgagg ggcggggcgg ggcgaggcgg agaggtgcgg cggcagccaa       480
tcagagcggc gcgctccgaa agtttccttt tatggcgagg cggcggcggc ggcggcccta       540
taaaaagcga agcgcgcggc gggcgggagt cgctgcgacg ctgccttcgc cccgtgcccc       600
gctccgccgc cgcctcgcgc cgcccgcccc ggctctgact gaccgcgtta ctcccacagg       660
tgagcgggcg gacggccct tctcctccgg gctgtaatta gctgagcaag aggtaagggt       720
ttaagggatg gttggttggt ggggtattaa tgtttaatta cctggagcac ctgcctgaaa       780
tcacttttttt tcaggttgga ccggtgccac catggactat aaggaccacg acggagacta       840
caaggatcat gatattgatt acaaagacga tgacgataag atggccccaa agaagaagcg       900
gaaggtcggt atccacggag tcccagcagc cgacaagaag tacagcatcg gcctggacat       960
cggcaccaac tctgtgggct gggccgtgat caccgacgag tacaaggtgc ccagcaagaa      1020
attcaaggtg ctgggcaaca ccgaccggca cagcatcaag aagaacctga tcggagccct      1080
gctgttcgac agcggcgaaa cagccgaggc caccccggctg aagagaaccg ccagaagaag      1140
atacaccaga cggaagaacc ggatctgcta tctgcaagag atcttcagca acgagatggc      1200
caaggtggac gacagcttct tccacagact ggaagagtcc ttcctggtgg aagaggataa      1260
gaagcacgag cggcacccca tcttcggcaa catcgtggac gaggtggcct accacgagaa      1320
gtaccccacc atctaccacc tgagaaagaa actggtggac agcaccgaca aggccgacct      1380
gcggctgatc tatctggccc tggcccacat gatcaagttc cggggccact tcctgatcga      1440
gggcgacctg aaccccgaca cagcgacgt ggacaagctg ttcatccagc tggtgcagac      1500
ctacaaccag ctgttcgagg aaaaccccat caacgccagc ggcgtggacg ccaaggccat      1560
cctgtctgcc agactgagca agagcagacg gctggaaaat ctgatcgccc agctgccgg      1620
cgagaagaag aatggcctgt tcggaaacct gattgccctg agcctgggcc tgaccccaa      1680
cttcaagagc aacttcgacc tggccgagga tgccaaactg cagctgagca aggacaccta      1740
cgacgacgac ctggacaacc tgctggccca gatcggcgac cagtacgccg acctgtttct      1800
ggccgccaag aacctgtccg acgccatcct gctgagcgac atcctgagag tgaacaccga      1860
gatcaccaag gcccccctga gcgcctctat gatcaagaga tacgacgagc accaccagga      1920
cctgaccctg ctgaaagctc tcgtgcggca gcagctgcct gagaagtaca agagattttt      1980
cttcgaccag agcaagaacg gctacgccgg ctacattgac ggcggagcca gcaggaaga      2040
gttctacaag ttcatcaagc ccatcctgga aaagatggac ggcaccgagg aactgctcgt      2100
gaagctgaac agagaggacc tgctgcggaa gcagcggacc ttcgacaacg gcagcatccc      2160
ccaccagatc cacctgggag agctgcacgc cattctgcgg cggcaggaag atttttaccc      2220
attcctgaag gacaaccggg aaaagatcga gaagatcctg accttccgca tcccctacta      2280
```

```
cgtgggccct ctggccaggg gaaacagcag attcgcctgg atgaccagaa agagcgagga    2340
aaccatcacc ccctggaact tcgaggaagt ggtggacaag ggcgcttccg cccagagctt    2400
catcgagcgg atgaccaact tcgataagaa cctgcccaac gagaaggtgc tgcccaagca    2460
cagcctgctg tacgagtact tcaccgtgta taacgagctg accaaagtga atacgtgac    2520
cgagggaatg agaaagcccg ccttcctgag cggcgagcag aaaaaggcca tcgtggacct    2580
gctgttcaag accaaccgga aagtgaccgt gaagcagctg aaagaggact acttcaagaa    2640
aatcgagtgc ttcgactccg tggaaatctc cggcgtggaa gatcggttca acgcctccct    2700
gggcacatac cacgatctgc tgaaaattat caaggacaag gacttcctgg acaatgagga    2760
aaacgaggac attctggaag atatcgtgct gaccctgaca ctgtttgagg acagagagat    2820
gatcgaggaa cggctgaaaa cctatgccca cctgttcgac gacaaagtga tgaagcagct    2880
gaagcggcgg agatacaccg gctggggcag gctgagccgg aagctgatca acggcatccg    2940
ggacaagcag tccggcaaga caatcctgga tttcctgaag tccgacggct cgccaacag    3000
aaacttcatg cagctgatcc acgacgacag cctgaccttt aaagaggaca tccagaaagc    3060
ccaggtgtcc ggccagggcg atagcctgca cgagcacatt gccaatctgg ccggcagccc    3120
cgccattaag aagggcatcc tgcagacagt gaaggtggtg gacgagctcg tgaaagtgat    3180
gggccggcac aagcccgaga acatcgtgat cgaaatggcc agagaaaacc agaccaccca    3240
gaagggacag aagaacagcc gcgagagaat gaagcggatc gaagagggca tcaaagagct    3300
gggcagccag atcctgaaag aacacccgt ggaaaacacc cagctgcaga acgagaagct    3360
gtacctgtac tacctgcaga atgggcggga tatgtacgtg gaccaggaac tggacatcaa    3420
ccggctgtcc gactacgatg tggaccatat cgtgcctcag agctttctga aggacgactc    3480
catcgacaac aaggtgctga ccagaagcga caagaaccgg ggcaagagcg acaacgtgcc    3540
ctccgaagag gtcgtgaaga gatgaagaa ctactggcgg cagctgctga acgccaagct    3600
gattacccag agaaagttcg acaatctgac caaggccgag agaggcggcc tgagcgaact    3660
ggataaggcc ggcttcatca agagacagct ggtggaaacc cggcagatca caaagcacgt    3720
ggcacagatc ctggactccc ggatgaacac taagtacgac gagaatgaca gctgatccg    3780
ggaagtgaaa gtgatcaccc tgaagtccaa gctggtgtcc gatttccgga aggatttcca    3840
gttttacaaa gtgcgcgaga tcaacaacta ccaccacgcc cacgacgcct acctgaacgc    3900
cgtcgtggga accgccctga tcaaaaagta ccctaagctg gaaagcgagt tcgtgtacgg    3960
cgactacaag gtgtacgacg tgcggaagat gatcgccaag agcgagcagg aaatcggcaa    4020
ggctaccgcc aagtacttct tctacagcaa catcatgaac ttttttcaaga ccgagattac    4080
cctggccaac ggcgagatcc ggaagcgcc tctgatcgaa acaaacgcg aaaccgggga    4140
gatcgtgtgg gataagggcc gggattttgc caccgtgcgg aaagtgctga gcatgcccca    4200
agtgaatatc gtgaaaaaga ccgaggtgca gacaggcggc ttcagcaaag agtctatcct    4260
gcccaagagg aacagcgata agctgatcgc cagaaagaag gactgggacc ctaagaagta    4320
cggcggcttc gacagcccca ccgtggccta ttctgtgctg gtggtggcca agtggaaaa    4380
gggcaagtcc aagaaactga agagtgtgaa agagctgctg gggatcacca tcatggaaag    4440
aagcagcttc gagaagaatc ccatcgactt tctggaagcc aagggctaca agaagtgaa    4500
aaaggacctg atcatcaagc tgcctaagta ctccctgttc gagctggaaa acggccggaa    4560
gagaatgctg gcctctgccg gcgaactgca gaagggaaac gaactggccc tgccctccaa    4620
```

| | |
|---|---|
| atatgtgaac ttcctgtacc tggccagcca ctatgagaag ctgaagggct cccccgagga | 4680 |
| taatgagcag aaacagctgt ttgtggaaca gcacaagcac tacctggacg agatcatcga | 4740 |
| gcagatcagc gagttctcca agagagtgat cctggccgac gctaatctgg acaaagtgct | 4800 |
| gtccgcctac aacaagcacc gggataagcc catcagagag caggccgaga atatcatcca | 4860 |
| cctgtttacc ctgaccaatc tgggagcccc tgccgccttc aagtactttg acaccaccat | 4920 |
| cgaccggaag aggtacacca gcaccaaaga ggtgctggac gccaccctga tccaccagag | 4980 |
| catcaccggc ctgtacgaga cacggatcga cctgtctcag ctgggaggcg acaaaaggcc | 5040 |
| ggcggccacg aaaaaggccg ccaggcaaa aagaaaaag gaattcggca gtggagaggg | 5100 |
| cagaggaagt ctgctaacat gcggtgacgt cgaggagaat cctggcccaa tgaccgagta | 5160 |
| caagcccacg gtgcgcctcg ccacccgcga cgacgtcccc agggccgtac gcaccctcgc | 5220 |
| cgccgcgttc gccgactacc ccgccacgcg ccacaccgtc gatccggacc gccacatcga | 5280 |
| gcgggtcacc gagctgcaag aactcttcct cacgcgcgtc gggctcgaca tcggcaaggt | 5340 |
| gtgggtcgcg gacgacggcg ccgcggtggc ggtctggacc acgccggaga gcgtcgaagc | 5400 |
| gggggcggtg ttcgccgaga tcggcccgcg catggccgag ttgagcggtt cccggctggc | 5460 |
| cgcgcagcaa cagatggaag gcctcctggc gccgcaccgg cccaaggagc ccgcgtggtt | 5520 |
| cctggccacc gtcggagtct cgcccgacca ccagggcaag ggtctgggca gcgccgtcgt | 5580 |
| gctcccggga gtggaggcgg ccgagcgcgc cggggtgccc gccttcctgg agacctccgc | 5640 |
| gccccgcaac ctcccctct acgagcggct cggcttcacc gtcaccgccg acgtcgaggt | 5700 |
| gcccgaagga ccgcgcacct ggtgcatgac ccgcaagccc ggtgcctgag aattctaact | 5760 |
| agagctcgct gatcagcctc gactgtgcct tctagttgcc agccatctgt tgtttgcccc | 5820 |
| tcccccgtgc cttccttgac cctggaaggt gccactccca ctgtcctttc ctaataaaat | 5880 |
| gaggaaattg catcgcattg tctgagtagg tgtcattcta ttctgggggg tggggtgggg | 5940 |
| caggacagca aggggagga ttgggaagag aatagcaggc atgctgggga | 5990 |

<210> SEQ ID NO 69
<211> LENGTH: 241
<212> TYPE: DNA
<213> ORGANISM: Artificial Sequence
<220> FEATURE:
<223> OTHER INFORMATION: Example 5: U6 promoter:

<400> SEQUENCE: 69

| | |
|---|---|
| tttcccatga ttccttcata tttgcatata cgatacaagg ctgttagaga gataattgga | 60 |
| attaatttga ctgtaaacac aaagatatta gtacaaaata cgtgacgtag aaagtaataa | 120 |
| tttcttgggt agtttgcagt tttaaaatta tgttttaaaa tggactatca tatgcttacc | 180 |
| gtaacttgaa agtatttcga tttcttggct ttatatatct tgtggaaagg acgaaacacc | 240 |
| g | 241 |

<210> SEQ ID NO 70
<211> LENGTH: 143
<212> TYPE: DNA
<213> ORGANISM: Artificial Sequence
<220> FEATURE:
<223> OTHER INFORMATION: Example 5: conserved portion of the gRNA

<400> SEQUENCE: 70

| | |
|---|---|
| gttttagagc taggccaaca tgaggatcac ccatgtctgc agggcctagc aagttaaaat | 60 |
| aaggctagtc cgttatcaac ttggccaaca tgaggatcac ccatgtctgc agggccaagt | 120 | ggcaccgagt cggtgctttt ttt                                        143

<210> SEQ ID NO 71
<211> LENGTH: 20
<212> TYPE: DNA
<213> ORGANISM: Artificial Sequence
<220> FEATURE:
<223> OTHER INFORMATION: Example 5: the guide targeting sequence 1
      (protospacer).

<400> SEQUENCE: 71
taattttgtg tgggtcaccc                                             20

<210> SEQ ID NO 72
<211> LENGTH: 20
<212> TYPE: DNA
<213> ORGANISM: Artificial Sequence
<220> FEATURE:
<223> OTHER INFORMATION: Example 5: the guide targeting sequence 2
      (protospacer).

<400> SEQUENCE: 72
tgaaaccagt ttggttaccc                                             20

<210> SEQ ID NO 73
<211> LENGTH: 784
<212> TYPE: DNA
<213> ORGANISM: Artificial Sequence
<220> FEATURE:
<223> OTHER INFORMATION: Example 5: Target genomic sequence

<400> SEQUENCE: 73
ccaccatacc cggccatctt ttagaatttc tatgtttaca ctctcccaag catttttatg    60
gttttatttc accccatgat agtaattata tcacttctga tctgttaaga atagaccttt   120
taaaagtatt ggataactta gagatgagac atcttcagtt actctgttat tcacctatta   180
ctccttaggt tacttgtgaa taattttgtg tgggtcaccc aggcaaatgt aaatagctct   240
tcatgtcttt tagcagactg gtatgttccc aataagatca tttaagtcct caaagcattc   300
ctaaatcatt gttagacttt ttttttttctt aaagattcgg caggatgata cgagttcatc   360
catcaatttc ctgactcgag ttagtggcat tgggtaagaa ctatttttta agcagacaca   420
atcgtcagtt agtttatttt tcctgttagc caaagtaaat tacatgctgt ttctcaaaac   480
ctgtacttca ccacctctgt accttagcca tacagttcac ccttccatag cttatgatct   540
gaggccgatt cttcagatag tgtctctact gtaaggtccc catccaaggc agatgttacc   600
tccttcatga aaccagtttg gttacccagg cagaaagaac ctctccctcc tctgaactcc   660
actaccattt cctccgtgtg catctatttc ctgctccagc ttggcctctt ttgtttctct   720
gagcatgata tttatcatag cacctcatga atttggaaca agccctcaag ctttttttaa   780
atta                                                              784

<210> SEQ ID NO 74
<211> LENGTH: 59
<212> TYPE: DNA
<213> ORGANISM: Artificial Sequence
<220> FEATURE:
<223> OTHER INFORMATION: Example 5: exon to be replaced (Polb-exon5)

<400> SEQUENCE: 74
attcggcagg atgatacgag ttcatccatc aatttcctga ctcgagttag tggcattgg    59

```
<210> SEQ ID NO 75
<211> LENGTH: 20
<212> TYPE: DNA
<213> ORGANISM: Artificial Sequence
<220> FEATURE:
<223> OTHER INFORMATION: Example 5: Cas9 Target Site 1

<400> SEQUENCE: 75
taattttgtg tgggtcaccc                                              20

<210> SEQ ID NO 76
<211> LENGTH: 20
<212> TYPE: DNA
<213> ORGANISM: Artificial Sequence
<220> FEATURE:
<223> OTHER INFORMATION: Example 5: Cas9 Target Site 2

<400> SEQUENCE: 76
tgaaaccagt ttggttaccc                                              20

<210> SEQ ID NO 77
<211> LENGTH: 24
<212> TYPE: DNA
<213> ORGANISM: Artificial Sequence
<220> FEATURE:
<223> OTHER INFORMATION: Figure 16: WT allele: protospacer and upstream
      PAM

<400> SEQUENCE: 77
ttgtgtgggt cacccaggca aatg                                         24

<210> SEQ ID NO 78
<211> LENGTH: 24
<212> TYPE: DNA
<213> ORGANISM: Artificial Sequence
<220> FEATURE:
<223> OTHER INFORMATION: Figure 16: WT allele: protospacer and
      downstream PAM

<400> SEQUENCE: 78
ccagtttggt tacccaggca gaaa                                         24

<210> SEQ ID NO 79
<211> LENGTH: 24
<212> TYPE: DNA
<213> ORGANISM: Artificial Sequence
<220> FEATURE:
<223> OTHER INFORMATION: Figure 16: Correctly targeted allele:

<400> SEQUENCE: 79
ttgtgtgggt catgacccac acaa                                         24

<210> SEQ ID NO 80
<211> LENGTH: 24
<212> TYPE: DNA
<213> ORGANISM: Artificial Sequence
<220> FEATURE:
<223> OTHER INFORMATION: Figure 16: Correctly targeted allele

<400> SEQUENCE: 80
agaagtcctg ggcccaggca gaaa                                         24

<210> SEQ ID NO 81
<211> LENGTH: 10
<212> TYPE: DNA
<213> ORGANISM: Artificial Sequence
```

```
<220> FEATURE:
<223> OTHER INFORMATION: Figure 16: Incorrectly targeted allele

<400> SEQUENCE: 81
caggcagaaa                                                                  10

<210> SEQ ID NO 82
<211> LENGTH: 25
<212> TYPE: DNA
<213> ORGANISM: Artificial Sequence
<220> FEATURE:
<223> OTHER INFORMATION: Figure 16: Incorrectly targeted allele

<400> SEQUENCE: 82
ttgtgtgggt cactgaccca cacaa                                                 25

<210> SEQ ID NO 83
<211> LENGTH: 22
<212> TYPE: DNA
<213> ORGANISM: Artificial Sequence
<220> FEATURE:
<223> OTHER INFORMATION: Figure 16: Incorrectly targeted allele

<400> SEQUENCE: 83
ttgtgtgggt tgacccacac aa                                                    22

<210> SEQ ID NO 84
<211> LENGTH: 25
<212> TYPE: DNA
<213> ORGANISM: Artificial Sequence
<220> FEATURE:
<223> OTHER INFORMATION: Figure 16: Incorrectly targeted allele

<400> SEQUENCE: 84
agaagtcctg ggtcccaggc agaaa                                                 25

<210> SEQ ID NO 85
<211> LENGTH: 25
<212> TYPE: DNA
<213> ORGANISM: Artificial Sequence
<220> FEATURE:
<223> OTHER INFORMATION: Figure 16: Incorrectly targeted allele

<400> SEQUENCE: 85
agaagtcctg ggacccaggc agaaa                                                 25

<210> SEQ ID NO 86
<211> LENGTH: 22
<212> TYPE: DNA
<213> ORGANISM: Artificial Sequence
<220> FEATURE:
<223> OTHER INFORMATION: primer

<400> SEQUENCE: 86
gactacacca tcgtggaaca gt                                                    22
```

NUCLEIC ACID SEQUENCE REPLACEMENT BY NHEJ

REFERENCE TO SEQUENCE LISTING

A Sequence Listing submitted as an ASCII text file via EFS-Web is hereby incorporated by reference in accordance with 35 U.S.C. § 1.52(e). The name of the ASCII 15 text file for the Sequence Listing is 34375976_1.TXT, the date of creation of the ASCII text file is Feb. 8, 2021, and the size of the ASCII text file is 122 KB.

DESCRIPTION

The invention relates to the field of molecular biology, in particular genetic engineering. The invention relates to a method for modifying double stranded DNA employing an RNA guided DNA endonuclease to generate two double strand breaks in the dsDNA molecule to be modified, and replacement of the sequence positioned between the double strand breaks with a substitute DNA sequence using the non-homologous end joining (NHEJ) pathway. The invention also relates to corresponding kits and compositions for modifying double stranded DNA molecules.

The invention relates in particular to an in vitro method for modifying a double stranded DNA (dsDNA) molecule in a cell, the method comprising a) introducing into the cell i) an RNA guided DNA endonuclease or a nucleic acid encoding an RNA guided DNA endonuclease, ii) at least one guide RNA, and iii) an exogenous nucleic acid molecule comprising or encoding a DNA substitute sequence, b) generating at least two double strand breaks of the dsDNA molecule to be modified, wherein i) the dsDNA molecule comprises at least two target sequences (target sequences 1 and 2) which are targeted by the at least one guide RNA, and ii) the at least two double strand breaks occur within or adjacent to the at least two target sequences, c) replacing a DNA sequence of the dsDNA molecule to be modified, wherein the replaced sequence is located between the double strand breaks (between target sequences 1 and 2) and is replaced by the DNA substitute sequence of the exogenous nucleic acid molecule by the non-homologous end joining (NHEJ) pathway.

BACKGROUND

With the rapid discovery and implementation of RNA guided nucleases such as SpCas9 or CPF1, the ability to probe biological questions and engineer biological systems is quickly expanding (Barrangou, R., and Doudna, J. A. (2016). Nat. Biotechnol. 34, 933-941). The use of such nucleases was originally shown to form a double strand break that would be rejoined and in some cases mutated by the non-homologous end joining (NHEJ) pathway to create small insertions and deletions (INDELs) that would cause damage to the loci and inhibit gene function, often to create protein knock-outs (Lieber, M. R. (2010). Annu. Rev. Biochem. 79, 181-211). This non-homologous end joining pathway is able to ligate DNA in all parts of the cell cycle.

Additionally, early studies showed that when the RNA-guided nuclease cuts the DNA in the presence of a "repair template" the cells can undergo homologous recombination using the supplied template DNA (Mali, P., et al. (2013). Science 339, 823-826); Jinek, M., et al. (2013). Elife 2, e00471; Heyer, W.-D., et al. (2010). Annu. Rev. Genet. 44, 113-139). This can create a precise insertion or a replacement of sequence. Initially the template was supplied as double stranded DNA, but it was also shown that single stranded DNA with homology arms can also be used to replace or add DNA sequences, using single strand template repair (SSTR) (Chen, F., et al. (2011). Nat. Methods 8, 753-755).

However, the replacement of sequences by knock-ins using homologous recombination or SSTR are frequently reported to be of low efficiency, raising the challenge of whether these pathways for DSB repair can be further improved or replaced (Danner, E. et al (2017), Mamm. Genome, 28, 262-274). Moreover, homologous recombination and SSTR require enzymatic processes that are relegated to the late S/G2 phases of the cell cycle and are therefore restricted to dividing and cycling cells. This ablates the ability to produce knock-ins in non-dividing or slowly dividing cells.

Replacement of DNA sequences located between two DSBs by a different DNA sequence by means of the NHEJ repair pathway has been described for systems employing Zinc Finger Nucleases (ZFNs) (Orlando S. J. et al. (2010). Nucleic Acids Research, Vol. 38, No. 15; Weinthal D. M. et al. (2013). Plant Physiology, Vol. 162, pp. 390-400). The use of Transcription Activator-like Effector Nuclease (TALENs) in such methods has also been suggested (U.S. Pat. No. 9,005,973B2).

However, the described replacement of DNA sequences by means of the NHEJ repair pathway and ZFNs is typically inefficient, exhibiting replacement rates of only around 5%. Furthermore, such methods depend on the generation of complementary single strand overhangs at the open ends of the DNA molecule to be modified and at the ends of the insert sequence. A further disadvantage of these replacement methods is that it is time-consuming to generate sequence specific ZFN and TALEN enzymes, and the use of known enzymes reduces the flexibility of the user to select suitable sites for generating DSBs. Accordingly, the methods of the prior art with respect to NHEJ-mediated sequence replacement are hampered by poor specificity and flexibility regarding election of insertion sites and require time- and cost-intensive preparation. Furthermore, the methods employing ZFNs are focused primarily on DNA replacement in plant cells, where HDR is inefficient. The application of such methods in mammalian cells is also of low efficiency.

Furthermore, NHEJ repair has been shown to ligate exogenously provided DNA segments in between the ends of a single DSB. For example, methods for homology-independent knock-in of a donor sequence into a single CRISPR/Cas9-generated DSB in zebra fish (Auer et al Genome Research 2013, vol. 24, no. 1, 31, 142-153) have been described. However, in approaches such as this, and also as shown for similar approaches in human cells, designated as Non-Homology (NH) Targeting (He X et al. 2016, Nucleic Acids Res 44:e85), the orientation of the inserted fragments is stochastic and cannot be controlled. This stochastic insertion has been recently overcome by a modification in the technique that allows a high degree of preference in the insertion orientation (Suzuki et al. (2016) Nature 540:144-149). This Homology-Independent Targeted Integration (HITI) method was shown to be effective in primary cells in vitro and in vivo, suggesting that c-NHEJ can be a method for achieving targeted integrations.

Furthermore, exon replacement in rice cells through NHEJ using CRISPR/Cas9 mediated-cleavage of genomic DNA employing two site-specific guide RNAs has been described (Jun Li et al, Nature Plants, vol. 2, no. 10, 2016, 16139). However, this method revealed a low efficiency for correct exon replacement.

NHEJ-based methods of the prior art such as those described above were not primarily designed for purposes that aim to replace a DNA sequence in a targeted and controlled manner. Due to the known problem of the uncontrolled and frequent generation of insertions and deletions at the DSB site, these methods are primarily intended for introducing genetic disruptions or insertions and have essentially been disqualified for targeted DNA editing approaches that are geared towards a controlled/pre-designed sequence replacement.

Importantly, previous references to NHEJ for ligating exogenously provided DNA segments between the ends of a DSB generated by a CRISPR/Cas system in vertebrate or mammalian systems are limited to the presence of a single DSB in the DNA molecule to be modified. As such, the methods of the prior art are limited to insertion events, in which DNA segments are introduced, but no sequence segment is removed or replaced from the dsDNA molecule to be modified. The previous technology is therefore seriously limited in the type of modifications possible to the DNA molecule to be modified. The targeted and efficient replacement of a portion of the target dsDNA molecule via CRISPR/Cas systems and the NHEJ mechanism for the purpose of precise genome editing was until now not thought to be possible.

Despite advances in methods for editing DNA molecules in a cell, improvements are needed that would overcome the disadvantages of the prior art.

SUMMARY OF THE INVENTION

In light of the prior art the technical problem underlying the present invention is the provision of alternative and/or improved means and methods for modifying dsDNA in cells. In particular, improved means for modifying the genome of eukaryotic cells, such as e.g. mammalian or vertebrate cells, are needed. More specifically, the provision of means for the replacement of a genomic sequence segment by a new segment harbored on a donor DNA molecule, especially in non-dividing or slowly dividing cells, is one aim of the present invention.

This problem is solved by the features of the independent claims. Preferred embodiments of the present invention are provided by the dependent claims.

The invention relates to a method for modifying double stranded DNA employing an RNA guided DNA endonuclease to generate two double strand breaks in the dsDNA molecule to be modified, and replacement of the sequence positioned between the double strand breaks with a substitute DNA sequence using the non-homologous end joining (NHEJ) pathway. The invention also relates to corresponding kits and compositions.

The invention therefore relates to an in vitro method for modifying a double stranded DNA (dsDNA) molecule in a cell, the method comprising:
  introducing into the cell
    i. an RNA guided DNA endonuclease or a nucleic acid encoding an RNA guided DNA endonuclease,
    ii. at least one guide RNA, and
    iii. an exogenous nucleic acid molecule comprising or encoding a DNA substitute sequence,
  generating at least two double strand breaks of the dsDNA molecule to be modified, wherein
    i. the dsDNA molecule comprises at least two target sequences (target sequences 1 and 2) which are targeted by the at least one guide RNA, and
    ii. the at least two double strand breaks occur within or adjacent to the at least two target sequences,
  replacing a DNA sequence of the dsDNA molecule to be modified, wherein the replaced sequence is located between the double strand breaks (between target sequences 1 and 2) and is replaced by the DNA substitute sequence of the exogenous nucleic acid molecule by the non-homologous end joining (NHEJ) pathway.

It was entirely surprising that it is possible to efficiently replace a sequence of a dsDNA molecule that is located between two cut sites or double strand breaks generated by an RNA guided endonuclease by a substitute DNA sequence that is ligated to the dsDNA molecule to be modified by means of the non-homologous end joining pathway in a targeted and controlled manner.

An entirely surprising effect or result of the method of the invention is that the generation of unwanted and/or uncontrolled DNA sequence modifications at the site of DNA sequence replacement can be largely avoided, although the method relies upon the NHEJ pathway. The method of the invention solves the problem of unwanted modifications frequently observed in DNA editing techniques that employ NHEJ repair. In a preferred embodiment, the replacement of a DNA sequence of the dsDNA molecule to be modified located between the at least two double strand breaks by the DNA substitute sequence by NHEJ occurs without the generation of INDELs or sequence modifications at the sites of the at least two DSBs.

It is unexpected for a person skilled in the art that a DNA sequence can be substituted or replaced by an exogenous DNA sequence using an RNA guided endonuclease and the NHEJ mechanism with high precision and efficiency without the generation of INDELs at the ligation sites, in the majority of sequence replacement events. Additionally, the desired, targeted replacement occurs with a high frequency in the method of the present invention. Furthermore, the method of the invention is relatively straightforward and user friendly, as it does not require the laborious design and generation of donor DNA molecules comprising homology sequences or suitable single strand overhangs, as required for the DNA replacement methods of the prior art. The present invention therefore opens a new field for the creation of pre-designed, controlled and targeted DNA replacement strategies using the NHEJ pathway, which is efficient, safe and user friendly.

So far, to the knowledge of the inventors, it was commonly accepted in the field that for targeted and controlled sequence replacement, the homology-directed repair (HDR) pathway has to be employed, which requires that the cells comprising the DNA to be modified must be cycling cells in S or G2 phase of the cell cycle. Furthermore, in HDR-mediated sequence replacement methods, a donor DNA molecule is typically provided that comprises homology arms flanking the DNA sequence to be inserted into the dsDNA molecule, wherein the homology arms share a high sequence identity with the DNA sequence adjacent to the cut sites of the DNA molecule to be modified, which enables physical interaction between the homology arms and the free ends at the double strand breaks.

According to the method of the present invention, two double strand breaks (DSBs) are generated in a dsDNA molecule present in a biological cell. The cut sites or locations of the DSBs are generated through cleavage by an RNA guided endonuclease, which is complexed with a guide RNA. The guide RNA leads the endonuclease to the target site where the RNA guided endonuclease is activated through the interaction of the guide RNA and the target sequence and the presence of a PAM sequence. The activated RNA guided endonuclease generates a DSB at or adjacent to the target sequence. The exact cut site of the RNA guided endonuclease and therefore the exact location of the DSB relative to the location of the target sequence and the PAM depends on the specific CRISPR/Cas system or RNA guided endonuclease used in the method of the present invention. Multiple CRISPR/Cas systems and corresponding RNA guided endonucleases are known to one skilled in the art and may therefore be selected appropriately, and target sequences may therefore be designed or selected appropriately, for use in the present invention.

It was surprising in the context of the present invention that DNA sequence replacement is possible between two cut sites (DSBs) that have been generated by RNA guided endonucleases in a way that is completely independent of homology arms or homology sequences present on the DNA substitute sequence and the open ends of the cut DNA molecule to be modified. Furthermore, no single strand sequence overhangs (sticky ends) need to be generated. Especially, no complementary single strand overhangs on the open ends of the cut DNA molecule or on the DNA substitute sequence need be present, as in known replacement methods employing ZFNs for generating DSBs. A further advantage of the method of the present invention in comparison to ZFN-mediated replacement methods is the dramatically increased flexibility with respect to the choice of the target sites for generating the DSBs. In the context of the present invention, such cut-sites can essentially be freely chosen, whereas in ZFN-mediated methods suitable enzymes for a specific target site have to be engineered.

In some embodiments of the invention one guide RNA is used. In other embodiments of the invention two or more guide RNAs are used.

In embodiments employing only one guide RNA, the specific sequence of the guide RNA recognizes at least two target sequences, which might be identical or highly homologous to each other, leading to the generation of two DSBs via the use of a single guide RNA.

Through the generation of two DSBs in the dsDNA molecule to be modified the DNA sequence located between the two DSBs can be excised and removed from the dsDNA molecule, leaving two open ends of the dsDNA molecule that are not comprised by the excised sequence. These two open ends can be ligated through NHEJ to the two ends of a DNA substitute sequence, which may be a linear or linearized dsDNA molecule, which has been introduced into the cell by means of an external nucleic acid molecule comprising or encoding the DNA substitute sequence and which thereby replaces or "substitutes" the sequence that had initially been located between the sites of the two DSB that are defined by the two target sequences.

Through ligation of the exogenous DNA substitute sequence, the target sequences of the dsDNA molecule may preferably be disrupted, preventing excision of the inserted substitute DNA sequence by means of the introduced RNA guided endonuclease and guide RNA. However, it is possible to design and/or select DNA substitute sequences and/or target sequences in such a manner, that the target sequences are only disrupted when the substitute DNA sequence has been ligated to the open ends of the dsDNA molecule in the desired orientation. This represents a great advantage of the present invention, which is based on the surprising observation that replacement of DNA sequences located between two DSBs by the DNA substitute sequence occurs primarily without the generation of INDELs.

Since the cut sites of the RNA guided endonuclease are known, it is possible to design and provide a linear dsDNA substitute sequence with nucleotide sequences at its ends that lead to either reconstitution or disruption of the target sequences upon ligation of the open ends of the dsDNA molecule to be modified and the DNA substitute sequence, depending on the orientation of the DNA substitute sequence after ligation. If the target sequences are reconstituted after ligation, the DNA substitute sequence can be excised again by the RNA guided endonuclease that is complexed with the guide RNA. This process can be repeated until the DNA substitute sequence has been inserted in the desired orientation leading to disruption or disappearance of the target sequence. This principle is further illustrated by FIG. 11.

Furthermore, it is possible to design or select the two target sequences 1 and 2 comprised by the dsDNA molecule to be modified in a way that—after generation of the two DSBs and excision of the DNA sequence located between the DSBs—a target sequence and/or target site that is recognized by the at least one guide RNA is generated upon ligation of the open ends of the dsDNA molecule that are not located on the excised DNA sequence. This enables recognition of the newly generated target sequence by the complex of RNA guided endonuclease and guide RNA leading to cleavage at the site of ligation of the two open ends of the dsDNA molecule. This may lead to the regeneration of the open ends of the dsDNA molecule, which are again available for ligation to the DNA substitute sequence. Moreover, upon re-ligation of the excised DNA sequence of the dsDNA molecule, the target sequences may be reconstituted leading to repeated excision of the DNA sequence to be replaced from the dsDNA molecule. Preferably, a further guide RNA may be used that targets the protospacer site formed by the deletion between the two original target sites enabling reopening of the ligated DNA. This allows for more chances to ligate in the replacement sequence. Furthermore, if the target is inserted in the inverted direction, this guide can excise out the incorrectly ligated sequence.

Accordingly, it is possible to design and select target sequences and DNA substitute sequences that favor replacement of the DNA sequence of the dsDNA molecule located between the DSBs by a DNA substitute sequence in a specific and desired orientation over re-ligation of the excised sequence, ligation of the open ends of the dsDNA molecule and ligation of the DNA substitute sequence in an undesired orientation.

In the context of the present invention, in some embodiments, target sequence 1 and target sequence 2 may be the same (meaning identical) or different from each other.

Furthermore, in some embodiments, target sequence 1 and target sequence 2 may be recognized by the same and/or different guide RNAs.

The use of two different target sequences may be advantageous in embodiments comprising the replacement of a genomic DNA sequence. However, in case of excision and replacement of repetitive sequences or gene duplications in the genome, two target sequences and/or target sites may be used that are identical or at least recognized by the same guide RNA.

Both the guide RNA and the RNA guided endonuclease may be introduced into the cell, either as a protein and an RNA molecule, respectively, or by introducing a nucleic acid molecule into the cell which encodes the RNA guided endonuclease and/or the guide RNA, allowing expression of the respective molecule inside the cell after introduction of the encoding nucleic acid. A person skilled in the art knows how to configure such nucleic acids with suitable promoters and other required or useful genetic elements.

The method of the present invention represents an improved and simplified method for sequence replacement in a dsDNA molecule located in a cell. Surprisingly, the method can be performed to modify any kind of dsDNA molecule present in a biological cell, such as, without limitation, a plant cell, a prokaryotic cell, a eukaryotic cell or an engineered artificial cell. The dsDNA molecule to be modified can be naturally present in the cell or can be introduced or inserted into the cell.

In some embodiments, the method of the invention is particularly suited to modify genomic DNA in eukaryotic cells, wherein the term genomic DNA comprises, for example, mitochondrial DNA and/or chromosomal DNA.

It was completely unexpected that it is possible to replace a DNA sequence located between two double strand breaks that are introduced into the dsDNA molecule to be modified through provision of an external DNA substitute sequence, such as a linear or linearized dsDNA molecule in a controlled manner. A skilled person would have expected that the two free or open ends of the dsDNA molecule that are not present on the excised DNA fragment (i.e. flanking the excised sequence of the dsDNA to be replaced) would be ligated with each other, leading to a simple deletion of the sequence positioned between the double strand breaks. Since the exogenous nucleic acid molecule and the DNA substitute sequence do not require sequences that are homologous to the target sites of the dsDNA molecule, a skilled person would not have thought that the exogenous DNA sequence will be present at the sites of both DSBs and will be available for ligation to the open ends of the dsDNA molecule through NHEJ, especially not when the open ends of the DNA molecule to be modified that should be ligated to the DNA substitute sequence are generated by two DNA independent DSBs that might be located at hundreds or thousands of base pairs distance from each other. Furthermore, it was surprisingly found that the method of the present invention is more efficient for site-specific sequence replacement compared to known HDR-mediated techniques.

Since NHEJ is also active in the G1 and G0 phase of the cell cycle, it is a great advantage of the method of the present invention that sequence replacement can also be performed in non-dividing or slowly dividing cells, which are not accessible to sequence replacement by HDR.

In the context of the present invention, the dsDNA molecule to be modified may also be referred to as the dsDNA molecule, target molecule, target DNA molecule, target dsDNA or target dsDNA molecule.

The present invention can be applied for engineering and manipulating dsDNA molecules in biological cells. The dsDNA molecules to be modified can be an artificial molecule or a naturally occurring molecule. One application of the present invention is the correction or modification of genetic sequences of a cell. For example, an exon of a gene or a complete gene could be replaced by a DNA substitute sequence provided by an exogenous nucleic acid molecule. It is possible to correct genetic mutations that are associated with diseases by replacing a mutated sequence, for example an exon comprising a pathological mutation, by a corrected exon sequence without the respective mutation. Furthermore, the method can be used to generate cells that carry modified genetic sequences, wherein an endogenous gene or part of a gene is replaced by an artificial genetic sequence, which might have, for example, a therapeutic effect.

The cells and the dsDNA molecule to be modified comprised by the cell, such as for example the genomic dsDNA, can be manipulated by the method of the present invention in vitro or in vivo. In case of in vitro manipulation of cells, which might be used for therapeutic applications, through sequence replacement according to the present invention, the modified cells can be administered subsequently to a subject in need thereof. Furthermore, it is possible by employing suitable delivery vehicles such as viral vectors, such as AAV or non-integrating lentiviruses, to introduce the components of the present invention into a target cell in vivo.

Another application of the method of the present invention is genetic engineering of complex dsDNA molecules, as for example artificial chromosomes. By using the method of the present invention, complex replacement steps of DNA sequences in dsDNA molecules can be performed in a facilitated way as compared to previous approaches, involving HDR-dependent methods or classical molecular cloning strategies.

Importantly, the use of NHEJ for replacing a DNA sequence of the dsDNA molecule to be modified by a DNA substitute sequence is identifiable by analyzing the genetic scar resulting from the ligation of the DNA substitute sequence caused by insertions and deletion at the site of cleavage and ligation. As such, the replacing of a DNA sequence by the DNA substitute sequence by the non-homologous end joining (NHEJ) pathway can be determined after replacement has occurred using methods known to a skilled person, for example by sequencing the relevant region of the DNA molecule that has been modified.

Further, the delivered DNA for integration might have its own unique scarring pattern. The inserted sequence may always have this scarring pattern, except when the DNA is not linearized in the cell by an RNA guided endonuclease such as Cas9.

Preferably, the exogenous nucleic acid molecule is a circular DNA molecule, preferably a plasmid or mini-circle. The use of a circular plasmid DNA and a mini-circle molecule as an exogenous nucleic acid molecule is particularly advantageous since delivery of such molecules to target cells is well established and highly efficient, for example through transfection, lipofection or electroporation.

Furthermore, such plasmids can be designed to comprise one or more target sequences that are recognized by the at least one guide RNA and are cleaved inside the cell by the complex of the RNA guided endonuclease and the associated guide RNA.

If the plasmid contains two target sequences, a linear dsDNA molecule serving as the DNA substitute sequence can be excised from the plasmid through generation of two DSBs.

Alternatively, the whole plasmid can be integrated into the dsDNA molecule to replace the sequence present between the cut sites if only one DSB in the plasmid is generated, leading to the provision of a linear dsDNA molecule.

The use of mini-circles as exogenous nucleic acid molecules is particularly advantageous because such molecules may substantially consist of the DNA substitute sequence in circular form, which can be linearized by generating a single DSB at the cut site marked by a target sequence comprised in the mini-circle sequence, which is recognized by the at least one guide RNA. Sequence replacement through provision of a mini-circle derived substitute sequence is particularly efficient compared to other exogenous DNA molecules serving as a source of the DNA substitute sequence.

Through the specific configuration, selection and/or localization of a target sequence comprised by the plasmid or mini-circle it is possible to direct a specific orientation of the DNA substitute sequence upon integration into the dsDNA molecule. A further advantage of plasmids as well as of mini-circles is the stability of these molecules, allowing prolonged storage before use in the method of the present invention.

According to a further embodiment of the method of the present invention, the exogenous nucleic acid molecule is a linear DNA molecule. This embodiment is particular advantageous because a linear dsDNA molecule does not have to be linearized and can serve as a DNA substitute sequence without further processing inside the cell. As such, PCR products or linear segments of synthetic DNA may be employed directly as the exogenous DNA molecule comprising or consisting of the substitute DNA sequence.

In a preferred embodiment, the linear DNA molecule serving as an exogenous nucleic acid molecule comprising the DNA substitute sequence is a PCR product. This is particularly advantageous because PCR fragments can be easily generated by amplifying the sequence of interest. Furthermore, PCR products are very stable and isolation, purification and delivery of PCR product is well established is well established.

According to a further preferred embodiment of the invention, the exogenous nucleic acid molecule is comprised by a viral vector, such as AAV or a non-integrating lentivirus. Delivery of the exogenous nucleic acid molecule through viral vectors is particularly advantageous for manipulation of dsDNA molecules in cells, in which delivery of exogenous nucleic acid molecules such as linear and circular dsDNA is difficult to achieve through other means, such as transfection, electroporation or microinjection. A skilled person is capable of determining the ability of the target cells to be transformed with an exogenous DNA molecule and is capable of selecting the form or structure of the exogenous DNA molecule appropriately. Transformation frequency using various vectors or structures of the exogenous DNA molecule can be measured and the transformation rate assessed accordingly.

Cells that are difficult to transform, in some embodiments, relate to slowly dividing or non-dividing cells. The frequency or rate of cell division can be established by a skilled person using known techniques, such as methods that measure proliferation of cells, for example by an estimation of DNA synthesis or the number of cells in cell culture in S phase. Direct measurement of cell proliferation may involve the incorporation of a labeled nucleoside into genomic DNA. Examples include the tritiated thymidine ([3H]dT) and BrdU (bromodeoxyuridine) methods.

Furthermore, the method of the invention allows to deliver nucleic acid molecules to cells that are inaccessible to other techniques, for example due to their localization. This relates in particular to cells that are present and integrated into complex structures such as organs or organisms or complex three-dimensional tissue culture systems.

Preferably, the DNA substitute sequence has a length of 25 bp to 1 Mega bp, 30 to 800.000, 40 to 600.000 bp, 50 to 500.000 bp, 60 to 400.000 bp, 70 to 300.000 bp, 80 to 200.000 bp, 90 to 100.000 bp, 100 to 90.000 bp, 110 to 80.000 bp, 120 to 70.000 bp, 130 to 60.000 bp, 140 to 50.000 bp, 150 to 40.000 bp, 160 to 30.000 bp, 180 to 20.000 bp, 200 to 10.000 bp, 220 to 9.000 bp, 240 to 8.000 bp, 260 to 7.500 bp, 280 to 7.000 bp, 300 to 6.500 bp, 320 to 6.000 bp, 340 to 5.500 bp, 360 to 5.000 bp, 380 to 4.500 bp, 400 to 4.000 bp, 420 to 3.800 bp, 440 to 3.600 bp, 460 to 3.400 bp, 480 to 3.200 bp, 500 to 3.000 bp, 520 to 2.800 bp, 540 to 2.600 bp, 560 to 2.400 bp, 580 to 2.200 bp, 600 to 2.000 bp, 650 to 1.800 bp, 700 to 1.750 bp, 750 to 1.700 bp, 800 to 1.650 bp, 850 to 1.650 bp, 900 to 1.600 bp, 950 to 1.550 bp, 1000 to 1.500 bp, 1.050 to 1.450 bp, 1.100 to 1.400 bp, 1.150 to 1.350 bp, 1.200 to 1.400 bp or 1.250 to 1.350 bp. It was shown that integration of sequences in the range of 200 to 10.000 bp is particularly efficient.

Furthermore, in preferred embodiments of the present invention the replaced sequence of the dsDNA molecule to be modified has a length of 25 bp to 1 Mega bp, 30 to 800.000, 40 to 600.000 bp, 50 to 500.000 bp, 60 to 400.000 bp, 70 to 300.000 bp, 80 to 200.000 bp, 90 to 100.000 bp, 100 to 90.000 bp, 110 to 80.000 bp, 120 to 70.000 bp, 130 to 60.000 bp, 140 to 50.000 bp, 150 to 40.000 bp, 160 to 30.000 bp, 180 to 20.000 bp, 200 to 10.000 bp, 220 to 9.000 bp, 240 to 8.000 bp, 260 to 7.500 bp, 280 to 7.000 bp, 300 to 6.500 bp, 320 to 6.000 bp, 340 to 5.500 bp, 360 to 5.000 bp, 380 to 4.500 bp, 400 to 4.000 bp, 420 to 3.800 bp, 440 to 3.600 bp, 460 to 3.400 bp, 480 to 3.200 bp, 500 to 3.000 bp, 520 to 2.800 bp, 540 to 2.600 bp, 560 to 2.400 bp, 580 to 2.200 bp, 600 to 2.000 bp, 650 to 1.800 bp, 700 to 1.750 bp, 750 to 1.700 bp, 800 to 1.650 bp, 850 to 1.650 bp, 900 to 1.600 bp, 950 to 1.550 bp, 1000 to 1.500 bp, 1.050 to 1.450 bp, 1.100 to 1.400 bp, 1.150 to 1.350 bp, 1.200 to 1.400 bp or 1.250 to 1.350 bp. It was shown that excision of sequences in the range of 100 to 10.000 bp is particularly efficient.

It is a great advantage of the present invention that neither the length of the DNA substitute sequence nor the length or the replaced DNA sequence is significantly limiting to the feasibility of the present invention.

In a preferred embodiment of the present invention, the exogenous nucleic acid molecule comprises at least one target sequence (target sequence 3) which is targeted by at least one guide RNA, wherein at least one double strand break occurs within or adjacent to target sequence 3 thereby resulting in a DNA substitute sequence.

In preferred embodiments, target sequence 3 may be the same or different from target sequence 1 and/or target sequence 2.

Furthermore, in some embodiments, target sequence 3 may be recognized by the same and/or different guide RNA as target sequence 1 and/or target sequence 2.

By providing a target sequence for the RNA guided endonuclease in the exogenous nucleic acid molecule it is possible that a dsDNA molecule that either is the exogenous nucleic acid molecule or is derived from the exogenous nucleic acid molecule is further processed inside the cell by the RNA guided endonuclease to generate the linear or linearized DNA substitute sequence for replacement of the sequence located between the DSBs. This feature allows generation of the DNA substitute sequence within the cell. Accordingly, the DNA substitute sequence does not have to be provided to the cell in a ready-to-use configuration.

Furthermore, through selection or design of a suitable target sequence and/or target site it is possible to influence the favored orientation of the DNA substitute sequence after integration between the two DSBs sites in the target DNA molecule, as explained above.

According to a further preferred embodiment of the invention, the exogenous nucleic acid molecule comprises at least two target sequences (target sequences 3 and 4) that are targeted by the at least one guide RNA, wherein double strand breaks occur within or adjacent to target sequences 3 and 4 thereby resulting in a DNA substitute sequence.

In preferred embodiments, target sequence 4 may be the same or different from target sequence 1, target sequence 2 and/or target sequence 3. Furthermore, in some embodiments, target sequence 4 may be recognized by the same and/or different guide RNAs as target sequence 1, target sequence 2 and/or target sequence 3.

In one embodiment of the present invention, the exogenous nucleic acid molecule neither comprises nor encodes homology arms targeted to the dsDNA molecule to be modified. Accordingly, in some embodiments, the DNA substitute sequence does not comprise homology arms targeted to the dsDNA molecule to be modified. In some embodiments, homology arms that are targeted to the dsDNA molecule to be modified are sequences flanking the DNA substitute sequence.

Homology arm sequences are homologous to the sequences of the target dsDNA present at the open ends of the dsDNA molecule, after creation of two double strand breaks, that are not comprised by the DNA sequence to be replaced. Homology arms have a length of at least 30 nucleotides, preferably at least 50 nucleotides, and may have 90%, preferably 95%, 97%, 98%, 99% or 100% sequence identity to the corresponding sequences flanking the open ends of the target dsDNA molecule.

It is a great advantage of the method of the present invention that it enables precise replacement of a DNA sequence located between two DSBs of the dsDNA molecule to be modified by a DNA substitute sequence in the absence of homology sequences or homology arms on the sequence to be inserted. This embodiment further differentiates the method of the present invention from methods known in the art that use HDR-mediated insertion or replacement of sequences, which require the presence of homology sequences.

One advantage of the invention is therefore that it is not necessary to design substitute DNA sequences that comprise homology arms, whereby the use of homology arms typically leads to extra complication in cloning or costs for synthesis of the substitute DNA for integration into the dsDNA to be modified.

However, the use of homology arms in the exogenous nucleic acid, flanking the substitute sequence to be inserted, may in some embodiments also lead to induction of the NHEJ pathway for ligation of the substitute sequence between the two DSBs. For example, the homology arms may be cleaved by any given endonuclease and NHEJ subsequently employed, if for example the homology arm containing exogenous nucleic acid sequence is provided to the cell when cell division is not taking place. Therefore, the exogenous nucleic acid molecule may in some embodiments comprise homology arms, when they are not determinative in inducing the HDR pathway.

According to a preferred embodiment of the present invention, the cell is a non-dividing cell, preferably a cell in the G1 or G0 phase. Alternatively, the cell can be a slowly dividing cell. In a further preferred embodiment of the invention, the cell is in G2 or in S phase.

It is particularly advantageous that the method of the invention can be performed in resting cells that are in G1 of the cell cycle for prolonged times, such as, for example, more than one day, preferably more than 1 week, 1 month or one year, or in cells, which have left the cell cycle and are in G0. Known methods for replacing DNA sequences in dsDNA molecules in cells, especially in eukaryotic cells, cannot be performed in G1 and G0 phase, since these methods depend on the HDR pathway that is only active in G2 and S phase or the cell cycle.

Preferably, the method of the present invention comprises introducing into the cell at least two guide RNAs (guide RNA 1 and 2), wherein guide RNA 1 targets at least target sequence 1 and guide RNA 2 targets at least target sequence 2.

The use of two guide RNAs with specificities to different target sequences provides more flexibility to the method of the present invention since DNA sequences located between the cut sites associated with two different target sequences can be excised and replaced by a DNA substitute sequence. This is a great advantage when modifying genomic DNA which comprises only few identical target sequences.

In a preferred embodiment of the invention, guide RNA 1 targets at least a target sequence 1 of the dsDNA molecule to be modified and a target sequence 3 of the exogenous nucleic acid molecule, and/or guide RNA 2 targets at least a target sequence 2 of the dsDNA molecule to be modified and a target sequence 4 of the exogenous nucleic acid molecule.

In a further embodiment of the invention, the RNA guided endonuclease generates blunt end double strand breaks and/or the target sequences are configured to generate blunt end double strand breaks.

The generation of blunt ended double strand breaks may be preferred in embodiments that aim to achieve integration of the DNA substitute sequence or ligation of open ends of the dsDNA molecules to be modified present after cleavage without the generation of INDELs at the site of ligation.

As shown in the examples, it was surprisingly found that blunt end cleavage allows perfect ligation and integration of DNA substitute sequences into the dsDNA molecule without the generation of INDELs in the vast majority of sequence replacement events. This can enable reconstitution of previously present or generation of newly formed target sequence that can be cleaved by the RNA guided endonuclease in cooperation with at least one of the guide RNAs. This enables the directed and/or favorable integration of the DNA substitute sequence to achieve a desired orientation of the integrated DNA substitute sequence. A skilled person is aware of suitable RNA guided endonucleases that preferably generate blunt ends, such as Cas9 and especially SpCas9. Furthermore, it is known that the target sequence and/or the target site influence the tendency of RNA guided endonucleases to generate blunt or sticky ends. Accordingly, a skilled person is able to configure the target sequences and/or target sites in a way that favors the generation of blunt or sticky ends, respectively.

It is possible to determine whether an RNA guided endonuclease generates or has generated blunt or sticky ends by sequencing the cut-site after cutting and subsequent ligation of the open ends. If there are base-insertions that match to the protospacer sequence, this indicates that a sticky end cut occurred. This is further illustrated in FIG. 7.

Preferred RNA guided DNA endonucleases that generate blunt end double strand breaks cuts and can be used in the context of the present invention comprise, without limitation, all RNA guided endonucleases of class 2 type II CRISPR systems, including, without limitation, Cas9 of *Streptococcus pyogenes, Streptococcus thermophiles, Streptococcus pasteurianus, Staphylococcus aureus, Neisseria cinerea, Campylobacter lari, Corynebacterium diphtheria* and *Parvibaculum lavamentivorans* (Ran, F. A. et al. (2015). Nature 520, 186-191; Murugan, K. et al. (2017). Mol. Cell 68, 15-25).

In another preferred embodiment of the invention, the RNA guided endonuclease generating the at least two double strand breaks of the dsDNA molecule to be modified is a nickase.

The use of nickases for the generation of DSBs may be particularly advantageous to increase the specificity of DSB generation. It is highly unlikely, that double strand breaks at undesired sites of the dsDNA molecule to be modified or in the genome of a cell are generated when nickases are used to generate single strand breaks on the (+) and the (−) strand of the dsDNA molecule that are so close to each other that a DSB is generated. In this case the presence of two different guide RNAs may be required for the generation of one DSB. This embodiment may be used in particular in therapeutic application of the method of the present invention, for example, when the cells are present in a patient after modification of the dsDNA molecule.

In a further embodiment of the invention the RNA guided endonuclease generates sticky end double strand breaks. The generation of sticky end DSB may be favorable in embodiments of the invention that aim to generate genetic scars or INDELs at the site of integration of the DNA substitute sequence. Also, it may be advantageous in certain embodiments that the target sequences of the dsDNA target molecule and potentially the exogenous nucleic acid molecules are disrupted after integration of the DNA substitute sequence. This normally is the case for sticky end DSBs, since the shorter strand will be filled up during ligation by NHEJ, leading to the insertion of additional base pairs at the site of ligation. Sticky-end DSB can be generated by RNA guided endonucleases in various ways known to the person skilled in the art. For example, two single-strand breaks on the (+) and the (−) strand of the dsDNA molecule can be generated by using a nickase. If these single-strand breaks are close to each other, for example within a distance of less than 30, preferably less than 20 nt, more preferably less than 10 nt, a DSB with sticky ends will be formed. Alternatively, an RNA guided endonuclease that regularly generates sticky end DSBs may be used, such as Cpf1. Furthermore, the target sequence or target site can be selected in a way that sticky-end DSB formation is favored.

Preferred RNA guided DNA endonucleases that generate sticky end double strand breaks cuts and can be used in the context of the present invention comprise, without limitation, all RNA guided endonucleases of class 2 type V or type V-A CRISPR systems, such as, without limitation, Cpf1 or Cas12a of *Acidaminococcus* sp. BV3L6 and Lachnospiraceae bacterium ND2006 (Zetsche, B. et al. (2015). Cell 163, 759-771; Murugan, K. et al (2017). Cell 68, 15-25).

Preferred RNA guided DNA endonucleases that generate sticky end double strand breaks cuts and can be used in the context of the present invention comprise, without limitation, SpCas9(D10A) and SpCas9(H840A) (Ran, F. A. et al. (2013). Cell 154, 1380-1389).

In a preferred embodiment of the method of the present invention, ligation of the DNA substitute sequence by the non-homologous end joining (NHEJ) pathway occurs in orientation 1 or orientation 2, wherein
  upon ligation in orientation 1, target sequences 1 and target sequence 2 are restored, and
  upon ligation in orientation 2, target sequences 1 and target sequence 2 are disrupted.

It is clear to a skilled person that a DNA substitute sequence, which is a dsDNA molecule, can be inserted into the dsDNA molecule to be modified in two orientations. However, one of the two orientations may be favored over the other, for example when a coding sequence or a genomic DNA molecule, such as an exon or a part of an exon, is replaced by a modified or corrected version of the sequence. In this case, the target sequences and/or target sites of the dsDNA molecule to be modified and the exogenous nucleic acid molecule may be configured in a way that favors integration in the desired orientation.

For example, if the DNA substitute sequence comprises a coding sequence with 5' to 3' directionality, for favoring the desired integration orientation, the exogenous nucleic acid molecule comprising the DNA substitute sequence may have the same target sequence located on the 5'-end of the DNA substitute sequence as the dsDNA molecule to be modified comprises at the cleavage site that should be ligated to the 3'-end of the DNA substitute sequence. Additionally, the exogenous nucleic acid molecule comprising the DNA substitute sequence may have the same target sequence located on the 3'-end of the DNA substitute sequence as the dsDNA molecule to be modified comprises at the cleavage site that should be ligated to the 5'-end of the DNA substitute sequence.

In that way, it is possible that the respective target sequences are restored upon integration of the DNA substitute sequence in the undesired orientation. Restoration of a target sequence means that the same sequence that is recognized by the at least one guide RNA is formed again after ligation of the DSB sites to the DNA substitute sequence. This allows re-excision of the DNA substitute sequence after ligation and integration so that the DNA substitute sequence and the open ends of the dsDNA molecule to be modified are again available for integration.

In contrast, upon integration of the DNA substitute sequence in the desired orientation, the respective target sequences will be disrupted, which prevents re-excision of the DNA substitute sequence. Disruption of the target sequence means that upon ligation of the DSB a new sequence is formed that is different from the previously target sequence and that is not recognized by the at least one guide RNA. As such, a bias for the desired integration orientation of the DNA substitute sequence can be created. This example demonstrates that the specific configuration of the target sequences employed in the method of the present invention can be used to direct the orientation of the integration of the DNA substitute sequence. A person skilled in the art is able to perform and/or design such configurations on the basis of the present description and the examples and figures provided herein.

According to a further embodiment of the invention, at least two guide RNAs (guide RNA 1 and 2) are introduced into the cell, wherein guide RNA 1 targets target sequence 1 and target sequence 3, and guide RNA 2 targets target sequence 2 and target sequence 4.

In a preferred embodiment of the invention, the exogenous nucleic acid molecule is an exogenous dsDNA molecule.

In a further preferred embodiment of the invention,
  target sequence 1 is positioned at a 5'-end and target sequence 2 is positioned at a 3'-end of a (preferably coding) sequence located between the double strand breaks of the dsDNA molecule to be modified, and
  target sequence 4 is positioned at a 5' end and target sequence 3 is positioned at a 3' end of a (preferably coding) DNA substitute sequence located between the double strand breaks within target sequences 3 and 4 of the exogenous nucleic acid or dsDNA molecule.

In a further embodiment of the invention, at least one additional guide RNA targets a sequence of the dsDNA molecule to be modified, wherein said sequence arises when the double strand breaks of the dsDNA molecule to be modified are ligated together, without a) introduction of the DNA substitute sequence and b) without reintroduction of the sequence located originally between the double strand breaks.

This method is particularly advantageous because in case of ligation of the open ends of the dsDNA molecule to be modified, which are not comprised by the excised DNA sequence to be replaced, a target sequence is generated that is recognized by a specific guide RNA, leading to separation of the open ends, which are then again available for the integration of the DNA substitute sequence. An example of this embodiment of the invention is illustrated in FIG. 10 and example 3 provided herein.

In another embodiment of the present invention,
a PAM associated with target sequence 1 and a PAM associated with target sequence 2 are comprised by the DNA sequence located between the double strand breaks of the dsDNA molecule to be modified, and/or
a PAM associated with target sequence 3 and a PAM associated with target sequence 4 are not comprised by the DNA substitute sequence.

This configuration of the target sequences 1 to 4 is particularly advantageous, because it was shown that it leads to a very efficient replacement of the DNA sequence located between the DSBs of the dsDNA molecule to be modified and integration of the DNA substitute sequence without the generation of INDELs. Therefore, this embodiment is particularly advantageous for the directed integration of the DNA substitute sequence.

According to a further embodiment of the method or the invention, the DNA sequence to be replaced between the DSBs of the dsDNA molecule to be modified and the DNA substitute sequence comprised by the exogenous dsDNA molecule are both coding DNA sequences and therefore define a (+)-strand and a (−)-strand of the dsDNA molecule to be modified and the exogenous dsDNA molecule, and
target sequences 1 and 2 are located on the (+)-strand and target sequence 3 and 4 are located on the (−)-strand,
target sequence 1 and 3 are located on the (+)-strand and target sequence 2 and 4 are located on the (−)-strand,
target sequences 1 and 4 are located on the (+)-strand and target sequence 2 and 3 are located on the (−)-strand,
target sequences 2 and 3 are located on the (+)-strand and target sequence 1 and 4 are located on the (−)-strand,
target sequences 2 and 4 are located on the (+)-strand and target sequence 1 and 3 are located on the (−)-strand, or
target sequences 3 and 4 are located on the (+)-strand and target sequence 1 and 2 are located on the (−)-strand.

The present invention further relates to a Kit for modifying a dsDNA molecule in a cell, comprising:
an RNA guided DNA endonuclease or a nucleic acid encoding an RNA guided DNA endonuclease,
at least one guide RNA, and
a nucleic acid molecule comprising or encoding a DNA substitute sequence,
wherein:
the at least one guide RNA is configured for generating at least two double strand breaks of a dsDNA molecule to be modified within or adjacent to a target sequence 1 and a target sequence 2 within the dsDNA molecule, and
the nucleic acid molecule comprising or encoding a DNA substitute sequence is configured for replacement of the DNA sequence of the dsDNA molecule located between the two double strand breaks with the DNA substitute sequence by the NHEJ pathway.

The at least one guide RNA that is configured for generating at least two double strand breaks of a dsDNA molecule to be modified within or adjacent to a target sequence 1 and a target sequence 2 may comprise a target specific sequence that is at least partially, preferably completely complementary to target sequences 1 and 2 and interacts with the RNA guided DNA endonuclease of the kit of the present invention.

A skilled person is therefore capable of configuring the guide RNA to target particular sequences in the dsDNA target. By analysis of the guide RNAs in the kit or composition a skilled person can determine whether and how the guide RNAs are configured for generating two double strand breaks. The presence of two guide RNAs in the kit is clearly indicative of generating two double strand breaks, for example in the context of editing genomic dsDNA sequences.

The DNA substitute sequence that is configured for replacement of the DNA sequence of the dsDNA molecule located between the two double strand breaks with the DNA substitute sequence by the NHEJ pathway may be a linear or linearized dsDNA molecule.

The nucleic acid molecule comprising or encoding a DNA substitute sequence may be configured for employing the NHEJ pathway by comprising a linearizable DNA element that is suitable as the substitute DNA sequence. The configuration of the DNA substitute sequence for employing the NHEJ pathway may in some embodiments relate to the absence of homology arms.

However, in some embodiments, the presence of homology arms may not be determinative for using the HDR pathway, and the presence of homology arms may in some embodiments lead also to the employment of the NHEJ pathway.

In a preferred embodiment of the kit of the invention the nucleic acid molecule comprising or encoding a DNA substitute sequence is configured
to restore target sequence 1 and target sequence 2 upon ligation of the DNA substitute sequence by the NHEJ pathway in orientation 1, and
to disrupt target sequence 1 and target sequence 2 upon ligation of the DNA substitute sequence by the NHEJ pathway in orientation 2.

Such a nucleic acid molecule may comprise target sequences 3 and 4, wherein target sequence 3 is the same as target sequence 1, and target sequence 4 is the same as target sequence 2, or target sequence 3 is the same as target sequence 2, and target sequence 4 is the same as target sequence 1. Suitable configurations of the nucleic acid molecule comprising or encoding a DNA substitute sequence have been described herein in the context of the method of the present invention and are obvious to the person skilled in the art in light of the disclosure of the present patent application.

In a preferred embodiment of the kit of the invention the RNA guided endonuclease generates blunt end double strand breaks and/or the target sequences are configured to generate blunt end double strand breaks.

In a preferred embodiment of the kit of the invention the RNA guided endonuclease generating the at least two double strand breaks of the dsDNA molecule to be modified is a nickase and/or the RNA guided endonuclease generates sticky end double strand breaks.

Furthermore, the present invention encompasses a composition for use as a medicament, for modifying a double stranded DNA (dsDNA) molecule in a cell, comprising:
an RNA guided DNA endonuclease or a nucleic acid encoding an RNA guided DNA endonuclease,
at least one guide RNA, and
a nucleic acid molecule comprising or encoding a DNA substitute sequence, wherein:
the at least one guide RNA is configured for generating at least two double strand breaks of a genomic dsDNA molecule within or adjacent to a target sequence 1 and a target sequence 2 within the genomic dsDNA molecule, and
the nucleic acid molecule comprising or encoding a DNA substitute sequence is configured for replacement of the DNA sequence of the genomic dsDNA molecule located between the two double strand breaks with the DNA substitute sequence by the NHEJ pathway.

Preferably, the dsDNA molecule of the composition of the present invention is a genomic dsDNA molecule. Furthermore, the cell of the preferentially is a eukaryotic cell.

The composition of the present invention is therefore suitable for the treatment of any given medical condition in which a change in the genomic DNA (including mitochondrial DNA) of a subject is necessary. Preferably, the change in the genomic DNA is to be carried out in somatic cells. This genetic modification may be employed potentially directly in vivo to a subject in need thereof, for example by modifying the genome of a subject, or may be employed in cells removed from a patient before subsequent transplantation, or may be employed to modify the genome or other genetic element of a pathogen inside a host.

In a preferred embodiment of the composition for use as a medicament the nucleic acid molecule comprising or encoding a DNA substitute sequence is configured
to restore target sequence 1 and target sequence 2 upon ligation of the DNA substitute sequence by the NHEJ pathway in orientation 1, and
to disrupt target sequence 1 and target sequence 2 upon ligation of the DNA substitute sequence by the NHEJ pathway in orientation 2.

In a further embodiment of the composition for use as a medicament of the invention the RNA guided endonuclease generates blunt end double strand breaks and/or the target sequences are configured to generate blunt end double strand breaks.

In an alternative embodiment of the composition for use as a medicament the RNA guided endonuclease generating the at least two double strand breaks of the dsDNA molecule to be modified is a nickase and/or the RNA guided endonuclease generates sticky end double strand breaks.

In further embodiments of the invention the method as described herein is used for exon replacement or exchange. Exon replacement allows coding regions in genes, which are later spliced into functional coding mRNA molecules, to be precisely and efficiently modified, for example by removing exons in which undesired gene sequences, such as mutations or other sequences encoding unwanted traits, are present. The present invention enables via the use of two DSBs the replacement of an entire exon, for example by targeting sites for DSB creation in the neighboring introns flanking an exon and providing to the cell a replacement exon in the form of an exogenous nucleic acid molecule for replacing the undesired exon.

All advantages and preferred features of the method of the present invention provided herein also apply to the kit and the composition of the invention, and vice versa.

The invention is further described by the following figures. These are not intended to limit the scope of the invention, but represent preferred embodiments of aspects of the invention provided for greater illustration of the invention described herein.

BRIEF DESCRIPTION OF THE DRAWINGS

FIG. 16: Sequence analysis of engineered Polb alleles. Sanger sequencing of mCherry sequence replacement targeted to POLB exon 5 in NHDF cells. The two regions highlighted are at the ligated interface of genomic and exogenous DNA. Sequences shown: SEQ ID NO: 77; SEQ ID NO: 78; SEQ ID NO: 79; SEQ ID NO: 80; SEQ ID NO: 81; and SEQ ID NO: 82; SEQ ID NO: 83; SEQ ID NO: 84; and SEQ ID NO: 85.

DETAILED DESCRIPTION OF THE INVENTION

Figure 1:
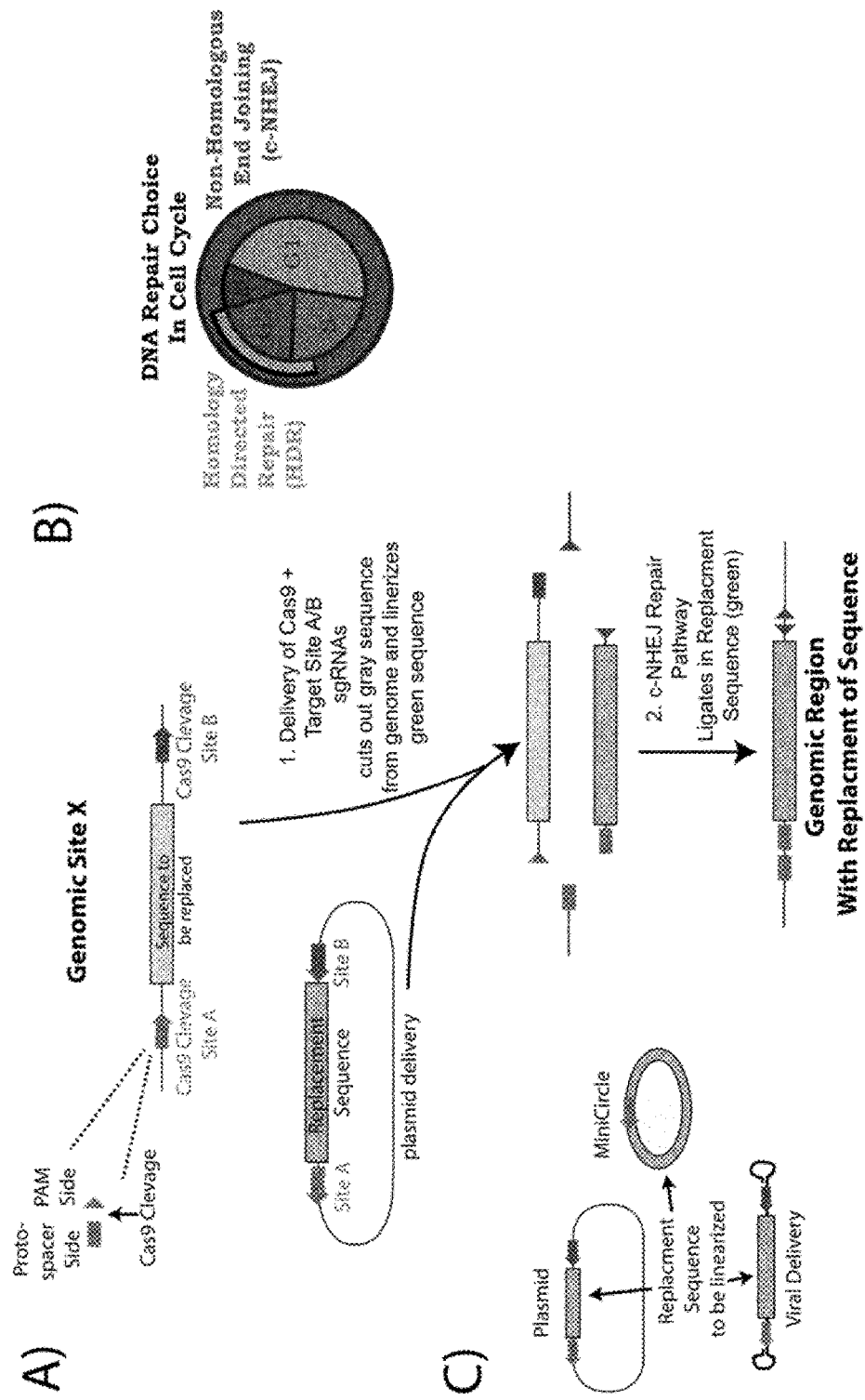
FIG. 1: Outline of use of RNA-guided nucleases for the replacement of sequences in cells using the non-homologous end joining pathway, as described in the present invention. A) This overview underlies the concept of the invention. It utilizes a RNA-guided nuclease, in our case CRISPR/Cas9, to create two double strand breaks flanking the sequence to be replaced. The cleavage sites in this figure are "Site A" and "Site B". The light and dark grey arrow symbolize this Cas9 recognition sequence and the triangle symbolizes the sequence on the PAM side of the break. At the same time as the Cas9/sgRNA, a sequence to be inserted in place of the original sequence is delivered into the cell. In part A this is exemplified by plasmid delivery. The new "replacement sequence" on the plasmid needs to be linearized and excised from the plasmid backbone; this excision is in this case done through the use of the same guide-RNA recognition sequences, cleaving out the replacement sequence. Finally the linear piece of replacement DNA is ligated in between the two sites of double strand breaks using the classic non-homologous end joining Pathway (c-NHEJ). It is important to note that religating the original sequence back into the genome reforms the original Cas9 recognition site which then can be cleaved out. The recognition site in the delivered replacement sequence has the recognition sequence pointing in the opposite direction so the CRISPR/Cas9 site is ablated when the replacement sequence is ligated in (notice the two light and dark grey rectangles together or two light and dark grey triangles indicating the loss of the functional recognition site). B) The use of c-NHEJ to replace sequence is a completely not enzymatic pathway for creating such a change in sequence. Due to the profoundly different enzymatic machinery, the method of the invention functions in all parts of the cell cycle, in particular G0/G1, besides S/G2 phase. In contrast, Homology Directed Repair (HDR) functions only in late S/G2 phase of the cell cycle-limiting its use to rapidly dividing cells. C) The delivery of the replacement sequence could be in multiple forms. It could be delivered in a plasmid such as in part of this figure. It could also be delivered by a virus such as AAV or non-integrating lentivirus. Further it could be delivered by a MiniCircle which is a plasmid like circular DNA that has had all other parts except the sequence of interest removed. Thus a single cut would linearize a fragment that is then ready to integrate.

The invention relates to a method for modifying double stranded DNA employing an RNA guided DNA endonuclease to generate two double strand breaks in the dsDNA molecule to be modified, and replacement of the sequence positioned between the double strand breaks with a substitute DNA sequence using the non-homologous end joining (NHEJ) pathway.

In the context of the present invention, the term "modifying" a double stranded DNA refers to any kind of alteration, modification or change of a dsDNA molecule. In particular, modifying relates to deleting, inserting, replacing, substituting or translocating one or one or more nucleotides or pairs of nucleotides or nucleotide sequences from a dsDNA molecule.

The term "replacement" or "substitution", as used herein, is defined in accordance with the pertinent art and refers to the replacement of nucleotides with other nucleotides. The term includes for example the replacement of single nucleotides resulting in point mutations. Said point mutations can lead to an amino acid exchange in the resulting protein product but may also not be reflected an the amino acid level (i.e. silent mutations). Also encompassed by the term "substitution" are mutations resulting in the replacement of multiple nucleotides, such as for example parts of genes, such as parts of exons or introns as well as the replacement of entire genes. The number of nucleotides that replace the originally present nucleotides may be the same or different (i.e. more or less) as compared to the number of nucleotides removed. Preferably, the number of replacement nucleotides corresponds to the number of originally present nucleotides that are substituted.

The term "insertion", in accordance with the present invention, is defined in accordance with the pertinent art and refers to the incorporation of one or more nucleotides into a nucleic acid molecule. Insertion of parts of genes, such as parts of exons or introns as well as insertion of entire genes is also encompassed by the term "insertion". When the number of inserted nucleotides is not dividable by three, the insertion can result in a frameshift mutation within a coding sequence of a gene. Such frameshift mutations will alter the amino acids encoded by a gene following the mutation. In some cases, such a mutation will cause the active translation of the gene to encounter a premature stop codon, resulting in an end to translation and the production of a truncated protein. When the number of inserted nucleotides is instead dividable by three, the resulting insertion is an "in-frame insertion". In this case, the reading frame remains intact after the insertion and translation will most likely run to completion if the inserted nucleotides do not code for a stop codon. However, because of the inserted nucleotides, the finished protein will contain, depending on the size of the insertion, one or multiple new amino acids that may affect the function of the protein.

The term "deletion", as used in accordance with the present invention, is defined in accordance with the pertinent art and refers to the loss of nucleotides or larger parts of genes, such as exons or introns as well as entire genes. As defined with regard to the term "insertion", the deletion of a number of nucleotides that is not evenly dividable by three will lead to a frameshift mutation, causing all of the codons occurring after the deletion to be read incorrectly during translation, potentially producing a severely altered and most likely nonfunctional protein. If a deletion does not result in a frameshift mutation, i.e. because the number of nucleotides deleted is dividable by three, the resulting protein is nonetheless altered as the finished protein will lack, depending on the size of the deletion, one or several amino acids that may affect the function of the protein.

The term double stranded DNA relates to two deoxyribonucleic acid polynucleotide strands that are bound together or hybridizes through pairing of the bases or nucleotides of the two strands through hydrogen bonds resulting in double-stranded DNA. The method of the present invention can be performed using any kind of dsDNA molecule, including, without limitation, genomic dsDNA of any origin or organism, synthetic dsDNA, amplified or isolated dsDNA.

A "cell" in the sense of the present invention refers to, without limitation, any biological cell, which might be derived from any kind of organism, comprising unicellular organisms as well as multicellular organisms, such as for example any kind of plant or animal, including mammals, fish, amphibians, reptiles, birds, molluscs, arthropods, annelids, nematodes, flatworms, cnidarians, ctenophores and sponges. Cells of the present invention further comprise prokaryotic cells, bacteria, eukaryotic cells, blood cells, stem cells, immune cells (such as B-cells, dendritic cells, granulocytes, innate lymphoid cells (ILCs), megakaryocytes, monocytes, macrophages, myeloid-derived Suppressor Cells (MDSC), natural killer (NK) cells, platelets, red blood cells (RBCs), T-cells or thymocytes), cancer cells, tumor cells and circulating tumor cells.

In some embodiments of the invention, the cell in which the dsDNA is to be modified is a vertebrate cell, more preferably a mammalian cell, such as a human cell. In some embodiments, the cell is not a rice cell. In some embodiments, the cell is not a plant cell.

The term "introducing into the cell", as used herein, relates to any known method of bringing a protein or a nucleic acid molecule into a cell. Non-limiting examples include microinjection, infection with viral vectors, electroporation, transfection, such as transfection using formulations with cationic lipids. Suitable methods for introducing the components of the present invention into a cell are known to the skilled person.

CRISPR is an abbreviation of Clustered Regularly Interspaced Short Palindromic Repeats and is a family of DNA sequences in bacteria. The sequences contain snippets of DNA from viruses that have attacked the bacterium. These snippets are used by the bacterium to detect and destroy DNA from further attacks by similar viruses. These sequences play a key role in a bacterial defense system, and form the basis of a technology known as CRISPR/Cas that effectively and specifically changes genes within organisms.

Sequences of the CRISPR loci are transcribed and processed into CRISPR RNAs (crRNAs) which, together with a trans-activating crRNAs (tracrRNAs), complex with CRISPR-associated (Cas) proteins to dictate specificity of DNA cleavage by Cas nucleases through Watson-Crick base pairing between nucleic acids (Wiedenheft, B et al (2012). Nature 482: 331-338; Horvath, P et al (2010). Science 327:167-170; Fineran, P C et a. (2012). Virology 434: 202-209).

It was shown that the three components required for the type II CRISPR nuclease system are the Cas9 protein, the mature crRNA and the tracrRNA, which can be reduced to two components by fusion of the crRNA and tracrRNA into a single guide RNA (sgRNA) and that re-targeting of the Cas9/sgRNA complex to new sites could be accomplished by altering the sequence of a short portion of the gRNA (Garneau, J E et al (2010). Nature 468: 67-71; Deltcheva, E et al. (2011). Nature 471: 602-607, Jinek, M et al (2012) Science 337: 816-821).

CRISPR-Cas systems are RNA-guided adaptive immune systems of bacteria and archaea that provide sequence-specific resistance against viruses or other invading genetic material. This immune-like response has been divided into two classes on the basis of the architecture of the effector module responsible for target recognition and the cleavage of the invading nucleic acid (Makarova K S et al. Nat Rev Microbiol. 2015 November; 13(11):722-36.). Class 1 comprises multi-subunit Cas protein effectors and Class 2 consists of a single large effector protein. Both Class 1 and 2 use CRISPR RNAs (crRNAs) to guide a Cas nuclease component to its target site where it cleaves the invading nucleic acids. Due to their simplicity, Class 2 CRISPR-Cas systems are the most studied and widely applied for genome editing. The most widely used CRISPR-Cas system is CRISPR-Cas9.

It was demonstrated that the CRISPR/Cas9 system could be engineered for efficient genetic modification in mammalian cells. The only sequence limitation of the CRISPR/Cas system appears to derive from the necessity of a protospacer-adjacent motif (PAM) located immediately 3' to the target site. The PAM sequence is specific to the species of Cas9. For example, the PAM sequence 5'-NGG-3' is necessary for binding and cleavage of DNA by the commonly used Cas9 from Streptococcus pyogenes. However, Cas9 variants with novel PAMs have been and may be engineered by directed evolution, thus dramatically expanding the number of potential target sequences. Cas9 complexed with the crRNA and tracrRNA undergoes a conformational change and associates with PAM motifs throughout the genome interrogating the sequence directly upstream to determine sequence complementarity with the gRNA. The formation of a DNA-RNA heteroduplex at a matched target site allows for cleavage of the target DNA by the Cas9-RNA complex. These methods and mechanisms are well known in the art.

As known in the art, CRISPR/Cas9 has been exploited to develop potent tools for genome manipulation in animals, plants and microorganisms. The RNA-guided Cas9 endonuclease first recognizes a 2- to 4-base-pair conserved sequence named the protospacer-adjacent motif (PAM), which flanks a target DNA site. Upon binding to the PAM, Cas9 interrogates the flanking DNA sequences for base-pairing complementarity to a guide RNA. If there is complementarity between the first 12 base pairs (the 'seed' sequence) of the guide RNA and the target DNA strand, RNA strand invasion accompanies local DNA unwinding to form an R-loop. Precise cleavage of each DNA strand by the RuvC and HNH domains of Cas9 generates a blunt double-strand DNA (dsDNA) break (DSB) at a position three base pairs upstream of the 3' edge of the protospacer sequence, measuring from the PAM.

CRISPR/Cas9 genome-editing experiments have been exploiting the host cell machinery to repair the genome precisely at the site of the Cas9-generated DSB. Mutations can arise either by non-homologous end joining (NHEJ) or homology-directed repair (HDR) of DSBs. NHEJ can produce small insertions or deletions (INDELs) at the cleavage site, whereas HDR uses a native (or engineered) DNA template to replace the targeted allele with an alternative sequence by recombination. Additional DNA repair pathways such as single-strand annealing, alternative end joining, microhomology-mediated joining, mismatch and base- and nucleotide-excision repair can also produce genome edits.

Cas9 variants derived from the Streptococcus pyogenes Cas9 (SpCas9) have been generated for use as nickases, dual nickases or FokI fusion variants. More recently, Cas9 orthologs, and other nucleases derived from class 2 CRISPR-Cas systems including Cpf1 and C2c1, have been added to the CRISPR toolbox. These ongoing efforts to mine the abundant bacterial and archaeal CRISPR-Cas systems should increase the range of molecular tools available to researchers.

In the context of the present invention, the term "RNA guided DNA endonuclease" refers to DNA endonucleases that interact with at least one RNA-Molecule. In the context of the present invention the terms RNA guided DNA endonuclease and RNA guided endonuclease are used interchangeably. DNA endonucleases are enzymes that cleave the phosphodiester bond within a DNA polynucleotide chain. In case of RNA guided DNA endonuclease the interacting RNA-Molecule may guide the RNA guided DNA endonuclease to the site or location in a DNA where the endonuclease becomes active. In particular, the term RNA guided DNA endonuclease refers to naturally occurring or genetically modified Cas nuclease components or CRISPR-Cas systems, which include, without limitation, multi-subunit Cas protein effectors of class 1 CRISPR-Cas systems as well as single large effector Cas proteins of class 2 systems.

Details of the technical application of CRISPR/Cas systems and suitable RNA guided endonuclease are known to the skilled person and have been described in detail in the literature, as for example by Barrangou R et al. (Nat Biotechnol. 2016 Sep. 8; 34(9):933-941), Maeder M L et al. (Mol Ther. 2016 March; 24(3):430-46) and Cebrian-Serrano A et al. (Mamm Genome. 2017; 28(7): 247-261). The present invention is not limited to the use specific RNA guided endonucleases and therefore comprises the use of any given RNA guided endonucleases in the sense of the present invention suitable for use in the method described herein.

Any RNA guided DNA endonuclease known in the art may be employed in accordance with the present invention. RNA guided DNA endonuclease comprise, without limitation, Cas proteins of class 1 CRISPR-Cas systems, such as Cas3, Cas8a, Cas5, Cas8b, Cas8c, Cas10d, Cse1, Cse2, Csy1, Csy2, Csy3, GSU0054, Cas10, Csm2, Cmr5, Csx11, Csx10 and Csf1; Cas proteins of class 2 CRISPR-Cas systems, such as Cas9, Csn2, Cas4, Cpf1, C2c1, C2c3 and C2c2; corresponding orthologous enzymes/CRISPR effectors from various bacterial and archeal species; engineered CRISPR effectors with for example novel PAM specificities, increased fidelity, such as SpCas9-HF1/eSpCas9, or altered functions, such as nickases. Particularly preferred RNA guided DNA endonuclease of the present invention are *Streptococcus pyogenes* Cas9 (SpCas9), *Staphylococcus aureus* Cas9, *Streptococcus thermophilus* Cas9, *Neisseria meningitidis* Cas9 (NmCas9), *Francisella novicida* Cas9 (FnCas9), *Campylobacter jejuni* Cas9 (CjCas9), Cas12a (Cpf1) and Cas13a (C2C2) (Makarova K S et al. (November 2015). Nature Reviews Microbiology. 13 (11): 722-36).

The definition and explanations provided herein are mainly focused on the SpCas9 Crispr/Cas system. However, the person skilled in the art is aware of how to use alternative Crispr/Cas systems as well as tools and methods that provide or allow the gain of information on the details of such alternative systems.

The use of Cpf1 in the context of the present invention can be advantageous because it requires only one associated guide RNA, it generates staggered/sticky end cuts and it cuts in non-dividing cells, such as nerve cells.

The RNA guided DNA endonuclease and in particular Cas9 may also be a modified protein, wherein the nuclease function of the protein is altered into a nicking endonuclease function, which only cuts one of the two DNA strands of the dsDNA. In other words, the naturally occurring endonucleases function of cleaving both strands of a double-stranded target DNA, is altered into an endonuclease that cleaves (i.e. nicks) only one of the strands. Such modified RNA guided DNA endonucleases are also calls "nickases" in the context of the present invention. Means and methods of modifying RNA guided DNA endonuclease such as Cas9 accordingly are well known in the art, and include for example the introduction of amino acid replacements into Cas9 that render one of the nuclease domains inactive. More specifically, aspartate can be replaced against alanine at position 10 of the *Streptococcus pyogenes* Cas9 (SpCas9 D10A; Cong et al. (2013) Science 339:819-823). Further examples are known in the art, for example the H840A replacement in SpCas9 (Mali P et al. Nat Biotechnol. 2013 September; 31(9):833-8; Ran F A et al. Cell. 2013 Sep. 12; 154(6):1380-9).

In accordance with the method of the invention, the RNA guided DNA endonuclease may be introduced as a protein, but alternatively the RNA guided DNA endonuclease may also be introduced in form of a nucleic acid molecule encoding said protein. It will be appreciated that the nucleic acid molecule encodes said RNA guided DNA endonuclease in expressible form such that expression in the cell results in a functional RNA guided DNA endonuclease protein such as Cas9 protein. Means and methods to ensure expression of a functional polypeptide are well known in the art.

For example, the coding sequences for the endonuclease may be comprised in a vector, such as for example a plasmid, cosmid, virus, bacteriophage or another vector used conventionally e.g. in genetic engineering. The coding sequences inserted in the vector can e.g. be synthesized by standard methods, or isolated from natural sources. The coding sequences may further be ligated to transcriptional regulatory elements and/or to other amino acid encoding sequences. Such regulatory sequences are well known to those skilled in the art and include, without being limiting, regulatory sequences ensuring the initiation of transcription, internal ribosomal entry sites (IRES) and optionally regulatory elements ensuring termination of transcription and stabilization of the transcript. Non-limiting examples for regulatory elements ensuring the initiation of transcription comprise a translation initiation codon, transcriptional enhancers such as e.g. the SV40-enhancer, insulators and/or promoters, such as for example the cytomegalovirus (CMV) promoter, SV40-promoter, RSV-promoter (Rous sarcoma virus), the lacZ promoter, chicken beta-actin promoter, CAG-promoter (a combination of chicken beta-actin promoter and cytomegalovirus immediate-early enhancer), the gai10 promoter, human elongation factor 1a-promoter, AOX1 promoter, GAL1 promoter CaM-kinase promoter, the lac, trp or tac promoter, the IacUV5 promoter, the *Autographa californica* multiple nuclear polyhedrosis virus (AcMNPV) polyhedral promoter or a globin intron in mammalian and other animal cells. Non-limiting examples for regulatory elements ensuring transcription termination include the V40-poly-A site, the tk-poly-A site or the SV40, lacZ or AcMNPV polyhedral polyadenylation signals, which are to be included downstream of the nucleic acid sequence of the invention. Additional regulatory elements may include translational enhancers, Kozak sequences and intervening sequences flanked by donor and acceptor sites for RNA splicing. Moreover, elements such as origin of replication, drug resistance gene or regulators (as part of an inducible promoter) may also be included.

Nucleic acid molecules encoding said RNA guided DNA endonuclease include DNA, such as cDNA or genomic DNA, as well as RNA and in particular mRNA. It will be readily appreciated by the skilled person that more than one nucleic acid molecule may encode an RNA guided DNA endonuclease in accordance with the present invention due to the degeneracy of the genetic code. Degeneracy results because a triplet code designates 20 amino acids and a stop codon. Because four bases exist which are utilized to encode genetic information, triplet codons are required to produce at least 21 different codes. The possible e possibilities for bases in triplets give 64 possible codons, meaning that some degeneracy must exist. As a result, some amino acids are encoded by more than one triplet, i.e. by up to six. The degeneracy mostly arises from alterations in the third position in a triplet. This means that nucleic acid molecules having different sequences, but still encoding the same RNA guided DNA endonuclease, can be employed in accordance with the present invention.

The nucleic acid molecules used in accordance with the present invention may be of natural as well as of (semi) synthetic origin. Thus, the nucleic acid molecules may, for example, be nucleic acid molecules that have been synthesized according to conventional protocols of organic chemistry. The person skilled in the art is familiar with the preparation and the use of said probes (see, e.g., Sambrook and Russel "Molecular Cloning, A Laboratory Manual", Cold Spring Harbor Laboratory, N.Y. (2001)).

As used herein "nucleic acid" shall mean any nucleic acid molecule, including, without limitation, DNA, RNA and hybrids or modified variants thereof. An "exogenous nucleic acid" or "exogenous genetic element" relates to any nucleic acid introduced into the cell, which is not a component of the cells "original" or "natural" genome. Exogenous nucleic acids may be integrated or nonintegrated in the genetic material of the target mesenchymal stem cell, or relate to stably transduced nucleic acids.

The nucleic acid molecules used in accordance with the invention may be nucleic acid mimicking molecules known in the art such as synthetic or semi-synthetic derivatives of nucleic acid molecules and mixed polymers. They may contain additional non-natural or derivatised nucleotide bases, as will be readily appreciated by those skilled in the art. Nucleic acid mimicking molecules or nucleic acid derivatives according to the invention include, without being limiting, phosphorothioate nucleic acid, phosphoramidate nucleic acid, morpholino nucleic acid, hexitol nucleic acid (HNA), peptide nucleic acid (PNA) and locked nucleic acid (LNA).

Furthermore, the method of the present invention comprises introducing into the cell at least one guide RNA. In the context of the present invention, a "guide RNA" refers to RNA molecules interacting with RNA guided DNA endonuclease leading to the recognition of the target sequence to be cleaved by the RNA guided DNA endonuclease. According to the present invention, the term "guide RNA" therefore comprises, without limitiation, target sequence specific CRISPR RNAs (crRNA), trans-activating crRNAs (tracrRNA) and chimeric single guide RNAs (sgRNA).

crRNAs differ depending on the RNA guided endonuclease and the CRISPR/Cas system but typically contain a target specific sequence of between 20 to 72 nucleotides in length, flanked by two direct repeats (DR) of a length of between 21 to 46 nucleotides. In the case of S. pyogenes, the DRs are 36 nucleotides long and the target sequence is 30 nucleotides long. The 3' located DR of the crRNA is complementary to and hybridizes with the corresponding tracr RNA, which in turn binds to the Cas9 protein.

As used herein, the term "trans-activating crRNA (tracr RNA)" refers to a small RNA, that is complementary to and base pairs with a pre-crRNA (3' located DR of the crRNA), thereby forming an RNA dupiex. This pre-crRNA is then cleaved by an RNA-specific ribonuclease, to form a crRNA/tracrRNA hybrid, which subsequently acts as a guide for the endonuclease Cas9, which cleaves the invading nucleic acid.

As described herein, the genes encoding the elements of a CRISPR/Cas system, such as for example Cas9, tracrRNA and crRNA, are typically organized in operon(s). DR sequences functioning together with RNA guided endonuclease such as Cas9 proteins of other bacterial species may be identified by bioinformatic analysis of sequence repeats occurring in the respective Crispr/Cas operons and by experimental binding studies of Cas9 protein and tracrRNA together with putative DR sequence flanked target sequences.

Alternatively, a chimeric single guide RNA sequence comprising such a target sequence specific crRNA and tracrRNA may be employed. Such a chimeric (ch) RNA may be designed by the fusion of a target specific sequence of 20 or more nucleotides (nt) with a part or the entire DR sequence (defined as part of a crRNA) with the entire or part of a tracrRNA, as shown by (Jinek et al. Science 337:816-821). Within the chimeric RNA a segment of the DR and the tracrRNA sequence are complementary able to hybridize and to form a hairpin structure.

Moreover, the at least one guide RNA of the present invention may also be encoded by a nucleic acid molecule, which is introduced into the cell. The definitions and preferred embodiments recited above with regard to the nucleic acid molecule encoding the endonuclease equally apply to the nucleic acid molecule encoding these RNAs. Regulatory elements for expressing RNAs are known to one skilled in the art, for example a U6 promoter.

The present invention relates to the generation of double strand beaks of the dsDNA molecule to be modified, wherein the dsDNA molecule comprises at least two target sequences, which are targeted by the at least one guide RNA.

In accordance with the present invention, a "target sequence" is a nucleotide sequence in the dsDNA molecule that is recognized by the at least one guide RNA that is associated with the RNA guided endonuclease due to the target specific sequence comprised by the guide RNA. The target sequence is at least partially complementary to the target specific sequence of the guide RNA and is associated with a so-called protospacer adjacent motif (PAM). The PAM is a 2-6 base pair DNA sequence located adjacent to the target sequence and can be located either at the 5'-end (for example for the Crispr/Cpf1 system) or at the 3'-end of the target sequence (for example for the Crispr/Cas9 system), depending on the Crispr/Cas system employed. An RNA guided endonuclease, such as Cas9 or Cpf1, will not successfully bind to and cleave the targeted dsDNA molecule if the recognized target sequence is not associated with a PAM sequence. The formation of a DNA-RNA heteroduplex between the target sequence and the target specific sequence of the guide RNA allows for cleavage of the target DNA by the guide RNA/RNA guided endonuclease complex. Cleavage of the targeted dsDNA molecule occurs within the target sequence or at a site adjacent to the target sequence, depending on the used RNA guided endonuclease and CRISPR/Cas system.

For example, in case of SpCas9 the DNA target sequence of at least 20 nucleotides is located directly upstream/at the 5'-end of an invariant 5'-NGG-3' PAM. Correct pairing of the guide RNA to the DNA target sequence leads to the generation of a double strand break in the dsDNA molecule ("cleavage" of the dsDNA molecule by SpCas9) 3 base-pairs (bp) upstream of the PAM within the target sequence.

In case of the CRISPR/Cpf1 system, the Cpf1-crRNA complex cleaves target DNA by identification of a target sequence that may be located downstream/at the 3' end of a protospacer adjacent motif (for example 5'-YTN-3' (where "Y" is a pyrimidine and "N" is any nucleobase) or 5'-TTN-3'). Cpf1 can introduce a sticky end/staggered end DNA double strand breaks. In case of AsCpf1 and LbCpf1 a double strand break with a 4 nucleotides overhang can be generated, which can occur 19 bp downstream of the PAM on the targeted (+)-strand and 23 bp downstream of the PAM on the (−)-strand.

As illustrated by the above examples, the exact site of the double strand break depends on the Crispr/Cas system or the RNA guided endonuclease employed in the method of the invention and can therefore be determined by the person skilled in the art upon selection of the RNA guided endonuclease. In the context of the present invention, a site of a double strand break "adjacent" to the target sequence is located within 100 nucleotides or base pairs upstream or downstream from the 5'- or 3'-end of the target sequence. Preferably, the double strand break is generated within 90, 80, 70, 60, 50, 40, 30, 20, 10, 5, 4, 3, 2 or 1 nucleotides/base pairs upstream or downstream from the 5'- or 3'-end of the target sequence or within the target sequence.

In the context of the present invention, the target sequence may also be called "protospacer". The term "target site" may refer to a location or sequence in the dsDNA molecule comprising the target sequence and an associated PAM.

In the context of the present invention, the term "double strand break" or "DSB" refers to interruption of both strands of a dsDNA molecule leading to the separation of the parts of the dsDNA molecule that lie upstream and downstream of the side of the double strand break. In contrast, a single strand break refers to the interruption of only one of the two DNA strands and will not lead to a separation of the parts of the dsDNA molecule that lie upstream and downstream of the side of the double strand break.

In the context of the present invention, double strand breaks can occur due to cleavage of both strands by one RNA guided endonuclease or due to two single-strand cuts on both the (+)- and the (−)-strand by nickases.

A double strand break can be generated by cleavage of both strands of the dsDNA at the same/corresponding position on the complementary strands, leading to the formation of blunt ends of the resulting separated ends of the dsDNA molecule, as it is mostly the case for Cas9 mediated cleavage. However, in case of non-canonical cleavage, Cas9 may also induce the formation of double strand breaks with sticky/staggered ends, wherein the strand breaks on the two complementary DNA strands of the dsDNA are located at different positions, leading to the formation of strand-overhangs on the ends of the cleaved dsDNA molecule.

Furthermore, certain RNA-guided endonucleases regularly generate sticky ends, such as for example Cpf1. It is also possible to influence the tendency of RNA guided endonucleases to generate sticky-ends or blunt ends through selection of certain target sequence.

Additionally, it is possible to intentionally generate sticky ended double strand breaks of a certain configuration by inducing single strand breaks on both the (+)- and the (−)-strand by individual nickases targeting different target sequences on the two strands. By using this approach, it is possible to precisely select the site of a single strand break. Induction of two single strand breaks on both complementary strands within a distance of no more than 50 nucleotides, preferably not more than 40 nt, 35 nt, 30 nt or 25, most preferably not more than 20, 19, 18, 17, 16, 15 14, 13, 12, 11, 10, 9, 8, 7, 6, 5, 4, 3, 2 or 1 nt will lead to a separation of the ends of the dsDNA molecule that are distal and proximal of the corresponding single strand breaks, resulting in the formation of stick ends with overhangs of the corresponding length. Importantly, the single strands sticky end overhangs might not be required for NHEJ repair and it might not be required that complimentary single strand overhangs are present on the open ends of the DNA molecule to be modified generated by a DSB and of the corresponding DNA substitute sequence to be ligated with each other.

In preferred embodiments, the DNA double strand breaks generate sticky ends with single strand overhangs of at least 5 nucleotides.

By using this approach of inducing a double strand break, it can be precisely selected what kind of overhang at the resulting separated ends of the dsDNA molecule is generated. For each double strand break, at least two guide RNA molecules may be required.

DNA double-strand breaks (DSBs) are produced intentionally by RNA guided nucleases to achieve genome editing through DSB repair. Two main branches of DSB repair mechanisms exist in cells. These either process DSB ends by strand resection and initiate repair by homology-directed repair (HDR) or template-free annealing (a-NHEJ), or seek for the immediate protection of free ends through relegation by classic-NHEJ (c-NHEJ).

While the c-NHEJ pathway operates throughout all phases of the cell cycle, HDR is restricted to the S and G2 phases, seeking for homologous sequences to repair the resected DSB ends. During mitosis, DSB repair is entirely shut down to guard the chromosomes against the fusion of telomeres. In the G1 (and G0) phase and in resting cells, c-NHEJ repair is dominant as HDR is silenced. All pathways are active and competing in the S/G2 phases. DSB induction in a population of cycling cells leads to a variety of edited alleles, with c-NHEJ as the dominant outcome.

In proliferating cells, HDR is mediated by the homologous recombination (HR) pathway, wherein the native pathway uses the intact homologous sequences of sister chromatids as template for the repair of DSB sites and leads to the reconstitution of the wild-type allele. It has been shown in the art that it is possible to achieve precise sequence modifications at targeted DSBs. Therefore, the HR pathway can be co-opted by providing an artificial DNA repair template containing sequence regions homologous the DSB ends. The sequence between the homologous ends, either an insertion or replacement, is then transferred into the targeted locus during HR, enabling the generation of precisely modified 'knockin' alleles, e.g., for codon replacements or the insertion of reporter genes.

Large sequence insertions require the use of double-stranded, plasmid-based gene-targeting vectors with homology regions of >500 bp. Shorter sequence modifications can be introduced by using synthetic single-stranded DNA oligodeoxynucleotides (ssODN) as repair templates. Repair using ssODNs is mediated by a poorly defined mechanism designated as single-strand template repair (SST-R).

In contrast to HDR, the c-NHEJ pathway mediates the relegation of DSB ends without the involvement of a repair template. Although some fraction of c-NHEJ repair events result in precisely reconstituted wild-type sequences, a fraction of cleaved sequences gain a random insertion or deletion of one or more nucleotides (INDELs). Therefore, DSB repair by the supposedly error-prone c-NHEJ pathway is frequently used to generate INDELs within coding regions, which often will cause a frameshift knockout mutation.

In the context of the present invention, the terms NHEJ and c-NHEJ are used interchangeably.

In further embodiments, the present invention further relates to a-NHEJ. In preferred embodiments, a-NHEJ is not comprised by the present invention.

NHEJ- and HDR-mediated DSB repair are well established processes or mechanisms that are known to the person skilled in the art and have been described by Danner et al. (Mamm Genome 28, 262-274-). The initiation of DSB repair is identical for both c-NHEJ and HDR. The ATM (ataxia telangiectasia mutated) protein kinase is a key initial regulator of the DNA damage response and coordinates DSB repair. ATM is activated by the MRN (Mre11-Rad50-Nibrin) complex and other factors at DNA breaks. Upon monomerization and autophosphorylation, ATM phosphorylates Serine 139 of histone H2AX, forming γH2AX. The phosphorylated residue on γH2AX is recognized by MDC1, which in turn recruits more MRN complexes. These further activate ATM and creates a positive feedback loop driving the expansion of γH2AX chromatin domains into γH2AX foci. MDC1 becomes phosphorylated by ATM at its TQXF repeats and initiates downstream signaling by recruiting the E3 ubiquitin ligase RNF8. RNF8 and its E2 enzyme partner UBC13 polyubiquitinate the H1 linker histone. This further promotes the recruitment of the E3 ubiquitin ligase RNF168 that ubiquitinates histone H2A at Lysine 13 and 15. H2A-K15Ub together with dimethylated Lysine 20 of histone H4 (H4K20me2) are chromatin marks for the recruitment of the checkpoint protein 53BP1. The control of accumulation of 53BP1 determines if the DSB event is repaired by c-NHEJ, or through resection and subsequent HDR.

The classical c-NHEJ pathway initiates with the localization of 53BP1 to a DSB and blocks 5' resectioning. 53BP1 blocks CtIP-based resectioning and recruits Rif1, which further blocks resectioning and inhibits BRCA1 accumulation. Unresected ends allow Ku70/80 to bind, further inhibiting resection. Ku proteins form a scaffold and recruit DNA-PKcs (catalytical subunit) to form the complete DNA-PK, which then recruits endprocessing factors (like Artemis) and the XRCC4/XLF/DNA Ligase-IV complex. The XRCC4/XLF factors stabilize and align the DNA fibers and DNA Ligase IV ligates the two strands. Repair of chemically or irradiation-induced DSBs is greatly complicated by the need to excise and repair damaged bases. However, this will be left out of this review as DSBs from Cas9 nucleases form blunt ends with 5' phosphorylated DNA, the substrate for DNA Ligase IV. The ability to excise damaged bases and then ligate non-complementary strands has resulted in c-NHEJ being often thought of as a mutagenic process. However given a complimentary cut, such as created by restriction enzymes, mutation-free ligation events can be 75% or higher. Error-prone mutations that have previously been attributed to c-NHEJ are often a result of DSB resectioning and annealing through the similarly named but mechanistically distinct a-NHEJ.

Alternative non-homologous end joining pathways (a-)NHEJ encompass microhomology-mediated end joining (MMEJ), single-strand annealing (SSA), and thetamediated end joining. Once thought to only be backup pathways, a-NHEJ events can in some cases occur up to 10% of the frequency of c-NHEJ. These repair events can result in deletions of various sizes, and only sometimes anneal and ligate through microhomologies. However, they always begin with the same resection steps as in homologous recombination, involving the MRE11 complex and CtIP. Resection can be <20 bp for microhomology or up to thousands of bps for SSA. The choice between a-NHEJ and HR comes from the inability of RPA to be replaced by Rad51 by Rad52/BRCA2. This limits the ssDNA to proceed through the HR pathway. Importantly, the extensive resection, when repaired by a-NHEJ, results in an increased chromosomal translocation frequency, a major driver of human cancer.

The homologous recombination pathway requires the exclusion of 53BP1 and resection in order to be initiated. H2A is de-ubiquitinated upon mitotic entry so 53BP1 is excluded from the chromatin. During the S/G2 phase, BRCA1 excludes Rif1 from the foci, and recruits CtIP and the MRN complex. This complex initiates a cleavage step which is then further 5'-resected by Exo1. The resection extends 2-4 kb on each side of the DSB. The exposed single-stranded DNA (ssDNA) is quickly bound by RPA for protection. RPA is replaced by Rad51 through the action of BRCA2 and Rad52 to form a nucleofilament competent for homology search. The Rad51 filaments maintain the ssDNA in a B-form which has triplets open for Watson-Crick pairing with complementary triplets in homologous duplex DNA. It should be noted that this review highlights only some of the key factors of the HR pathway and more complete reviews are available.

In contrast to HDR, replacement of a DNA sequence of a dsDNA molecule by a DNA substitute sequence of an exogenous nucleic acid molecule according to the method of the present invention does not require that the exogenous nucleic acid molecule comprises or encodes homology arms targeted to the dsDNA molecule to be modified.

In the context of the present invention, the terms "homology arms" or "homology arms that are targeted to the dsDNA molecule to be modified" refer to regions or sequences of the exogenous nucleic acid molecule that are homologous to the sequences at the two double strand break ends of the dsDNA molecule to be modified that are not located on the DNA sequence to be replaced.

This means that for performing the method of the present invention it is not required that there is a sequence homology between the sequences of the dsDNA molecule to be modified that are adjacent to the at least two target sequences and sequences comprised by the exogenous DNA molecule comprising the DNA substitute sequence.

Homology arms have a length of at least 30 nucleotides, preferably at least 50 nucleotides, and may have 90%, preferably 95%, 97%, 98%, 99% or 100% sequence identity to the corresponding sequences flanking the open ends of the target dsDNA molecule. In preferred embodiments of the present invention, homology arms have a length of at least 30 nucleotides, preferably more than 35 nt, 40 nt, 45 nt, 50 nt, 60 nt, 80 nt, 100 nt or 500 nt.

Homology arms have sufficient sequence identity to ensure specific binding to the target sequence. Methods to evaluate the identity level between two nucleic acid sequences are well known in the art. For example, the sequences can be aligned electronically using suitable computer programs known in the art. Such programs comprise BLAST (Altschul et al. (1990) J. Mol. Biol. 215, 403), variants thereof such as WU-BLAST (Altschul and Gish (1996) Methods Enzymol. 266, 460), FASTA (Pearson and Lipman (1988) Proc. Natl. Acad. Sci. USA 85, 2444) or implementations of the Smith-Waterman algorithm (SSEARCH, Smith and Waterman (1981) J. Mol. Biol., 147, 195). These programs, in addition to providing a pairwise sequence alignment, also report the sequence identity level (usually in percent identity) and the probability for the occurrence of the alignment by chance (P-value). In accordance with the present invention it is preferred that BLAST is used to determine the identify level between two nucleic acid sequences.

The method of the invention further comprises introducing into the cell an exogenous nucleic acid molecule comprising or encoding a DNA substitute sequence. An "exogenous nucleic acid" or "exogenous genetic element" relates to any nucleic acid introduced into the cell, which is not a component of the cells "original" or "natural" genome. Exogenous nucleic acids may be integrated or not integrated in the genetic material of the target cell, or relate to stably transduced nucleic acids.

In the context of the present invention, the "DNA substitute sequence", which might also be called a "replacement sequence", is a DNA sequence that is introduced into the dsDNA molecule to be modified at the location between the at least two double strand breaks leading to replacement of the sequence of the dsDNA molecule that was initially located between the at least two double strand breaks.

The DNA substitute sequence may be introduced into the dsDNA molecule to be modified as a linear or linearizable dsDNA molecule that can be generated from the exogenous nucleic acid molecule. The exogenous nucleic acid molecule comprising or encoding a DNA substitute sequence can be, for example, a dsDNA molecule, such as a linear dsDNA molecule, which can result from a PCR amplification, a DNA plasmid or a DNA mini-circle.

In preferred embodiments, the exogenous nucleic acid molecules consist of the DNA substitute sequence. This is possible, for example, if the exogenous nucleic acid molecule is a linear dsDNA molecule, such as for example a PCR amplification product, or a DNA mini-circle. A mini-circle is a plasmid like circular DNA that has had all other parts except the sequence of interest removed. Thus a single cut can linearize a fragment that is then ready to integrate.

In certain embodiments, the DNA substitute sequence can be introduced into the cell through delivery of a nucleic acid encoding for the DNA substitute sequence, for example by means of viral delivery through Adeno-associated viruses (AAV), retroviruses, non-integrating or integrating lentiviruses.

Genetically modified viruses have been widely applied for the delivery of genes into cells. A viral vector may be employed in the context of the present invention.

Non-viral methods may also be employed, such as alternative strategies that include conventional plasmid and nucleic acid transfer and delivery. Physical methods to introduce vectors and nucleic acid molecules or proteins into cells are known to a skilled person. One example relates to electroporation, which relies on the use of brief, high voltage electric pulses, which create transient pores in the membrane by overcoming its capacitance. One advantage of this method is that it can be utilized for both stable and transient gene expression in most cell types. Furthermore, gold nanoparticles for delivery of PCR-like double strand DNA products attached to the gold nanoparticle can be used. Alternative methods relate to the use of liposomes or protein transduction domains. Appropriate methods are known to a skilled person and are not intended as limiting embodiments of the present invention.

In preferred embodiments of the method of the present invention, the cell is a non-dividing or a slowly dividing cell, preferably a cell in the G1 or G0 phase.

The cell cycle or cell division cycle is the series of events that take place in a cell leading to its division and duplication of its DNA (DNA replication) to produce two daughter cells. In cells with a nucleus, as in eukaryotes, the cell cycle consists of four distinct phases: G1 phase, S phase (synthesis), G2 phase (collectively known as interphase) and M phase (mitosis). M phase is itself composed of two tightly coupled processes: karyokinesis, in which the cell's chromosomes are divided, and cytokinesis, in which the cell's cytoplasm divides forming two daughter cells. G0 is a resting phase where the cell has left the cycle and has stopped dividing.

The word "post-mitotic" is sometimes used to refer to both quiescent and senescent cells. Non-proliferative (non-dividing) cells in multicellular eukaryotes generally enter the quiescent G0 state from G1 and may remain quiescent for long periods of time, possibly indefinitely (as is often the case for neurons). This is very common for cells that are fully differentiated. Some cells enter the G0 phase semi-permanently and are considered post-mitotic, e.g., some liver, kidney, and stomach cells. Many cells do not enter G0 and continue to divide throughout an organism's life, e.g., epithelial cells.

In the context of the present invention, a non-dividing cell is a cell that is in the G0 phase where the cell has left the cycle and has stopped dividing. A slowly dividing cell is a cell that has not yet left the cell cycle, but remains in the G1 or G0 phase for a prolonged period, such as more than 1 day, 2 days, 1 week, 2 weeks, 1 month, 2 months, 1 year, 2 years, 5 years, 10 year, or 20 years before reentering the cell cycle and transitioning to the S phase. Importantly, HDR is only active in the S and G2 phase of the cell cycle, whereas NHEJ is active in G0, G1, S, and G2. During the M phase no DNA repair mechanisms are active.

The ability to manipulate any genomic sequence by gene editing has created diverse opportunities to treating many different diseases and disorders (For a review see Maeder et al, Molecular Therapy, 24:3, 2016, 430-446). Of relevance to the present invention is the opportunity of correcting deficient gene sequences in vivo. The present invention enables gene therapy for correcting pathogenic gene sequences by DNA sequence replacement according to the method described herein. For example, hematologic disorders associated with genetic defects could be treated by gene correction in hematopoetic stem cells. Of further relevance is the treatment of liver disease, by liver-targeted gene editing and the treatment of muscle disease by gene correction in muscle stem cells. Respiratory disorders may be treated, for example, cystic fibrosis, which is caused by mutations to the CFTR chloride channel. Gene editing according to the present invention may be employed to repair the CFTR mutations in patient lung cells. Antimicrobials are another potential therapeutic target of the present invention, i.e. by targeting the genomes of other organisms, for example bacterial genes could be replaced by the method described herein.

The present invention encompasses administration of the composition of the present invention to a subject. As used herein, "administration" or "administering" shall include, without limitation, introducing the composition by oral administration. Such administering can also be performed, for example, once, a plurality of times, and/or over one or more extended periods. A single administration is preferred, but repeated administrations over time (e.g., hourly, daily, weekly, monthly, quarterly, half-yearly or yearly) may be necessary in some instances. Such administering is also preferably performed using an admixture and a pharmaceutically acceptable carrier. Pharmaceutically acceptable carriers are well known to those skilled in the art.

Administration may also occur locally, for example by injection at the site where the cells comprising the dsDNA to be modified are located, for example by endoscopic or microinvasive means.

The composition described herein may comprise different types of carriers depending on whether it is to be administered in solid, liquid or aerosol form, and whether it need to be sterile for such routes of administration as injection. The composition of the present invention can be administered intravenously, intradermally, intraarterially, intraperitoneally, intralesionally, intracranially, intraarticularly, intraprostaticaly, intrapleurally, intratracheally, intranasally, intravitreally, intravaginally, intrarectally, topically, intratumorally, intramuscularly, intraperitoneally, subcutaneously, subconjunctival, intravesicularlly, mucosally, intrapericardially, intraumbilically, intraocularally, orally, topically, locally, inhalation (e.g., aerosol inhalation), injection, infusion, continuous infusion, localized perfusion bathing target cells directly, via a catheter, via a lavage, in cremes, in lipid compositions (e.g., liposomes), nanoparticles, or by other method or any combination of the forgoing as would be known to one of ordinary skill in the art (see, for example, Remington's Pharmaceutical Sciences, 18th Ed. Mack Printing Company, 1990, incorporated herein by reference).

Additionally, such compositions can comprise pharmaceutically acceptable carriers that can be aqueous or non-aqueous solutions, suspensions, and emulsions, most preferably aqueous solutions or solid formulations of various types known in the art. Aqueous carriers include water, alcoholic/aqueous solutions, emulsions and suspensions, including saline and buffered media. Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as Ringer's dextrose, those based on Ringer's dextrose, and the like. Fluids used commonly for i.v. administration are found, for example, in Remington: The Science and Practice of Pharmacy, 20th Ed., p. 808, Lippincott Williams S-Wilkins (2000). Preservatives and other additives may also be present, such as, for example, antimicrobials, antioxidants, chelating agents, inert gases, and the like.

Sequences

The invention is further described by the following sequences. These are not intended to limit the scope of the invention, but represent preferred embodiments of aspects of the invention provided for greater illustration of the invention described herein.

| SEQ ID No | Description | Sequence |
|---|---|---|
| SEQ ID NO: 1 | Plasmid 'Target Site A'-sgRNA CAG-Cas9-2A-Puro for targeting Reporter 1 (#481) | ACTGCGGCCAACTTACTTCTGACAACGATCGGAGGACCGAAGGAGCTAACCG<br>CTTTTTTGCACAACATGGGGGATCATGTAACTCGCCTTGATCGTTGGGAACCG<br>GAGCTGAATGAAGCCATACCAAACGACGAGCGTGACACCACGATGCCTGTAG<br>CAATGGCAACAACGTTGCGCAAACTATTAACTGGCGAACTACTTACTCTAGCT<br>TCCCGGCAACAATTAATAGACTGGATGGAGGCGGATAAAGTTGCAGGACCAC<br>TTCTGCGCTCGGCCCTTCCGGCTGGCTGGTTTATTGCTGATAAATCTGGAGC<br>CGGTGAGCGTGGAAGCCGCGGTATCATTGCAGCACTGGGGCCAGATGGTAA<br>GCCCTCCCGTATCGTAGTTATCTACACGACGGGGAGTCAGGCAACTATGGAT<br>GAACGAAATAGACAGATCGCTGAGATAGGTGCCTCACTGATTAAGCATTGGT<br>AACTGTCAGACCAAGTTTACTCATATATACTTTAGATTGATTTAAAACTTCATTT<br>TTAATTTAAAAGGATCTAGGTGAAGATCCTTTTTGATAATCTCATGACCAAAAT<br>CCCTTAACGTGAGTTTTCGTTCCACTGAGCGTCAGACCCCGTAGAAAAGATCA<br>AAGGATCTTCTTGAGATCCTTTTTTTCTGCGCGTAATCTGCTGCTTGCAAACAA<br>AAAAACCACCGCTACCAGCGGTGGTTTGTTTGCCGGATCAAGAGCTACCAAC<br>TCTTTTTCCGAAGGTAACTGGCTTCAGCAGAGCGCAGATACCAAATACTGTCC<br>TTCTAGTGTAGCCGTAGTTAGGCCACCACTTCAAGAACTCTGTAGCACCGCCT<br>ACATACCTCGCTCTGCTAATCCTGTTACCAGTGGCTGCTGCCAGTGGCGATA<br>AGTCGTGTCTTACCGGGTTGGACTCAAGACGATAGTTACCGGATAAGGCGCA<br>GCGGTCGGGCTGAACGGGGGGTTCGTGCACACAGCCCAGCTTGGAGCGAA<br>CGACCTACACCGAACTGAGATACCTACAGCGTGAGCTATGAGAAAGCGCCAC<br>GCTTCCCGAAGGGAGAAAGGCGGACAGGTATCCGGTAAGCGGCAGGGTCG<br>GAACAGGAGAGCGCACGAGGGAGCTTCCAGGGGGAAACGCCTGGTATCTTT<br>ATAGTCCTGTCGGGTTTCGCCACCTCTGACTTGAGCGTCGATTTTTGTGATGC<br>TCGTCAGGGGGGCGGAGCCTATGGAAAAACGCCAGCAACGCGGCCTTTTTA<br>CGGTTCCTGGCCTTTTGCTGGCCTTTTGCTCACATGTGAGGGCCTATTTCCCA<br>TGATTCCTTCATATTTGCATATACGATACAAGGCTGTTAGAGAGATAATTGGAA<br>TTAATTTGACTGTAAACACAAAGATATTAGTACAAAATACGTGACGTAGAAAGT<br>AATAATTTCTTGGGTAGTTTGCAGTTTTAAAATTATGTTTTAAAATGGACTATCA<br>TATGCTTACCGTAACTTGAAAGTATTTCGATTTCTTGGCTTTATATATCTTGTG<br>GAAAGGACGAAACACCGACTCCAGTCTTTCTAGAAGAGTTTTAGAGCTAGAAA<br>TAGCAAGTTAAAATAAGGCTAGTCCGTTATCAACTTGAAAAAGTGGCACCGAG<br>TCGGTGCTTTTTTGTTTTAGAGCTAGAAATAGCAAGTTAAAATAAGGCTAGTCC<br>GTTTTTAGCGCGTGCGCCAATTCTGCAGACAAATGGCTCTAGAGGTACCCGT<br>TACATAACTTACGGTAAATGGCCCGCCTGGCTGACCGCCCAACGACCCCCGC<br>CCATTGACGTCAATAGTAACGCCAATAGGGACTTTCCATTGACGTCAATGGGT<br>GGAGTATTTACGGTAAACTGCCCACTTGGCAGTACATCAAGTGTATCATATGC<br>CAAGTACGCCCCCTATTGACGTCAATGACGGTAAATGGCCCGCCTGGCATTG<br>TGCCCAGTACATGACCTTATGGGACTTTCCTACTTGGCAGTACATCTACGTAT<br>TAGTCATCGCTATTACCATGGTCGAGGTGAGCCCCACGTTCTGCTTCACTCTC<br>CCCATCTCCCCCCCTCCCCACCCCCAATTTTGTATTTATTTATTTTTTAATTAT<br>TTTGTGCAGCGATGGGGCGGGGGGGGGGGGGGGCGCGCGCCAGGCGG<br>GGCGGGGCGGGCGAGGGCGGGCGGGCGAGGCGGAGAGGTGCGC<br>GGCAGCCAATCAGAGCGGCGCGCTCCGAAAGTTTCCTTTTATGGCGAGGCG<br>GCGGCGGCGGCGGCCCTATAAAAAGCGAAGCGCGCGGCGGCGGGAGTCG<br>CTGCGACGCTGCCTTCGCCCCGTGCCCCGCTCCGCCGCCGCCTCGCGCCG<br>CCCGCCCCGGCTCTGACTGACCGCGTTACTCCCACAGGTGAGCGGGCGGGA<br>CGGCCCTTCTCCTCCGGGCTGTAATTAGCTGAGCAAGAGGTAAGGGTTTAAG<br>GGATGGTTGGTTGGTGGGGTATTAATGTTTAATTACCTGGAGCACCTGCCTG<br>AAATCACTTTTTTTCAGGTTGGACCGGTGCCACCATGGACTATAAGGACCACG |

| SEQ ID No | Description | Sequence |
|---|---|---|
| | | ACGGAGACTACAAGGATCATGATATTGATTACAAAGACGATGACGATAAGATG |
| | | GCCCCAAAGAAGAAGCGGAAGGTCGGTATCCACGGAGTCCCAGCAGCCGAC |
| | | AAGAAGTACAGCATCGGCCTGGACATCGGCACCAACTCTGTGGGCTGGGCC |
| | | GTGATCACCGACGAGTACAAGGTGCCCAGCAAGAAATTCAAGGTGCTGGGCA |
| | | ACACCGACCGGCACAGCATCAAGAAGAACCTGATCGGAGCCCTGCTGTTCGA |
| | | CAGCGGCGAAACAGCCGAGGCCACCCGGCTGAAGAGAACCGCCAGAAGAA |
| | | GATACACCAGACGGAAGAACCGGATCTGCTATCTGCAAGAGATCTTCAGCAA |
| | | CGAGATGGCCAAGGTGGACGACAGCTTCTTCCACAGACTGGAAGAGTCCTTC |
| | | CTGGTGGAAGAGGATAAGAAGCACGAGCGGCACCCCATCTTCGGCAACATC |
| | | GTGGACGAGGTGGCCTACCACGAGAAGTACCCCACCATCTACCACCTGAGAA |
| | | AGAAACTGGTGGACAGCACCGACAAGGCCGACCTGCGGCTGATCTATCTGG |
| | | CCCTGGCCCACATGATCAAGTTCCGGGGCCACTTCCTGATCGAGGGCGACC |
| | | TGAACCCCGACAACAGCGACGTGGACAAGCTGTTCATCCAGCTGGTGCAGAC |
| | | CTACAACCAGCTGTTCGAGGAAAACCCCATCAACGCCAGCGGCGTGGACGC |
| | | CAAGGCCATCCTGTCTGCCAGACTGAGCAAGAGCAGACGGCTGGAAAATCTG |
| | | ATCGCCCAGCTGCCCGGCGAGAAGAAGAATGGCCTGTTCGGAAACCTGATT |
| | | GCCCTGAGCCTGGGCCTGACCCCCAACTTCAAGAGCAACTTCGACCTGGCC |
| | | GAGGATGCCAAACTGCAGCTGAGCAAGGACACCTACGACGACGACCTGGAC |
| | | AACCTGCTGGCCCAGATCGGCGACCAGTACGCCGACCTGTTTCTGGCCGCC |
| | | AAGAACCTGTCCGACGCCATCCTGCTGAGCGACATCCTGAGAGTGAACACCG |
| | | AGATCACCAAGGCCCCCCTGAGCGCCTCTATGATCAAGAGATACGACGAGCA |
| | | CCACCAGGACCTGACCCTGCTGAAAGCTCTCGTCGGCAGCAGCTGCCTGA |
| | | GAAGTACAAAGAGATTTTCTTCGACCAGAGCAAGAACGGCTACGCCGGCTAC |
| | | ATTGACGGCGGAGCCAGCCAGGAAGAGTTCTACAAGTTCATCAAGCCCATCC |
| | | TGGAAAAGATGGACGGCACCGAGGAACTGCTCGTGAAGCTGAACAGAGAGG |
| | | ACCTGCTGCGGAAGCAGCGGACCTTCGACAACGGCAGCATCCCCCACCAGA |
| | | TCCACCTGGGAGAGCTGCACGCCATTCTGCGGCGGCAGGAAGATTTTTACCC |
| | | ATTCCTGAAGGACAACCGGGAAAAGATCGAGAAGATCCTGACCTTCCGCATC |
| | | CCCTACTACGTGGGCCCTCTGGCCAGGGGAAACAGCAGATTCGCCTGGATG |
| | | ACCAGAAAGAGCGAGGAAACCATCACCCCCTGGAACTTCGAGGAAGTGGTG |
| | | GACAAGGGCGCTTCCGCCCAGAGCTTCATCGAGCGGATGACCAACTTCGATA |
| | | AGAACCTGCCCAACGAGAAGGTGCTGCCCAAGCACAGCCTGCTGTACGAGT |
| | | ACTTCACCGTGTATAACGAGCTGACCAAAGTGAAATACGTGACCGAGGGAAT |
| | | GAGAAAGCCCGCCTTCCTGAGCGGCGAGCAGAAAAAGGCCATCGTGGACCT |
| | | GCTGTTCAAGACCAACCGGAAAGTGACCGTGAAGCAGCTGAAAGAGGACTAC |
| | | TTCAAGAAAATCGAGTGCTTCGACTCCGTGGAAATCTCCGGCGTGGAAGATC |
| | | GGTTCAACGCCTCCCTGGGCACATACCACGATCTGCTGAAAATTATCAAGGA |
| | | CAAGGACTTCCTGGACAATGAGGAAAACGAGGACATTCTGGAAGATATCGTG |
| | | CTGACCCTGACACTGTTTGAGGACAGAGAGATGATCGAGGAACGGCTGAAAA |
| | | CCTATGCCCACCTGTTCGACGACAAAGTGATGAAGCAGCTGAAGCGGCGGA |
| | | GATACACCGGCTGGGGCAGGCTGAGCCGGAAGCTGATCAACGGCATCCGGG |
| | | ACAAGCAGTCCGGCAAGACAATCCTGGATTTCCTGAAGTCCGACGGCTTCGC |
| | | CAACAGAAACTTCATGCAGCTGATCCACGACGACAGCCTGACCTTTAAAGAG |
| | | GACATCCAGAAAGCCCAGGTGTCCGGCCAGGGCGATAGCCTGCACGAGCAC |
| | | ATTGCCAATCTGGCCGGCAGCCCCGCCATTAAGAAGGGCATCCTGCAGACA |
| | | GTGAAGGTGGTGGACGAGCTCGTGAAAGTGATGGGCCGGCACAAGCCCGAG |
| | | AACATCGTGATCGAAATGGCCAGAGAGAACCAGACCACCCAGAAGGGACAG |
| | | AAGAACAGCCGCGAGAGAATGAAGCGGATCGAAGAGGGCATCAAAGAGCTG |
| | | GGCAGCCAGATCCTGAAAGAACACCCCGTGGAAAACACCCAGCTGCAGAAC |
| | | GAGAAGCTGTACCTGTACTACCTGCAGAATGGGCGGGATATGTACGTGGACC |
| | | AGGAACTGGACATCAACCGGCTGTCCGACTACGATGTGGACCATATCGTGCC |
| | | TCAGAGCTTTCTGAAGGACGACTCCATCGACAACAAGGTGCTGACCAGAAGC |
| | | GACAAGAACCGGGGCAAGAGCGACAACGTGCCCTCCGAAGAGGTCGTGAAG |
| | | AAGATGAAGAACTACTGGCGGCAGCTGCTGAACGCCAAGCTGATTACCCAGA |
| | | GAAAGTTCGACAATCTGACCAAGGCCGAGAGAGGCGGCCTGAGCGAACTGG |
| | | ATAAGGCCGGCTTCATCAAGAGACAGCTGGTGGAAACCCGGCAGATCACAAA |
| | | GCACGTGGCACAGATCCTGGACTCCCGGATGAACACTAAGTACGACGAGAAT |
| | | GACAAGCTGATCCGGGAAGTGAAAGTGATCACCCTGAAGTCCAAGCTGGTGT |
| | | CCGATTTCCGGAAGGATTTCCAGTTTTACAAAGTGCGCGAGATCAACAACTAC |
| | | CACCACGCCCACGACGCCTACCTGAACGCCGTCGTGGGAACCGCCCTGATC |
| | | AAAAAGTACCCTAAGCTGGAAAGCGAGTTCGTGTACGGCGACTACAAGGTGT |
| | | ACGACGTGCGGAAGATGATCGCCAAGAGCGAGCAGGAAATCGGCAAGGCTA |
| | | CCGCCAAGTACTTCTTCTACAGCAACATCATGAACTTTTTCAAGACCGAGATT |
| | | ACCCTGGCCAACGGCGAGATCCGGAAGCGGCCTCTGATCGAGACAAACGGC |
| | | GAAACCGGGGAGATCGTGTGGGATAAGGGCCGGGATTTTGCCACCGTGCGG |
| | | AAAGTGCTGAGCATGCCCCAAGTGAATATCGTGAAAAAGACCGAGGTGCAGA |
| | | CAGGCGGCTTCAGCAAAGAGTCTATCCTGCCCAAGAGGAACAGCGATAAGCT |
| | | GATCGCCAGAAAGAAGGACTGGGACCCTAAGAAGTACGGCGGCTTCGACAG |
| | | CCCCACCGTGGCCTATTCTGTGCTGGTGGTGGCCAAAGTGGAAAAGGGCAA |
| | | GTCCAAGAAACTGAAGAGTGTGAAAGAGCTGCTGGGGATCACCATCATGGAA |
| | | AGAAGCAGCTTCGAGAAGAATCCCATCGACTTTCTGGAAGCCAAGGGCTACA |
| | | AAGAAGTGAAAAAGGACCTGATCATCAAGCTGCCTAAGTACTCCCTGTTCGA |
| | | GCTGGAAAACGGCCGGAAGAGAATGCTGGCCTCTGCCGGCGAACTGCAGAA |
| | | GGGAAACGAACTGGCCCTGCCCTCCAAATATGTGAACTTCCTGTACCTGGCC |
| | | AGCCACTATGAGAAGCTGAAGGGCTCCCCCGAGGATAATGAGCAGAAACAG |

| SEQ ID No | Description | Sequence |
|---|---|---|
| | | CTGTTTGTGGAACAGCACAAGCACTACCTGGACGAGATCATCGAGCAGATCA
GCGAGTTCTCCAAGAGAGTGATCCTGGCCGACGCTAATCTGGACAAAGTGCT
GTCCGCCTACAACAAGCACCGGGATAAGCCCATCAGAGAGCAGGCCGAGAA
TATCATCCACCTGTTTACCCTGACCAATCTGGGAGCCCCTGCCGCCTTCAAGT
ACTTTGACACCACCATCGACCGGAAGAGGTACACCAGCACCAAAGAGGTGCT
GGACGCCACCCTGATCCACCAGAGCATCACCGGCCTGTACGAGACACGGAT
CGACCTGTCTCAGCTGGGAGGCGACAAAAGGCCGGCGGCCACGAAAAAGGC
CGGCCAGGCAAAAAGAAAAAGGAATTCGGCAGTGGAGAGGGCAGAGGAAG
TCTGCTAACATGCGGTGACGTCGAGGAGAATCCTGGCCCAATGACCGAGTAC
AAGCCCACGGTGCGCCTCGCCACCCGCGACGACGTCCCCAGGGCCGTACG
CACCCTCGCCGCCGCGTTCGCCGACTACCCCGCCACGCGCCACACCGTCGA
TCCGGACCGCCACATCGAGCGGGTCACCGAGCTGCAAGAACTCTTCCTCAC
GCGCGTCGGGCTCGACATCGGCAAGGTGTGGGTCGCGGACGACGGCGCCG
CGGTGGCGGTCTGGACCACGCCGGAGAGCGTCGAAGCGGGGGCGGTGTTC
GCCGAGATCGGCCCGCGCATGGCCGAGTTGAGCGGTTCCCGGCTGGCCGC
GCAGCAACAGATGGAAGGCCTCCTGGCGCCGCACCGGCCCAAGGAGCCCG
CGTGGTTCCTGGCCACCGTCGGAGTCTCGCCCGACCACCAGGGCAAGGGTC
TGGGCAGCGCCGTCGTGCTCCCCGGAGTGGAGGCGGCCGAGCGCGCCGGG
GTGCCCGCCTTCCTGGAGACCTCCGCGCCCCGCAACCTCCCCTTCTACGAG
CGGCTCGGCTTCACCGTCACCGCCGACGTCGAGGTGCCCGAAGGACCGCG
CACCTGGTGCATGACCCGCAAGCCCGGTGCCTGAGAATTCTAACTAGAGCTC
GCTGATCAGCCTCGACTGTGCCTTCTAGTTGCCAGCCATCTGTTGTTTGCCC
CTCCCCCGTGCCTTCCTTGACCCTGGAAGGTGCCACTCCCACTGTCCTTTCC
TAATAAAATGAGGAAATTGCATCGCATTGTCTGAGTAGGTGTCATTCTATTCTG
GGGGGTGGGGTGGGGCAGGACAGCAAGGGGGAGGATTGGGAAGAGAATAG
CAGGCATGCTGGGGAGCGGCCGCAGGAACCCCTAGTGATGGAGTTGGCCAC
TCCCTCTCTGCGCGCTCGCTCGCTCACTGAGGCCGGGCGACCAAAGGTCGC
CCGACGCCCGGGCTTTGCCCGGGCGGCCTCAGTGAGCGAGCGAGCGCGCA
GCTGCCTGCAGGGGCGCCTGATGCGGTATTTTCTCCTTACGCATCTGTGCGG
TATTTCACACCGCATACGTCAAAGCAACCATAGTACGCGCCCTGTAGCGGCG
CATTAAGCGCGGCGGGTGTGGTGGTTACGCGCAGCGTGACCGCTACACTTG
CCAGCGCCCTAGCGCCCGCTCCTTTCGCTTTCTTCCCTTCCTTTCTCGCCAC
GTTCGCCGGCTTTCCCCGTCAAGCTCTAAATCGGGGGCTCCCTTTAGGGTTC
CGATTTAGTGCTTTACGGCACCTCGACCCCAAAAAACTTGATTTGGGTGATGG
TTCACGTAGTGGGCCATCGCCCTGATAGACGGTTTTTCGCCCTTTGACGTTG
GAGTCCACGTTCTTTAATAGTGGACTCTTGTTCCAAACTGGAACAACACTCAA
CCCTATCTCGGGCTATTCTTTTGATTTATAAGGGATTTTGCCGATTTCGGCCTA
TTGGTTAAAAAATGAGCTGATTTAACAAAAATTTAACGCGAATTTTAACAAAAT
ATTAACGTTTACAATTTTATGGTGCACTCTCAGTACAATCTGCTCTGATGCCGC
ATAGTTAAGCCAGCCCCGACACCCGCCAACACCCGCTGACGCGCCCTGACG
GGCTTGTCTGCTCCCGGCATCCGCTTACAGACAAGCTGTGACCGTCTCCGGG
AGCTGCATGTGTCAGAGGTTTTCACCGTCATCACCGAAACGCGCGAGACGAA
AGGGCCTCGTGATACGCCTATTTTTATAGGTTAATGTCATGATAATAATGGTTT
CTTAGACGTCAGGTGGCACTTTTCGGGGAAATGTGCGCGGAACCCCTATTTG
TTTATTTTTCTAAATACATTCAAATATGTATCCGCTCATGAGACAATAACCCTG
ATAAATGCTTCAATAATATTGAAAAAGGAAGAGTATGAGTATTCAACATTTCCG
TGTCGCCCTTATTCCCTTTTTTGCGGCATTTTGCCTTCCTGTTTTTGCTCACCC
AGAAACGCTGGTGAAAGTAAAAGATGCTGAAGATCAGTTGGGTGCACGAGTG
GGTTACATCGAACTGGATCTCAACAGCGGTAAGATCCTTGAGAGTTTTCGCC
CCGAAGAACGTTTTCCAATGATGAGCACTTTTAAAGTTCTGCTATGTGGCGCG
GTATTATCCCGTATTGACGCCGGGCAAGAGCAACTCGGTCGCCGCATACACT
ATTCTCAGAATGACTTGGTTGAGTACTCACCAGTCACAGAAAAGCATCTTACG
GATGGCATGACAGTAAGAGAATTATGCAGTGCTGCCATAACCATGAGTGATAA
C |
| SEQ ID NO: 2 | PAM + Protosp acer for 'Target Site A' Sequence used for Cas9 cleavage in Reporter 1 | ACTCCAGTCTTTCTAGAAGATGG |
| SEQ ID NO: 3 | Reporter 1 sequence (FIG. 2) integrated into the AAVSI loci | CTAGTTATTAATAGTAATCAATTACGGGGTCATTAGTTCATAGCCCATATATGG
AGTTCCGCGTTACATAACTTACGGTAAATGGCCCGCCTGGCTGACCGCCCAA
CGACCCCCGCCCATTGACGTCAATAATGACGTATGTTCCCATAGTAACGCCA
ATAGGGACTTTCCATTGACGTCAATGGGTGGAGTATTTACGGTAAACTGCCCA
CTTGGCAGTACATCAAGTGTATCATATGCCAAGTACGCCCCCTATTGACGTCA
ATGACGGTAAATGGCCCGCCTGGCATTATGCCCAGTACATGACCTTATGGGA
CTTTCCTACTTGGCAGTACATCTACGTATTAGTCATCGCTATTACCATGGTCG
AGGTGAGCCCCACGTTCTGCTTCACTCTCCCCATCTCCCCCCCCTCCCCACC
CCCAATTTTGTATTTATTTATTTTTAATTATTTTGTGCAGCGATGGGGGCGGG
GGGGGGGGGGGCGCGCGCCAGGCGGGGCGGGGCGGGGCGAGGGGCG
GGGCGGGGCGAGGCGGAGAGGTGCGGCGGCAGCCAATCAGAGCGGCGCG
CTCCGAAAGTTTCCTTTTATGGCGAGGCGGCGGCGGCGGCGGCCCTATAAA |

| SEQ ID No | Description | Sequence |
|---|---|---|
| | | AAGCGAAGCGCGCGGCGGGCGGGGAGTCGCTGCGACGCTGCCTTCGCCCC<br>GTGCCCCGCTCCGCCGCCGCCTCGCGCCGCCCGCCCCGGCTCTGACTGAC<br>CGCGTTACTCCCACAGGTGAGCGGGCGGGACGGCCCTTCTCCTCCGGGCTG<br>TAATTAGCGCTTGGTTTAATGACGGCTTGTTTCTTTTCTGTGGCTGCGTGAAA<br>GCCTTGAGGGGCTCCGGGAGGGCCCTTTGTGCGGGGGGAGCGGCTCGGGG<br>GGTGCGTGCGTGTGTGTGCGTGGGGAGCGCCGCGTGCGGCTCCGCGCT<br>GCCCGGCGGCTGTGAGCGCTGCGGGCGCGGCGCGGGGCTTTGTGCGCTCC<br>GCAGTGTGCGCGAGGGGAGCGCGGCCGGGGCGGTGCCCGCGGTGCGG<br>GGGGGGCTGCGAGGGGAACAAAGGCTGCGTGCGGGGTGTGTGCGTGGGGG<br>GGTGAGCAGGGGGTGTGGGCGCGTCGGTCGGGCTGCAACCCCCCCTGCAC<br>CCCCCTCCCCGAGTTGCTGAGCACGGCCCGGCTTCGGGTGCGGGGCTCCGT<br>ACGGGGCGTGGCGCGGGGCTCGCCGTGCCGGGCGGGGGGTGGCGGCAGG<br>TGGGGGTGCCGGCGGGGCGGGGCCGCCTCGGGCCGGGGAGGGCTCGGG<br>GGAGGGGCGCGGCGGCCCCCGGAGCGCCGGCGGCTGTCGAGGCGCGGCG<br>AGCCGCAGCCATTGCCTTTTATGGTAATCGTGCGAGAGGGCGCAGGGACTTC<br>CTTTGTCCCAAATCTGTGCGGAGCCGAAATCTGGGAGGCGCCGCCGCACCC<br>CCTCTAGCGGGCGCGGGGCGAAGCGGTGCGGCGCCGGCAGGAAGGAAATG<br>GGCGGGGAGGGCCTTCGTGCGTCGCCGCGCCGCCGTCCCCTTCTCCCTCTC<br>CAGCCTCGGGGCTGTCCGCGGGGGGACGGCTGCCTTCGGGGGGGACGGG<br>GCAGGGCGGGGTTCGGCTTCTGGCGTGTGACCGGCGGCTCTAGAGCCTCTG<br>CTAACCATGTTCATGCCTTCTTCTTTTTCCTACAGCTCCTGGGCAACGTGCTG<br>GTTATTGTGCTGTCTCATCATTTTGGCAAAGAATTCCGCTCCATCTTCTAGAAA<br>GACTGGAGTGCGATCGCGCCACCATGGTGAGCAAGGGCGAGGAGCTGTTCA<br>CCGGGGTGGTGCCCATCCTGGTCGAGCTGGACGGCGACGTAAACGGCCACA<br>AGTTCAGCGTGAGGGGCGAGGGCGAGGGCGATGCCACCAACGGCAAGCTG<br>ACCCTGAAGTTCATCTGCACCACCGGCAAGCTGCCCGTGCCCTGGCCCACC<br>CTCGTGACCACCCTGAGCCACGGCGTGCAGTGCTTCGCCCGCTACCCCGAC<br>CACATGAAGCAGCACGACTTCTTCAAGTCCGCCATGCCCGAAGGCTACGTCC<br>AGGAGCGCACCATCTTCTTCAAGGACGACGGCACCTACAAGACCCGCGCCG<br>AGGTGAAGTTCGAGGGCGACACCCTGGTGAACCGCATCGAGCTGAAGGGCG<br>TCGACTTCAAGGAGGACGGCAACATCCTGGGGCACAAGCTGGAGTACAACTT<br>CAACAGCCACAACATCTATATCATGGCCGTCAAGCAGAAGAACGGCATCAAG<br>GTGAACTTCAAGATCCGCCACAACGTGGAGGACGGCAGCGTGCAGCTCGCC<br>GACCACTACCAGCAGAACACCCCCATCGGCGACGGCCCCGTGCTGCTGCCC<br>GACAGCCACTACCTGAGCACCCAGTCCGTGCTGAGCAAAGACCCCAACGAG<br>AAGCGCGATCACATGGTCCTGCTGGAGTTCGCACCGCCGCCGGGATCACT<br>CTCGGCATGGACGAGCTGTACAAGTGAGAATTCCTAGAGCTCGCTGATCAGC<br>CTCGACTGTGCCTTCTAGTTGCCAGCCATCTGTTGTTTGCCCCTCCCCCGTG<br>CCTTCCTTGACCCTGGAAGGTGCCACTCCCACTGTCCTTTCCTAATAAAATGA<br>GGAAATTGCATCGCATTGTCTGAGTAGGTGTCATTCTATTCTGGGGGGTGGG<br>GTGGGGCAGGACAGCAAGGGGGAGGATTGGGAAGAGAATAGCAGGCATGC<br>CTCCATCTTCTAGAAAGACTGGAGTTTAATTAAGCCACCATGGTGAGCAAGGG<br>CGAGGAGCTGTTCACCGGGGTGGTGCCCATCCTGGTCGAGCTGGACGGCGA<br>CGTAAACGGCCACAAGTTCAGCGTGTCCGGCGAGGGCGAGGGCGATGCCAC<br>CTACGGCAAGCTGACCCTGAAGCTGATCTGCACCACCGGCAAGCTGCCCGT<br>GCCCTGGCCCACCCTCGTGACCACCCTGGGCTACGGCCTGCAGTGCTTCGC<br>CCGCTACCCCGACCACATGAAGCAGCACGACTTCTTCAAGTCCGCCATGCCC<br>GAAGGCTACGTCCAGGAGCGCACCATCTTCTTCAAGGACGACGGCAACTACA<br>AGACCCGCGCCGAGGTGAAGTTCGAGGGCGACACCCTGGTGAACCGCATCG<br>AGCTGAAGGGCATCGACTTCAAGGAGGACGGCAACATCCTGGGGCACAAGC<br>TGGAGTACAACTACAACAGCCACAACGTCTATATCACCGCCGACAAGCAGAA<br>GAACGGCATCAAGGCCAACTTCAAGATCCGCCACAACATCGAGGACGGCGG<br>CGTGCAGCTCGCCGACCACTACCAGCAGAACACCCCCATCGGCGACGGCCC<br>CGTGCTGCTGCCCGACAACCACTACCTGAGCTACCAGTCCGCCCTGAGCAAA<br>GACCCCAACGAGAAGCGCGATCACATGGTCCTGCTGGAGTTCGTGACCGCC<br>GCCGGGATCACTCTCGGCATGGACGAGCTGTACAAGTAACGCGTGAATTCAC<br>TCCTCAGGTGCAGGCTGCCTATCAGAAGGTGGTGGCTGGTGTGGCCAATGC<br>CCTGGCTCACAAATACCACTGAGATCTTTTTCCCTCTGCCAAAAATTATGGGG<br>ACATCATGAAGCCCCTTGAGCATCTGACTTCTGGCTAATAAAGGAAATTTATTT<br>TCATTGCAATAGTGTGTTGGAATTTTTTGTGTCTCTCACTCGGAAGGACATAT<br>GGGAGGGCAAATCATTTAAAACATCAGAATGAGTATTTGGTTTAGAGTTTGGC<br>AACATATGCCCATATGCTGGCTGCCATGAACAAAGGTTGGCTATAAAGAGGT<br>CATCAGTATATGAAACAGCCCCCTGCTGTCCATTCCTTATTCCATAGAAAAGC<br>CTTGACTTGAGGTTAGATTTTTTTTATATTTTGTTTTGTGTTATTTTTTTCTTTAA<br>CATCCCTAAAATTTTCCTTACATGTTTTACTAGCCAGATTTTTCCTCCTCTCCT<br>GACTACTCCCAGTCATAGCTGTCCCTCTTCTCTTATGGAGATC |
| SEQ ID NO: 4 | Reporter 1 with mCherry Replacing BFP in the AAVSI loci | CTAGTTATTAATAGTAATCAATTACGGGGTCATTAGTTCATAGCCCATATATGG<br>AGTTCCGCGTTACATAACTTACGGTAAATGGCCCGCCTGGCTGACCGCCCAA<br>CGACCCCCGCCCATTGACGTCAATAATGACGTATGTTCCCATAGTAACGCCA<br>ATAGGGACTTTCCATTGACGTCAATGGGTGGAGTATTTACGGTAAACTGCCCA<br>CTTGGCAGTACATCAAGTGTATCATATGCCAAGTACGCCCCCTATTGACGTCA<br>ATGACGGTAAATGGCCCGCCTGGCATTATGCCCAGTACATGACCTTATGGGA<br>CTTTCCTACTTGGCAGTACATCTACGTATTAGTCATCGCTATTACCATGGTCG<br>AGGTGAGCCCCACGTTCTGCTTCACTCTCCCCATCTCCCCCCCCTCCCCACC |

| SEQ ID No | Description | Sequence |
|---|---|---|
| | | CCCAATTTTGTATTTATTTATTTTTTAATTATTTTTGTGCAGCGATGGGGCGGG |
| | | GGGGGGGGGGGGGCGCGCGCCAGGCGGGGCGGGGCGGGGCGAGGGGCG |
| | | GGGCGGGGCGAGGCGGAGAGGTGCGGCGGCAGCCAATCAGAGCGGCGCG |
| | | CTCCGAAAGTTTCCTTTTATGGCGAGGCGGCGGCGGCGGCCCTATAAA |
| | | AAGCGAAGCGCGCGGCGGGCGGGGAGTCGCTGCGACGCTGCCTTCGCCCC |
| | | GTGCCCCGCTCCGCCGCCGCCTCGCGCCGCCCGCCCCGGCTCTGACTGAC |
| | | CGCGTTACTCCCACAGGTGAGCGGGCGGGACGGCCCTTCTCCTCCGGGCTG |
| | | TAATTAGCGCTTGGTTTAATGACGGCTTGTTTCTTTTCTGTGGCTGCGTGAAA |
| | | GCCTTGAGGGGCTCCGGGAGGGCCCTTTGTGCGGGGGGAGCGGCTCGGGG |
| | | GGTGCGTGCGTGTGTGTGCGTGGGGAGCGCCGCGTGCGGCTCCGCGCT |
| | | GCCCGGCGGCTGTGAGCGCTGCGGGCGCGGCGCGGGGCTTTGTGCGCTCC |
| | | GCAGTGTGCGCGAGGGGAGCGCGGCCGGGGCGGTGCCCGCGGTGCGG |
| | | GGGGGGCTGCGAGGGGAACAAAGGCTGCGTGCGGGGTGTGTGCGTGGGGG |
| | | GGTGAGCAGGGGGTGTGGGCGCGTCGGTCGGGCTGCAACCCCCCCTGCAC |
| | | CCCCCTCCCCGAGTTGCTGAGCACGGCCCGGCTTCGGGTGCGGGGCTCCGT |
| | | ACGGGGCGTGCGCGGGGCTCGCCGTGCCGGGCGGGGGGTGGCGGCAGG |
| | | TGGGGGTGCCGGGCGGGGCGGGGCGCCTCGGGCCGGGGAGGGCTCGGG |
| | | GGAGGGGCGCGGCGGCCCCCGGAGCGCCGGCGGCTGTCGAGGCGCGGCG |
| | | AGCCGCAGCCATTGCCTTTTATGGTAATCGTGCGAGAGGGCGCAGGGACTTC |
| | | CTTTGTCCCAAATCTGTGCGGAGCCGAAATCTGGGAGGCGCCGCCGCACCC |
| | | CCTCTAGCGGGCGCGGGGCGAAGCGGTGCGGCGCCGGCAGGAAGGAAATG |
| | | GGCGGGGAGGGCCTTCGTGCGTCGCCGCGCCGTCCCCTTCTCCCTCTC |
| | | CAGCCTCGGGGCTGTCCGCGGGGGGACGGCTGCCTTCGGGGGGGACGGG |
| | | GCAGGGCGGGGTTCGGCTTCTGGCGTGTGACCGGCGGCTCTAGAGCCTCTG |
| | | CTAACCATGTTCATGCCTTCTTCTTTTTCCTACAGCTCCTGGGCAACGTGCTG |
| | | GTTATTGTGCTGTCTCATCATTTTGGCAAAGAATTCCGCTCCATCTAGATGGG |
| | | GGGACGTGGTTTTCCTTTGAAAAACACGATGATAATATGGCCACAACCATGGT |
| | | GAGCAAGGGCGAGGAGGATAACATGGCCATCATCAAGGAGTTCATGCGCTTC |
| | | AAGGTGCACATGGAGGGCTCCGTGAACGGCCACGAGTTCGAGATCGAGGGC |
| | | GAGGGCGAGGGCCGCCCCTACGAGGGCACCCAGACCGCCAAGCTGAAGGT |
| | | GACCAAGGGTGGCCCCCTGCCCTTCGCCTGGGACATCCTGTCCCCTCAGTT |
| | | CATGTACGGCTCCAAGGCCTACGTGAAGCACCCCGCCGACATCCCCGACTA |
| | | CTTGAAGCTGTCCTTCCCCGAGGGCTTCAAGTGGGAGCGCGTGATGAACTTC |
| | | GAGGACGGCGGCGTGGTGACCGTGACCCAGGACTCCTCCCTGCAGGACGG |
| | | CGAGTTCATCTACAAGGTGAAGCTGCGCGGCACCAACTTCCCCTCCGACGGC |
| | | CCCGTAATGCAGAAGAAGACCATGGGCTGGGAGGCCTCCTCCGAGCGGATG |
| | | TACCCCGAGGACGGCGCCCTGAAGGGCGAGATCAAGCAGAGGCTGAAGCTG |
| | | AAGGACGGCGGCCACTACGACGCTGAGGTCAAGACCACCTACAAGGCCAAG |
| | | AAGCCCGTGCAGCTGCCCGGCGCCTACAACGTCAACATCAAGTTGGACATCA |
| | | CCTCCCACAACGAGGACTACACCATCGTGGAACAGTACGAACGCGCCGAGG |
| | | GCCGCCACTCCACCGGCGGCATGGACGAGCTGTACAAGTAATGAACTCCAG |
| | | TCTTTCTAGATCTAGAAAGACTGGAGTTTAATTAAGCCACCATGGTGAGCAAG |
| | | GGCGAGGAGCTGTTCACCGGGGTGGTGCCCATCCTGGTCGAGCTGGACGG |
| | | CGACGTAAACGGCCACAAGTTCAGCGTGTCCGGCGAGGGCGAGGGCGATGC |
| | | CACCTACGGCAAGCTGACCCTGAAGCTGATCTGCACCACCGGCAAGCTGCC |
| | | CGTGCCCTGGCCCACCCTCGTGACCACCCTGGGCTACGGCCTGCAGTGCTT |
| | | CGCCCGCTACCCCGACCACATGAAGCAGCACGACTTCTTCAAGTCCGCCATG |
| | | CCCGAAGGCTACGTCCAGGAGCGCACCATCTTCTTCAAGGACGACGGCAACT |
| | | ACAAGACCCGCGCCGAGGTGAAGTTCGAGGGCGACACCCTGGTGAACCGCA |
| | | TCGAGCTGAAGGGCATCGACTTCAAGGAGGACGGCAACATCCTGGGGCACA |
| | | AGCTGGAGTACAACTACAACAGCCACAACGTCTATATCACCGCCGACAAGCA |
| | | GAAGAACGGCATCAAGGCCAACTTCAAGATCCGCCACAACATCGAGGACGG |
| | | CGGCGTGCAGCTCGCCGACCACTACCAGCAGAACACCCCCATCGGCGACGG |
| | | CCCCGTGCTGCTGCCCGACAACCACTACCTGAGCTACCAGTCCGCCCTGAG |
| | | CAAAGACCCCAACGAGAAGCGCGATCACATGGTCCTGCTGGAGTTCGTGACC |
| | | GCCGCCGGGATCACTCTCGGCATGGACGAGCTGTACAAGTAACGCGTGAATT |
| | | CACTCCTCAGGTGCAGGCTGCCTATCAGAAGGTGGTGGCTGGTGTGGCCAA |
| | | TGCCCTGGCTCACAAATACCACTGAGATCTTTTTCCCTCTGCCAAAAATTATG |
| | | GGGACATCATGAAGCCCCTTGAGCATCTGACTTCTGGCTAATAAAGGAAATTT |
| | | ATTTTCATTGCAATAGTGTGTTGGAATTTTTTGTGTCTCTCACTCGGAAGGACA |
| | | TATGGGAGGGCAAATCATTTAAAACATCAGAATGAGTATTTGGTTTAGAGTTT |
| | | GGCAACATATGCCCATATGCTGGCTGCCATGAACAAAGGTTGGCTATAAAGA |
| | | GGTCATCAGTATATGAAACAGCCCCCTGCTGTCCATTCCTTATTCCATAGAAA |
| | | AGCCTTGACTTGAGGTTAGATTTTTTTTATATTTTGTTTTGTGTTATTTTTTCTT |
| | | TAACATCCCTAAAATTTTCCTTACATGTTTTACTAGCCAGATTTTTCCTCCTCTC |
| | | CTGACTACTCCCAGTCATAGCTGTCCCTCTTCTCTTATGGAGATC |
| SEQ ID NO: 5 | Cas9 protein (Amino acid sequence) | MDYKDHDGDYKDHDIDYKDDDDKMAPKKKRKVGIHGVPAADKKYSIGLDIGINS VGWAVITDEYKVPSKKFKVLGNTDRHSIKKNLIGALLFDSGETAEATRLKRTARRR YTRRKNRICYLQEIFSNEMAKVDDSFFHRLEESFLVEEDKKHERHPIFGNIVDEVA YHEKYPTIYHLRKKLVDSTDKADLRLIYLALAHMIKFRGHFLIEGDLNPDNSDVDKL FIQLVQTYNQLFEENPINASGVDAKAILSARLSKSRRLENLIAQLPGEKKNGLFGN LIALSLGLTPNFKSNFDLAEDAKLQLSKDTYDDDLDNLLAQIGDQYADLFLAAKNL SDAILLSDILRVNTEITKAPLSASMIKRYDEHHQDLTLLKALVRQQLPEKYKEIFFDQ SKNGYAGYIDGGASQEEFYKFIKPILEKMDGTEELLVKLNREDLLRKQRTFDNGSI |

| SEQ ID No | Description | Sequence |
|---|---|---|
| | | PHQIHLGELHAILRRQEDFYPFLKDNREKIEKILTFRIPYYVGPLARGNSRFAWMT<br>RKSEETITPWNFEEVVDKGASAQSFIERMTNFDKNLPNEKVLPKHSLLYEYFTVY<br>NELTKVKYVTEGMRKPAFLSGEQKKAIVDLLFKTNRKVTVKQLKEDYFKKIECFDS<br>VEISGVEDRFNASLGTYHDLLKIIKDKDFLDNEENEDILEDIVLTLTLFEDREMIEER<br>LKTYAHLFDDKVMKQLKRRRYTGWGRLSRKLINGIRDKQSGKTILDFLKSDGFAN<br>RNFMQLIHDDSLIFKEDIQKAQVSGQGDSLHEHIANLAGSPAIKKGILQTVKVVDE<br>LVKVMGRHKPENIVIEMARENQTTQKGQKNSRERMKRIEEGIKELGSQILKEHPV<br>ENTQLQNEKLYLYYLQNGRDMYVDQELDINRLSDYDVDHIVPQSFLKDDSIDNKV<br>LTRSDKNRGKSDNVPSEEVVKKMKNYWRQLLNAKLITQRKFDNLTKAERGGLSE<br>LDKAGFIKRQLVETRQITKHVAQILDSRMNTKYDENDKLIREVKVITLKSKLVSDFR<br>KDFQFYKVREINNYHHAHDAYLNAVVGTALIKKYPKLESEFVYGDYKVYDVRKMI<br>AKSEQEIGKATAKYFFYSNIMNFFKTEITLANGEIRKRPLIETNGETGEIVWDKGRD<br>FATVRKVLSMPQVNIVKKTEVQTGGFSKESILPKRNSDKLIARKKDWDPKKYGGF<br>DSPTVAYSVLVVAKVEKGKSKKLKSVKELLGITIMERSSFEKNPIDFLEAKGYKEV<br>KKDLIIKLPKYSLFELENGRKRMLASAGELQKGNELALPSKYVNFLYLASHYEKLK<br>GSPEDNEQKQLFVEQHKHYLDEIIEQISEFSKRVILADANLDKVLSAYNKHRDKPI<br>REQAENIIHLFTLTNLGAPAAFKYFDTTIDRKRYTSTKEVLDATLIHQSITGLYETRI<br>DLSQLGGDKRPAATKKAGQAKKKKEF |
| SEQ ID NO: 6 | Plasmid containing mCherry flanked by two cut sites for Integration in Reporter 1 | CTAAATTGTAAGCGTTAATATTTTGTTAAAATTCGCGTTAAATTTTTGTTAAATC<br>AGCTCATTTTTTAACCAATAGGCCGAAATCGGCAAAATCCCTTATAAATCAAAA<br>GAATAGACCGAGATAGGGTTGAGTGGCCGCTACAGGGCGCTCCCATTCGCC<br>ATTCAGGCTGCGCAACTGTTGGGAAGGGCGTTTCGGTGCGGGCCTCTTCGC<br>TATTACGCCAGCTGGCGAAAGGGGGATGTGCTGCAAGGCGATTAAGTTGGGT<br>AACGCCAGGGTTTTCCCAGTCACGACGTTGTAAAACGACGGCCAGTGAGCGC<br>GACGTAATACGACTCACTATAGGGCGAATTGAAGGAAGGCCGTCAAGGCCGC<br>ATTTAATTAAACTCCAGTCTTTCTAGAAGATGGGGGGACGTGGTTTTCCTTTG<br>AAAAACACGATGATAATATGGCCACAACCATGGTGAGCAAGGGCGAGGAGGA<br>TAACATGGCCATCATCAAGGAGTTCATGCGCTTCAAGGTGCACATGGAGGGC<br>TCCGTGAACGGCCACGAGTTCGAGATCGAGGGCGAGGGCGAGGGCCGCCC<br>CTACGAGGGCACCCAGACCGCCAAGCTGAAGGTGACCAAGGGTGGCCCCCT<br>GCCCTTCGCCTGGGACATCCTGTCCCCTCAGTTCATGTACGGCTCCAAGGCC<br>TACGTGAAGCACCCCGCCGACATCCCCGACTACTTGAAGCTGTCCTTCCCCG<br>AGGGCTTCAAGTGGGAGCGCGTGATGAACTTCGAGGACGGCGGCGTGGTGA<br>CCGTGACCCAGGACTCCTCCCTGCAGGACGGCGAGTTCATCTACAAGGTGAA<br>GCTGCGCGGCACCAACTTCCCCTCCGACGGCCCCGTAATGCAGAAGAAGAC<br>CATGGGCTGGGAGGCCTCCTCCGAGCGGATGTACCCCGAGGACGGCGCCC<br>TGAAGGGCGAGATCAAGCAGAGGCTGAAGCTGAAGGACGGCGGCCACTACG<br>ACGCTGAGGTCAAGACCACCTACAAGGCCAAGAAGCCCGTGCAGCTGCCCG<br>GCGCCTACAACGTCAACATCAAGTTGGACATCACCTCCCACAACGAGGACTA<br>CACCATCGTGGAACAGTACGAACGCGCCGAGGGCCGCCACTCCACCGGCGG<br>CATGGACGAGCTGTACAAGTAATGAACTCCAGTCTTTCTAGAAGATGGcgatcga<br>tcatCTGGGCCTCATGGGCCTTCCTTTCACTGCCCGCTTTCCAGTCGGGAAACC<br>TGTCGTGCCAGCTGCATTAACATGGTCATAGCTGTTTCCTTGCGTATTGGGCG<br>CTCTCCGCTTCCTCGCTCACTGACTCGCTGCGCTCGGTCGTTCGGGTAAAGC<br>CTGGGGTGCCTAATGAGCAAAAGGCCAGCAAAAGGCCAGGAACCGTAAAAA<br>GGCCGCGTTGCTGGCGTTTTTCCATAGGCTCCGCCCCCCTGACGAGCATCAC<br>AAAAATCGACGCTCAAGTCAGAGGTGGCGAAACCCGACAGGACTATAAAGAT<br>ACCAGGCGTTTCCCCCTGGAAGCTCCCTCGTGCGCTCTCCTGTTCCGACCCT<br>GCCGCTTACCGGATACCTGTCCGCCTTTCTCCCTTCGGGAAGCGTGGCGCTT<br>TCTCATAGCTCACGCTGTAGGTATCTCAGTTCGGTGTAGGTCGTTCGCTCCAA<br>GCTGGGCTGTGTGCACGAACCCCCCGTTCAGCCCGACCGCTGCGCCTTATC<br>CGGTAACTATCGTCTTGAGTCCAACCCGGTAAGACACGACTTATCGCCACTG<br>GCAGCAGCCACTGGTAACAGGATTAGCAGAGCGAGGTATGTAGGCGGTGCT<br>ACAGAGTTCTTGAAGTGGTGGCCTAACTACGGCTACACTAGAAGAACAGTATT<br>TGGTATCTGCGCTCTGCTGAAGCCAGTTACCTTCGGAAAAAGAGTTGGTAGC<br>TCTTGATCCGGCAAACAAACCACCGCTGGTAGCGGTGGTTTTTTTGTTTGCAA<br>GCAGCAGATTACGCGCAGAAAAAAAGGATCTCAAGAAGATCCTTTGATCTTTT<br>CTACGGGGTCTGACGCTCAGTGGAACGAAAACTCACGTTAAGGGATTTTGGT<br>CATGAGATTATCAAAAAGGATCTTCACCTAGATCCTTTTAAATTAAAAATGAAG<br>TTTTAAATCAATCTAAAGTATATATGAGTAAACTTGGTCTGACAGTTATTAGAA<br>AAATTCATCCAGCAGACGATAAAACGCAATACGCTGGCTATCCGGTGCCGCA<br>ATGCCATACAGCACCAGAAAACGATCCGCCCATTCGCCGCCCAGTTCTTCCG<br>CAATATCACGGGTGGCCAGCGCAATATCCTGATAACGATCCGCCACGCCCAG<br>ACGGCCGCAATAATAAAGCCGCTAAAACGGCCATTTTCCACCATAATGTTCG<br>GCAGGCACGCATCACCATGGGTCACCACCAGATCTTCGCCATCCGGCATGCT<br>CGCTTTCAGACGCGCAAACAGCTCTGCCGGTGCCAGGCCCTGATGTTCTTCA<br>TCCAGATCATCCTGATCCACCAGGCCCGCTTCCATACGGGTACGCGCACGTT<br>CAATACGATGTTTCGCCTGATGATCAAACGGACAGGTCGCGGGTCCAGGGT<br>ATGCAGACGACGCATGGCATCCGCCATAATGCTCACTTTTTCTGCCGGCGCC<br>AGATGGCTAGACAGCAGATCCTGACCCGGCACTTCGCCCAGCAGCAGCCAA<br>TCACGGCCCGCTTCGGTCACCACATCCAGCACCGCCGCACACGGAACACCG<br>GTGGTGGCCAGCCAGCTCAGACGCGCCGCTTCATCCTGCAGCTCGTTCAGC<br>GCACCGCTCAGATCGGTTTTCACAAACAGCACCGGACGACCCTGCGCGCTCA<br>GACGAAACACCGCCGCATCAGAGCAGCCAATGGTCTGCTGCGCCCAATCATA |

| SEQ ID No | Description | Sequence |
|---|---|---|
| | | GCCAAACAGACGTTCCACCCACGCTGCCGGGCTACCCGCATGCAGGCCATC<br>CTGTTCAATCATACTCTTCCTTTTTCAATATTATTGAAGCATTTATCAGGGTTAT<br>TGTCTCATGAGCGGATACATATTTGAATGTATTTAGAAAAATAAACAAATAGGG<br>GTTCCGCGCACATTTCCCCGAAAAGTGCCAC |
| SEQ ID NO: 7 | MC plasmid mCherry Insert for Integrating in Reporter 1 | TTGGGCTCCCCGGGCGCGACTAGTGAATTCAGATCTGATATCTCTAGAGTCG<br>AGCTAGCACTCCAGTCTTTCTAGAAGAAGGGCCACAACCATGGTGAGCAAGG<br>GCGAGGAGGATAACATGGCCATCATCAAGGAGTTCATGCGCTTCAAGGTGCA<br>CATGGAGGGCTCCGTGAACGGCCACGAGTTCGAGATCGAGGGCGAGGGCG<br>AGGGCCGCCCCTACGAGGGCACCCAGACCGCCAAGCTGAAGGTGACCAAG<br>GGTGGCCCCCTGCCCTTCGCCTGGGACATCCTGTCCCCTCAGTTCATGTACG<br>GCTCCAAGGCCTACGTGAAGCACCCCGCCGACATCCCCGACTACTTGAAGCT<br>GTCCTTCCCCGAGGGCTTCAAGTGGGAGCGCGTGATGAACTTCGAGGACGG<br>CGGCGTGGTGACCGTGACCCAGGACTCCTCCCTGCAGGACGGCGAGTTCAT<br>CTACAAGGTGAAGCTGCGCGGCACCAACTTCCCCTCCGACGGCCCCGTAAT<br>GCAGAAGAAGACCATGGGCTGGGAGGCCTCCTCCGAGCGGATGTACCCCGA<br>GGACGGCGCCCTGAAGGGCGAGATCAAGCAGAGGCTGAAGCTGAAGGACG<br>GCGGCCACTACGACGCTGAGGTCAAGACCACCTACAAGGCCAAGAAGCCCG<br>TGCAGCTGCCCGGCGCCTACAACGTCAACATCAAGTTGGACATCACCTCCCA<br>CAACGAGGACTACACCATCGTGGAACAGTACGAACGCGCCGAGGGCCGCCA<br>CTCCACCGGCGGCATGGACGAGCTGTACAAGTAATGAGTCGACCCATGGGG<br>GCCCGCCCCAACTGGGGTAACCT |
| SEQ ID NO: 8 | Example full PCR product of 5' end sequencing in Reporter 1 | TTGTCCCAAATCTGTGCGGAGCCGAAATCTGGGAGGCGCCGCCGCACCCCC<br>TCTAGCGGGCGCGGGGCGAAGCGGTGCGGCGCCGGCAGGAAGGAAATGGG<br>CGGGGAGGGCCTTCGTGCGTCGCCGCGCCGCCGTCCCCTTCTCCCTCTCCA<br>GCCTCGGGGCTGTCCGCGGGGGACGGCTGCCTTCGGGGGGGACGGGGC<br>AGGGCGGGGTTCGGCTTCTGGCGTGTGACCGGCGGCTCTAGAGCCTCTGCT<br>AACCATGTTCATGCCTTCTTCTTTTTCCTACAGCTCCTGGGCAACGTGCTGGT<br>TATTGTGCTGTCTCATCATTTTGGCAAAGAATTCcgctCCATCTAGATGGGGGG<br>ACGTGGTTTTCCTTTGAAAAACACGATGATAATATGGCCACAACCATGGTGAG<br>CAAGGGCGAGGAGGATAACATGGCCATCATCAAGGAGTTCATGCGCTTCAAG<br>GTGCACATGGAGGGCTCCGTGAACGGCCACGAGTTCGAGATCGAGGGCGAG<br>GGCGAGGGCCGCCCCTACGAGGGCACCCAGACCGCCAAGCTGAAGGTGAC<br>CAAGGGTGGCCCCCTGCCCTTCGCCTGGGACATCCTGTCCCCTCAGTTCATG<br>TACGGCTCCAAGGCCTACGTGAAGCACCCCGCCGACATCCCCGACTACTTG |
| SEQ ID NO: 9 | Example full PCR product of 3' end sequencing in Reporter 1 | GACTACACCATCGTGGAACAGTACGAACGCGCCGAGGGCCGCCACTCCACC<br>GGCGGCATGGACGAGCTGTACAAGTAATGAACTCCAGTCTTTCTAGATCTAG<br>AAAGACTGGAGTTTAATTAAGCCACCATGGTGAGCAAGGGCGAGGAGCTGTT<br>CACCGGGGTGGTGCCCATCCTGGTCGAGCTGGACGGCGACGTAAACGGCCA<br>CAAGTTCAGCGTGTCCGGCGAGGGCGAGGGCGATGCCACCTACGGCAAGCT<br>GACCCTGAAGCTGATCTGCACCACCGGCAAGCTGCCCGTGCCCTGGCCCAC<br>CCTCGTGACCACCCTGGGCTACGGCCTGCAGTGCTTCGCCCGCTACCCCGA<br>CCACATGAAGCAGCACGACTTCTTCAAGTCCGCCATGCCCGAAGGCTACGTC<br>CAGGAGCGCACCATCTTCTTCAAGGACGACGGCAACTACAAGACCCGCGCC<br>GAGGTGAAGTTCGAGGGCGACACCCTGGTGAACCGCATCGAGCTGAAGGGC<br>ATCGACTTCAAGGAGGACGGCAACATCCTGGGGCACAAGCTGGAGTACAACT<br>ACAACAGCCACAACGTCTATATCACCGCCGACAAGCAGAAGAACGGCATCAA<br>GGCCAACTTCAAGATCCGCCACAACATCGAGGACGGCGGCGTGCAGCTCGC<br>CGACCACTACCAGCAGAACACCCCCATCGGCGACGGCCCCGTGCTGCTGCC<br>CGACAACCACTACCTGAGCTACCAGTCCGCCCTGAGCAAAGACCCCAACGAG<br>AAGCGCGATCACATGGTCCTGCTGGAGTTCGTGACCGCCGCGGGATCACT<br>CTCGGCATGGACGAGCTGTACAAGTAACGCGTGAATTCACTCCTCAGGTGCA<br>GGCTGCCTATCAGAAGGTGGTGGCTGGTGTGGCCAATGCCCTGGCTCACAA<br>ATACCACTGAGATCTTTTTCCCTCTGCCAAAAATTATGGGGACATCATGAAGC<br>CCCTTGAGCATCTGACTTCTGGCTAATAAAGGAAATTTATTTTCATTGCAATAG<br>TGTGTTGGAATTTTTTGTGTCTCTCACTCGGAAGGACATATGGG |
| SEQ ID NO: 10 | Reporter 2 sequence in the AAVSI loci in HEK293 Cells | GACATTGATTATTGACTAGTTATTAATAGTAATCAATTACGGGGTCATTAGTTC<br>ATAGCCCATATATGGAGTTCCGCGTTACATAACTTACGGTAAATGGCCCGCCT<br>GGCTGACCGCCCAACGACCCCCGCCCATTGACGTCAATAATGACGTATGTTC<br>CCATAGTAACGCCAATAGGGACTTTCCATTGACGTCAATGGGTGGACTATTTA<br>CGGTAAACTGCCCACTTGGCAGTACATCAAGTGTATCATATGCCAAGTACGC<br>CCCCTATTGACGTCAATGACGGTAAATGGCCCGCCTGGCATTATGCCCAGTA<br>CATGACCTTATGGGACTTTCCTACTTGGCAGTACATCTACGTATTAGTCATCG<br>CTATTACCATGGTCGAGGTGAGCCCCACGTTCTGCTTCACTCTCCCCATCT<br>CCCCCCCCTCCCCACCCCCAATTTTGTATTTTATTTTTTAATTATTTTGTGC<br>AGCGATGGGGGCGGGGGGGGGGGGCGCGCCAGGCGGGGCGGGGC<br>GGGGCGAGGGGCGGGGGGGGAGGCGGAGAGGTGCGGCGGCAGCCAA<br>TCAGAGCGGCGCGCTCCGAAAGTTTCCTTTTATGGCGAGGCGGCGGCGGCG<br>GCGGCCCTATAAAAAGCGAAGCGCGCGGCGGGCGGGAGTCGCTGCGTTGC<br>CTTCGCCCCGTGCCCCGCTCCGCGCCGCCTCGCGCCGCCCGCCCCGGCTC<br>TGACTGACCGCGTTACTCCCACAGGTGAGCGGGCGGGACGGCCCTTCTCCT<br>CCGGGCTGTAATTAGCGCTTGGTTTAATGACGGCTCGTTTCTTTTCTGTGGCT |

| SEQ ID No | Description | Sequence |
|---|---|---|
| | | GCGTGAAAGCCTTAAAGGGCTCCGGGAGGGCCCTTTGTGCGGGGGGGAGC<br>GGCTCGGGGGGTGCGTGCGTGTGTGTGCGTGGGGAGCGCCGCGTGCGG<br>CCCGCGCTGCCCGGCGGCTGTGAGCGCTGCGGGCGCGGCGCGGGGCTTTG<br>TGCGCTCCGCGTGTGCGCGAGGGGAGCGCGGCCGGGGGCGGTGCCCCGC<br>GGTGCGGGGGGGCTGCGAGGGGAACAAAGGCTGCGTGCGGGGTGTGTGCG<br>TGGGGGGGTGAGCAGGGGGTGTGGGCGCGGCGGTCGGGCTGTAACCCCCC<br>CCTGCACCCCCTCCCCGAGTTGCTGAGCACGGCCCGGCTTCGGGTGCGGG<br>GCTCCGTGCGGGCGTGGCGCGGGGCTCGCCGTGCCGGGCGGGGGGTGG<br>CGGCAGGTGGGGGTGCCGGGCGGGGCGGGGCCGCCTCGGGCCGGGGAGG<br>GCTCGGGGGAGGGGCGCGGCGGCCCCGGAGCGCCGGCGGCTGTCGAGGC<br>GCGGCGAGCCGCAGCCATTGCCTTTTATGGTAATCGTGCGAGAGGGCGCAG<br>GGACTTCCTTTGTCCCAAATCTGGCGGAGCCGAAATCTGGGAGGCGCCGCC<br>GCACCCCCTCTAGCGGGCGCGGGCGAAGCGGTGCGGCGCCGGCAGGAAGG<br>AAATGGGCGGGGAGGGCCTTCGTGCGTCGCCGCGCCGCCGTCCCCTTCTCC<br>ATCTCCAGCCTCGGGGCTGCCGCAGGGGGACGGCTGCCTTCGGGGGGGAC<br>GGGGCAGGGCGGGGTTCGGCTTCTGGCGTGTGACCGGCGGCTCTAGAGCC<br>TCTGCTAACCATGTTCATGCCTTCTTCTTTTTCCTACAGATCCTTAATTAAGCC<br>GCCACCATGGTGAGCAAGGGCGAGGAGCTGTTCACCGGGGTGGTGCCCATC<br>CTGGTCGAGCTGGACGGCGACGTAAACGGCCACAAGTTCAGCGTGTCCGGC<br>GAGGGCGAGGGCGATGCCACCTACGGCAAGCTGACCCTGAAGCTGATCTGC<br>ACCACCGGCAAGCTGCCCGTGCCCTGGCCCACCCTCGTGACCACCCTGGGC<br>TACGGCCTGCAGTGCTTCGCCCGCTACCCCGACCACATGAAGCAGCACGAC<br>TTCTTCAAGTCCGCCATGCCCGAAGGCTACGTCCAGGAGCGCACCATCTTCT<br>TCAAGGACGACGGCAACTACAAGACCCGCGCCGAGGTGAAGTTCGAGCTGC<br>AACTCCAGTCTTTCTAGAAGATGGGCGGGAGTCTTCTGGGCAGGCTTATATC<br>AAGCGCTATGTGCACCAAAACTTCTCCTCGCACTACCGGGCCACCATTGGTG<br>ATCACCGCCGACAAGCAGAAGAACGGCATCAAGGCCAACTTCAAGATCCGCC<br>ACAACATCGAGGACGGCGGCGTGCAGCTCGCCGACCACTACCAGCAGAACA<br>CCCCCATCGGCGACGGCCCCGTGCTGCTGCCCGACAACCACTACCTGAGCT<br>ACCAGTCCGCCCTGAGCAAAGACCCCAACGAGAAGCGCGATCACATGGTCC<br>TGCTGGAGTTCGTGACCGCCGCCGGGATCACTCTCGGCATGGACGAGCTGT<br>ACAAGTAGACGCGTTGGCCACGAACTTCTCTCTGTTAAAGCAAGCAGGAGAT<br>GTTGAAGAAAACCCCGGGCCTATGGTGTCTAAGGGCGAAGAGCTGATTAAGG<br>AGAACATGCACATGAAGCTGTACATGGAGGGCACCGTGAACAACCACCACTT<br>CAAGTGCACATCCGAGGGCGAAGGCAAGCCCTACGAGGGCACCCAGACCAT<br>GAGAATCAAGGTGGTCGAGGGCGGCCCTCTCCCCTTCGCCTTCGACATCCT<br>GGCTACCAGCTTCATGTACGGCAGCAGAACCTTCATCAACCACACCCAGGGC<br>ATCCCCGACTTCTTTAAGCAGTCCTTCCCTGAGGGCTTCACATGGGAGAGAG<br>TCACCACATACGAAGACGGGGGCGTGCTGACCGCTACCCAGGACACCAGCC<br>TCCAGGACGGCTGCCTCATCTACAACGTCAAGATCAGAGGGGTGAACTTCCC<br>ATCCAACGGCCCTGTGATGCAGAAGAAAACACTCGGCTGGGAGGCCAACAC<br>CGAGATGCTGTACCCCGCTGACGGCGGCCTGGAAGGCAGAAGCGACATGGC<br>CCTGAAGCTCGTGGGCGGGGGCCACCTGATCTGCAACTTCAAGACCACATAC<br>AGATCCAAGAAACCCGCTAAGAACCTCAAGATGCCCGGCGTCTACTATGTGG<br>ACCACAGACTGGAAAGAATCAAGGAGGCCGACAAAGAGACCTACGTCGAGC<br>AGCACGAGGTGGCTGTGGCCAGATACTGCGACCTCCCTAGCAAACTGGGGC<br>ACAAACTTAATTGAGCGATCGCACGCGTAAATGATTGCAGATCCACTAGTTCT<br>AGAGCTCGCTGATCAGCCTCGACTGTGCCTTCTAGTTGCCAGCCATCTGTTG<br>TTTGCCCCTCCCCCGTGCCTTCCTTGACCCTGGAAGGTGCCACTCCCACTGT<br>CCTTTCCTAATAAAATGAGGAAATTGCATCGCATTGTCTGAGTAGGTGTCATT<br>CTATTCTGGGGGGTGGGGTGGGGCAGGACAGCAAGGGGGAGGATTGGGAA<br>GACAATAGCAGGCATGCTGGGGATGCGGTGGGCTCTATGGCTTCTGAGGCG<br>GAAAGAACCAGCTGGGG |
| SEQ ID NO: 11 | Plasmid targeting replacement of sequence in Reporter 2: All-in-one plasmid containing sequence for replacement (turboGFP), Cas9, guide RNA | CCCGGATTCGACATTGATTATTGACTAGTCCATGGTGGCGGCTTAATTAAGGA<br>TCGATTTAGCAGCCACCATGGTGAGCAAGGGCGAGGAGGATAACATGGCCT<br>CTCTCCCAGCGACACATGAGTTACACATCTTTGGCTCCATCAACGGTGTGGA<br>CTTTGACATGGTGGGTCAGGGCACCGGCAATCCAAATGATGGTTATGAGGAG<br>TTAAACCTGAAGTCCACCAAGGGTGACCTCCAGTTCTCCCCCTGGATTCTGG<br>TCCCTCATATCGGGTATGGCTTCCATCAGTACCTGCCCTACCCTGACGGGAT<br>GTCGCCTTTCCAGGCCGCCATGGTAGATGGCTCCGGATACCAAGTCCATCGC<br>ACAATGCAGTTTGAAGATGGTGCCTCCCTTACTGTTAACTACCGCTACACCTA<br>CGAGGGAAGCCACATCAAAGGAGAGGCCCAGGTGAAGGGGACTGGTTTCCC<br>TGCTGACGGTCCTGTGATGACCAACTCGCTGACCGCTGCGGACTGGTGCAG<br>GTCGAAGAAGACTTACCCCAACGACAAAACCATCATCAGTACCTTTAAGTGGA<br>GTTACACCACTGGAAATGGCAAGCGCTACCGGAGCACTGCGCGGACCACCT<br>ACACCTTTGCCAAGCCAATGGCGGCTAACTATCTGAAGAACCAGCCGATGTA<br>CGTGTTCCGTAAGACGGAGCTCAAGCACTCCAAGACCGAGCTCAACTTCAAG<br>GAGTGGCAAAAGGCCTTTACCGATGTGATGGGCATGGACGAGCTGTACAAGT<br>AAATCGATTGCAGATCCCCTGGGTGTGGTTGATGAAGGTCGATTAATAATACG<br>ACTCACTATAGGGGCCGCCACCATGGGACCTAAGAAAAAGAGGAAGGTGGC<br>GGCCCCGGTGCCTAGAGAAGGTGGCGCGGGGTAAACTGGGAAAGTGATGTC<br>GTGTACTGGCTCCGCCTTTTTCCCGAGGGTGGGGGAGAACCGTATATAAGTG<br>CAGTAGTCGCCGTGAACGTTCTTTTTCGCAACGGGTTTGCCGCCAGAACACA<br>GGTAAGTGCCGTGTGTGGTTCCCGCGGGCCTGGCCTCTTTACGGGTTATGG |

| SEQ ID No | Description | Sequence |
|---|---|---|
| | | CCCTTGCGTGCCTTGAATTACTTCCACCTGGCTGCAGTACGTGATTCTTGATC |
| | | CCGAGCTTCGGGTTGGAAGTGGGTGGGAGAGTTCGAGGCCTTGCGCTTAAG |
| | | GAGCCCCTTCGCCTCGTGCTTGAGTTGAGGCCTGGCCTGGGCGCTGGGGCC |
| | | GCCGCGTGCGAATCTGGTGGCACCTTCGCGCCTGTCTCGCTGCTTTCGATAA |
| | | GTCTCTAGCCATTTAAAATTTTTGATGACCTGCTGCGACGCTTTTTTTCTGGCA |
| | | AGATAGTCTTGTAAATGCGGGCCAAGATCTGCACACTGGTATTTCGGTTTTTG |
| | | GGGCCGCGGGCGGCGACGGGGCCCGTGCGTCCCAGCGCACATGTTCGGCG |
| | | AGGCGGGGCCTGCGAGCGCGGCCACCGAGAATCGGACGGGGGTAGTCTCA |
| | | AGCTGGCCGGCCTGCTCTGGTGCCTGGCCTCGCGCCGCCGTGTATCGCCCC |
| | | GCCCTGGGCGGCAAGGCTGGCCCGGTCGGCACCAGTTGCGTGAGCGGAAA |
| | | GATGGCCGCTTCCCGGCCCTGCTGCAGGGAGCTCAAAATGGAGGACGCGGC |
| | | GCTCGGGAGAGCGGGCGGGTGAGTCACCCACACAAAGGAAAAGGGCCTTTC |
| | | CGTCCTCAGCCGTCGCTTCATGTGACTCCACGGAGTACCGGGCGCCGTCCA |
| | | GGCACCTCGATTAGTTCTCGAGCTTTTGGAGTACGTCGTCTTTAGGTTGGGG |
| | | GGAGGGGTTTTATGCGATGGAGTTTCCCCACACTGAGTGGGTGGAGACTGAA |
| | | GTTAGGCCAGCTTGGCACTTGATGTAATTCTCCTTGGAATTTGCCCTTTTTGA |
| | | GTTTGGATCTTGGTTCATTCTCAAGCCTCAGACAGTGGTTCAAAGTTTTTTCT |
| | | TCCATTTCAGGTGTCGTGAGCGATCGCATCGACAGTGTTTAAACGCCACCAT |
| | | GGTGAGCAAGGGCGAGGAGCTGTTCACCGGGGTGGTGCCCATCCTGGTCGA |
| | | GCTGGACGGCGACGTAAACGGCCACAAGTTCAGCGTGAGGGGCGAGGGCG |
| | | AGGGCGATGCCACCAACGGCAAGCTGACCCTGAAGTTCATCTGCACCACCG |
| | | GCAAGCTGCCCGTGCCCTGGCCCACCCTCGTGACCACCCTGAGCCACGGCG |
| | | TGCAGTGCTTCGCCCGCTACCCCGACCACATGAAGCAGCACGACTTCTTCAA |
| | | GTCCGCCATGCCCGAAGGCTACGTCCAGGAGCGCACCATCTTCTTCAAGGAC |
| | | GACGGCACCTACAAGACCCGCGCCGAGGTGAAGTTCGAGGGCGACACCCTG |
| | | GTGAACCGCATCGAGCTGAAGGGCGTCGACTTCAAGGAGGACGGCAACATC |
| | | CTGGGGCACAAGCTGGAGTACAACTTCAACAGCCACAACATCTATATCATGG |
| | | CCGTCAAGCAGAAGAACGGCATCAAGGTGAACTTCAAGATCCGCCACAACGT |
| | | GGAGGACGGCAGCGTGCAGCTCGCCGACCACTACCAGCAGAACACCCCCAT |
| | | CGGCGACGGCCCCGTGCTGCTGCCCGACAGCCACTACCTGAGCACCCAGTC |
| | | CGTGCTGAGCAAAGACCCCAACGAGAAGCGCGATCACATGGTCCTGCTGGA |
| | | GTTCCGCACCGCCGCCGGGATCACTCTCGGCATGGACGAGCTGTACAAGTG |
| | | AGAATTCCTAGAGCTCGCTGATCAGCCTCGACTGTGCCTTCTAGTTGCCAGC |
| | | CATCTGTTGTTTGCCCCTCCCCCGTGCCTTCCTTGACCCTGGAAGGTGCCAC |
| | | TCCCACTGTCCTTTCCTAATAAAATGAGGAAATTGCATCGCATTGTCTGAGTA |
| | | GGTGTCATTCTATTCTGGGGGGTGGGGTGGGCAGGACAGCAAGGGGGAG |
| | | GATTGGGAAGAGAATAGCAGGCATGCGTTTAAACATTAGTCGACAGGGCCGC |
| | | CACTGGCCGTCGTTTTACAACGTCGTGACTGGGAAAAACCCTGGCGTTACCCA |
| | | ACTTAATCGCCTTGCAGCACATCCCCCTTTCGCCAGCTGGCGTAATAGCGAA |
| | | GAGGCCCGCACCGATCGCCCTTCCCAACAGTTGCGCAGCCTGAATGGCGAA |
| | | TGGGACGCGCCCTGTAGCGGCGCATTAAGCGCGGCGGGTGTGGTGGTTACG |
| | | CGCAGCGTGACCGCTACACTTGCCAGCGCCCTAGCGCCCGCTCCTTTCGCTT |
| | | TCTTCCCTTCCTTTCTCGCCACGTTCGCCGGCTTTCCCCGTCAAGCTCTAAAT |
| | | CGGGGGCTCCCTTTAGGGTTCCGATTTAGTGCTTTACGGCACCTCGACCCCA |
| | | AAAAACTTGATTAGGGTGATGGTTCACGTAGTGGGCCATCGCCCTGATAGAC |
| | | GGTTTTTCGCCCTTTGACGTTGGAGTCCACGTTCTTTAATAGTGGACTCTTGT |
| | | TCCAAACTGGAACAACACTCAACCCTATCTCGGTCTATTCTTTTGATTTATAAG |
| | | GGATTTTGCCGATTTCGGCCTATTGGTTAAAAAATGAGCTGATTTAACAAAAAT |
| | | TTAACGCGAATTTTAACAAAATATTAACGCTTACAATTTAGGTGGCACTTTTCG |
| | | GGGAAATGTGCGCGGAACCCCTATTTGTTTATTTTTCTAAATACATTCAAATAT |
| | | GTATCCGCTCATGAGACAATAACCCTGATAAATGCTTCAATAATATTGAAAAAG |
| | | GAAGAGTATGAGTATTCAACATTTCCGTGTCGCCCTTATTCCCTTTTTTGCGG |
| | | CATTTTGCCTTCCTGTTTTTGCTCACCCAGAAACGCTGGTGAAAGTAAAAGAT |
| | | GCTGAAGATCAGTTGGGTGCACGAGTGGGTTACATCGAACTGGATCTCAACA |
| | | GCGGTAAGATCCTTGAGAGTTTTCGCCCCGAAGAACGTTTTCCAATGATGAG |
| | | CACTTTTAAAGTTCTGCTATGTGGCGCGGTATTATCCCGTATTGACGCCGGGC |
| | | AAGAGCAACTCGGTCGCCGCATACACTATTCTCAGAATGACTTGGTTGAGTAC |
| | | TCACCAGTCACAGAAAAGCATCTTACGGATGGCATGACAGTAAGAGAATTATG |
| | | CAGTGCTGCCATAACCATGAGTGATAACACTGCGGCCAACTTACTTCTGACAA |
| | | CGATCGGAGGACCGAAGGAGCTAACCGCTTTTTTGCACAACATGGGGGATCA |
| | | TGTAACTCGCCTTGATCGTTGGGAACCGGAGCTGAATGAAGCCATACCAAAC |
| | | GACGAGCGTGACACCACGATGCCTGTAGCAATGGCAACAACGTTGCGCAAAC |
| | | TATTAACTGGCGAACTACTTACTCTAGCTTCCCGGCAACAATTAATAGACTGG |
| | | ATGGAGGCGGATAAAGTTGCAGGACCACTTCTGCGCTCGGCCCTTCCGGCT |
| | | GGCTGGTTTATTGCTGATAAATCTGGAGCCGGTGAGCGTGGGTCTCGCGGTA |
| | | TCATTGCAGCACTGGGGCCAGATGGTAAGCCCTCCCGTATCGTAGTTATCTA |
| | | CACGACGGGGAGTCAGGCAACTATGGATGAACGAAATAGACAGATCGCTGA |
| | | GATAGGTGCCTCACTGATTAAGCATTGGTAACTGTCAGACCAAGTTTACTCAT |
| | | ATATACTTTAGATTGATTTAAAACTTCATTTTTAATTTAAAAGGATCTAGGTGAA |
| | | GATCCTTTTTGATAATCTCATGACCAAAATCCCTTAACGTGAGTTTTCGTTCCA |
| | | CTGAGCGTCAGACCCCGTAGAAAAGATCAAAGGATCTTCTTGAGATCCTTTTT |
| | | TTCTGCGCGTAATCTGCTGCTTGCAAACAAAAAAACCACCGCTACCAGCGGT |
| | | GGTTTGTTTGCCGGATCAAGAGCTACCAACTCTTTTTCCGAAGGTAACTGGCT |
| | | TCAGCAGAGCGCAGATACCAAATACTGTCCTTCTAGTGTAGCCGTAGTTAGG |
| | | CCACCACTTCAAGAACTCTGTAGCACCGCCTACATACCTCGCTCTGCTAATCC |

| SEQ ID No | Description | Sequence |
|---|---|---|
| | | TGTTACCAGTGGCTGCTGCCAGTGGCGATAAGTCGTGTCTTACCGGGTTGGA<br>CTCAAGACGATAGTTACCGGATAAGGCGCAGCGGTCGGGCTGAACGGGGGG<br>TTCGTGCACACAGCCCAGCTTGGAGCGAACGACCTACACCGAACTGAGATAC<br>CTACAGCGTGAGCTATGAGAAAGCGCCACGCTTCCCGAAGGGAGAAAGGCG<br>GACAGGTATCCGGTAAGCGGCAGGGTCGGAACAGGAGAGCGCACGAGGGA<br>GCTTCCAGGGGAAACGCCTGGTATCTTTATAGTCCTGTCGGGTTTCGCCAC<br>CTCTGACTTGAGCGTCGATTTTTGTGATGCTCGTCAGGGGGGCGGAGCCTAT<br>GGAAAAACGCCAGCAACGCGGCCTTTTTACGGTTCCTGGCCTTTTGCTGGCC<br>TTTTGCTCACATGTTCTTTCCTGCGTTATCCCCTGATTCTGTGGATAACCGTAT<br>TACCGCCTTTGAGTGAGCTGATACCGCTCGCCGCAGCCGAACGACCGAGCG<br>CAGCGAGTCAGTGAGCGAGGAAGCGGAAGAGCGCCCAATACGCAAACCGCC<br>TCTCCCCGCGCGTTGGCCGATTCATTAATGCAGCTGGCACGACAGGTTTCCC<br>GACTGGAAAGCGGGCAGTGAGCGCAACGCAATTAATGTGAGTTAGCTCACTC<br>ATTAGGCACCCCAGGCTTTACACTTTATGCTTCCGGCTCGTATGTTGTGTGGA<br>ATTGTGAGCGGATAACAATTTCACACAGGAAACAGCTATGACCATGAGGGGC<br>CCCCTTCACCGAGGGCCTATTTCCCATGATTCCTTCATATTTGCATATACGAT<br>ACAAGGCTGTTAGAGAGATAATTGGAATTAATTTGACTGTAAACACAAAGATAT<br>TAGTACAAAATACGTGACGTAGAAAGTAATAATTTCTTGGGTAGTTTGCAGTTT<br>TAAAATTATGTTTTAAAATGGACTATCATATGCTTACCGTAACTTGAAAGTATTT<br>CGATTTCTTGGCTTTATATATCTTGTGGAAAGGACGAAACACCGCCTTAATTAA<br>GCCGCCACCAGTTTTAGAGCTAGGCCAACATGAGGATCACCCATGTCTGCAG<br>GGCCTAGCAAGTTAAAATAAGGCTAGTCCGTTATCAACTTGGCCAACATGAG<br>GATCACCCATGTCTGCAGGGCCAAGTGGCACCGAGTCGGTGCTTTTTTTGAT<br>CACAGCATCGGCCTGGCCATCGGGCCCCCTTCACCGAGGGCCTATTTCCCAT<br>GATTCCTTCATATTTGCATATACGATACAAGGCTGTTAGAGAGATAATTGGAAT<br>TAATTTGACTGTAAACACAAAGATATTAGTACAAAATACGTGACGTAGAAAGTA<br>ATAATTTCTTGGGTAGTTTGCAGTTTTAAAATTATGTTTTAAAATGGACTATCAT<br>ATGCTTACCGTAACTTGAAAGTATTTCGATTTCTTGGCTTTATATATCTTGTGG<br>AAAGGACGAAACACCGACCTTCATCAACCACACCCAGTTTTAGAGCTAGGCC<br>AACATGAGGATCACCCATGTCTGCAGGGCCTAGCAAGTTAAAATAAGGCTAG<br>TCCGTTATCAACTTGGCCAACATGAGGATCACCCATGTCTGCAGGGCCAAGT<br>GGCACCGAGTCGGTGCTTTTTTTGAT |
| SEQ ID NO: 12 | Target Site B PAM + Protospacer Sequence for targeting Reporter 2 in HEK293 Cells | CCATGGTGGCGGCTTAATTAAGG |
| SEQ ID NO: 13 | Target Site C PAM + Protospacer Sequence for targeting Reporter 2 in HEK293 Cells | CCCTGGGTGTGGTTGATGAAGGT |
| SEQ ID NO: 14 | Human Lamin A Exon 2 Sequence | AGGCAAGCAGATGCAAACCAACCTAATGCAAGGATGCCCTCTCCTGGTAATT<br>GCAGGCATAGCAGCGCCAGCCCCCATGGCTGACCTCCTGGGAGCCTGGCAC<br>TGTCTAGGCACACAGACTCCTTCTCTTAAATCTACTCTCCCCTCTCTTCTTTAG<br>CAATACCAAGAAGGAGGGTGACCTGATAGCTGCTCAGGCTCGGCTGAAGGA<br>CCTGGAGGCTCTGCTGAACTCCAAGGAGGCGCACTGAGCACTGCTCTCAG<br>TGAGAAGCGCACGCTGGAGGGCGAGCTGCATGATCTGCGGGCCAGGTGG<br>CCAAGGTGAGGCCACCCTGCAGGGCCCACCCATGGCCCCACCTAACACATG<br>TACACTCACTCTTCTACCTAGGCCCTCCCCCATGTGGTGCCTGGTCTGACCT<br>GTCACCTGATTTCAGAGCCATTCACCTGTCCTAGAGTCATTTTACCCACTGAG<br>GTCACATCTTATCCTAATTTGGCTGCAATGGGATCTACCACAGTGAATTTAA<br>AATAATCCAGGAGGCCGGGCATGGTGGTTCACGCCTGTAATCCCAGCACTTT<br>AGGAGGCCGAGGTGGGCCGATCACGAGGTCAGGAGATCGAGATCATCCTGA<br>CTAACATGGTGAAACCCCGTCTCTACTAAAAATACAAAAAATTA |
| SEQ ID NO: 15 | hLMNA guide 1 | GCTCCCAGGAGGTCAGCCATGTTTTAGAGCTAGAAATAGCAAGTTAAAATAAG<br>GCTAGTCCGTTATCAACTTGAAAAAGTGGCACCGAGTCGGTGCTTTTTT |
| SEQ ID NO: 16 | hLMNA guide 2 | TTCACTGTGGTAGATCCCATGTTTTAGAGCTAGAAATAGCAAGTTAAAATAAG<br>GCTAGTCCGTTATCAACTTGAAAAAGTGGCACCGAGTCGGTGCTTTTTT |

| SEQ ID No | Description | Sequence |
|---|---|---|
| SEQ ID NO: 17 | hLMNA Deleted Section guide 3 | TTCACTGTGGTAGATCCCATGTTTTAGAGCTAGAAATAGCAAGTTAAAATAAG GCTAGTCCGTTATCAACTTGAAAAAGTGGCACCGAGTCGGTGCTTTTTT |
| SEQ ID NO: 18 | hLMNA Replacement Sequence Plasmid | ACTCGACATTGATTATTGACTAGTGCTCCCAGGAGGTCAGCCATGGGGGAG CCTGGCACTGTCTAGGCACACAGACTCCTTCTCTTAAATCTACTCTCCCCTCT CTTCTTTAGCAATGAGGGCAGAGGAAGTCTGCTAACATGCGGTGACGTGGAG GAGAATCCCGGCCCTGCTAGCATGGTGAGCAAGGGCGAGGAGGATAACATG GCCATCATCAAGGAGTTCATGCGCTTCAAGGTGCACATGGAGGGCTCCGTGA ACGGCCACGAGTTCGAGATCGAGGGCGAGGGCGAGGGCCGCCCCTACGAG GGCACCCAGACCGCCAAGCTGAAGGTGACCAAGGGTGGCCCCCTGCCCTTC GCCTGGGACATCCTGTCCCCTCAGTTCATGTACGGCTCCAAGGCCTACGTGA AGCACCCCGCCGACATCCCCGACTACTTGAAGCTGTCCTTCCCCGAGGGCTT CAAGTGGGAGCGCGTGATGAACTTCGAGGACGGCGGCGTGGTGACCGTGAC CCAGGACTCCTCCCTGCAGGACGGCGAGTTCATCTACAAGGTGAAGCTGCG CGGCACCAACTTCCCCCTCAGACGGCCCCGTAATGCAGAAGAAACCATGGG CTGGGAGGCCTCCTCCGAGCGGATGTACCCCGAGGACGGCGCCCTGAAGG GCGAGATCAAGCAGAGGCTGAAGCTGAAGGACGGCGGCCACTACGACGCTG AGGTCAAGACCACCTACAAGGCCAAGAAGCCCGTGCAGCTGCCCGGCGCCT ACAACGTCAACATCAAGTTGGACATCACCTCCCACAACGAGGACTACACCAT CGTGGAACAGTACGAACGCGCCGAGGGCCGCCACTCCACCGGCGGCATGG ACGAGCTGTACAAGTAAGAATTCCTAGAGCTCGCTGATCAGCCTCGACTGTG CCTTCTAGTTGCCAGCCATCTGTTGTTTGCCCCTCCCCCGTGCCTTCCTTGAC CCTGGAAGGTGCCACTCCCACTGTCCTTTCCTAATAAAATGAGGAAATTGCAT CGCATTGTCTGAGTAGGTGTCATTCTATTCTGGGGGGTGGGGTGGGGCAGG ACAGCAAGGGGGAGGATTGGGAAGAGAATAGCAGGCATGCTGGGGGCTCCC AGGAGGTCAGCCATGGGTTAATTAATAATACGACTCACTATAGGGGCCGCCC CGCCACTGGCCGTCGTTTTACAACGTCGTGACTGGGAAAACCCTGGCGTTAC CCAACTTAATCGCCTTGCAGCACATCCCCCTTTCGCCAGCTGGCGTAATAGC GAAGAGGCCCGCACCGATCGCCCTTCCCAACAGTTGCGCAGCCTGAATGGC GAATGGGACGCGCCCTGTAGCGGCGCATTAAGCGCGGCGGGTGTGGTGGTT ACGCGCAGCGTGACCGCTACACTTGCCAGCGCCCTAGCGCCCGCTCCTTTC GCTTTCTTCCCTTCCTTTCTCGCCACGTTCGCCGGCTTTCCCCGTCAAGCTCT AAATCGGGGGCTCCCTTTAGGGTTCCGATTTAGTGCTTTACGGCACCTCGAC CCCAAAAAACTTGATTAGGGTGATGGTTCACGTAGTGGGCCATCGCCCTGAT AGACGGTTTTTCGCCCTTTGACGTTGGAGTCCACGTTCTTTAATAGTGGACTC TTGTTCCAAACTGGAACAACACTCAACCCTATCTCGGTCTATTCTTTTGATTTA TAAGGGATTTTGCCGATTTCGGCCTATTGGTTAAAAAATGAGCTGATTTAACA AAAATTTAACGCGAATTTTAACAAAATATTAACGCTTACAATTTAGGTGGCACT TTTCGGGGAAATGTGCGCGGAACCCCTATTTGTTTATTTTTCTAAATACATTCA AATATGTATCCGCTCATGAGACAATAACCCTGATAAATGCTTCAATAATATTGA AAAAGGAAGAGTATGAGTATTCAACATTTCCGTGTCGCCCTTATTCCCTTTTTT GCGGCATTTTGCCTTCCTGTTTTTGCTCACCCAGAAACGCTGGTGAAAGTAAA AGATGCTGAAGATCAGTTGGGTGCACGAGTGGGTTACATCGAACTGGATCTC AACAGCGGTAAGATCCTTGAGAGTTTTCGCCCCGAAGAACGTTTTCCAATGAT GAGCACTTTTAAAGTTCTGCTATGTGGCGCGGTATTATCCCGTATTGACGCCG GGCAAGAGCAACTCGGTCGCCGCATACACTATTCTCAGAATGACTTGGTTGA GTACTCACCAGTCACAGAAAAGCATCTTACGGATGGCATGACAGTAAGAGAA TTATGCAGTGCTGCCATAACCATGAGTGATAACACTGCGGCCAACTTACTTCT GACAACGATCGGAGGACCGAAGGAGCTAACCGCTTTTTTTGCACAACATGGGG GATCATGTAACTCGCCTTGATCGTTGGGAACCGGAGCTGAATGAAGCCATAC CAAACGACGAGCGTGACACCACGATGCCTGTAGCAATGGCAACAACGTTGCG CAAACTATTAACTGGCGAACTACTTACTCTAGCTTCCCGGCAACAATTAATAG ACTGGATGGAGGCGGATAAAGTTGCAGGACCACTTCTGCGCTCGGCCCTTCC GGCTGGCTGGTTTATTGCTGATAAATCTGGAGCCGGTGAGCGTGGGTCTCGC GGTATCATTGCAGCACTGGGGCCAGATGGTAAGCCCTCCCGTATCGTAGTTA TCTACACGACGGGGAGTCAGGCAACTATGGATGAACGAAATAGACAGATCGC TGAGATAGGTGCCTCACTGATTAAGCATTGGTAACTGTCAGACCAAGTTTACT CATATATACTTTAGATTGATTTAAAACTTCATTTTTAATTTAAAAGGATCTAGGT GAAGATCCTTTTTGATAATCTCATGACCAAAATCCCTTAACGTGAGTTTTCGTT CCACTGAGCGTCAGACCCCGTAGAAAAGATCAAAGGATCTTCTTGAGATCCTT TTTTTCTGCGCGTAATCTGCTGCTTGCAAACAAAAAAACCACCGCTACCAGCG GTGGTTTGTTTGCCGGATCAAGAGCTACCAACTCTTTTTCCGAAGGTAACTGG CTTCAGCAGAGCGCAGATACCAAATACTGTCCTTCTAGTGTAGCCGTAGTTAG GCCACCACTTCAAGAACTCTGTAGCACCGCCTACATACCTCGCTCTGCTAATC CTGTTACCAGTGGCTGCTGCCAGTGGCGATAAGTCGTGTCTTACCGGGTTGG ACTCAAGACGATAGTTACCGGATAAGGCGCAGCGGTCGGGCTGAACGGGGG GTTCGTGCACACAGCCCAGCTTGGAGCGAACGACCTACACCGAACTGAGATA CCTACAGCGTGAGCTATGAGAAAGCGCCACGCTTCCCGAAGGGAGAAAGGC GGACAGGTATCCGGTAAGCGGCAGGGTCGGAACAGGAGAGCGCACGAGGG AGCTTCCAGGGGGAAACGCCTGGTATCTTTATAGTCCTGTCGGGTTTCGCCA CCTCTGACTTGAGCGTCGATTTTTGTGATGCTCGTCAGGGGGCGGAGCCTA TGGAAAAACGCCAGCAACGCGGCCTTTTTACGGTTCCTGGCCTTTTGCTGGC CTTTTGCTCACATGTTCTTTCCTGCGTTATCCCCTGATTCTGTGGATAACCGTA |

| SEQ ID No | Description | Sequence |
|---|---|---|
| | | TTACCGCCTTTGAGTGAGCTGATACCGCTCGCCGCAGCCGAACGACCGAGC<br>GCAGCGAGTCAGTGAGCGAGGAAGCGGAAGAGCGCCCAATACGCAAACCGC<br>CTCTCCCCGCGCGTTGGCCGATTCATTAATGCAGCTGGCACGACAGGTTTCC<br>CGACTGGAAAGCGGGCAGTGAGCGCAACGCAATTAATGTGAGTTAGCTCACT<br>CATTAGGCACCCCAGGCTTTACACTTTATGCTTCCGGCTCGTATGTTGTGTGG<br>AATTGTGAGCGGATAACAATTTCAC |
| SEQ ID NO: 19 | Human Sarcoglycan A (hSCGA) Exon 7 with mutation (premature stop codon) | CTTGTCTGAGTCTGGATTCAAACCAGGAGGTCAGACCCTAGAGCTGTGCGCT<br>AACCAGTGCACTGTCCCGCCTCTGCTGGACTTTGTGTCTCCTGCCTCCTAGT<br>CCTGGCCCCTGCCATGTTCCTGGGGACCTCTGTGTCCAGCCAGCCACTTCCT<br>GCGTCAGCCCTGAGCTCTCTGTGCAGGTGGATAAGTAAGTGCCGGAGCCTG<br>CAGATGAGGTGCCCACCCCAGGTGATGGGATCCTGGAGCATGACCCGTTCTT<br>CTGCCCACCCACTGAGGCCCCAGACCGTGACTTCTTGGTGGATGCTCTGGTC<br>ACCCTCCTGGTGCCCCTGCTGGTGGCCCTGCTTCTCACCTTGCTGCTGGCCT<br>ATGTCATGTGCTGCCGGCGGGAGGGAAGGTGAATGTGGGCATGAAGGGCGG<br>GGGAGCACCTGCTGGAGCTCACACCCATGGGACTCACAGTGGCACTTGTGC<br>TGTATGGGACCCAGACACCATGGGAATGGGGTTCTCAGGCACAAAAGGAGT<br>GTGGGGCCCCTTTCTAGGCAACTTGGGGCTTGAGACCTGCCTGGCCTGGCA<br>CCAGGA |
| SEQ ID NO: 20 | hSCGA guide 1, 2, and 3 in AAV | TTACCGGATAAGGCGCAGCGGTCGGGCTGAACGGGGGGTTCGTGCACACAG<br>CCCAGCTTGGAGCGAACGACCTACACCGAACTGAGATACCTACAGCGTGAGC<br>TATGAGAAAGCGCCACGCTTCCCGAAGGGAGAAAGGCGGACAGGTATCCGG<br>TAAGCGGCAGGGTCGGAACAGGAGAGCGCACGAGGGAGCTTCCAGGGGGA<br>AACGCCTGGTATCTTTATAGTCCTGTCGGGTTTCGCCACCTCTGACTTGAGCG<br>TCGATTTTTGTGATGCTCGTCAGGGGGCGGAGCCTATGGAAAAACGCCAGC<br>AACGCGGCCTTTTTACGGTTCCTGGCCTTTTGCTGGCCTTTTGCTCACATGTC<br>CTGCAGGCAGCTGCGCGCTCGCTCGCTCACTGAGGCCGCCCGGGCGTCGG<br>GCGACCTTTGGTCGCCCGGCCTCAGTGAGCGAGCGAGCGCGCAGAGAGGG<br>AGTGGCCAACTCCATCACTAGGGGTTCCTGCGGCCGCAGAAATAGCAATTTC<br>CCATGATTCCTTCATATTTGCATATACGATACAAGGCTGTTAGAGAGATAATTG<br>GAATTAATTTGACTGTAAACACAAAGATATTAGTACAAAATACGTGACGTAGAA<br>AGTAATAATTTCTTGGGTAGTTTGCAGTTTTAAAATTATGTTTTAAAATGGACTA<br>TCATATGCTTACCGTAACTTGAAAGTATTTCGATTTCTTGGCTTTATATATCTTG<br>TGGAAAGGACGAAACACCGAGCTCTAGGGTCTGACCTCCGTTTTAGAGCTAG<br>AAATAGCAAGTTAAAATAAGGCTAGTCCGTTATCAACTTGAAAAAGTGGCACC<br>GAGTCGGTGCTTTTTTGCTTGCTAGAAATAGCAATTTCCCATGATTCCTTCATA<br>TTTGCATATACGATACAAGGCTGTTAGAGAGATAATTGGAATTAATTTGACTGT<br>AAACACAAAGATATTAGTACAAAATACGTGACGTAGAAAGTAATAATTTCTTGG<br>GTAGTTTGCAGTTTTAAAATTATGTTTTAAAATGGACTATCATATGCTTACCGT<br>AACTTGAAAGTATTTCGATTTCTTGGCTTTATATATCTTGTGGAAAGGACGAAA<br>CACCGAAGCCCCAAGTTGCCTAGAAGTTTTAGAGCTAGAAATAGCAAGTTAAA<br>ATAAGGCTAGTCCGTTATCAACTTGAAAAAGTGGCACCGAGTCGGTGCTTTTT<br>TGCTTGGGCTCGAGTTTCCCATGATTCCTTCATATTTGCATATACGATACAAG<br>GCTGTTAGAGAGATAATTGGAATTAATTTGACTGTAAACACAAAGATATTAGTA<br>CAAAATACGTGACGTAGAAAGTAATAATTTCTTGGGTAGTTTGCAGTTTTAAAA<br>TTATGTTTTAAAATGGACTATCATATGCTTACCGTAACTTGAAAGTATTTCGATT<br>TCTTGGCTTTATATATCTTGTGGAAAGGACGAAACACCGAAGCCCCAAGTTGC<br>CTATCCGTTTTAGAGCTAGAAATAGCAAGTTAAAATAAGGCTAGTCCGTTATC<br>AACTTGAAAAAGTGGCACCGAGTCGGTGCTTTTTTGCTTAAGGATGGTGAGC<br>AAGGGCGAGGAGCTGTTCACCGGGGTGGTGCCCATCCTGGTCGAGCTGGAC<br>GGCGACGTAAACGGCCACAAGTTCAGCGTGAGGGGCGAGGGCGAGGGCGA<br>TGCCACCAACGGCAAGCTGACCCTGAAGTTCATCTGCACCACCGGCAAGCTG<br>CCCGTGCCCTGGCCCACCCTCGTGACCACCCTGAGCCACGGCGTGCAGTGC<br>TTCGCCCGCTACCCCGACCACATGAAGCAGCACGACTTCTTCAAGTCCGCCA<br>TGCCCGAAGGCTACGTCCAGGAGCGCACCATCTTCTTCAAGGACGACGGCA<br>CCTACAAGACCCGCGCCGAGGTGAAGTTCGAGGGCGACACCCTGGTGAACC<br>GCATCGAGCTGAAGGGCGTCGACTTCAAGGAGGACGGCAACATCCTGGGGC<br>ACAAGCTGGAGTACAACTTCAACAGCCACAACATCTATATCATGGCCGTCAAG<br>CAGAAGAACGGCATCAAGGTGAACTTCAAGATCCGCCACAACGTGGAGGAC<br>GGCAGCGTGCAGCTCGCCGACCACTACCAGCAGAACACCCCCATCGGCGAC<br>GGCCCCGTGCTGCTGCCCGACAGCCACTACCTGAGCACCCAGTCCGTGCTG<br>AGCAAAGACCCCAACGAGAAGCGCGATCACATGGTCCTGCTGGAGTTCGC<br>ACCGCCGCCGGGATCACTCTCGGCATGGACGAGCTGTACAAGTGAGAATTC<br>CTAGAGCTCGCTGATCAGCCTCGACTGTGCCTTCTAGTTGCCAGCCATCTGT<br>TGTTTGCCCCTCCCCCGTGCCTTCCTTGACCCTGGAAGGTGCCACTCCCACT<br>GTCCTTTCCTAATAAAATGAGGAAATTGCATCGCATTGTCTGAGTAGGTGTCA<br>TTCTATTCTGGGGGGTGGGGTGGGCAGGACAGCAAGGGGGAGGATTGGG<br>AAGAGAATAGCAGGCATGCGCTTAATTAATATGCTAGCCAGCACGTGCGGAC<br>CGAGCGGCCGCAGGAACCCTAGTGATGGAGTTGGCCACTCCCTCTCTGCG<br>CGCTCGCTCGCTCACTGAGGCCGGGCGACCAAAGGTCGCCCGACGCCCGG<br>GCTTTGCCCGGGCGGCCTCAGTGAGCGAGCGAGCGCGCAGCTGCCTGCAG<br>GGGCGCCTGATGCGGTATTTTCTCCTTACGCATCTGTGCGGTATTTCACACC<br>GCATACGTCAAAGCAACCATAGTACGCGCCCTGTAGCGGCGCATTAAGCGCG<br>GCGGGTGTGGTGGTTACGCGCAGCGTGACCGCTACACTTGCCAGCGCCCTA |

| SEQ ID No | Description | Sequence |
|---|---|---|
| | | GCGCCCGCTCCTTTCGCTTTCTTCCCTTCCTTTCTCGCCACGTTCGCCGGCTT<br>TCCCCGTCAAGCTCTAAATCGGGGGCTCCCTTTAGGGTTCCGATTTAGTGCTT<br>TACGGCACCTCGACCCCAAAAAACTTGATTTGGGTGATGGTTCACGTAGTGG<br>GCCATCGCCCTGATAGACGGTTTTTCGCCCTTTGACGTTGGAGTCCACGTTC<br>TTTAATAGTGGACTCTTGTTCCAAACTGGAACAACACTCAACCCTATCTCGGG<br>CTATTCTTTTGATTTATAAGGGATTTTGCCGATTTCGGCCTATTGGTTAAAAAA<br>TGAGCTGATTTAACAAAAATTTAACGCGAATTTTAACAAAATATTAACGTTTAC<br>AATTTTATGGTGCACTCTCAGTACAATCTGCTCTGATGCCGCATAGTTAAGCC<br>AGCCCCGACACCCGCCAACACCCGCTGACGCGCCCTGACGGGCTTGTCTGC<br>TCCCGGCATCCGCTTACAGACAAGCTGTGACCGTCTCCGGGAGCTGCATGTG<br>TCAGAGGTTTTCACCGTCATCACCGAAACGCGCGAGACGAAAGGGCCTCGTG<br>ATACGCCTATTTTTATAGGTTAATGTCATGATAATAATGGTTTCTTAGACGTCA<br>GGTGGCACTTTTCGGGGAAATGTGCGCGGAACCCCTATTTGTTTATTTTTCTA<br>AATACATTCAAATATGTATCCGCTCATGAGACAATAACCCTGATAAATGCTTCA<br>ATAATATTGAAAAAGGAAGAGTATGAGTATTCAACATTTCCGTGTCGCCCTTAT<br>TCCCTTTTTTGCGGCATTTTGCCTTCCTGTTTTTGCTCACCCAGAAACGCTGG<br>TGAAAGTAAAAGATGCTGAAGATCAGTTGGGTGCACGAGTGGGTTACATCGA<br>ACTGGATCTCAACAGCGGTAAGATCCTTGAGAGTTTTCGCCCCGAAGAACGT<br>TTTCCAATGATGAGCACTTTTAAAGTTCTGCTATGTGGCGCGGTATTATCCCG<br>TATTGACGCCGGGCAAGAGCAACTCGGTCGCCGCATACACTATTCTCAGAAT<br>GACTTGGTTGAGTACTCACCAGTCACAGAAAAGCATCTTACGGATGGCATGA<br>CAGTAAGAGAATTATGCAGTGCTGCCATAACCATGAGTGATAACACTGCGGC<br>CAACTTACTTCTGACAACGATCGGAGGACCGAAGGAGCTAACCGCTTTTTTG<br>CACAACATGGGGGATCATGTAACTCGCCTTGATCGTTGGGAACCGGAGCTGA<br>ATGAAGCCATACCAAACGACGAGCGTGACACCACGATGCCTGTAGCAATGGC<br>AACAACGTTGCGCAAACTATTAACTGGCGAACTACTTACTCTAGCTTCCCGGC<br>AACAATTAATAGACTGGATGGAGGCGGATAAAGTTGCAGGACCACTTCTGCG<br>CTCGGCCCTTCCGGCTGGCTGGTTTATTGCTGATAAATCTGGAGCCGGTGAG<br>CGTGGGTCTCGCGGTATCATTGCAGCACTGGGGCCAGATGGTAAGCCCTCC<br>CGTATCGTAGTTATCTACACGACGGGGAGTCAGGCAACTATGGATGAACGAA<br>ATAGACAGATCGCTGAGATAGGTGCCTCACTGATTAAGCATTGGTAACTGTCA<br>GACCAAGTTTACTCATATATACTTTAGATTGATTTAAAACTTCATTTTTAATTTA<br>AAAGGATCTAGGTGAAGATCCTTTTTGATAATCTCATGACCAAAATCCCTTAAC<br>GTGAGTTTTCGTTCCACTGAGCGTCAGACCCCGTAGAAAAGATCAAAGGATC<br>TTCTTGAGATCCTTTTTTTCTGCGCGTAATCTGCTGCTTGCAAACAAAAAAACC<br>ACCGCTACCAGCGGTGGTTTGTTTGCCGGATCAAGAGCTACCAACTCTTTTTC<br>CGAAGGTAACTGGCTTCAGCAGAGCGCAGATACCAAATACTGTCCTTCTAGT<br>GTAGCCGTAGTTAGGCCACCACTTCAAGAACTCTGTAGCACCGCCTACATAC<br>CTCGCTCTGCTAATCCTGTTACCAGTGGCTGCTGCCAGTGGCGATAAGTCGT<br>GTCTTACCGGGTTGGACTCAAGACGATAG |
| SEQ ID NO: 21 | hSCGA replacement in AAV with no premature stop codon | TTACCGGATAAGGCGCAGCGGTCGGGCTGAACGGGGGGTTCGTGCACACAG<br>CCCAGCTTGGAGCGAACGACCTACACCGAACTGAGATACCTACAGCGTGAGC<br>TATGAGAAAGCGCCACGCTTCCCGAAGGGAGAAAGGCGGACAGGTATCCGG<br>TAAGCGGCAGGGTCGGAACAGGAGAGCGCACGAGGGAGCTTCCAGGGGGA<br>AACGCCTGGTATCTTTATAGTCCTGTCGGGTTTCGCCACCTCTGACTTGAGCG<br>TCGATTTTTGTGATGCTCGTCAGGGGGCGGAGCCTATGGAAAAACGCCAGC<br>AACGCGGCCTTTTTACGGTTCCTGGCCTTTTGCTGGCCTTTTGCTCACATGTC<br>CTGCAGGCAGCTGCGCGCTCGCTCGCTCACTGAGGCCGCCCGGGCGTCGG<br>GCGACCTTTGGTCGCCCGGCCTCAGTGAGCGAGCGAGCGCGCAGAGAGGG<br>AGTGGCCAACTCCATCACTAGGGGTTCCTGCGGCCGCAGAAATAGCAAAGCT<br>CTAGGGTCTGACCTCCTGGGTGCGCTAACCAGTGCACTGTCCCGCCTCTGCT<br>GGACTTTGTGTCTCCTGCCTCCTAGTCCTGGCCCTGCCATGTTCCTGGGGA<br>CCTCTGTGTCCAGCCAGCCACTTCCTGCGTCAGCCCTGAGCTCTCTGTGCAG<br>GTGGATAAGTCAGTGCCGGAGCCTGCAGATGAGGTGCCCACCCCAGGTGAT<br>GGGATCCTGGAGCATGACCCGTTCTTCTGCCCACCCACTGAGGCCCCAGAC<br>CGTGACTTCTTGGTGGATGCTCTGGTCACCCTCCTGGTGCCCCTGCTGGTGG<br>CCCTGCTTCTCACCTTGCTGCTGGCCTATGTCATGTGCTGCCGGCGGGAGG<br>GAAGGTGAATGTGGGCATGAAGGGCGGGGAGCACCTGCTGGAGCTCACAC<br>CCATGGGACTCACAGTGGCACTTGTGCTGTATGGGACCCAGACACCATGGGA<br>ATGGGGTTCTCAGGCACAAAAGGAGTGTGGGGCCAGCTCTAGGGTCTGACC<br>TCCTGGGCTTAAGGATGGTGAGCAAGGGCGAGGAGCTGTTCACCGGGGTGG<br>TGCCCATCCTGGTCGAGCTGGACGGCGACGTAAACGGCCACAAGTTCAGCG<br>TGAGGGGCGAGGGCGAGGGCGATGCCACCAACGGCAAGCTGACCCTGAAG<br>TTCATCTGCACCACCGGCAAGCTGCCCGTGCCCTGGCCCACCCTCGTGACC<br>ACCCTGAGCCACGGCGTGCAGTGCTTCGCCCGCTACCCCGACCACATGAAG<br>CAGCACGACTTCTTCAAGTCCGCCATGCCCGAAGGCTACGTCCAGGAGCGC<br>ACCATCTTCTTCAAGGACGACGGCACCTACAAGACCCGCGCCGAGGTGAAGT<br>TCGAGGGCGACACCCTGGTGAACCGCATCGAGCTGAAGGGCGTCGACTTCA<br>AGGAGGACGGCAACATCCTGGGGCACAAGCTGGAGTACAACTTCAACAGCC<br>ACAACATCTATATCATGGCCGTCAAGCAGAAGAACGGCATCAAGGTGAACTT<br>CAAGATCCGCCACAACGTGGAGGACGGCAGCGTGCAGCTCGCCGACCACTA<br>CCAGCAGAACACCCCCATCGGCGACGGCCCCGTGCTGCTGCCCGACAGCCA<br>CTACCTGAGCACCCAGTCCGTGCTGAGCAAAGACCCCAACGAGAAGCGCGA<br>TCACATGGTCCTGCTGGAGTTCGCACCGCCGCCGGGATCACTCTCGGCAT |

| SEQ ID No | Description | Sequence |
|---|---|---|
| | | GGACGAGCTGTACAAGTGAGAATTCCTAGAGCTCGCTGATCAGCCTCGACTG<br>TGCCTTCTAGTTGCCAGCCATCTGTTGTTTGCCCCTCCCCCGTGCCTTCCTTG<br>ACCCTGGAAGGTGCCACTCCCACTGTCCTTTCCTAATAAAATGAGGAAATTGC<br>ATCGCATTGTCTGAGTAGGTGTCATTCTATTCTGGGGGGTGGGGTGGGGCAG<br>GACAGCAAGGGGGAGGATTGGGAAGAGAATAGCAGGCATGCGCTTAATTAAT<br>ATGCTAGCCAGCACGTGCGGACCGAGCGGCCGCAGGAACCCCTAGTGATGG<br>AGTTGGCCACTCCCTCTCTGCGCGCTCGCTCGCTCACTGAGGCCGGGCGAC<br>CAAAGGTCGCCCGACGCCCGGGCTTTGCCCGGGCGGCCTCAGTGAGCGAG<br>CGAGCGCGCAGCTGCCTGCAGGGGCGCCTGATGCGGTATTTTCTCCTTACG<br>CATCTGTGCGGTATTTCACACCGCATACGTCAAAGCAACCATAGTACGCGCC<br>CTGTAGCGGCGCATTAAGCGCGGCGGGTGTGGTGGTTACGCGCAGCGTGAC<br>CGCTACACTTGCCAGCGCCCTAGCGCCCGCTCCTTTCGCTTTCTTCCCTTCC<br>TTTCTCGCCACGTTCGCCGGCTTTCCCCGTCAAGCTCTAAATCGGGGGCTCC<br>CTTTAGGGTTCCGATTTAGTGCTTTACGGCACCTCGACCCCAAAAAACTTGAT<br>TTGGGTGATGGTTCACGTAGTGGGCCATCGCCCTGATAGACGGTTTTTCGCC<br>CTTTGACGTTGGAGTCCACGTTCTTTAATAGTGGACTCTTGTTCCAAACTGGA<br>ACAACACTCAACCCTATCTCGGGCTATTCTTTTGATTTATAAGGGATTTTGCCG<br>ATTTCGGCCTATTGGTTAAAAAATGAGCTGATTTAACAAAAATTTAACGCGAAT<br>TTTAACAAAATATTAACGTTTACAATTTTATGGTGCACTCTCAGTACAATCTGC<br>TCTGATGCCGCATAGTTAAGCCAGCCCCGACACCCGCCAACACCCGCTGAC<br>GCGCCCTGACGGGCTTGTCTGCTCCCGGCATCCGCTTACAGACAAGCTGTG<br>ACCGTCTCCGGGAGCTGCATGTGTCAGAGGTTTTCACCGTCATCACCGAAAC<br>GCGCGAGACGAAAGGGCCTCGTGATACGCCTATTTTTATAGGTTAATGTCAT<br>GATAATAATGGTTTCTTAGACGTCAGGTGGCACTTTTCGGGGAAATGTGCGC<br>GGAACCCCTATTTGTTTATTTTTCTAAATACATTCAAATATGTATCCGCTCATG<br>AGACAATAACCCTGATAAATGCTTCAATAATATTGAAAAAGGAAGAGTATGAG<br>TATTCAACATTTCCGTGTCGCCCTTATTCCCTTTTTTGCGGCATTTTGCCTTCC<br>TGTTTTTGCTCACCCAGAAACGCTGGTGAAAGTAAAAGATGCTGAAGATCAGT<br>TGGGTGCACGAGTGGGTTACATCGAACTGGATCTCAACAGCGGTAAGATCCT<br>TGAGAGTTTTCGCCCCGAAGAACGTTTTCCAATGATGAGCACTTTTAAAGTTC<br>TGCTATGTGGCGCGGTATTATCCCGTATTGACGCCGGGCAAGAGCAACTCGG<br>TCGCCGCATACACTATTCTCAGAATGACTTGGTTGAGTACTCACCAGTCACAG<br>AAAAGCATCTTACGGATGGCATGACAGTAAGAGAATTATGCAGTGCTGCCATA<br>ACCATGAGTGATAACACTGCGGCCAACTTACTTCTGACAACGATCGGAGGAC<br>CGAAGGAGCTAACCGCTTTTTTGCACAACATGGGGGATCATGTAACTCGCCT<br>TGATCGTTGGGAACCGGAGCTGAATGAAGCCATACCAAACGACGAGCGTGAC<br>ACCACGATGCCTGTAGCAATGGCAACAACGTTGCGCAAACTATTAACTGGCG<br>AACTACTTACTCTAGCTTCCCGGCAACAATTAATAGACTGGATGGAGGCGGAT<br>AAAGTTGCAGGACCACTTCTGCGCTCGGCCCTTCCGGCTGGCTGGTTTATTG<br>CTGATAAATCTGGAGCCGGTGAGCGTGGGTCTCGCGGTATCATTGCAGCACT<br>GGGGCCAGATGGTAAGCCCTCCCGTATCGTAGTTATCTACACGACGGGGAGT<br>CAGGCAACTATGGATGAACGAAATAGACAGATCGCTGAGATAGGTGCCTCAC<br>TGATTAAGCATTGGTAACTGTCAGACCAAGTTTACTCATATATACTTTAGATTG<br>ATTTAAAACTTCATTTTTAATTTAAAAGGATCTAGGTGAAGATCCTTTTTGATAA<br>TCTCATGACCAAAATCCCTTAACGTGAGTTTTCGTTCCACTGAGCGTCAGACC<br>CCGTAGAAAAGATCAAAGGATCTTCTTGAGATCCTTTTTTTCTGCGCGTAATCT<br>GCTGCTTGCAAACAAAAAAACCACCGCTACCAGCGGTGGTTTGTTTGCCGGA<br>TCAAGAGCTACCAACTCTTTTTCCGAAGGTAACTGGCTTCAGCAGAGCGCAG<br>ATACCAAATACTGTCCTTCTAGTGTAGCCGTAGTTAGGCCACCACTTCAAGAA<br>CTCTGTAGCACCGCCTACATACCTCGCTCTGCTAATCCTGTTACCAGTGGCTG<br>CTGCCAGTGGCGATAAGTCGTGTCTTACCGGGTTGGACTCAAGACGATAG |
| SEQ ID NO: 22 | spCas9 in AAV | GGCGTCGGGCGACCTTTGGTCGCCCGGCCTCAGTGAGCGAGCGAGCGCGC<br>AGAGAGGGAGTGGCCAACTCCATCACTAGGGGTTCCTGCGGCCTCTAGAAA<br>GCTTAGCTGAATGGGGTCCGCCTCTTTTCCCTGCCTAAACAGACAGGAACTC<br>CTGCCAATTGAGGGCGTCACCGCTAAGGCTCCGCCCCAGCCTGGGCTCCAC<br>AACCAATGAAGGGTAATCTCGACAAAGAGCAAGGGTGGGGCGCGGGCGCG<br>CAGGTGCAGCAGCACACAGGCTGGTCGGGAGGGCGGGGCGCGACGTCTGC<br>CGTGCGGGGTCCCGGCATCGGTTGCGCGCACCGGTGCCACCATGTACCCAT<br>ACGATGTTCCAGATTACGCTTCGCCGAAGAAAAAGCGCAAGGTCGAAGCGTC<br>CGACAAGAAGTACAGCATCGGCCTGGACATCGGCACCAACTCTGTGGGCTG<br>GGCCGTGATCACCGACGAGTACAAGGTGCCCAGCAAGAAATTCAAGGTGCT<br>GGGCAACACCGACCGGCACAGCATCAAGAAGAACCTGATCGGAGCCCTGCT<br>GTTCGACAGCGGCGAAACAGCCGAGGCCACCCGGCTGAAGAGAACCGCCAG<br>AAGAAGATACACCAGACGGAAGAACCGGATCTGCTATCTGCAAGAGATCTTC<br>AGCAACGAGATGGCCAAGGTGGACGACAGCTTCTTCCACAGACTGGAAGAGT<br>CCTTCCTGGTGGAAGAGGATAAGAAGCACGAGCGGCACCCCATCTTCGGCA<br>ACATCGTGGACGAGGTGGCCTACCACGAGAAGTACCCCACCATCTACCACCT<br>GAGAAAGAAACTGGTGGACAGCACCGACAAGGCCGACCTGCGGCTGATCTA<br>TCTGGCCCTGGCCCACATGATCAAGTTCCGGGGCCACTTCCTGATCGAGGG<br>CGACCTGAACCCCGACAACAGCGACGTGGACAAGCTGTTCATCCAGCTGGT<br>GCAGACCTACAACCAGCTGTTCGAGGAAAACCCCATCAACGCCAGCGGCGT<br>GGACGCCAAGGCCATCCTGTCTGCCAGACTGAGCAAGAGCAGACGGCTGGA<br>AAATCTGATCGCCCAGCTGCCCGGCGAGAAGAAGAATGGCCTGTTCGGAAAC<br>CTGATTGCCCTGAGCCTGGGCCTGACCCCCAACTTCAAGAGCAACTTCGACC |

| SEQ ID No | Description | Sequence |
|---|---|---|
| | | TGGCCGAGGATGCCAAACTGCAGCTGAGCAAGGACACCTACGACGACGACC TGGACAACCTGCTGGCCCAGATCGGCGACCAGTACGCCGACCTGTTTCTGG CCGCCAAGAACCTGTCCGACGCCATCCTGCTGAGCGACATCCTGAGAGTGAA CACCGAGATCACCAAGGCCCCCCTGAGCGCCTCTATGATCAAGAGATACGAC GAGCACCACCAGGACCTGACCCTGCTGAAAGCTCTCGTGCGGCAGCAGCTG CCTGAGAAGTACAAAGAGATTTTCTTCGACCAGAGCAAGAACGGCTACGCCG GCTACATTGACGGCGGAGCCAGCCAGGAAGAGTTCTACAAGTTCATCAAGCC CATCCTGGAAAAGATGGACGGCACCGAGGAACTGCTCGTGAAGCTGAACAG AGAGGACCTGCTGCGGAAGCAGCGGACCTTCGACAACGGCAGCATCCCCCA CCAGATCCACCTGGGAGAGCTGCACGCCATTCTGCGGCGGCAGGAAGATTT TTACCCATTCCTGAAGGACAACCGGGAAAAGATCGAGAAGATCCTGACCTTC CGCATCCCCTACTACGTGGGCCCTCTGGCCAGGGGAAACAGCAGATTCGCC TGGATGACCAGAAAGAGCGAGGAAACCATCACCCCCTGGAACTTCGAGGAA GTGGTGGACAAGGGCGCTTCCGCCCAGAGCTTCATCGAGCGGATGACCAAC TTCGATAAGAACCTGCCCAACGAGAAGGTGCTGCCCAAGCACAGCCTGCTGT ACGAGTACTTCACCGTGTATAACGAGCTGACCAAAGTGAAATACGTGACCGA GGGAATGAGAAAGCCCGCCTTCCTGAGCGGCGAGCAGAAAAAGGCCATCGT GGACCTGCTGTTCAAGACCAACCGGAAAGTGACCGTGAAGCAGCTGAAAGA GGACTACTTCAAGAAAATCGAGTGCTTCGACTCCGTGGAAATCTCCGGCGTG GAAGATCGGTTCAACGCCTCCCTGGGCACATACCACGATCTGCTGAAAATTA TCAAGGACAAGGACTTCCTGGACAATGAGGAAAACGAGGACATTCTGGAAGA TATCGTGCTGACCCTGACACTGTTTGAGGACAGAGAGATGATCGAGGAACGG CTGAAAACCTATGCCCACCTGTTCGACGACAAAGTGATGAAGCAGCTGAAGC GGCGGAGATACACCGGCTGGGGCAGGCTGAGCCGGAAGCTGATCAACGGC ATCCGGGACAAGCAGTCCGGCAAGACAATCCTGGATTTCCTGAAGTCCGACG GCTTCGCCAACAGAAACTTCATGCAGCTGATCCACGACGACAGCCTGACCTT TAAAGAGGACATCCAGAAAGCCCAGGTGTCCGGCCAGGGCGATAGCCTGCA CGAGCACATTGCCAATCTGGCCGGCAGCCCCGCCATTAAGAAGGGCATCCT GCAGACAGTGAAGGTGGTGGACGAGCTCGTGAAAGTGATGGGCCGGCACAA GCCCGAGAACATCGTGATCGAAATGGCCAGAGAGAACCAGACCACCCAGAA GGGACAAGAACAGCCGCGAGAGAATGAAGCGGATCGAAGAGGGCATCAA AGAGCTGGGCAGCCAGATCCTGAAAGAACACCCCGTGGAAAACACCCAGCT GCAGAACGAGAAGCTGTACCTGTACTACCTGCAGAATGGGCGGGATATGTAC GTGGACCAGGAACTGGACATCAACCGGCTGTCCGACTACGATGTGGACCATA TCGTGCCTCAGAGCTTTCTGAAGGACGACTCCATCGACAACAAGGTGCTGAC CAGAAGCGACAAGAACCGGGGCAAGAGCGACAACGTGCCCTCCGAAGAGGT CGTGAAGAAGATGAAGAACTACTGGCGGCAGCTGCTGAACGCCAAGCTGATT ACCCAGAGAAAGTTCGACAATCTGACCAAGGCCGAGAGAGGCGGCCTGAGC GAACTGGATAAGGCCGGCTTCATCAAGAGACAGCTGGTGGAAACCCGGCAG ATCACAAAGCACGTGGCACAGATCCTGGACTCCCGGATGAACACTAAGTACG ACGAGAATGACAAGCTGATCCGGGAAGTGAAAGTGATCACCCTGAAGTCCAA GCTGGTGTCCGATTTCCGGAAGGATTTCCAGTTTTACAAAGTGCGCGAGATC AACAACTACCACCACGCCCACGACGCCTACCTGAACGCCGTCGTGGGAACC GCCCTGATCAAAAAGTACCCTAAGCTGGAAAGCGAGTTCGTGTACGGCGACT ACAAGGTGTACGACGTGCGGAAGATGATCGCCAAGAGCGAGCAGGAAATCG GCAAGGCTACCGCCAAGTACTTCTTCTACAGCAACATCATGAACTTTTTCAAG ACCGAGATTACCCTGGCCAACGGCGAGATCCGGAAGCGGCCTCTGATCGAG ACAAACGGCGAAACCGGGGAGATCGTGTGGGATAAGGGCCGGGATTTTGCC ACCGTGCGGAAAGTGCTGAGCATGCCCCAAGTGAATATCGTGAAAAAGACCG AGGTGCAGACAGGCGGCTTCAGCAAAGAGTCTATCCTGCCCAAGAGGAACA GCGATAAGCTGATCGCCAGAAAGAAGGACTGGGACCCTAAGAAGTACGGCG GCTTCGACAGCCCCACCGTGGCCTATTCTGTGCTGGTGGTGGCCAAAGTGG AAAAGGGCAAGTCCAAGAAACTGAAGAGTGTGAAAGAGCTGCTGGGGATCAC CATCATGGAAAGAAGCAGCTTCGAAGAATCCCATCGACTTTCTGGAAGCC AAGGGCTACAAAGAAGTGAAAAAGGACCTGATCATCAAGCTGCCTAAGTACT CCCTGTTCGAGCTGGAAAACGGCCGGAAGAGAATGCTGGCCTCTGCCGGCG AACTGCAGAAGGGAAACGAACTGGCCCTGCCCTCCAAATATGTGAACTTCCT GTACCTGGCCAGCCACTATGAGAAGCTGAAGGGCTCCCCCGAGGATAATGA GCAGAAACAGCTGTTTGTGGAACAGCACAAGCACTACCTGGACGAGATCATC GAGCAGATCAGCGAGTTCTCCAAGAGAGTGATCCTGGCCGACGCTAATCTGG ACAAAGTGCTGTCCGCCTACAACAAGCACCGGGATAAGCCCATCAGAGAGCA GGCCGAGAATATCATCCACCTGTTTACCCTGACCAATCTGGGAGCCCCTGCC GCCTTCAAGTACTTTGACACCACCATCGACCGGAAGAGGTACACCAGCACCA AAGAGGTGCTGGACGCCACCCTGATCCACCAGAGCATCACCGGCCTGTACG AGACACGGATCGACCTGTCTCAGCTGGGAGGCGACAGCCCCAAGAAGAAGA GAAAGGTGGAGGCCAGCTAAGAATTCAATAAAAGATCTTTATTTTCATTAGAT CTGTGTGTTGGTTTTTTGTGTGCGGCCGCAGGAACCCCTAGTGATGGAGTTG GCCACTCCCTCTCTGCGCGCTCGCTCGCTCACTGAGGCCGGGCGACCAAAG GTCGCCCGACGCCCGGGCTTTGCCCGGGCGGCCTCAGTGAGCGAGCGAGC GCGCAGCTGCCTGCAGGGGCGCCTGATGCGGTATTTTCTCCTTACGCATCTG TGCGGTATTTCACACCGCATACGTCAAAGCAACCATAGTACGCGCCCTGTAG CGGCGCATTAAGCGCGGCGGGTGTGGTGGTTACGCGCAGCGTGACCGCTAC ACTTGCCAGCGCCTTAGCGCCCGCTCCTTTCGCTTTCTTCCCTTCCTTTCTCG CCACGTTCGCCGGCTTTCCCCGTCAAGCTCTAAATCGGGGGCTCCCTTTAGG GTTCCGATTTAGTGCTTTACGGCACCTCGACCCCAAAAAACTTGATTTGGGTG |

Figure 3:
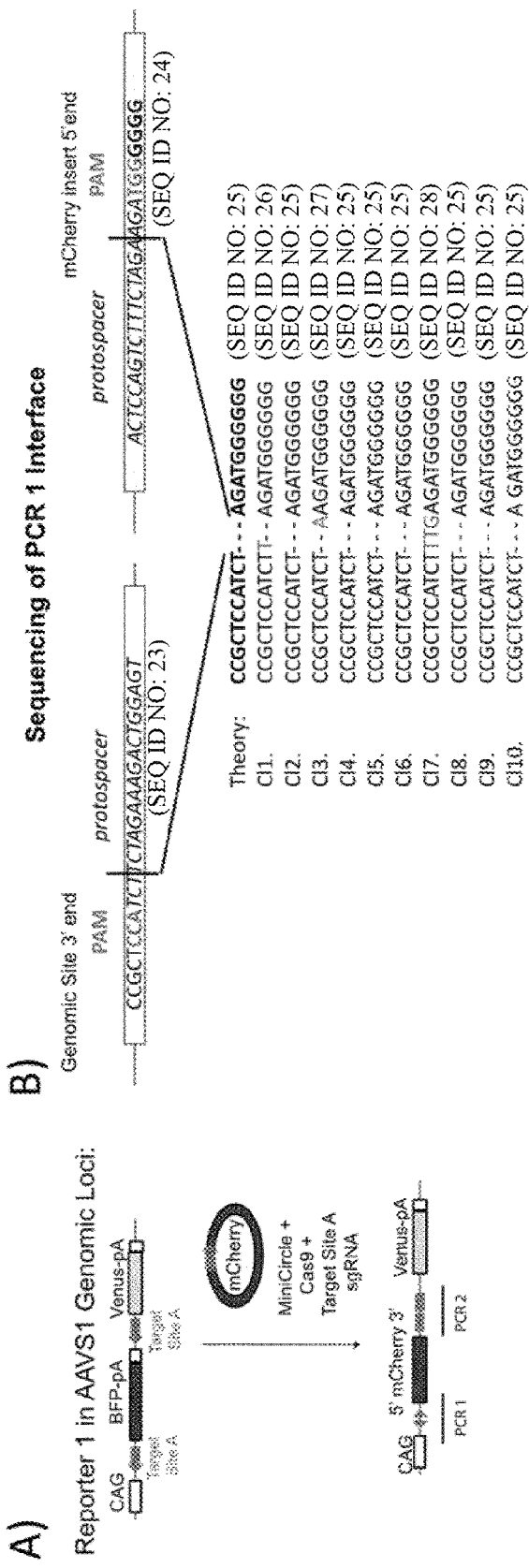
FIG. 3: Sequencing of 5' end PCR1 of the replaced sequence in Reporter 1. A) This schematic explains the PCR fragment shown in (B). PCR 1 is between the genomic sequence near the CAG reporter and the 5' end of the mCherry replacement sequence. This PCR sequence shows that the mCherry sequence was integrated into the target of interest. B) The figure at the top of B shows the original uncleaved genomic cut site on the left and the uncleaved mCherry sequence on the right; both are then cleaved by Cas9. The lines then indicate how the cleaved sequences are ligated together to form the final product (CAG-mCherry) as shown in the bottom of portion A. In this case 70% of the targets are Insertion-Deletion Mutation (INDEL) free. 2 of the INDELs were created by sticky end cleavage explained in FIG. 7. If the formation of these INDELs were problematic for a replacement (such as in a coding region), reversal of the direction of the cut site chosen (5' protospacer—PAM 3') can ameliorate this situation (explained in FIG. 7). In this case and in many possible uses of c-NHEJ for replacement of sequence, these small INDELs would not be problematic. Sequences shown: SEQ ID NO: 23; SEQ ID NO: 24; SEQ ID NO: 25; SEQ ID NO: 26; SEQ ID NO: 27; and SEQ ID NO: 28.

| SEQ ID No | Description | Sequence |
|---|---|---|
| | | ATGGTTCACGTAGTGGGCCATCGCCCTGATAGACGGTTTTTCGCCCTTTGAC<br>GTTGGAGTCCACGTTCTTTAATAGTGGACTCTTGTTCCAAACTGGAACAACAC<br>TCAACTCTATCTCGGGCTATTCTTTTGATTTATAAGGGATTTTGCCGATTTCGG<br>TCTATTGGTTAAAAAATGAGCTGATTTAACAAAAATTTAACGCGAATTTTAACA<br>AAATATTAACGTTTACAATTTTATGGTGCACTCTCAGTACAATCTGCTCTGATG<br>CCGCATAGTTAAGCCAGCCCCGACACCCGCCAACACCCGCTGACGCGCCCT<br>GACGGGCTTGTCTGCTCCCGGCATCCGCTTACAGACAAGCTGTGACCGTCTC<br>CGGGAGCTGCATGTGTCAGAGGTTTTCACCGTCATCACCGAAACGCGCGAGA<br>CGAAAGGGCCTCGTGATACGCCTATTTTTATAGGTTAATGTCATGATAATAAT<br>GGTTTCTTAGACGTCAGGTGGCACTTTTCGGGGAAATGTGCGCGGAACCCCT<br>ATTTGTTTATTTTTCTAAATACATTCAAATATGTATCCGCTCATGAGACAATAAC<br>CCTGATAAATGCTTCAATAATATTGAAAAAGGAAGAGTATGAGTATTCAACATT<br>TCCGTGTCGCCCTTATTCCCTTTTTTGCGGCATTTTGCCTTCCTGTTTTTGCTC<br>ACCCAGAAACGCTGGTGAAAGTAAAAGATGCTGAAGATCAGTTGGGTGCACG<br>AGTGGGTTACATCGAACTGGATCTCAACAGCGGTAAGATCCTTGAGAGTTTTC<br>GCCCCGAAGAACGTTTTCCAATGATGAGCACTTTTAAAGTTCTGCTATGTGGC<br>GCGGTATTATCCCGTATTGACGCCGGGCAAGAGCAACTCGGTCGCCGCATAC<br>ACTATTCTCAGAATGACTTGGTTGAGTACTCACCAGTCACAGAAAAGCATCTT<br>ACGGATGGCATGACAGTAAGAGAATTATGCAGTGCTGCCATAACCATGAGTG<br>ATAACACTGCGGCCAACTTACTTCTGACAACGATCGGAGGACCGAAGGAGCT<br>AACCGCTTTTTTGCACAACATGGGGGATCATGTAACTCGCCTTGATCGTTGGG<br>AACCGGAGCTGAATGAAGCCATACCAAACGACGAGCGTGACACCACGATGC<br>CTGTAGCAATGGCAACAACGTTGCGCAAACTATTAACTGGCGAACTACTTACT<br>CTAGCTTCCCGGCAACAATTAATAGACTGGATGGAGGCGGATAAAGTTGCAG<br>GACCACTTCTGCGCTCGGCCCTTCCGGCTGGCTGGTTTATTGCTGATAAATC<br>TGGAGCCGGTGAGCGTGGAAGCCGCGGTATCATTGCAGCACTGGGGCCAGA<br>TGGTAAGCCCTCCCGTATCGTAGTTATCTACACGACGGGGAGTCAGGCAACT<br>ATGGATGAACGAAATAGACAGATCGCTGAGATAGGTGCCTCACTGATTAAGC<br>ATTGGTAACTGTCAGACCAAGTTTACTCATATATACTTTAGATTGATTTAAAAC<br>TTCATTTTTAATTTAAAAGGATCTAGGTGAAGATCCTTTTTGATAATCTCATGAC<br>CAAAATCCCTTAACGTGAGTTTTCGTTCCACTGAGCGTCAGACCCCGTAGAAA<br>AGATCAAAGGATCTTCTTGAGATCCTTTTTTTCTGCGCGTAATCTGCTGCTTG<br>CAAACAAAAAAACCACCGCTACCAGCGGTGGTTTGTTTGCCGGATCAAGAGC<br>TACCAACTCTTTTTCCGAAGGTAACTGGCTTCAGCAGAGCGCAGATACCAAAT<br>ACTGTTCTTCTAGTGTAGCCGTAGTTAGGCCACCACTTCAAGAACTCTGTAGC<br>ACCGCCTACATACCTCGCTCTGCTAATCCTGTTACCAGTGGCTGCTGCCAGT<br>GGCGATAAGTCGTGTCTTACCGGGTTGGACTCAAGACGATAGTTACCGGATA<br>AGGCGCAGCGGTCGGGCTGAACGGGGGGTTCGTGCACACAGCCCAGCTTG<br>GAGCGAACGACCTACACCGAACTGAGATACCTACAGCGTGAGCTATGAGAAA<br>GCGCCACGCTTCCCGAAGGGAGAAAGGCGGACAGGTATCCGGTAAGCGGCA<br>GGGTCGGAACAGGAGAGCGCACGAGGGAGCTTCCAGGGGGAAACGCCTGG<br>TATCTTTATAGTCCTGTCGGGTTTCGCCACCTCTGACTTGAGCGTCGATTTTT<br>GTGATGCTCGTCAGGGGGGCGGAGCCTATGGAAAAACGCCAGCAACGCGGC<br>CTTTTTACGGTTCCTGGCCTTTTGCTGGCCTTTTGCTCACATGTCCTGCAGGC<br>AGCTGCGCGCTCGCTCGCTCACTGAGGCCGCCCG |
| SEQ ID NO: 23 | FIG. 3, Genomic Site 3' end | CCGCTCCATCTTCTAGAAAGACTGGAGT |
| SEQ ID NO: 24 | FIG. 3, mCherry insert 5'end | ACTCCAGTCTTTCTAGAAGATGGGGGG |
| SEQ ID NO: 25 | FIG. 3, Theory = CI2 = CI4 =CI5 = CI6 =CI8 = CI9 =CI10 | CCGCTCCATCTAGATGGGGGG |
| SEQ ID NO: 26 | FIG. 3, CI1 | CCGCTCCATCTTAGATGGGGGG |
| SEQ ID NO: 27 | FIG. 3, CI3 | CCGCTCCATCTAAGATGGGGGG |

Figure 4:
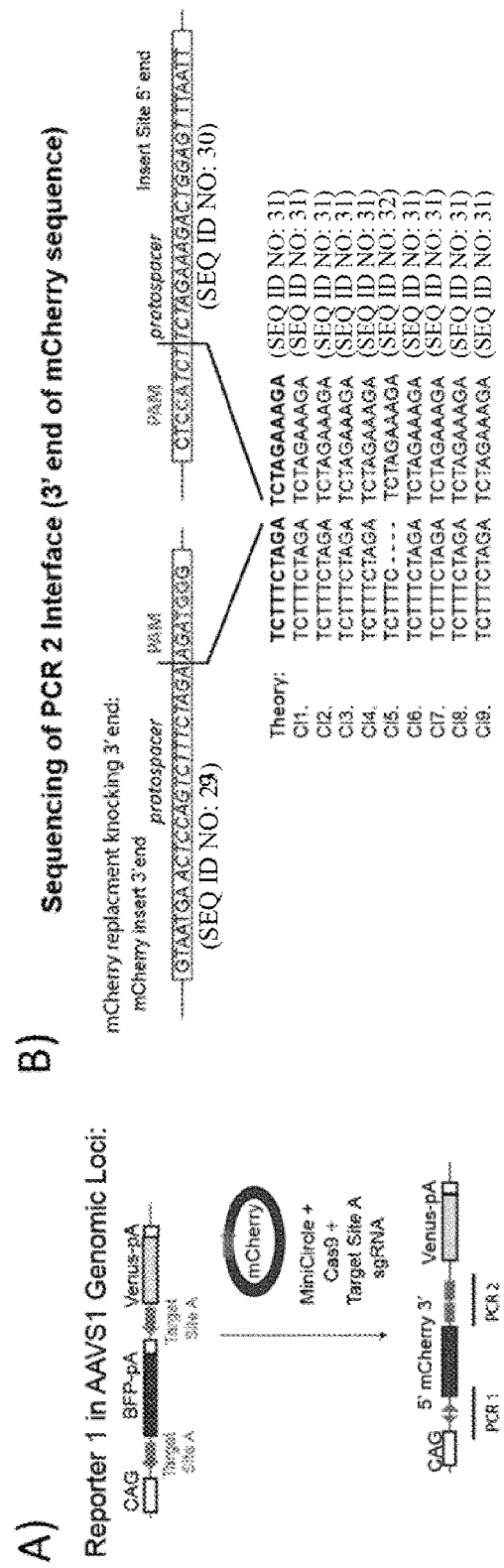
FIG. 4: Sequencing of the 3' end PCR 2 of the replaced sequence in Reporter 1. A) This schematic explains the PCR fragment shown in B. PCR 2 is between the 3' end of the mCherry replacement sequence and the 5' end of the genomic DNA. This PCR sequence shows that the mCherry sequence was integrated into the target of interest. B) The figure at the top of B shows the original uncleaved genomic cut site on the right and the uncleaved mCherry sequence on the left; both are then cleaved by Cas9. The lines then indicate how the cleaved sequences are ligated together to form the final product (CAG-mCherry) as shown in the bottom of part A). In this case 90% of the targets are Insertion-Deletion Mutation (INDEL) free. The one clone with an INDEL is a deletion formed during the c-NHEJ end processing. Sequences shown include: SEQ ID NO: 29; SEQ ID NO: 30; SEQ ID NO: 31; and SEQ ID NO: 32. The lack of "insertion" INDELs is due to the portions of the Cas9 cut sequences that are being ligated. The mechanism is more clearly explained in FIG. 7. For design purposes it should be noted that the two protospacer containing sides may results in more perfect ligations compared to the ligation of the PAM containing sides (due to the sticky cleavage of Cas9).
Figure 7:
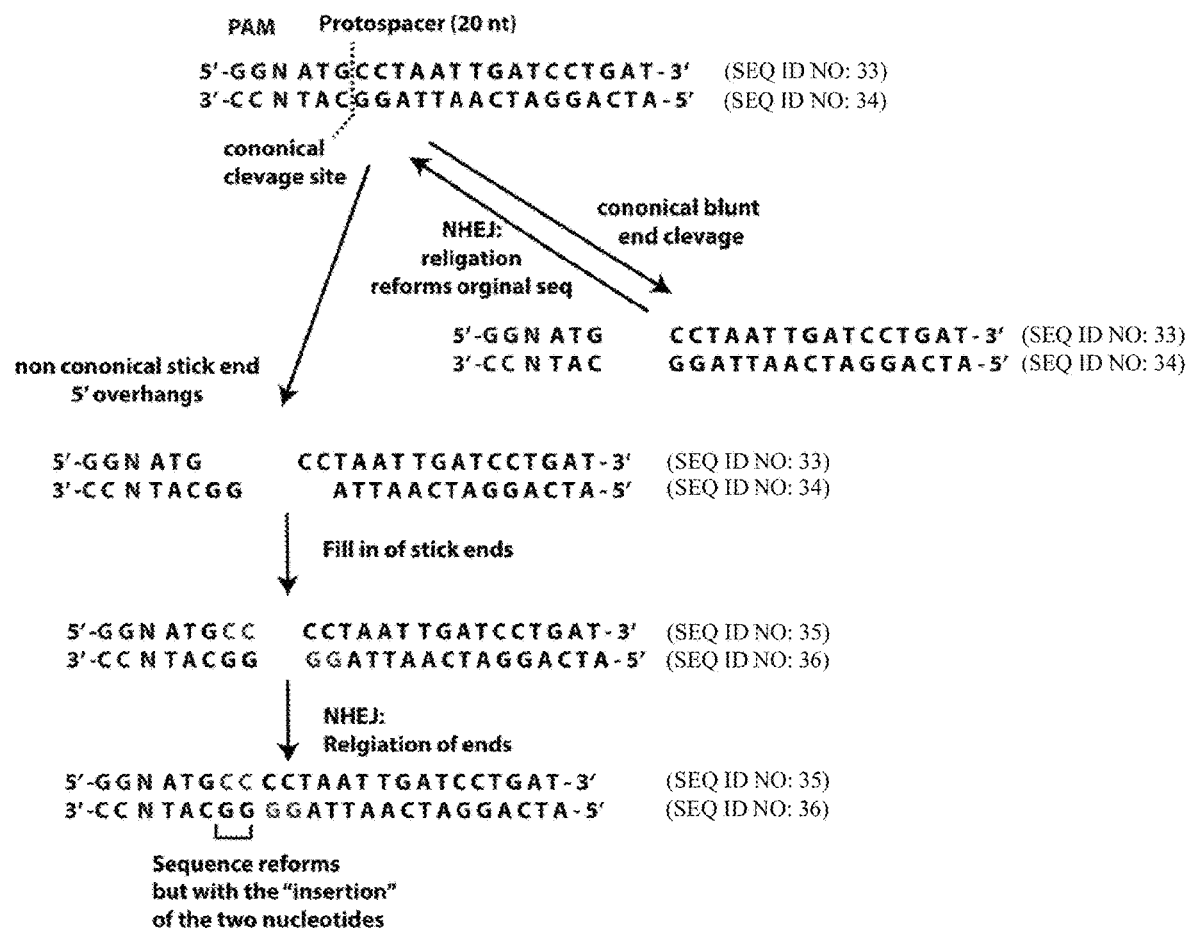
FIG. 7: Showing the staggered cleavage and filling in caused by Cas9. This figure explains how NHEJ after Cas9 cutting can relegate perfectly the restriction site or create some inserted nucleotides depending on how the Cas9 cleaves the genome. It is commonly accepted that Cas9 can blunt end cleave the genome. When this happens the double strand break can relegate and reform the original sequence with no mutations. In this case the genome could be cut again if Cas9 is still around. However it is less well known that Cas9 can cut to create 5' stick ends. In this case the sticky end overhangs are filled in by the NHEJ machinery (in grey) and then the sequence can be relegated. When this happens it appears that there has been an insertion, and this destroys the PAM site upon ligation. This figure does not discuss deletions that can form during NHEJ which is a well known phenomena, nor insertions that can also be randomly created during NHEJ, but rather focuses on insertions formed due non-canonical cleavage of the genome by Cas9 that creates sticky ends. Sequences shown include: SEQ ID NO: 33; SEQ ID NO: 34; SEQ ID NO: 35; and SEQ ID NO: 36.
Figure 9:
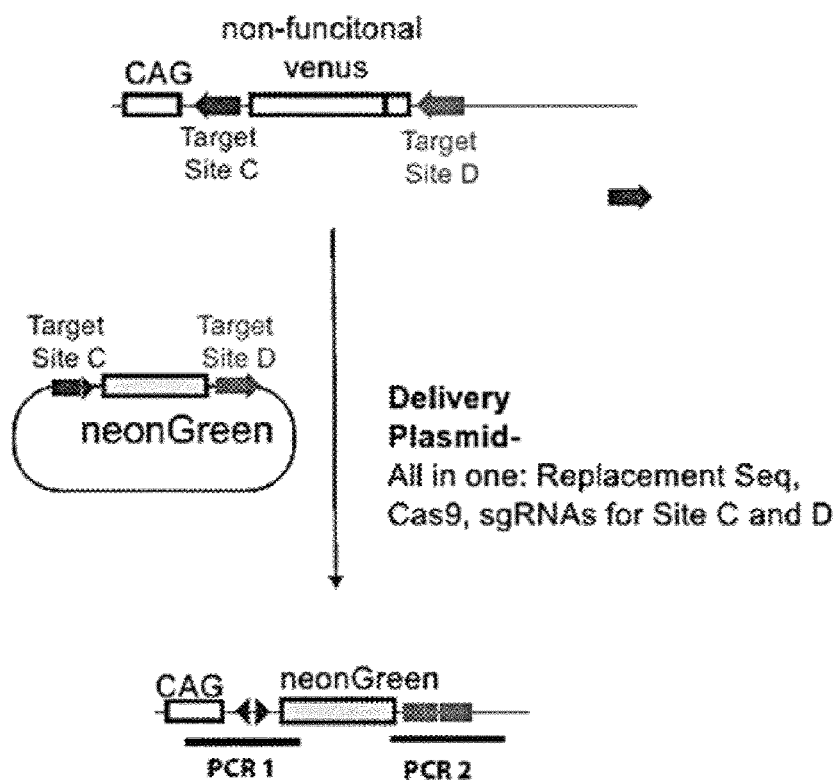
FIG. 9: Sequencing of 5' end and 3' end showing the replacement of sequence in Reporter 2. A) Shows a schematic of the transfected replacement of a sequence in HEK293 Cells. A dysfunctional fluorescent sequence was replaced by a functional turboGFP sequence. The cells were sorted and single cell colonies expanded. The gDNA was extracted from each single colony and PCR at the interface of the replacement sequence was done. B) In the 5' end there was an unusual and highly atypical resection pattern. Sequences shown: SEQ ID NO: 37; SEQ ID NO: 38; SEQ ID NO: 39; and SEQ ID NO: 40. C) At the 3' end there was insertions and deletions. However both shows that the turboGFP was correctly integrated into the genome, replacing the sequence in the correct location. Sequences shown: SEQ ID NO: 41; SEQ ID NO: 42; SEQ ID NO: 43; SEQ ID NO: 44; SEQ ID NO: 45; and SEQ ID NO: 46.
Figure 9:
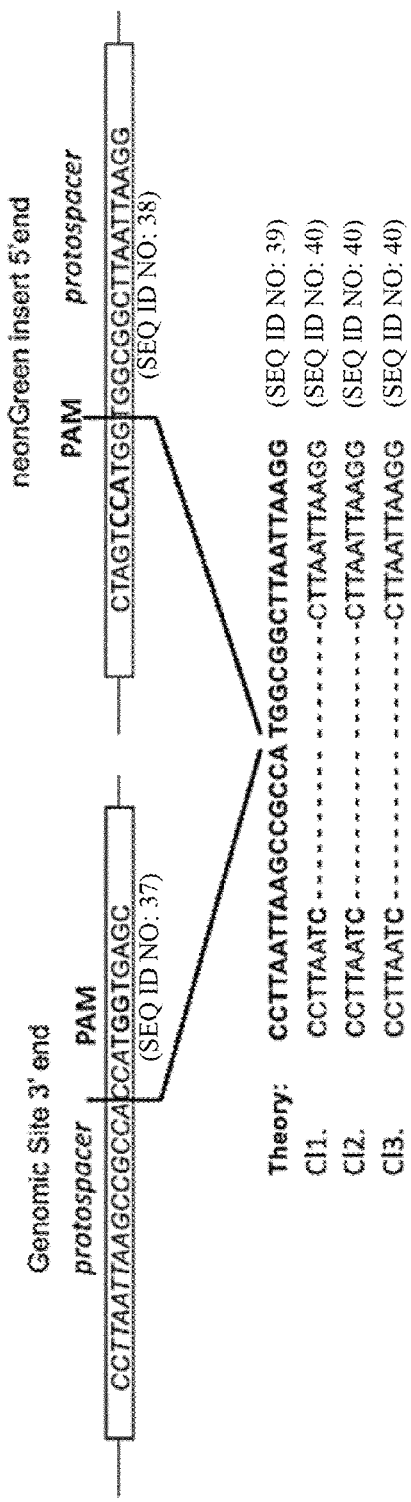
Figure 9:
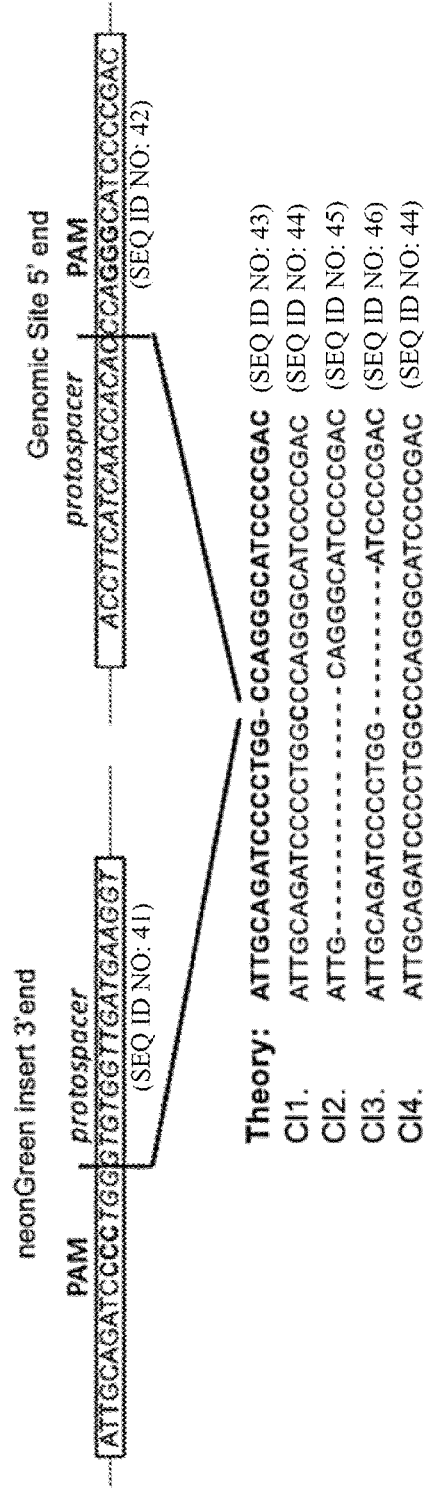

| SEQ ID No | Description | Sequence |
|---|---|---|
| SEQ ID NO: 28 | FIG. 3, CI7 | CCGCTCCATCTTTGAGATGGGGGG |
| SEQ ID NO: 29 | FIG. 4, mCherry insert 3' end | GTAATGAACTCCAGTCTTTCTAGAAGATGGG |
| SEQ ID NO: 30 | FIG. 4, Insert Site 5' end | CTCCATCTTCTAGAAAGACTGGAGTTTAATT |
| SEQ ID NO: 31 | FIG. 4, Theory = CI1 = CI2 =CI3 = CI4 =CI6 = CI7 =CI8 = CI9 | TCTTTCTAGATCTAGAAAGA |
| SEQ ID NO: 32 | FIG. 4, CI5 | TCTTTCTCTAGAAAGA |
| SEQ ID NO: 33 | FIG. 7, PAM Protospacer 5' to 3' = Religation reforms original seq 5' to 3' = non cononical stick end 5' to 3' | GGNATGCCTAATTGATCCTGAT |
| SEQ ID NO: 34 | FIG. 7, PAM Protospacer 3' to 5' = Religation reforms original seq 3' to 5' = non canonical stick end 3' to 5' | CCNTACGGATTAACTAGGACTA |
| SEQ ID NO: 35 | FIG. 7, Fill in of stick ends 5' to 3' = Religation of ends 5' to 3' | GGNATGCCCCTAATTGATCCTGAT |
| SEQ ID NO: 36 | FIG. 7, Fill in of stick ends 3' to 5' = Religation of ends 3' to 5' | CCNTACGGGGATTAACTAGGACTA |
| SEQ ID NO: 37 | FIG. 9 b, Genomic Site 3' end | CCTTAATTAAGCCGCCACCATGGTGAGC |
| SEQ ID NO: 38 | FIG. 9 b, turboGFP insert 5' end | CTAGTCCATGGTGGCGGCTTAATTAAGG |
| SEQ ID NO: 39 | FIG. 9 b, Theory | TTAATTAAGCCGCCATGGCGGCTTAATTAAGG |

Figure 2:
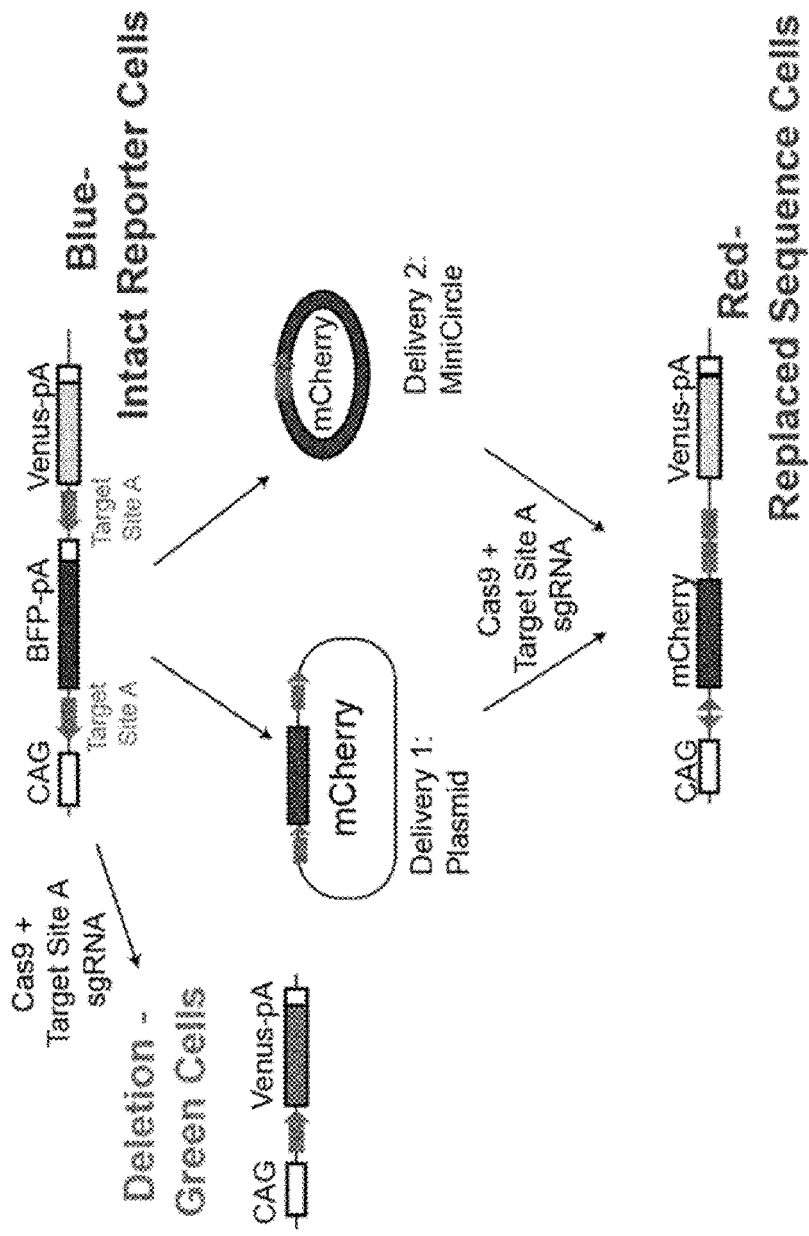
FIG. 2: Replacement of Sequence by fluorophore reporter in Reporter 1 cell line in Example 1. This is an overview of the genetic 'Reporter 1' that is used in Example 1 to show a replacement of sequence using the c-NHEJ pathway. The reporter is integrated into both copies of the AAVS1 Locus. A CAG promoter drives a BFP-pA sequence resulting in all cells being blue. This BFP sequence is flanked by a Cas9 recognition site "Site A". If Cas9 cleaves both sides and excises out the BFP-pA, the following Venus-pA that had not been coding, now is moved behind the CAG promoter and turns the cells green—indicating a deletion. The replacement sequence, in this case an mCherry coding sequence, is delivered by plasmid (Delivery option 1) or by MiniCircle (Delivery option 2). When the replacement sequence is co-delivered with Cas9 and the sgRNA the mCherry sequence replaces the BFP-pA sequence, turning the cells Red.

| SEQ ID No | Description | Sequence |
|---|---|---|
| SEQ ID NO: 40 | FIG. 9 b, CI1 = CI2 = CI3 | CCTTAATCCTTAATTAAGG |
| SEQ ID NO: 41 | FIG. 9 c, turboGFP insert 3'end | ATTGCAGATCCCCTGGGTGTGGTTGATGAAGGT |
| SEQ ID NO: 42 | FIG. 9 c, Genomic Site 5end | ACCTTCATCAACCACACCCAGGGCATCCCCGAC |
| SEQ ID NO: 43 | FIG. 9 c, Theory | ATTGCAGATCCCCTGGCCAGGGCATCCCCGAC |
| SEQ ID NO: 44 | FIG. 9 c, CI1 = CI4 | ATTGCAGATCCCCTGGCCCAGGGCATCCCCGAC |
| SEQ ID NO: 45 | FIG. 9 c, CI2 | ATTGCAGGGCATCCCCGAC |
| SEQ ID NO: 46 | FIG. 9 c, CI3 | ATTGCAGATCCCCTGGATCCCCGAC |
| SEQ ID NO: 47 | 5' junction PCR primer 1 (PCR 1 on FIG. 2) | TTGTCCCAAATCTGTGCGGA |
| SEQ ID NO: 48 | 5' junction PCR primer 2 (PCR 1 on FIG. 2) | CAAGTAGTCGGGGATGTCGG |
| SEQ ID NO: 49 | 3' junction PCR primer 1 (mCherry insert with the 5' region of genomic DNA, PCR 2 noted on FIG. 2) | CCGACTACTTGAAGCTGTCCTT |
| SEQ ID NO: 50 | 3' junction PCR primer 2 (mCherry insert with the 5' region of genomic DNA, PCR 2 noted on FIG. 2) | CCCATATGTCCTTCCGAGTGAG |
| SEQ ID NO: 51 | 5' end PCR primer 1 (HEK293 Cells with Reporter 2) | CGTAGGTGTAGCGGTAGTTAAC |
| SEQ ID NO: 52 | 5' end PCR primer 2 (HEK293 Cells with Reporter 2) | TTCGGCTTCTGGCGTGTGACC |

| SEQ ID No | Description | Sequence |
|---|---|---|
| SEQ ID NO: 53 | 3' end PCR primer 1 (HEK293 Cells with Reporter 2) | GTTAACTACCGCTACACCTACG |
| SEQ ID NO: 54 | 3' end PCR primer 2 (HEK293 Cells with Reporter 2) | GGTACAGCATCTCGGTGTTGG |
| SEQ ID NO: 55 | Example 5: Polb-Minicircle (circular DNA) | TGACCCACACAAAATTAGTCTTTTAGCAGACTGGTATGTTTCCAATAAGATCAT<br>TTAAGTCCTCAAAGCATTCCTAAATCATTGTTAGACTTTTTTTTTCTTAAAGAT<br>TGAGGGCAGAGGAAGTCTGCTAACATGCGGTGACGTGGAGGAGAATCCCGG<br>CCCTGCTAGCATGGTGAGCAAGGGCGAGGAGGATAACATGGCCATCATCAA<br>GGAGTTCATGCGCTTCAAGGTGCACATGGAGGGCTCCGTGAACGGCCACGA<br>GTTCGAGATCGAGGGCGAGGGCGAGGGCCGCCCCTACGAGGGCACCCAGA<br>CCGCCAAGCTGAAGGTGACCAAGGGTGGCCCCCTGCCCTTCGCCTGGGACA<br>TCCTGTCCCCTCAGTTCATGTACGGCTCCAAGGCCTACGTGAAGCACCCCGC<br>CGACATCCCCGACTACTTGAAGCTGTCCTTCCCCGAGGGCTTCAAGTGGGAG<br>CGCGTGATGAACTTCGAGGACGGCGGCGTGGTGACCGTGACCCAGGACTCC<br>TCCCTGCAGGACGGCGAGTTCATCTACAAGGTGAAGCTGCGCGGCACCAAC<br>TTCCCCTCAGACGGCCCCGTAATGCAGAAGAAAACCATGGGCTGGGAGGCC<br>TCCTCCGAGCGGATGTACCCCGAGGACGGCGCCCTGAAGGGCGAGATCAAG<br>CAGAGGCTGAAGCTGAAGGACGGCGGCCACTACGACGCTGAGGTCAAGACC<br>ACCTACAAGGCCAAGAAGCCCGTGCAGCTGCCCGGCGCCTACAACGTCAAC<br>ATCAAGTTGGACATCACCTCCCACAACGAGGACTACACCATCGTGGAACAGT<br>ACGAACGCGCCGAGGGCCGCCACTCCACCGGCGGCATGGACGAGCTGTAC<br>AAGTAAGAATTCCTAGAGCTCGCTGATCAGCCTCGACTGTGCCTTCTAGTTGC<br>CAGCCATCTGTTGTTTGCCCCTCCCCCGTGCCTTCCTTGACCCTGGAAGGTG<br>CCACTCCCACTGTCCTTTCCTAATAAAATGAGGAAATTGCATCGCATTGTCTG<br>AGTAGGTGTCATTCTATTCTGGGGGGTGGGTGGGCAGGACAGCAAGGGG<br>GAGGATTGGGAAGAGAATAGCAGGCATGCTGGGGGGATCCCTGCAGGAGCT<br>CGTCGACCCATGGGGCCCGCCCCAACTGGGGTAACCTTTGGGCTCCCCGG<br>GCGCGACTAGTGAATTCAGATCTGATATCTCTAGAAGTCCTGGG |
| SEQ ID NO: 56 | Example 5: Mini circle target 1: the beginning and end of the MC when combined form a Cas9 recognition site. This is the same site targeting upstream of POLB exon 5. It cuts the mini-circle plasmid, linearizing it, and allowing for c-NHEJ/a-EJ to ligate in the MC sequence | TGACCCACACAAAATTA |
| SEQ ID NO: 57 | Example 5: Native gene exon splice acceptor + 50-80 bp of sequence upstream (each gene has a different sequence) | GTCTTTTAGCAGACTGGTATGTTTCCAATAAGATCATTTAAGTCCTCAAAGCAT<br>TCCTAAATCATTGTTAGACTTTTTTTTTCTTAAA |

| SEQ ID No | Description | Sequence |
|---|---|---|
| SEQ ID NO: 58 | Example 5: 2A sequence | GAGGGCAGAGGAAGTCTGCTAACATGCGGTGACGTGGAGGAGAATCCCGGC<br>CCT |
| SEQ ID NO: 59 | Example 5: mCherry seq | ATGGTGAGCAAGGGCGAGGAGGATAACATGGCCATCATCAAGGAGTTCATGC<br>GCTTCAAGGTGCACATGGAGGGCTCCGTGAACGGCCACGAGTTCGAGATCG<br>AGGGCGAGGGCGAGGGCCGCCCCTACGAGGGCACCCAGACCGCCAAGCTG<br>AAGGTGACCAAGGGTGGCCCCCTGCCCTTCGCCTGGGACATCCTGTCCCCT<br>CAGTTCATGTACGGCTCCAAGGCCTACGTGAAGCACCCCGCCGACATCCCC<br>GACTACTTGAAGCTGTCCTTCCCCGAGGGCTTCAAGTGGGAGCGCGTGATGA<br>ACTTCGAGGACGGCGGCGTGGTGACCGTGACCCAGGACTCCTCCCTGCAGG<br>ACGGCGAGTTCATCTACAAGGTGAAGCTGCGCGGCACCAACTTCCCCCTCAGA<br>CGGCCCCGTAATGCAGAAGAAAACCATGGGCTGGGAGGCCTCCTCCGAGCG<br>GATGTACCCCGAGGACGGCGCCCTGAAGGGCGAGATCAAGCAGAGGCTGAA<br>GCTGAAGGACGGCGGCCACTACGACGCTGAGGTCAAGACCACCTACAAGGC<br>CAAGAAGCCCGTGCAGCTGCCCGGCGCCTACAACGTCAACATCAAGTTGGA<br>CATCACCTCCCACAACGAGGACTACACCATCGTGGAACAGTACGAACGCGCC<br>GAGGGCCGCCACTCCACCGGCGGCATGGACGAGCTGTACAAGTAA |
| SEQ ID NO: 60 | Example 5: pA | GAATTCCTAGAGCTCGCTGATCAGCCTCGACTGTGCCTTCTAGTTGCCAGCC<br>ATCTGTTGTTTGCCCCTCCCCCGTGCCTTCCTTGACCCTGGAAGGTGCCACT<br>CCCACTGTCCTTTCCTAATAAAATGAGGAAATTGCATCGCATTGTCTGAGTAG<br>GTGTCATTCTATTCTGGGGGGTGGGGTGGGGCAGGACAGCAAGGGGGAGGA<br>TTGGGAAGAGAATAGCAGGCATGCTGGGG |
| — | Example 5: Mini circle target 2: the beginning and end of the MC when combined form a Cas9 recognition site. This is the same site targeting upstream of POLB exon 5. It cuts the mini-circle plasmid, linearizing it, and allowing for c-NHEJ/a-EJ to ligate in the MC sequence | CCTGGG |
| SEQ ID NO: 61 | Example 5: PolbP1 primer | CCATACCCGGCCATCTTTTAGA |
| SEQ ID NO: 62 | Example 5: PolbP2 primer | GCTTGAGGGCTTGTTCCAAATT |
| SEQ ID NO: 63 | Example 5: PolbP3 primer | CCATACCCGGCCATCTTTTAGA |
| SEQ ID NO: 64 | Example 5: PolbP4 primer | ACTCCTTGATGATGGCCATGTT |
| SEQ ID NO: 65 | Example 5: PolbP5 primer | ATCAAGTTGGACATCACCTCCC |
| SEQ ID NO: 66 | Example 5: PolbP6 primer | GCTTGAGGGCTTGTTCCAAATT |
| SEQ ID NO: 67 | Example 5: Plasmid DNA (circular): Expression vector for Cas9 + two POLB specific Guide RNAs | CCGTTACATAACTTACGGTAAATGGCCCGCCTGGCTGACCGCCCAACGACCC<br>CCGCCCATTGACGTCAATAGTAACGCCAATAGGGACTTTCCATTGACGTCAAT<br>GGGTGGAGTATTTACGGTAAACTGCCCACTTGGCAGTACATCAAGTGTATCAT<br>ATGCCAAGTACGCCCCCTATTGACGTCAATGACGGTAAATGGCCCGCCTGGC<br>ATTGTGCCCAGTACATGACCTTATGGGACTTTCCTACTTGGCAGTACATCTAC<br>GTATTAGTCATCGCTATTACCATGGTCGAGGTGAGCCCCACGTTCTGCTTCAC<br>TCTCCCCATCTCCCCCCCCTCCCCACCCCCAATTTTGTATTTATTTATTTTTA<br>ATTATTTTGTGCAGCGATGGGGGCGGGGGGGGGGGGGCGCGCGCCAG<br>GCGGGGCGGGCGGGCGAGGGCGGGGCGGGGCGAGGCGGAGAGGTG |

| SEQ ID No | Description | Sequence |
|---|---|---|
| | | CGGCGGCAGCCAATCAGAGCGGCGCGCTCCGAAAGTTTCCTTTTATGGCGA |
| | | GGCGGCGGCGGCGGCGCCCTATAAAAAGCGAAGCGCGCGGCGGGCGGG |
| | | AGTCGCTGCGACGCTGCCTTCGCCCCGTGCCCCGCTCCGCCGCCGCCTCGC |
| | | GCCGCCCGCCCCGGCTCTGACTGACCGCGTTACTCCCACAGGTGAGCGGGC |
| | | GGGACGGCCCTTCTCCTCCGGGCTGTAATTAGCTGAGCAAGAGGTAAGGGTT |
| | | TAAGGGATGGTTGGTTGGTGGGGTATTAATGTTTAATTACCTGGAGCACCTGC |
| | | CTGAAATCACTTTTTTTCAGGTTGGACCGGTGCCACCATGGACTATAAGGACC |
| | | ACGACGGAGACTACAAGGATCATGATATTGATTACAAAGACGATGACGATAAG |
| | | ATGGCCCCAAAGAAGAAGCGGAAGGTCGGTATCCACGGAGTCCCAGCAGCC |
| | | GACAAGAAGTACAGCATCGGCCTGGACATCGGCACCAACTCTGTGGGCTGG |
| | | GCCGTGATCACCGACGAGTACAAGGTGCCCAGCAAGAAATTCAAGGTGCTG |
| | | GGCAACACCGACCGGCACAGCATCAAGAAGAACCTGATCGGAGCCCTGCTG |
| | | TTCGACAGCGGCGAAACAGCCGAGGCCACCCGGCTGAAGAGAACCGCCAGA |
| | | AGAAGATACACCAGACGGAAGAACCGGATCTGCTATCTGCAAGAGATCTTCA |
| | | GCAACGAGATGGCCAAGGTGGACGACAGCTTCTTCCACAGACTGGAAGAGT |
| | | CCTTCCTGGTGGAAGAGGATAAGAAGCACGAGCGGCACCCCATCTTCGGCA |
| | | ACATCGTGGACGAGGTGGCCTACCACGAGAAGTACCCCACCATCTACCACCT |
| | | GAGAAAGAAACTGGTGGACAGCACCGACAAGGCCGACCTGCGGCTGATCTA |
| | | TCTGGCCCTGGCCCACATGATCAAGTTCCGGGGCCACTTCCTGATCGAGGG |
| | | CGACCTGAACCCCGACAACAGCGACGTGGACAAGCTGTTCATCCAGCTGGT |
| | | GCAGACCTACAACCAGCTGTTCGAGGAAAACCCCATCAACGCCAGCGGCGT |
| | | GGACGCCAAGGCCATCCTGTCTGCCAGACTGAGCAAGAGCAGACGGCTGGA |
| | | AAATCTGATCGCCCAGCTGCCCGGCGAGAAGAAGAATGGCCTGTTCGGAAAC |
| | | CTGATTGCCCTGAGCCTGGGCCTGACCCCCAACTTCAAGAGCAACTTCGACC |
| | | TGGCCGAGGATGCCAAACTGCAGCTGAGCAAGGACACCTACGACGACGACC |
| | | TGGACAACCTGCTGGCCCAGATCGGCGACCAGTACGCCGACCTGTTTCTGG |
| | | CCGCCAAGAACCTGTCCGACGCCATCCTGCTGAGCGACATCCTGAGAGTGAA |
| | | CACCGAGATCACCAAGGCCCCCCTGAGCGCCTCTATGATCAAGAGATACGAC |
| | | GAGCACCACCAGGACCTGACCCTGCTGAAAGCTCTCGTGCGGCAGCAGCTG |
| | | CCTGAGAAGTACAAAGAGATTTTCTTCGACCAGAGCAAGAACGGCTACGCCG |
| | | GCTACATTGACGGCGGAGCCAGCCAGGAAGAGTTCTACAAGTTCATCAAGCC |
| | | CATCCTGGAAAAGATGGACGGCACCGAGGAACTGCTCGTGAAGCTGAACAG |
| | | AGAGGACCTGCTGCGGAAGCAGCGGACCTTCGACAACGGCAGCATCCCCCA |
| | | CCAGATCCACCTGGGAGAGCTGCACGCCATTCTGCGGCGGCAGGAAGATTT |
| | | TTACCCATTCCTGAAGGACAACCGGGAAAAGATCGAGAAGATCCTGACCTTC |
| | | CGCATCCCCTACTACGTGGGCCCTCTGGCCAGGGGAAACAGCAGATTCGCC |
| | | TGGATGACCAGAAAGAGCGAGGAAACCATCACCCCCTGGAACTTCGAGGAA |
| | | GTGGTGGACAAGGGCGCTTCCGCCCAGAGCTTCATCGAGCGGATGACCAAC |
| | | TTCGATAAGAACCTGCCCAACGAGAAGGTGCTGCCCAAGCACAGCCTGCTGT |
| | | ACGAGTACTTCACCGTGTATAACGAGCTGACCAAAGTGAAATACGTGACCGA |
| | | GGGAATGAGAAAGCCCGCCTTCCTGAGCGGCGAGCAGAAAAAGGCCATCGT |
| | | GGACCTGCTGTTCAAGACCAACCGGAAAGTGACCGTGAAGCAGCTGAAAGA |
| | | GGACTACTTCAAGAAAATCGAGTGCTTCGACTCCGTGGAAATCTCCGGCGTG |
| | | GAAGATCGGTTCAACGCCTCCCTGGGCACATACCACGATCTGCTGAAAATTA |
| | | TCAAGGACAAGGACTTCCTGGACAATGAGGAAAACGAGGACATTCTGGAAGA |
| | | TATCGTGCTGACCCTGACACTGTTTGAGGACAGAGAGATGATCGAGGAACGG |
| | | CTGAAAACCTATGCCCACCTGTTCGACGACAAAGTGATGAAGCAGCTGAAGC |
| | | GGCGGAGATACACCGGCTGGGGCAGGCTGAGCCGGAAGCTGATCAACGGC |
| | | ATCCGGGACAAGCAGTCCGGCAAGACAATCCTGGATTTCCTGAAGTCCGACG |
| | | GCTTCGCCAACAGAAACTTCATGCAGCTGATCCACGACGACAGCCTGACCTT |
| | | TAAAGAGGACATCCAGAAAGCCCAGGTGTCCGGCCAGGGCGATAGCCTGCA |
| | | CGAGCACATTGCCAATCTGGCCGGCAGCCCCGCCATTAAGAAGGGCATCCT |
| | | GCAGACAGTGAAGGTGGTGGACGAGCTCGTGAAAGTGATGGGCCGGCACAA |
| | | GCCCGAGAACATCGTGATCGAAATGGCCAGAGAGAACCAGACCACCCAGAA |
| | | GGGACAGAAGAACAGCCGCGAGAGAATGAAGCGGATCGAAGAGGGCATCAA |
| | | AGAGCTGGGCAGCCAGATCCTGAAAGAACACCCCGTGGAAAACACCCAGCT |
| | | GCAGAACGAGAAGCTGTACCTGTACTACCTGCAGAATGGGCGGGATATGTAC |
| | | GTGGACCAGGAACTGGACATCAACCGGCTGTCCGACTACGATGTGGACCATA |
| | | TCGTGCCTCAGAGCTTTCTGAAGGACGACTCCATCGACAACAAGGTGCTGAC |
| | | CAGAAGCGACAAGAACCGGGGCAAGAGCGACAACGTGCCCTCCGAAGAGGT |
| | | CGTGAAGAAGATGAAGAACTACTGGCGGCAGCTGCTGAACGCCAAGCTGATT |
| | | ACCCAGAGAAAGTTCGACAATCTGACCAAGGCCGAGAGAGGCGGCCTGAGC |
| | | GAACTGGATAAGGCCGGCTTCATCAAGAGACAGCTGGTGGAAACCCGGCAG |
| | | ATCACAAAGCACGTGGCACAGATCCTGGACTCCCGGATGAACACTAAGTACG |
| | | ACGAGAATGACAAGCTGATCCGGGAAGTGAAAGTGATCACCCTGAAGTCCAA |
| | | GCTGGTGTCCGATTTCCGGAAGGATTTCCAGTTTTACAAAGTGCGCGAGATC |
| | | AACAACTACCACCACGCCCACGACGCCTACCTGAACGCCGTCGTGGGAACC |
| | | GCCCTGATCAAAAAGTACCCTAAGCTGGAAAGCGAGTTCGTGTACGGCGACT |
| | | ACAAGGTGTACGACGTGCGGAAGATGATCGCCAAGAGCGAGCAGGAAATCG |
| | | GCAAGGCTACCGCCAAGTACTTCTTCTACAGCAACATCATGAACTTTTTCAAG |
| | | ACCGAGATTACCCTGGCCAACGGCGAGATCCGGAAGCGGCCTCTGATCGAG |
| | | ACAAACGGCGAAACCGGGGAGATCGTGTGGGATAAGGGCCGGGATTTTGCC |
| | | ACCGTGCGGAAAGTGCTGAGCATGCCCCAAGTGAATATCGTGAAAAAGACCG |
| | | AGGTGCAGACAGGCGGCTTCAGCAAAGAGTCTATCCTGCCCAAGAGGAACA |
| | | GCGATAAGCTGATCGCCAGAAAGAAGGACTGGGACCCTAAGAAGTACGGCG |

| SEQ ID No | Description | Sequence |
|---|---|---|
| | | GCTTCGACAGCCCCACCGTGGCCTATTCTGTGCTGGTGGTGGCCAAAGTGG |
| | | AAAAGGGCAAGTCCAAGAAACTGAAGAGTGTGAAAGAGCTGCTGGGGATCAC |
| | | CATCATGGAAAGAAGCAGCTTCGAGAAGAATCCCATCGACTTTCTGGAAGCC |
| | | AAGGGCTACAAAGAAGTGAAAAAGGACCTGATCATCAAGCTGCCTAAGTACT |
| | | CCCTGTTCGAGCTGGAAAACGGCCGGAAGAGAATGCTGGCCTCTGCCGGCG |
| | | AACTGCAGAAGGGAAACGAACTGGCCCTGCCCTCCAAATATGTGAACTTCCT |
| | | GTACCTGGCCAGCCACTATGAGAAGCTGAAGGGCTCCCCCGAGGATAATGA |
| | | GCAGAAACAGCTGTTTGTGGAACAGCACAAGCACTACCTGGACGAGATCATC |
| | | GAGCAGATCAGCGAGTTCTCCAAGAGAGTGATCCTGGCCGACGCTAATCTGG |
| | | ACAAAGTGCTGTCCGCCTACAACAAGCACCGGGATAAGCCCATCAGAGAGCA |
| | | GGCCGAGAATATCATCCACCTGTTTACCCTGACCAATCTGGGAGCCCCTGCC |
| | | GCCTTCAAGTACTTTGACACCACCATCGACCGGAAGAGGTACACCAGCACCA |
| | | AAGAGGTGCTGGACGCCACCCTGATCCACCAGAGCATCACCGGCCTGTACG |
| | | AGACACGGATCGACCTGTCTCAGCTGGGAGGCGACAAAAGGCCGGCGGCCA |
| | | CGAAAAAGGCCGGCCAGGCAAAAAAGAAAAAGGAATTCGGCAGTGGAGAGG |
| | | GCAGAGGAAGTCTGCTAACATGCGGTGACGTCGAGGAGAATCCTGGCCCAA |
| | | TGACCGAGTACAAGCCCACGGTGCGCCTCGCCACCCGCGACGACGTCCCCA |
| | | GGGCCGTACGCACCCTCGCCGCCGCGTTCGCCGACTACCCCGCCACGCGC |
| | | CACACCGTCGATCCGGACCGCCACATCGAGCGGGTCACCGAGCTGCAAGAA |
| | | CTCTTCCTCACGCGCGTCGGGCTCGACATCGGCAAGGTGTGGGTCGCGGAC |
| | | GACGGCGCCGCGGTGGCGGTCTGGACCACGCCGGAGAGCGTCGAAGCGGG |
| | | GGCGGTGTTCGCCGAGATCGGCCCGCGCATGGCCGAGTTGAGCGGTTCCC |
| | | GGCTGGCCGCGCAGCAACAGATGGAAGGCCTCCTGGCGCCGCACCGGCCC |
| | | AAGGAGCCCGCGTGGTTCCTGGCCACCGTCGGAGTCTCGCCCGACCACCAG |
| | | GGCAAGGGTCTGGGCAGCGCCGTCGTGCTCCCCGGAGTGGAGGCGGCCGA |
| | | GCGCGCCGGGGTGCCCGCCTTCCTGGAGACCTCCGCGCCCCGCAACCCTCC |
| | | CCTTCTACGAGCGGCTCGGCTTCACCGTCACCGCCGACGTCGAGGTGCCCG |
| | | AAGGACCGCGCACCTGGTGCATGACCCGCAAGCCCGGTGCCTGAGAATTCT |
| | | AACTAGAGCTCGCTGATCAGCCTCGACTGTGCCTTCTAGTTGCCAGCCATCT |
| | | GTTGTTTGCCCCTCCCCCGTGCCTTCCTTGACCCTGGAAGGTGCCACTCCCA |
| | | CTGTCCTTTCCTAATAAAATGAGGAAATTGCATCGCATTGTCTGAGTAGGTGT |
| | | CATTCTATTCTGGGGGGTGGGGTGGGGCAGGACAGCAAGGGGGAGGATTGG |
| | | GAAGAGAATAGCAGGCATGCTGGGGAGCGGCCGCAGGAACCCCTAGTGATG |
| | | GAGTTGGCCACTCCCTCTCTGCGCGCTCGCTCGCTCACTGAGGCCGGGCGA |
| | | CCAAAGGTCGCCCGACGCCCGGGCTTTGCCCGGGCGGCCTCAGTGAGCGA |
| | | GCGAGCGCGCAGCTGCCTGCAATCACTACATTCACATCTGATTTCAGTAGTTC |
| | | CTTACGAGAGTTCCTCCGCGCGGGTTTAAAGGGCCTCGTGATACGCCTATTT |
| | | TTATAGGTTAATGTCATGATAATAATGGTTTCTTAGACGTCAGGTGGCACTTTT |
| | | CGGGGAAATGTGCGCGGAACCCCTATTTGTTTATTTTTCTAAATACATTCAAAT |
| | | ATGTATCCGCTCATGAGACAATAACCCTGATAAATGCTTCAATAATATTGAAAA |
| | | AGGAAGAGTATGAGTATTCAACATTTCCGTGTCGCCCTTATTCCCTTTTTTGC |
| | | GGCATTTTGCCTTCCTGTTTTTGCTCACCCAGAAACGCTGGTGAAAGTAAAAG |
| | | ATGCTGAAGATCAGTTGGGTGCACGAGTGGGTTACATCGAACTGGATCTCAA |
| | | CAGCGGTAAGATCCTTGAGAGTTTTCGCCCCGAAGAACGTTTTCCAATGATGA |
| | | GCACTTTTAAAGTTCTGCTATGTGGCGCGGTATTATCCCGTATTGACGCCGG |
| | | GCAAGAGCAACTCGGTCGCCGCATACACTATTCTCAGAATGACTTGGTTGAG |
| | | TACTCACCAGTCACAGAAAAGCATCTTACGGATGGCATGACAGTAAGAGAATT |
| | | ATGCAGTGCTGCCATAACCATGAGTGATAACACTGCGGCCAACTTACTTCTGA |
| | | CAACGATCGGAGGACCGAAGGAGCTAACCGCTTTTTTGCACAACATGGGGGA |
| | | TCATGTAACTCGCCTTGATCGTTGGGAACCGGAGCTGAATGAAGCCATACCA |
| | | AACGACGAGCGTGACACCACGATGCCTGTAGCAATGGCAACAACGTTGCGCA |
| | | AACTATTAACTGGCGAACTACTTACTCTAGCTTCCCGGCAACAATTAATAGAC |
| | | TGGATGGAGGCGGATAAAGTTGCAGGACCACTTCTGCGCTCGGCCCTTCCG |
| | | GCTGGCTGGTTTATTGCTGATAAATCTGGAGCCGGTGAGCGTGGAAGCCGC |
| | | GGTATCATTGCAGCACTGGGGCCAGATGGTAAGCCCTCCCGTATCGTAGTTA |
| | | TCTACACGACGGGGAGTCAGGCAACTATGGATGAACGAAATAGACAGATCGC |
| | | TGAGATAGGTGCCTCACTGATTAAGCATTGGTAACTGTCAGACCAAGTTTACT |
| | | CATATATACTTTAGATTGATTTAAAACTTCATTTTTAATTTAAAAGGATCTAGGT |
| | | GAAGATCCTTTTTGATAATCTCATGACCAAATCCCTTAACGTGAGTTTTCGTT |
| | | CCACTGAGCGTCAGACCCCGTAGAAAAGATCAAAGGATCTTCTTGAGATCCTT |
| | | TTTTTCTGCGCGTAATCTGCTGCTTGCAAACAAAAAAACCACCGCTACCAGCG |
| | | GTGGTTTGTTTGCCGGATCAAGAGCTACCAACTCTTTTTCCGAAGGTAACTGG |
| | | CTTCAGCAGAGCGCAGATACCAAATACTGTCCTTCTAGTGTAGCCGTAGTTAG |
| | | GCCACCACTTCAAGAACTCTGTAGCACCGCCTACATACCTCGCTCTGCTAATC |
| | | CTGTTACCAGTGGCTGCTGCCAGTGGCGATAAGTCGTGTCTTACCGGGTTGG |
| | | ACTCAAGACGATAGTTACCGGATAAGGCGCAGCGGTCGGGCTGAACGGGGG |
| | | GTTCGTGCACACAGCCCAGCTTGGAGCGAACGACCTACACCGAACTGAGATA |
| | | CCTACAGCGTGAGCTATGAGAAAGCGCCACGCTTCCCGAAGGGAGAAAGGC |
| | | GGACAGGTATCCGGTAAGCGGCAGGGTCGGAACAGGAGAGCGCACGAGGG |
| | | AGCTTCCAGGGGGAAACGCCTGGTATCTTTATAGTCCTGTCGGGTTTCGCCA |
| | | CCTCTGACTTGAGCGTCGATTTTTGTGATGCTCGTCAGGGGGCGGAGCCTA |
| | | TGGAAAAACGCCAGCAACGCGGCCTTTTTACGGTTCCTGGCCTTTTGCTGGC |
| | | CTTTTGCTCACATGTGAGGGCCTATTTCCCATGATTCCTTCATATTTGCATATA |
| | | CGATACAAGGCTGTTAGAGAGATAATTGGAATTAATTTGACTGTAAACACAAA |
| | | GATATTAGTACAAAATACGTGACGTAGAAAGTAATAATTTCTTGGGTAGTTTGC |

| SEQ ID No | Description | Sequence |
|---|---|---|
| | | AGTTTTAAAATTATGTTTTAAAATGGACTATCATATGCTTACCGTAACTTGAAA<br>GTATTTCGATTTCTTGGCTTTATATATCTTGTGGAAAGGACGAAACACCGGGT<br>CTTCGAGAAGACCTGTTTTAGAGCTAGAAATAGCAAGTTAAAATAAGGCTAGT<br>CCGTTATCAACTTGAAAAAGTGGCACCGAGTCGGTGCTTTTTTGTTTTAGAGC<br>TAGAAATAGCAAGTTAAAATAAGGCTAGTCCGTTTTTAGCGCGTGCGCCAATT<br>CTGCAGACAAATGGCTCTAGAGCGAGGGCCTATTTCCCATGATTCCTTCATAT<br>TTGCATATACGATACAAGGCTGTTAGAGAGATAATTGGAATTAATTTGACTGTA<br>AACACAAAGATATTAGTACAAAATACGTGACGTAGAAAGTAATAATTTCTTGGG<br>TAGTTTGCAGTTTTAAAATTATGTTTTAAAATGGACTATCATATGCTTACCGTAA<br>CTTGAAAGTATTTCGATTTCTTGGCTTTATATATCTTGTGGAAAGGACGAAACA<br>CCGTAATTTTGTGTGGGTCACCCGTTTTAGAGCTAGGCCAACATGAGGATCA<br>CCCATGTCTGCAGGGCCTAGCAAGTTAAAATAAGGCTAGTCCGTTATCAACTT<br>GGCCAACATGAGGATCACCCATGTCTGCAGGGCCAAGTGGCACCGAGTCGG<br>TGCTTTTTTTGAGATATCCGAGGGCCTATTTCCCATGATTCCTTCATATTTGCA<br>TATACGATACAAGGCTGTTAGAGAGATAATTGGAATTAATTTGACTGTAAACAC<br>AAAGATATTAGTACAAAATACGTGACGTAGAAAGTAATAATTTCTTGGGTAGTT<br>TGCAGTTTTAAAATTATGTTTTAAAATGGACTATCATATGCTTACCGTAACTTG<br>AAAGTATTTCGATTTCTTGGCTTTATATATCTTGTGGAAAGGACGAAACACCGT<br>GAAACCAGTTTGGTTACCCGTTTTAGAGCTAGGCCAACATGAGGATCACCCAT<br>GTCTGCAGGGCCTAGCAAGTTAAAATAAGGCTAGTCCGTTATCAACTTGGCC<br>AACATGAGGATCACCCATGTCTGCAGGGCCAAGTGGCACCGAGTCGGTGCTT<br>TTTTTGA |
| SEQ ID NO: 68 | Example 5:<br>Cbh promoter<br>(small letters)-<br>Cas9-2A-puro-<br>pA (capital) | CGTTACATAACTTACGGTAAATGGCCCGCCTGGCTGACCGCCCAACGACCCC<br>CGCCCATTGACGTCAATAGTAACGCCAATAGGGACTTTCCATTGACGTCAATG<br>GGTGGAGTATTTACGGTAAACTGCCCACTTGGCAGTACATCAAGTGTATCATA<br>TGCCAAGTACGCCCCCTATTGACGTCAATGACGGTAAATGGCCCGCCTGGCA<br>TTGTGCCCAGTACATGACCTTATGGGACTTTCCTACTTGGCAGTACATCTACG<br>TATTAGTCATCGCTATTACCATGGTCGAGGTGAGCCCCACGTTCTGCTTCACT<br>CTCCCCATCTCCCCCCCCTCCCCACCCCCAATTTTGTATTTATTTATTTTTTAA<br>TTATTTTGTGCAGCGATGGGGGCGGGGGGGGGGGGGGGCGCGCGCCAGG<br>CGGGGCGGGCGGGCGAGGGGCGGGCGGGCGAGGCGGAGAGGTGC<br>GGCGGCAGCCAATCAGAGCGGCGCGCTCCGAAAGTTTCCTTTTATGGCGAG<br>GCGGCGGCGGCGGCCCTATAAAAAGCGAAGCGCGCGGCGGGCGGGA<br>GTCGCTGCGACGCTGCCTTCGCCCCGTGCCCCGCTCCGCCGCCGCCTCGC<br>GCCGCCCGCCCCGGCTCTGACTGACCGCGTTACTCCCACAGGTGAGCGGGC<br>GGGACGGCCCTTCTCCTCCGGGCTGTAATTAGCTGAGCAAGAGGTAAGGGTT<br>TAAGGGATGGTTGGTTGGTGGGGTATTAATGTTTAATTACCTGGACGCACCTGC<br>CTGAAATCACTTTTTTTCAGGTTGGACCGGTGCCACCATGGACTATAAGGACC<br>ACGACGGAGACTACAAGGATCATGATATTGATTACAAAGACGATGACGATAAG<br>ATGGCCCCAAAGAAGAAGCGGAAGGTCGGTATCCACGGAGTCCCAGCAGCC<br>GACAAGAAGTACAGCATCGGCCTGGACATCGGCACCAACTCTGTGGGCTGG<br>GCCGTGATCACCGACGAGTACAAGGTGCCCAGCAAGAAATTCAAGGTGCTG<br>GGCAACACCGACCGGCACAGCATCAAGAAGAACCTGATCGGAGCCCTGCTG<br>TTCGACAGCGGCGAAACAGCCGAGGCCACCCGGCTGAAGAGAACCGCCAGA<br>AGAAGATACACCAGACGGAAGAACCGGATCTGCTATCTGCAAGAGATCTTCA<br>GCAACGAGATGGCCAAGGTGGACGACAGCTTCTTCCACAGACTGGAAGAGT<br>CCTTCCTGGTGGAAGAGGATAAGAAGCACGAGCGGCACCCCATCTTCGGCA<br>ACATCGTGGACGAGGTGGCCTACCACGAGAAGTACCCCACCATCTACCACCT<br>GAGAAAGAAACTGGTGGACAGCACCGACAAGGCCGACCTGCGGCTGATCTA<br>TCTGGCCCTGGCCCACATGATCAAGTTCCGGGGCCACTTCCTGATCGAGGG<br>CGACCTGAACCCCGACAACAGCGACGTGGACAAGCTGTTCATCCAGCTGGT<br>GCAGACCTACAACCAGCTGTTCGAGGAAAACCCCATCAACGCCAGCGGCGT<br>GGACGCCAAGGCCATCCTGTCTGCCAGACTGAGCAAGAGCAGACGGCTGGA<br>AAATCTGATCGCCCAGCTGCCCGGCGAGAAGAAGAATGGCCTGTTCGGAAAC<br>CTGATTGCCCTGAGCCTGGGCCTGACCCCCAACTTCAAGAGCAACTTCGACC<br>TGGCCGAGGATGCCAAACTGCAGCTGAGCAAGGACACCTACGACGACGACC<br>TGGACAACCTGCTGGCCCAGATCGGCGACCAGTACGCCGACCTGTTTCTGG<br>CCGCCAAGAACCTGTCCGACGCCATCCTGCTGAGCGACATCCTGAGAGTGAA<br>CACCGAGATCACCAAGGCCCCCCTGAGCGCCTCTATGATCAAGAGATACGAC<br>GAGCACCACCAGGACCTGACCCTGCTGAAAGCTCTCGTGCGGCAGCAGCTG<br>CCTGAGAAGTACAAAGAGATTTTCTTCGACCAGAGCAAGAACGGCTACGCCG<br>GCTACATTGACGGCGGAGCCAGCCAGGAAGAGTTCTACAAGTTCATCAAGCC<br>CATCCTGGAAAAGATGGACGGCACCGAGGAACTGCTCGTGAAGCTGAACAG<br>AGAGGACCTGCTGCGGAAGCAGCGGACCTTCGACAACGGCAGCATCCCCCA<br>CCAGATCCACCTGGGAGAGCTGCACGCCATTCTGCGGCGGCAGGAAGATTT<br>TTACCCATTCCTGAAGGACAACCGGGAAAAGATCGAGAAGATCCTGACCTTC<br>CGCATCCCCTACTACGTGGGCCCTCTGGCCAGGGGAAACAGCAGATTCGCC<br>TGGATGACCAGAAAGAGCGAGGAAACCATCACCCCCTGGAACTTCGAGGAA<br>GTGGTGGACAAGGGCGCTTCCGCCCAGAGCTTCATCGAGCGGATGACCAAC<br>TTCGATAAGAACCTGCCCAACGAGAAGGTGCTGCCCAAGCACAGCCTGCTGT<br>ACGAGTACTTCACCGTGTATAACGAGCTGACCAAAGTGAAATACGTGACCGA<br>GGGAATGAGAAAGCCCGCCTTCCTGAGCGGCGAGCAGAAAAAGGCCATCGT<br>GGACCTGCTGTTCAAGACCAACCGGAAAGTGACCGTGAAGCAGCTGAAAGA<br>GGACTACTTCAAGAAAATCGAGTGCTTCGACTCCGTGGAAATCTCCGGCGTG |

| SEQ ID No | Description | Sequence |
|---|---|---|
| | | GAAGATCGGTTCAACGCCTCCCTGGGCACATACCACGATCTGCTGAAAATTA<br>TCAAGGACAAGGACTTCCTGGACAATGAGGAAAACGAGGACATTCTGGAAGA<br>TATCGTGCTGACCCTGACACTGTTTGAGGACAGAGAGATGATCGAGGAACGG<br>CTGAAAACCTATGCCCACCTGTTCGACGACAAAGTGATGAAGCAGCTGAAGC<br>GGCGGAGATACACCGGCTGGGGCAGGCTGAGCCGGAAGCTGATCAACGGC<br>ATCCGGGACAAGCAGTCCGGCAAGACAATCCTGGATTTCCTGAAGTCCGACG<br>GCTTCGCCAACAGAAACTTCATGCAGCTGATCCACGACGACAGCCTGACCTT<br>TAAAGAGGACATCCAGAAAGCCCAGGTGTCCGGCCAGGGCGATAGCCTGCA<br>CGAGCACATTGCCAATCTGGCCGGCAGCCCCGCCATTAAGAAGGGCATCCT<br>GCAGACAGTGAAGGTGGTGGACGAGCTCGTGAAAGTGATGGGCCGGCACAA<br>GCCCGAGAACATCGTGATCGAAATGGCCAGAGAGAACCAGACCACCCAGAA<br>GGGACAGAAGAACAGCCGCGAGAGAATGAAGCGGATCGAAGAGGGCATCAA<br>AGAGCTGGGCAGCCAGATCCTGAAAGAACACCCCGTGGAAAACACCCAGCT<br>GCAGAACGAGAAGCTGTACCTGTACTACCTGCAGAATGGGCGGGATATGTAC<br>GTGGACCAGGAACTGGACATCAACCGGCTGTCCGACTACGATGTGGACCATA<br>TCGTGCCTCAGAGCTTTCTGAAGGACGACTCCATCGACAACAAGGTGCTGAC<br>CAGAAGCGACAAGAACCGGGGCAAGAGCGACAACGTGCCCTCCGAAGAGGT<br>CGTGAAGAAGATGAAGAACTACTGGCGGCAGCTGCTGAACGCCAAGCTGATT<br>ACCCAGAGAAAGTTCGACAATCTGACCAAGGCCGAGAGAGGCGGCCTGAGC<br>GAACTGGATAAGGCCGGCTTCATCAAGAGACAGCTGGTGGAAACCCGGCAG<br>ATCACAAAGCACGTGGCACAGATCCTGGACTCCCGGATGAACACTAAGTACG<br>ACGAGAATGACAAGCTGATCCGGGAAGTGAAAGTGATCACCCTGAAGTCCAA<br>GCTGGTGTCCGATTTCCGGAAGGATTTCCAGTTTTACAAAGTGCGCGAGATC<br>AACAACTACCACCACGCCCACGACGCCTACCTGAACGCCGTCGTGGGAACC<br>GCCCTGATCAAAAAGTACCCTAAGCTGGAAAGCGAGTTCGTGTACGGCGACT<br>ACAAGGTGTACGACGTGCGGAAGATGATCGCCAAGAGCGAGCAGGAAATCG<br>GCAAGGCTACCGCCAAGTACTTCTTCTACAGCAACATCATGAACTTTTTCAAG<br>ACCGAGATTACCCTGGCCAACGGCGAGATCCGGAAGCGGCCTCTGATCGAG<br>ACAAACGGCGAAACCGGGGAGATCGTGTGGGATAAGGGCCGGGATTTTGCC<br>ACCGTGCGGAAAGTGCTGAGCATGCCCCAAGTGAATATCGTGAAAAAGACCG<br>AGGTGCAGACAGGCGGCTTCAGCAAAGAGTCTATCCTGCCCAAGAGGAACA<br>GCGATAAGCTGATCGCCAGAAAGAAGGACTGGGACCCTAAGAAGTACGGCG<br>GCTTCGACAGCCCCACCGTGGCCTATTCTGTGCTGGTGGTGGCCAAAGTGG<br>AAAAGGGCAAGTCCAAGAAACTGAAGAGTGTGAAAGAGCTGCTGGGGATCAC<br>CATCATGGAAAGAAGCAGCTTCGAGAAGAATCCCATCGACTTTCTGGAAGCC<br>AAGGGCTACAAAGAAGTGAAAAAGGACCTGATCATCAAGCTGCCTAAGTACT<br>CCCTGTTCGAGCTGGAAAACGGCCGGAAGAGAATGCTGGCCTCTGCCGGCG<br>AACTGCAGAAGGGAAACGAACTGGCCCTGCCCTCCAAATATGTGAACTTCCT<br>GTACCTGGCCAGCCACTATGAGAAGCTGAAGGGCTCCCCCGAGGATAATGA<br>GCAGAAACAGCTGTTTGTGGAACAGCACAAGCACTACCTGGACGAGATCATC<br>GAGCAGATCAGCGAGTTCTCCAAGAGAGTGATCCTGGCCGACGCTAATCTGG<br>ACAAAGTGCTGTCCGCCTACAACAAGCACCGGGATAAGCCCATCAGAGAGCA<br>GGCCGAGAATATCATCCACCTGTTTACCCTGACCAATCTGGGAGCCCCTGCC<br>GCCTTCAAGTACTTTGACACCACCATCGACCGGAAGAGGTACACCAGCACCA<br>AAGAGGTGCTGGACGCCACCCTGATCCACCAGAGCATCACCGGCCTGTACG<br>AGACACGGATCGACCTGTCTCAGCTGGGAGGCGACAAAAGGCCGGCGGCCA<br>CGAAAAAGGCCGGCCAGGCAAAAAAGAAAAAGGAATTCGGCAGTGGAGAGG<br>GCAGAGGAAGTCTGCTAACATGCGGTGACGTCGAGGAGAATCCTGGCCCAA<br>TGACCGAGTACAAGCCCACGGTGCGCCTCGCCACCCGCGACGACGTCCCCA<br>GGGCCGTACGCACCCTCGCCGCCGCGTTCGCCGACTACCCCGCCACGCGC<br>CACACCGTCGATCCGGACCGCCACATCGAGCGGGTCACCGAGCTGCAAGAA<br>CTCTTCCTCACGCGCGTCGGGCTCGACATCGGCAAGGTGTGGGTCGCGGAC<br>GACGGCGCCGCGGTGGCGGTCTGGACCACGCCGGAGAGCGTCGAAGCGGG<br>GGCGGTGTTCGCCGAGATCGGCCCGCGCATGGCCGAGTTGAGCGGTTCCC<br>GGCTGGCCGCGCAGCAACAGATGGAAGGCCTCCTGGCGCCGCACCGGCCC<br>AAGGAGCCCGCGTGGTTCCTGGCCACCGTCGGAGTCTCGCCCGACCACCAG<br>GGCAAGGGTCTGGGCAGCGCCGTCGTGCTCCCCGGAGTGGAGGCGGCCGA<br>GCGCGCCGGGGTGCCCGCCTTCCTGGAGACCTCCGCGCCCCGCAACCTCC<br>CCTTCTACGAGCGGCTCGGCTTCACCGTCACCGCCGACGTCGAGGTGCCCG<br>AAGGACCGCGCACCTGGTGCATGACCCGCAAGCCCGGTGCCTGAGAATTCT<br>AACTAGAGCTCGCTGATCAGCCTCGACTGTGCCTTCTAGTTGCCAGCCATCT<br>GTTGTTTGCCCCTCCCCCGTGCCTTCCTTGACCCTGGAAGGTGCCACTCCCA<br>CTGTCCTTTCCTAATAAAATGAGGAAATTGCATCGCATTGTCTGAGTAGGTGT<br>CATTCTATTCTGGGGGGTGGGGTGGGGCAGGACAGCAAGGGGGAGGATTGG<br>GAAGAGAATAGCAGGCATGCTGGGA |
| SEQ ID NO: 69 | Example 5: U6 promoter promoter for our guides (there are 3 U6 promoters in each plasmid, but only 2 are | TTTCCCATGATTCCTTCATATTTGCATATACGATACAAGGCTGTTAGAGAGATA<br>ATTGGAATTAATTTGACTGTAAACACAAAGATATTAGTACAAAATACGTGACGT<br>AGAAAGTAATAATTTCTTGGGTAGTTTGCAGTTTTAAAATTATGTTTTAAAATG<br>GACTATCATATGCTTACCGTAACTTGAAAGTATTTCGATTTCTTGGCTTTATAT<br>ATCTTGTGGAAAGGACGAAACACCG |

| SEQ ID No | Description | Sequence |
|---|---|---|
| | used to make a functional guide) | |
| SEQ ID NO: 70 | Example 5: conserved portion of the gRNA | GTTTTAGAGCTAGGCCAACATGAGGATCACCCATGTCTGCAGGGCCTAGCAA GTTAAAATAAGGCTAGTCCGTTATCAACTTGGCCAACATGAGGATCACCCATG TCTGCAGGGCCAAGTGGCACCGAGTCGGTGCTTTTTTT |
| SEQ ID NO: 71 | Example 5: the guide targeting sequence 1 (protospacer). This is unique for each guide targeting the genome before or after the exon to be excised. | TAATTTTGTGTGGGTCACCC |
| SEQ ID NO: 72 | Example 5: the guide targeting sequence 2 (protospacer). This is unique for each guide targeting the genome before or after the exon to be excised. | TGAAACCAGTTTGGTTACCC |
| SEQ ID NO: 73 | Example 5: Target genomic sequence | CCACCATACCCGGCCATCTTTTAGAATTTCTATGTTACACTCTCCCAAGCATT TTTATGGTTTTATTTCACCCCATGATAGTAATTATATCACTTCTGATCTGTTAAG AATAGACCTTTTAAAAGTATTGGATAACTTAGAGATGAGACATCTTCAGTTACT CTGTTATTCACCTATTACTCCTTAGGTTACTTGTGAATAATTTTGTGTGGGTCA CCCAGGCAAATGTAAATAGCTCTTCATGTCTTTTAGCAGACTGGTATGTTTCC AATAAGATCATTTAAGTCCTCAAAGCATTCCTAAATCATTGTTAGACTTTTTTTT TTCTTAAAGATTCGGCAGGATGATACGAGTTCATCCATCAATTTCCTGACTCG AGTTAGTGGCATTGGGTAAGAACTATTTTTTAAGCAGACACAATCGTCAGTTA GTTTATTTTTCCTGTTAGCCAAAGTAAATTACATGCTGTTTCTCAAAACCTGTA CTTCACCACCTCTGTACCTTAGCCATACAGTTCACCCTTCCATAGCTTATGAT CTGAGGCCGATTCTTCAGATAGTGTCTCTACTGTAAGGTCCCCATCCAAGGC AGATGTTACCTCCTTCATGAAACCAGTTTGGTTACCCAGGCAGAAAGAACCTC TCCCTCCTCTGAACTCCACTACCATTTCCTCCGTGTGCATCTATTTCCTGCTC CAGCTTGGCCTCTTTTGTTTCTCTGAGCATGATATTTATCATAGCACCTCATGA ATTTGGAACAAGCCCTCAAGCTTTTTTTAAATTA |
| SEQ ID NO: 74 | Example 5: exon to be replaced (Polb-exon5) | ATTCGGCAGGATGATACGAGTTCATCCATCAATTTCCTGACTCGAGTTAGTGG CATTGG |
| SEQ ID NO: 75 | Example 5: Cas9 Target Site 1 (each is unique) | TAATTTTGTGTGGGTCACCC |
| SEQ ID NO: 76 | Example 5: Cas9 Target Site 2 (each is unique) | TGAAACCAGTTTGGTTACCC |
| SEQ ID NO: 77 | FIG. 16: WT allele: protospacer and upstream PAM | TTGTGTGGGTCACCCAGGCAAATG |
| SEQ ID NO: 78 | FIG. 16: WT allele: protospacer | CCAGTTTGGTTACCCAGGCAGAAA |

| SEQ ID No | Description | Sequence |
|---|---|---|
| | and downstream PAM | |
| SEQ ID NO: 79 | FIG. 16: Correctly targeted allele: Upstream integration site | TTGTGTGGGTCATGACCCACACAA |
| SEQ ID NO: 80 | FIG. 16: Correctly targeted allele: Downstream integration site, with PAM | AGAAGTCCTGGGCCCAGGCAGAAA |
| SEQ ID NO: 81 | FIG. 16: Incorrectly targeted allele: Clone 1 downstream | CAGGCAGAAA |
| SEQ ID NO: 82 | FIG. 16: Incorrectly targeted allele: Clone 2 upstream | TTGTGTGGGTCACTGACCCACACAA |
| SEQ ID NO: 83 | FIG. 16: Incorrectly targeted allele: Clone 3 upstream | TTGTGTGGGTTGACCCACACAA |
| SEQ ID NO: 84 | FIG. 16: Incorrectly targeted allele: Clone 5 downstream | AGAAGTCCTGGGTCCCAGGCAGAAA |
| SEQ ID NO: 85 | FIG. 16: Incorrectly targeted allele: Clone 8 downstream | AGAAGTCCTGGGACCCAGGCAGAAA |

EXAMPLES

The invention is further described by the following examples. These are not intended to limit the scope of the invention, but represent preferred embodiments of aspects of the invention provided for greater illustration of the invention described herein.

Materials and Methods of the Examples

Plasmid Construction:

For SEQ ID NO: 1: oligonucleotides matching the protospacer of SEQ ID NO: 2: named Rosa26 were ordered from IDT Biologika. The oligonucleotides were hybridized and ligated into a backbone vector (Addgene #62988; www.addgene.org) containing the rest of the sgRNA as well as CAG-Cas9-2A-puro.

For SEQ ID NO: 6 (plasmid mCherry): The mCherry coding sequence was amplified from a plasmid. Both primers contained the Target Site A+PAM sequence (SEQ ID NO: 2) and each contained either PacI or PvuI for ligation into a backbone vector.

For SEQ ID NO: 7 (MC mCherry): The mCherry coding sequence was amplified from SEQ ID NO: 6. Primer included restriction sites for cloning into the MiniCircle SBI MC-Easy production system. MiniCircles were produced as per the manufactures instructions.

Cell Transfection, Sorting, Expansion

Reporter HeLa cells containing the CAG-BFP-pA-Venus-pA sequence in the AAVSI loci (FIG. 2, SEQ ID NO: 3) where transfected with the plasmid (SEQ ID NO: 1). This plasmid drives Cas9 production, the guide for the targeting sequences flanking the BFP-pA, and contains a puromycin resistance gene. This was co-transfected with the replacement mCherry sequence on either the full plasmid (SEQ ID NO: 6) or the minimal MiniCircle plasmid (SEQ ID NO: 7). Plasmids were delivered by reverse transfection using Lipofectamine 3000. After 24 hours selection began for puromycin resistance; selection was carried out for 48 hours. The cells were expanded for 10 days and then FACS sorted. mCherry+ cells were collected both as a mixed population and also mCherry+ cells were plated for single cell colonies. Single Cell colonies were expanded and gDNA extracted for genotyping. Cells were cultured in DMEM/10% FBS/1% Pen/Strep.

Reporter HEK293 cells containing the nonfunctional Venus in the AAVS1 loci (FIG. 8 and SEQ ID NO: 10) were transected with a plasmid containing Cas9, sgRNAs for two cut sites, and a turboGFP sequence that could be linearized and excised (SEQ ID NO: 11) using Lipofectamine 2000. These cells were cultured 10 days and FACS sorted for GFP+ cells. Single clonal colonies were made and expanded. The gDNA was extracted from such colonies.

Genotyping Cells:

For cells that were a mixed population of mCherry+ or single cell derived clones, the interface was sequenced at the 5' and 3' ends of the insert. The 5' junction (PCR 1 on FIG. 2) the primers 5'-TTGTCCCAAATCTGTGCGGA-3'; (SEQ ID NO: 47) and 5'-CAAGTAGTCGGGGATGTCGG-3'; (SEQ ID NO: 48) were used. The 3' junction of the mCherry insert with the 5' region of genomic DNA (PCR 2 noted on FIG. 2) primers 5'-CCGACTACTTGAAGCTGTCCTT-3'; (SEQ ID NO: 49) and 5'-CCCATATGTCCTTCCGAGT-GAG-3'; (SEQ ID NO: 50). Sequencing of this PCR product was done with primer 5'-GACTACACCATCGTG-GAACAGT-3'; (SEQ ID NO: 86). Both PCRs reactions were done with Hurculase 35× cycles, 98 C-30 s, 58 C-30 s, 72 C-45 s. For the mixed population mCherry cell PCR, the fragments were ligated into the CloneJET PCR Cloning kit. Mini-preps were made and sent for sequencing (FIGS. 3 and 4) (SEQ ID NO: 8 and SEQ ID NO; 9).

For HEK293 Cells with Reporter 2 that were GFP+10 days after transfection, single cell colonies were made. These colonies were expanded and gDNA extracted. The 5' end PCR was done with primers 5'-CGTAGGTGTAGCGGTAGTTAAC-3'; (SEQ ID NO: 51) and 5'-TTCGGCTTCTGGCGTGTGACC-3'; (SEQ ID NO: 52). The 3' end PCR was done with 5'-GTTAAC-TACCGCTACACCTACG-3'; (SEQ ID NO: 53) and 5'-GGTACAGCATCTCGGTGTTGG-3'; (SEQ ID NO: 54). The PCR was done 35× cycles, 98 C-30 s, 55 C-30 s, 72 C-30 s.

Methods for NHDF Polb Knock-In:

The human POLB exon 5 genomic region, the expression vector for Cas9 and guide RNAs, as well as the minicircle with the cherry reporter sequences are shown in the sequence section below. For a given experiment 1 µg of a plasmid containing Cas9 and guide RNAs were co-nucleofected with 3 µg of the POLB-Minicircle containing the replacement mCherry sequence (Lonza program DS-150) into 500.000 NHDF cells. Upon correct integration of the minicircle, the transcript contains a 2A-mCherry-pA sequence. NHDF cells (human juvenile foreskin fibroblasts, purchased from Promocell, Heidelberg, Germany) were cultured in DMEM/10% FCS/1% Pen/Strep. Expression of mCherry was measured by FACS after 8 days. An overview is shown in FIG. 1. Sanger sequencing shown in FIG. 3: the genomic DNA of the entire population of Polb Targeted NHDF cells was extracted with QuickExtract and amplified by primers POLBP3/POLBP4 or POLBP5/POLBP6 to amplify the 5' or 3' end respectively. The bands were gel extracted, purified, and Topo-cloned. The clones were Sanger sequenced using primer POLBP1 or POLBP2 to obtain sequence.

Primers for Topo Cloning/Sanger Sequencing of POLB Exon 5:

```
                                         (SEQ ID NO: 61)
PolbP1:  5' CCATACCCGGCCATCTTTTAGA 3';

(SEQ ID NO: 62)
PolbP2:  5' GCTTGAGGGCTTGTTCCAAATT 3';

(SEQ ID NO: 63)
PolbP3:  5' CCATACCCGGCCATCTTTTAGA 3';

(SEQ ID NO: 64)
PolbP4:  5' ACTCCTTGATGATGGCCATGTT 3';

(SEQ ID NO: 65)
PolbP5:  5' ATCAAGTTGGACATCACCTCCC '3;

(SEQ ID NO: 66)
PolbP6:  5' GCTTGAGGGCTTGTTCCAAATT 3';
```

Results of the Examples

Example 1: Replacement of Sequence in Reporter 1 Cell Line: Replacing a Blue Fluorescent Protein (BFP) with a Red Fluorescent Protein (mCherry) Sequence Using Non-Homologous End Joining after Two Genomic Cleavages by CRISPR/Cas9

To test if it is possible to cut out a piece of the genome and insert in another linear fragment in its place all at once, a florescent reporter was used (FIGS. 1 and 2). Reporter 1 in HeLa cells contains the CAG-BFP-pA-Venus-pA sequence inserted into the AAVSI loci (SEQ ID NO: 3). This sequence ccatacccggccatcttttagahas a Cas9 "target site A" inserted on both sides of the BFP so that when Cas9+ Target Site A sgRNA are introduced the reporter can excise out this sequence. Normally this would require two unique guides, but a single one was used for simplicity in this reporter. These Reporter 1 containing HeLa cells where transfected with the plasmid (SEQ ID NO: 1). This plasmid drives (i) Cas9 production, (ii) the guide for the targeting Target Site A flanking the BFP-pA, (iii) a Puromycin resistance gene. A second plasmid was added in addition to the Cas9 containing plasmid. This second plasmid contained the mCherry sequence required for sequence replacement in either a plasmid or MiniCircle form. If the plasmid was used, the Cas9 was designed to cut two places on the plasmid, freeing a linear piece of mCherry coding DNA. If the MiniCircle was used, a single cut site linearized the small plasmid and it was then ready for integration (FIG. 2).

Figure 6:
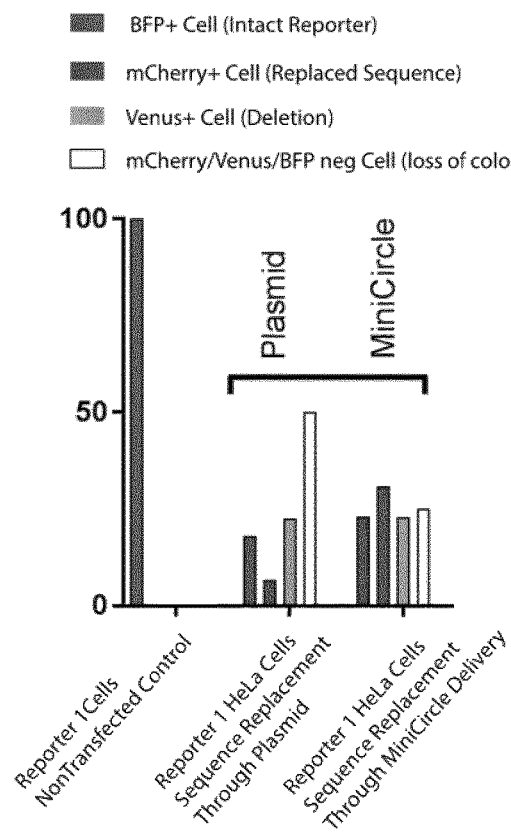
FIG. 6: Figure showing the Florescence Readout for Reporter 1 containing Cells and Wild Type Cells. A) This figure shows an example transfection of the Reporter 1 containing HeLa cells. This shows that initially all cells are blue. However after transfection with Cas9/gRNA and the replacement sequence (delivered either through plasmid or MiniCircle) the cells undergo a number of outcomes as noted in FIG. 2. Notably both the plasmid and MiniCircle delivery resulted in cells that took up and integrated the mCherry sequence. The plasmid based delivery was about 4% mCherry+ cells, while the MiniCircle delivery showed ~30% mCherry+ cells. Further genomic characterization of cells that underwent plasmid based or MC transfection is shown in FIGS. 3-5. B) The same transfection was done in WildType HeLa cells. These cells are identical to the reporter except they did not have the reporter placed in AAVS1. The aim of this experiment was to show that if any of the mCherry+ cells in part A were due to off target integration that somehow integrated into a reading frame, then the WT cells should also undergo a similar off target integration. As none of the WT HeLa cells became mCherry+, it points to the mCherry+ cells in part A originating from on target integration. This is further shown by the genotyping in FIGS. 3-5.
Figure 6:
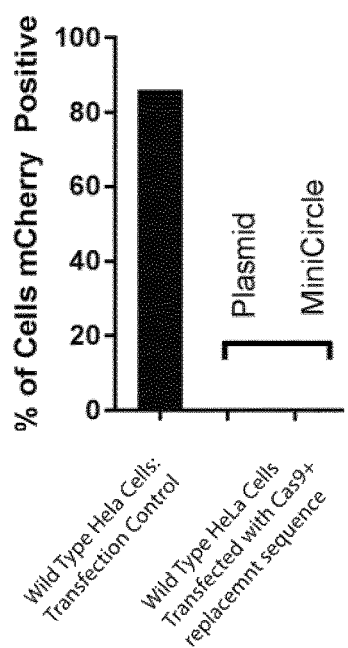

These reporter cells were selected by Puromycin to enrich for plasmid-transfected cells and analyzed by flow cytometry The cells could be red (mCherry), blue (BFP), green (Venus), or colorless. If they were red, this was due to the integration of the mCherry coding sequence into the reporter. Green was due to a deletion. BFP was due to a maintenance in the native gene, and colorless was due to some unspecific damage to the loci. Using the plasmid based mCherry delivery, about 5% of the cells were red (FIG. 6a). Using the MiniCircle delivery, about 30% of the cells became red. Further when wild type HeLa cells (without the Reporter 1 construct) were transfected with these plasmids, no cells became red (FIG. 6b). Noting that the red cells were due to on target integration.

To check that the mCherry was correctly inserted the cells were genotyped. First, the gDNA was extracted out of the transfected cells. Genotyping PCRs of the 5' end integration site (FIG. 3, SEQ ID NO: 8) show that the mCherry was correctly inserted. PCRs of the 3' end show that the integrate mCherry is correctly inserted. It would be possible that the cells turn red on insertion of the mCherry even if the original genomic DNA was not deleted. However sequencing in FIG. 4 (SEQ ID NO: 12) shows that the region behind the mCherry show that the mCherry replaced the original sequence and did not simply insert.

Figure 5:
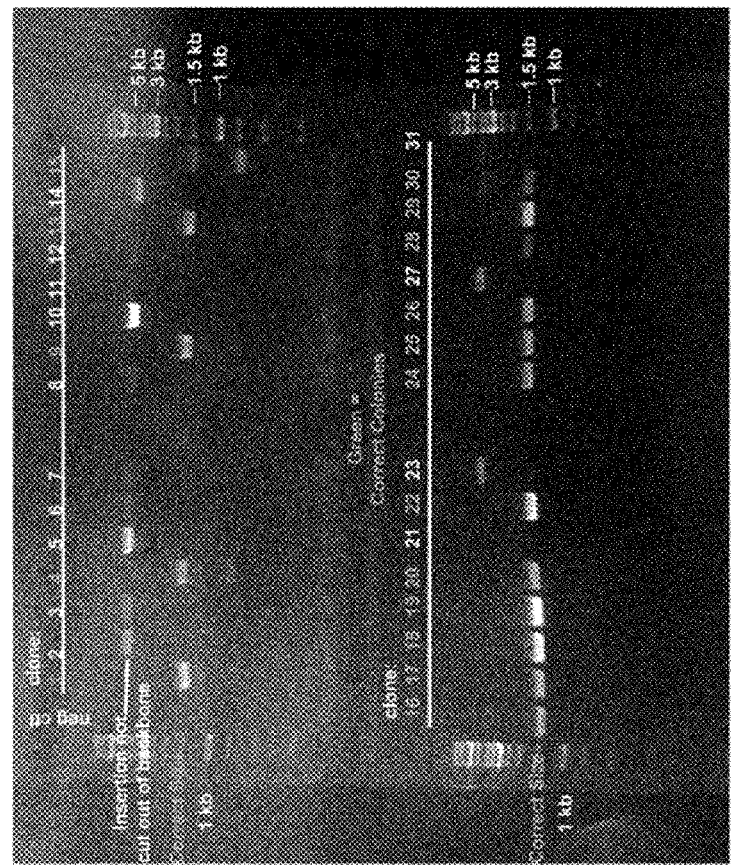
FIG. 5: Gel Showing Replacement of Sequence and larger Replacement. A) This figure highlights that when using a plasmid delivery option it could be possible to cleave only one side of the mCherry and then integrate the entire plasmid (Option 2) instead of the desired replacement sequence (Option 1). The Figure highlights the PCR band in the gel in B is the 5' region of the integrate. If the integration of mCherry was the small portion cleaved out of the backbone the size is 1.4 kb. If the entire plasmid is integrated it is nearly 4 kb. B) PCR 2 of single colonies of mCherry+ cells sorted after plasmid transfection. About 50% of the integrates integrated the entire plasmid and about 50% integrated the replacement sequence. While MiniCircle delivery avoids this backbone integration problem, this highlights that larger sequences (up to 4 kb in this case) can be used. Other data (not included) show 6 kb sequences inserted.

In comparison to the MiniCircle delivery, the plasmid based delivery requires two cuts to excise the sequence and prepare it for integration into the genomic region. However if it is not completely cut out of the backbone, then the entire sequence can be integrated into the region of interest. While this points to the utility of MiniCircle delivery, it also shows that larger sequences can be effectively integrated into the site. FIG. 5 shows that genotyping of the single cell colonies (single cells expanded to allow for easy genotyping) derived from plasmid based replacement show ~½ of the colonies that were mCherry+ had the entire 3 kb plasmid integrated.

Example 2: Replacement of a Nonfunctional Venus Fluorophore Encoding Sequence in Reporter 2: Replacing the Sequence with TurboGFP Using Non-Homologous End Joining after Two Genomic Cleavages by CRISPR/Cas9

Figure 8:
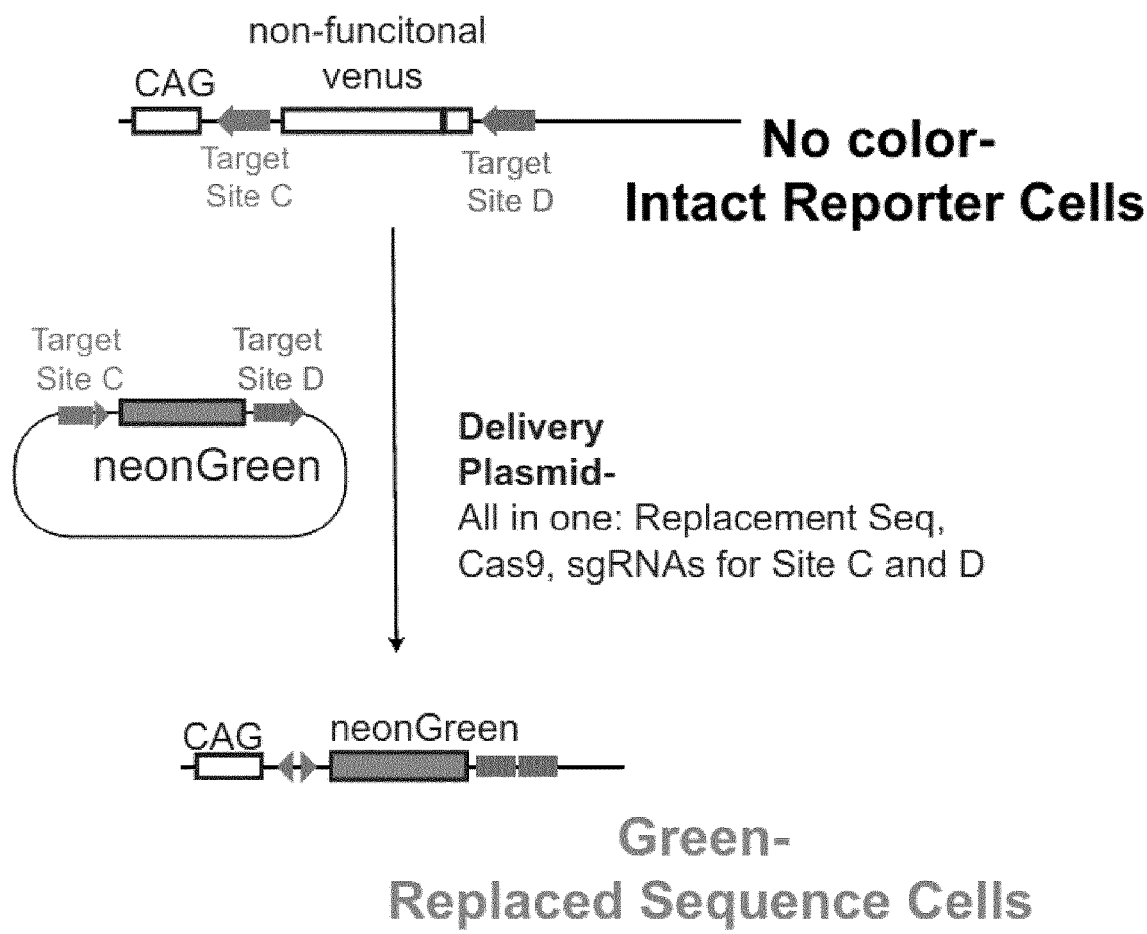
FIG. 8: Replacement of Sequence by fluorophore reporter in Reporter 2 cell line in Example 2. This figure shows an overview of the sequence put into the AAVS1 loci of HEK293 cells. There is a defective Venus in the loci so the cells are colorless. The sequence has two unique Cas9 recognition sites "Site C and Site D". A plasmid is transfected that contains Cas9, sgRNAs for Site C and D, and a turboGFP sequence to replace the excised defective Venus sequence. After the turboGFP sequence and the defective Venus are cleaved out of the plasmid and genome respectively, the turboGFP can be ligated in using the c-NHEJ pathway. This results in green cells that can be sorted and genotyped.

A second reporter cell line containing a nonfunctional venus existed in HEK293 cells as shown in FIG. 8 (SEQ ID NO: 10). This reporter was targeted as a second example of sequence replacement. The targeting of the sequence used two unique guide sites "Target Site B" and "Target Site C" (Figure (SEQ ID NO: 12 and SEQ ID NO: 13). The transfected vector (SEQ ID NO: 11) contained the Cas9, two guides, and the turboGFP to replace the excised genomic sequence. The turboGFP on the transfected plasmid was flanked by Target Site B and Target Site C. After the HEK293 cells with Reporter 2 were transfected with the plasmid, the cells were cultured for 10 days and then FACS sorted. GFP cells were taken and single colonies grown. Genotyping of the insert was done and shown in FIG. 9. While the 5' end shows an unusual deletion pattern, both ends show correct replacement of sequence in the turboGFP in the colonies.

Example 3: Using Replacement of Sequence on Native Gene

Figure 10:
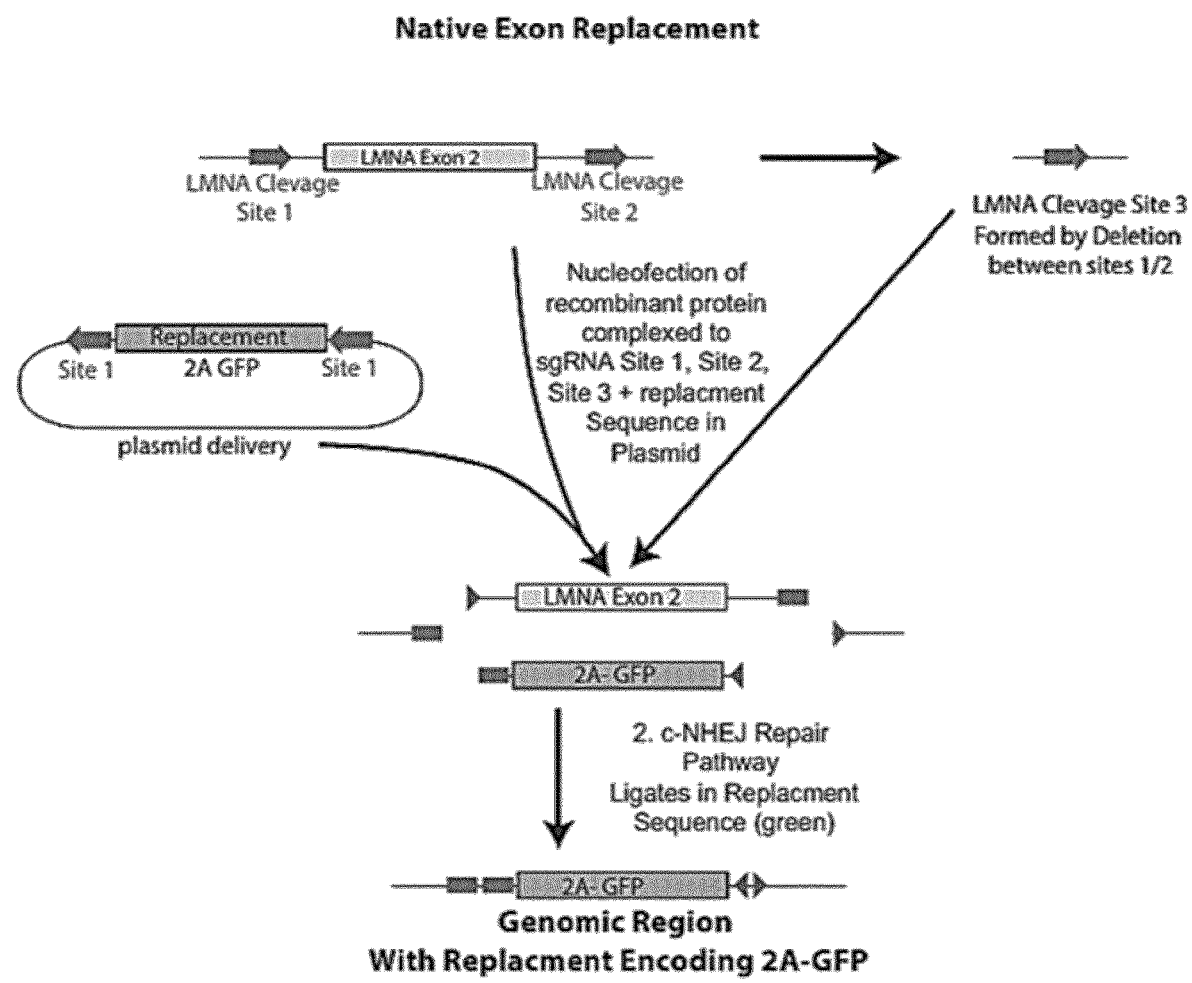
FIG. 10: Native Gene or Exon Replacement. The gene Lamin A is targeted for replacement of Exon 2 with with a fluorophore (GFP) as described in example 3.
Figure 11:
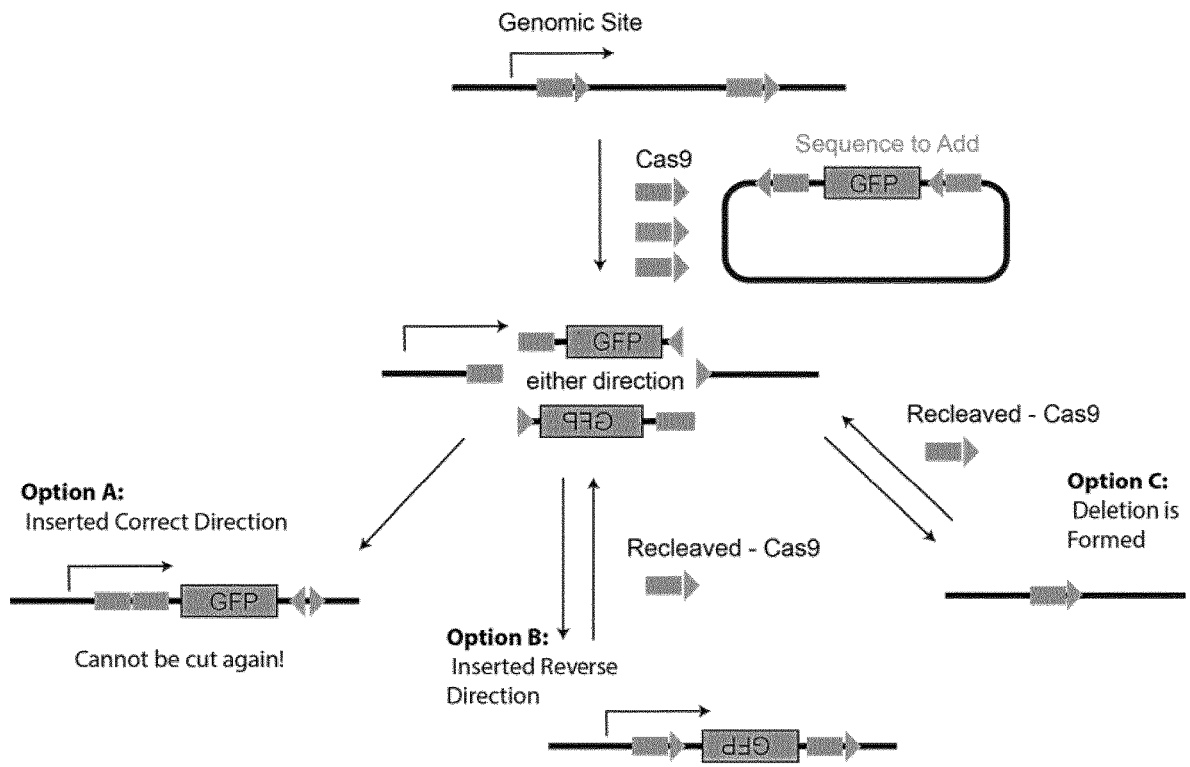
FIG. 11: Schematic representation of a strategy for directed insertion of a DNA substitute sequence (sequence to add). Directed integration of a DNA substitute sequence can be achieved by using three different guide RNAs. Guide RNA 1 (dark grey) recognizes a target side upstream of the DNA sequence to be replaced and downstream of the DNA substitute sequence (sequence to add). Guide RNA 2 (light grey) recognizes a target side downstream of the DNA sequence to be replaced and upstream of the DNA substitute sequence (sequence to add). Upon cleavage and removal of the DNA sequence to be replaced the DNA substitute sequence can either integrate in the desired orientation (Option A, inserted correct direction), in the undesired orientation (Option B, inserted reverse direction) or the open ends of the DNA molecule to be modified can be ligated with each other without insertion of the DNA substitute sequence (Option C, deletion is formed). If option A occurs, the resulting DNA molecule cannot be cut again, whereas in case of option B or C, a target side that is recognized by Guide RNA 3 (dark grey rectangle and light grey arrow head) is formed and can be cut again (recleavage) to recover the open ends for another integration event.
Figure 12:
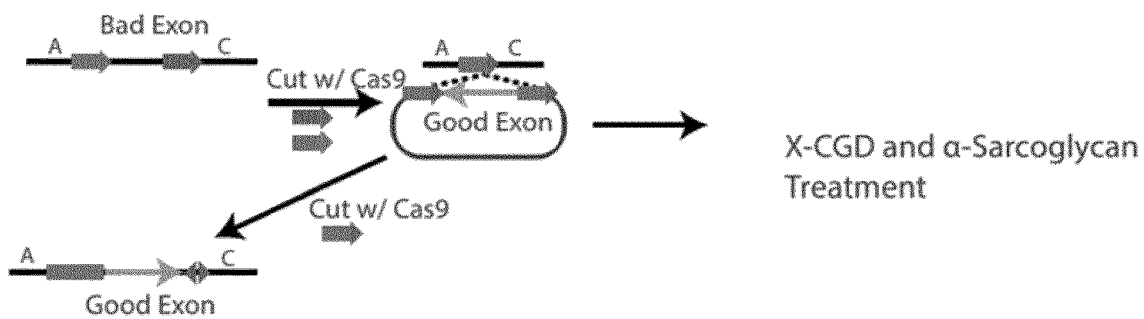
FIG. 12: Schematic representation of exon replacement therapy for X-linked chronic granulomatous disease (X-CGD) and α-sarcoglycanopathy. In this schematic representation of a treatment strategy aiming to replace a bad exon carrying a disease-causing mutation, for example in X-CGD or α-sarcoglycanopathy, directed integration of a DNA substitute sequence comprising the corrected/non-pathological exon sequence can be achieved by employing the directed integration strategy describe in FIG. 11.

The gene Lamin A is targeted for replacement of Exon 2 with a fluorophore (GFP) (FIG. 10). ~200 nucleotides upstream and downstream of Exon 2, Cas9 Pam/Protospacers sequences are identified (cut site 1 and 2). These two sequences have the same directionality with regard to the protospacer/Pam and so a new sequence is formed when the two sites are cut and the region in-between is excised. A third guide RNA targeting this newly formed cut-site (cut site 3) is to be used. Synthetic guides that target sites 1, 2, and 3 are complexed with recombinant Cas9 protein, and then are nucleofected along with the MiniCircle plasmid into the host HeLa cells. This minicricle sequence has a PAM/Protospacer sequence that matches the cut site 1, upstream of the exon. Further it also contains the intronic region flanking Exon 2 so that it can be spliced into the mature mRNA correctly. Within the coding region, the exon 2 sequence is replaced with a in-frame 2A-GFP sequence so that correctly inserted sequence causes the cells to become blue. Cells are cultured for 3-5 days to recover and then FACS sorted for GFP+ cells. These cells are taken for single colony sorting. Further, pooled populations of GFP+ cells are analyzed through PCR through the entire genomic region and sequencing with long read PacBio sequencing to quantify successful replacement and the mutation frequency.

Example 4: Using Replacement of Sequence for Therapeutic Applications In Vivo For the use of the replacement of sequence for gene therapy patients with Limb Girdle Muscular Dystrophy 2D. A mutation in the Sarcoglycan A (SCGA) gene in Exon 7 results in the slow deterioration of the muscles throughout the body. A mouse model with the patient mutation is generated. A C>A mutation in exon 7 results in Ser>Stop (ochre). Treatment of this using replacement of sequence utilizes three Cas9 gRNAs. Guide 1 is 200 nt downstream of Exon 7. Guide 2 is ~200 nt upstream of Exon 7. Guide 3 is formed from the deletion of the genetic region between guide 1 and 2. These three guides are driven by a U6 promoter and encapsulated in an AAV Virus. Cas9 driven by a truncated promoter is also encapsulated in an AAV virus. A third AAV virus contains the replacement sequence. The replacement sequence is the same Exon 7 sequence without the disease causing mutation. The replacement sequence in the AAV is flannel by cut site 1 and 2 in such a way that correct orientation of the integration destroys the Cas9 cut sites, but reverse integration causes reformed cut sites 1 and 2. Injection into the musculature of the mouse is performed with the three viruses. After 3 weeks the muscle is sectioned and stained for correct SGCA sequence and protein production.

Example 5: Replacement of the POLB Gene Exon 5 in Primary Human Fibroblasts

Figure 13:
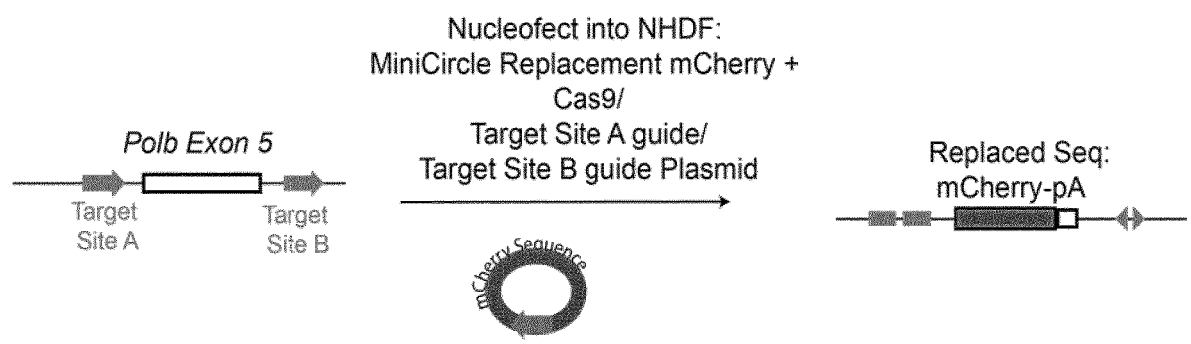
FIG. 13: Exon replacement in the Polb gene in human NHDF cells. For targeting of POLB exon 5 in NHDF cells, a Cas9 plasmid containing two guide RNAs targeting sequences upstream and downstream of exon 5, as well as an mCherry containing mini-circle were nucleofected into NHDF cells. The cells were analysed by flow cytometry and sequencing after a week.

In this example it is demonstrated that an exon of an endogenous target gene, specifically the exon 5 comprising 59 basepairs of the Polymerase-3 (POLB) gene, can be replaced in primary human fibroblasts by an artificial exon consisting of a splice acceptor element and a fluorescent Cherry reporter coding sequence (FIG. 13).

Figure 14:
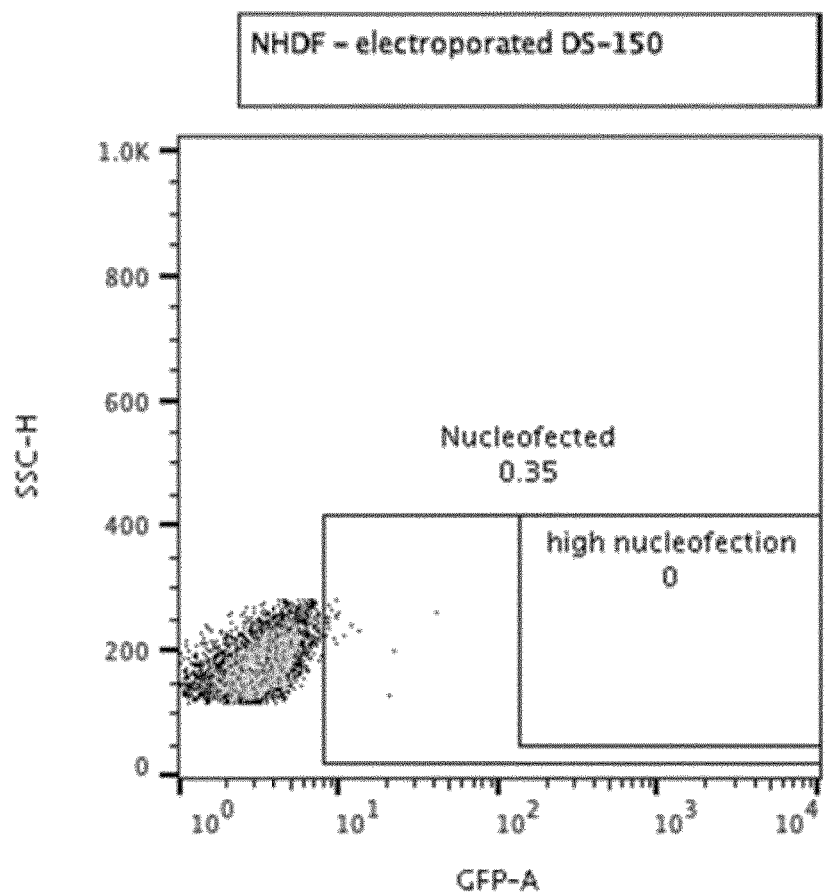
FIG. 14: Transfection control. FACS Analysis of Control nucleofection for estimation of transfection efficiency. A CAG-Venus plasmid was nucleofected into NHDF cells. Right panel: 53% of the cells were positive for GFP as compared to the negative control (left panel). The number of highly positive GFP cells (inserted box) reached 23.9% of the cells, i.e. about half of the transfected cell population.
Figure 14:
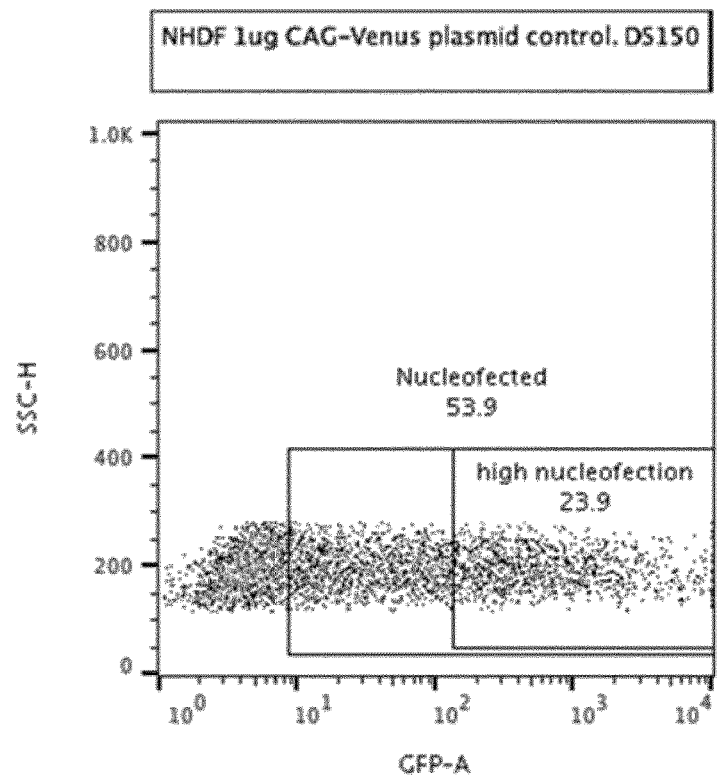

Sequence replacement was achieved by transfection of Normal Human Dermal Fibroblasts (NHDF) cells with a minicircle plasmid (carrying a splice acceptor and cherry reporter gene) together with an expression vector for Cas9 and two POLB specific guide RNAs that target sequences up- and downstream of exon 5 at a distance of 407 basepairs (FIG. 13). The efficiency of transfection was controlled by using a GFP expression plasmid and FACS analysis. As shown in FIG. 14, 53.9% of the cells were transfected, 23.9% showed high expression levels.

Figure 15:
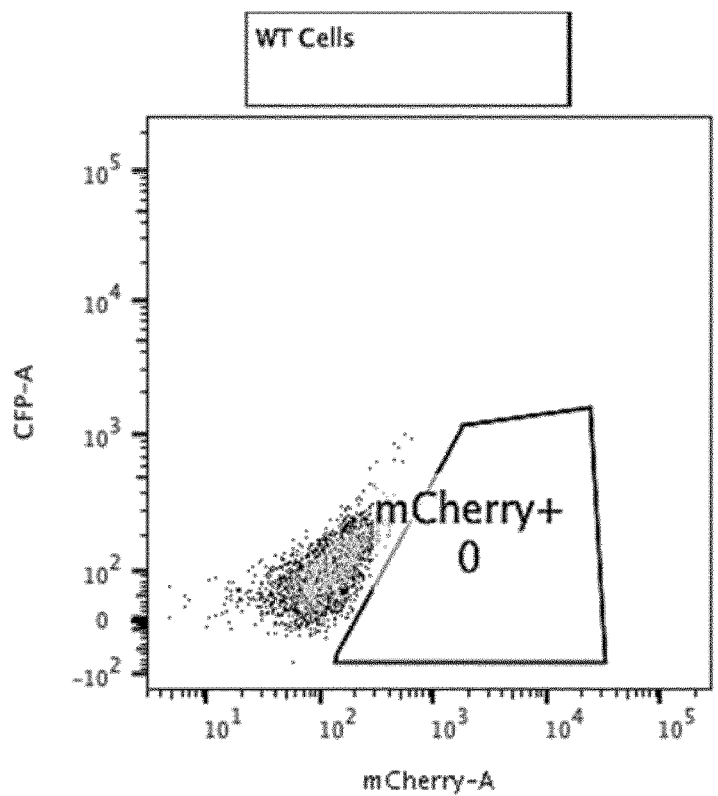
FIG. 15: Analysis of Polb gene exon replacement. FACS analysis one week after nucleofection of the Cas9 plasmid and the POLB-Minicircle containing the Cherry reporter gene into NHDF cells. 14% of the fibroblasts are mCherry positive. The mCherry MC alone contains no promoter.

Eight days after transfection, the population was analyzed for Cherry expression by flow cytometry to detect successful replacement events. This analysis showed that 14.1% of the transfected cell population were Cherry positive cells, indicating successful exon replacement at the POLB locus (FIG. 15). Since the transfection reached only 53.9% of the cells it can be estimated that exon replacement occurred within the transfected cell population at a frequency of approximately 26%. Under the assumption that exon replacement may occur only in the fraction of highly transfected cells (23.9%) the efficiency of exon replacement would be extrapolated to occur in 59% of the cells.

PCR amplification followed by Sanger sequencing proved the successful replacement of POLB exon 5 with the reporter gene together with minimal end resections (FIG. 16).

The invention claimed is:

1. An in vitro method for modifying a double stranded DNA (dsDNA) molecule in a mammalian cell, the method comprising:
   introducing into the cell
   i. a Cas9 endonuclease or a nucleic acid encoding a Cas9 endonuclease,
   ii. at least two Cas9-specific guide RNAs (guide RNA 1 and 2), and
   iii. an exogenous nucleic acid molecule comprising or encoding a DNA substitute sequence,
   generating at least two double strand breaks (DSBs) of the dsDNA molecule to be modified, wherein
   i. the dsDNA molecule comprises at least two target sequences (target sequences 1 and 2) which are targeted by the at least two Cas9-specific guide RNAs,
   ii. wherein guide RNA 1 targets target sequence 1 and guide RNA 2 targets target sequence 2, wherein the guide RNAs are complementary to the corresponding target sequences in the dsDNA molecule,
iii. wherein each target sequence in the dsDNA molecule is located adjacently to a protospacer-adjacent motif (PAM) sequence,
iv. wherein each guide RNA interacts with the Cas9 endonuclease to form a complex that specifically cleaves the dsDNA to create DSBs adjacent to each of the PAM sequences, and replacing a DNA sequence of the dsDNA molecule to be modified, wherein the replaced sequence is located between the double strand breaks (between target sequences 1 and 2) and wherein the sequence between the DSBs is replaced by the DNA substitute sequence of the exogenous nucleic acid molecule by the non-homologous end joining (NHEJ) pathway, wherein the exogenous nucleic acid molecule comprising or encoding the DNA substitute sequence has nucleotide sequences at its ends that lead to either reconstitution or disruption of the target sequences upon ligation of open ends of the dsDNA molecule to be modified and the DNA substitute sequence, depending on the orientation of the DNA substitute sequence after ligation, wherein if the target sequences are reconstituted after ligation, the DNA substitute sequence can be excised again by the Cas9 endonuclease that is complexed with the Cas9-specific guide RNA and wherein this process can be repeated until the DNA substitute sequence has been inserted in the desired orientation leading to disruption of the target sequences,
i. wherein ligation of the DNA substitute sequence by the NHEJ pathway occurs in orientation 1 or orientation 2,
ii. wherein upon ligation in orientation 1, target sequences 1 and target sequence 2 are restored, and upon ligation in orientation 2, target sequences 1 and target sequence 2 are disrupted.

2. The method according to claim 1, wherein said exogenous nucleic acid molecule is a circular DNA molecule.

3. The method according to claim 1, wherein said exogenous nucleic acid molecule is a linear DNA molecule.

4. The method according to claim 1, wherein said exogenous nucleic acid molecule is comprised by a viral vector.

5. The method according to claim 2, wherein the exogenous nucleic acid molecule comprises at least one target sequence (target sequence 3) which is targeted by at least one Cas9-specific guide RNA of the at least two guide Cas9-specific RNAs, wherein at least one double strand break occurs within or adjacent to target sequence 3 thereby resulting in a DNA substitute sequence.

6. The method according to claim 5, wherein the exogenous nucleic acid molecule comprises at least two target sequences (target sequences 3 and 4) that are targeted by the at least one Cas9-specific guide RNA, wherein double strand breaks occur within or adjacent to target sequences 3 and 4 thereby resulting in a DNA substitute sequence.

7. The method according to claim 1, wherein the cell is a non-dividing or slowly dividing cell.

8. The method according to claim 1, wherein the Cas9 endonuclease generates blunt end double strand breaks or wherein the target sequences are configured to generate blunt end double strand breaks.

9. The method according to claim 1, wherein the Cas9 endonuclease generating the at least two double strand breaks of the dsDNA molecule to be modified is a nickase or wherein the Cas9 endonuclease generates sticky end double strand breaks.

10. The method according to claim 8, wherein at least one additional guide RNA targets a sequence of the dsDNA molecule to be modified, wherein said sequence arises when the double strand breaks of the dsDNA molecule to be modified are ligated together, without a) introduction of the DNA substitute sequence and b) without reintroduction of the sequence located originally between the double strand breaks.

11. The method according to claim 2, wherein the circular DNA molecule is a plasmid or mini-circle.

12. The method according to claim 4, wherein the viral vector is an adenovirus, Adeno-associated virus (AAV), retrovirus or a non-integrating lentivirus.

13. The method according to claim 7, wherein the non-dividing or slowly dividing cell is cell in the G1 or G0 phase.

14. The method of claim 1, wherein the replaced DNA sequence of the dsDNA includes one or more exons.

* * * * *